(12) United States Patent
Bergman et al.

(10) Patent No.: US 10,494,376 B2
(45) Date of Patent: Dec. 3, 2019

(54) TETRAHYDROISOQUINOLINE DERIVED PRMT5-INHIBITORS

(71) Applicant: CTXT PTY LTD, Victoria (AU)

(72) Inventors: Ylva Elisabet Bergman, Victoria (AU); Richard Charles Foitzik, Victoria (AU); Benjamin Joseph Morrow, Victoria (AU); Michelle Ang Camerino, Victoria (AU); Scott Raymond Walker, Victoria (AU); H. Rachel Lagiakos, Victoria (AU); John Feutrill, Victoria (AU); Graeme Irvine Stevenson, Victoria (AU); Paul Anthony Stupple, Victoria (AU)

(73) Assignee: CTXT PTY. LTD., Victoria (AU)

( * ) Notice: Subject to any disclaimer, the term of this patent is extended or adjusted under 35 U.S.C. 154(b) by 0 days.

(21) Appl. No.: 15/508,053

(22) PCT Filed: Sep. 3, 2015

(86) PCT No.: PCT/EP2015/070149
§ 371 (c)(1),
(2) Date: Mar. 1, 2017

(87) PCT Pub. No.: WO2016/034673
PCT Pub. Date: Mar. 10, 2016

(65) Prior Publication Data
US 2017/0298075 A1 Oct. 19, 2017

(30) Foreign Application Priority Data

Sep. 3, 2014 (GB) .................................. 1415571.7
May 16, 2015 (GB) .................................. 1508454.4

(51) Int. Cl.
| | | |
|---|---|---|
| C07D 413/12 | (2006.01) |
| C07D 491/08 | (2006.01) |
| C07D 401/14 | (2006.01) |
| C07D 413/14 | (2006.01) |
| C07D 217/00 | (2006.01) |
| C07D 231/12 | (2006.01) |
| C07D 239/42 | (2006.01) |
| C07D 271/10 | (2006.01) |
| C07D 295/18 | (2006.01) |
| C07D 217/16 | (2006.01) |
| C07D 401/12 | (2006.01) |
| C07D 405/12 | (2006.01) |
| C07D 405/14 | (2006.01) |
| C07D 409/12 | (2006.01) |
| C07D 417/12 | (2006.01) |
| C07D 471/04 | (2006.01) |
| C07D 487/08 | (2006.01) |
| C07D 491/048 | (2006.01) |

(52) U.S. Cl.
CPC ......... *C07D 491/08* (2013.01); *C07D 217/00* (2013.01); *C07D 217/16* (2013.01); *C07D 231/12* (2013.01); *C07D 239/42* (2013.01); *C07D 271/10* (2013.01); *C07D 295/18* (2013.01); *C07D 401/12* (2013.01); *C07D 401/14* (2013.01); *C07D 405/12* (2013.01); *C07D 405/14* (2013.01); *C07D 409/12* (2013.01); *C07D 413/12* (2013.01); *C07D 413/14* (2013.01); *C07D 417/12* (2013.01); *C07D 471/04* (2013.01); *C07D 487/08* (2013.01); *C07D 491/048* (2013.01)

(58) Field of Classification Search
CPC .................................................... C07D 413/12
USPC ........................... 546/146; 514/307; 517/307
See application file for complete search history.

(56) References Cited

U.S. PATENT DOCUMENTS

| 6,008,219 A | 12/1999 | Stemp et al. |
| 6,046,210 A | 4/2000 | Stemp et al. |

(Continued)

FOREIGN PATENT DOCUMENTS

| CN | 102417483 A | 4/2012 |
| DE | 261153 A1 | 10/1988 |

(Continued)

OTHER PUBLICATIONS

Golub et al, Science, vol. 286, Oct. 15, 1999, pp. 531-537.*

(Continued)

*Primary Examiner* — Patricia L Morris
(74) *Attorney, Agent, or Firm* — Stites & Harbison PLLC; Richard S. Myers, Jr.

(57) ABSTRACT

A compound of formula I wherein: n is 1 or 2; p is 0 or 1; $R^1$ is optionally one or more halo or methyl groups; $R^{2a}$ and $R^{2b}$ are independently selected from the group consisting of: (i) F; (ii) H; (iii) Me; and (iv) $CH_2OH$; $R^{2c}$ and $R^{2d}$ are independently selected from the group consisting of: (i) F; (ii) H; (iii) Me; and (iv) $CH_2OH$; $R^{3a}$ and $R^{3b}$ are independently selected from H and Me; $R^4$ is either H or Me; $R^5$ is either H or Me; $R^{6a}$ and $R^{6b}$ are independently selected from H and Me; A is either (i) optionally substituted phenyl; (ii) optionally substituted naphthyl; or (iii) optionally substituted $C_{5-12}$ heteroaryl.

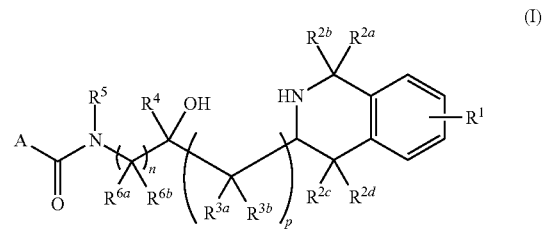

22 Claims, No Drawings

(56) References Cited

U.S. PATENT DOCUMENTS

| | | | |
|---|---|---|---|
| 6,274,593 | B1 | 8/2001 | Johns et al. |
| 6,579,892 | B1 | 6/2003 | Starck et al. |
| 2005/0101647 | A1 | 5/2005 | Oda et al. |
| 2005/0107398 | A1 | 5/2005 | Mach et al. |
| 2006/0235037 | A1 | 10/2006 | Purandare |
| 2010/0069431 | A1 | 3/2010 | Iwata et al. |
| 2016/0222005 | A1 | 8/2016 | Stupple et al. |

FOREIGN PATENT DOCUMENTS

| | | |
|---|---|---|
| GB | 2286395 A | 8/1995 |
| WO | WO96/30333 | 10/1996 |
| WO | WO97/43262 A1 | 11/1997 |
| WO | WO98/49145 | 11/1998 |
| WO | WO2003035065 A1 | 5/2003 |
| WO | WO2003082186 A2 | 10/2003 |
| WO | WO2004016611 A1 | 2/2004 |
| WO | WO2004024897 A2 | 3/2004 |
| WO | WO2005030206 A1 | 4/2005 |
| WO | WO2005042495 A1 | 5/2005 |
| WO | WO2006/008133 A2 | 1/2006 |
| WO | WO2006080821 A1 | 8/2006 |
| WO | WO2008061303 A1 | 5/2008 |
| WO | WO2009005551 A2 | 1/2009 |
| WO | WO2009113085 A1 | 9/2009 |
| WO | WO2009139076 A1 | 11/2009 |
| WO | WO2010025295 A2 | 3/2010 |
| WO | WO2012108689 A2 | 8/2012 |
| WO | WO2014100695 A1 | 6/2014 |
| WO | WO2014100716 A1 | 6/2014 |
| WO | WO2014100719 A2 | 6/2014 |
| WO | WO2014100730 A1 | 6/2014 |
| WO | WO2014100734 A1 | 6/2014 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Simone, Oncology:Introduction, Cecil Textbook of Medicine, ed Bennett et al. W.B.Saunders CO. 20th ed, vol. 1, 1996, pp. 1004-1010.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Ouaissi et al., "Rationale for Possible, etc.," Journal of Biomedicine and Biotechnology, 2011, Article: ID 315939, 1-8.*
K Vijayakumar et al: "Available on line www Synthesis, Anti-Tumor, Anti-Diabetic, and Anti-Asthmatic Activitives of Some Novel Benzimidazole Derivatives", Pharm. Res, vol. 2, No. 4 Jan. 1, 2010 (Jan. 1, 2010), 2010, pp. 215-224.
Richards M L et al: "Substituted 2-phenyl-benzimidazole derivatives: novel compounds that suppress key markers of allergy", European Journal of Medicinal Chemistry, Editions Scientifique Elsevier, Paris, FR, vol. 41, No. 8, Aug. 1, 2006 (Aug. 1, 2006), pp. 950-969.
Aggarwal, et al., Nuclear Cyclin D1/CDK4 Kinase Regulates CUL4 Expression and Triggers Neoplastic Growth via Activation of the PRMT5 Methyltransferase; Cancer Cell, 2010, 18, 329-340.
Berger, Shelley L., Out of the jaws of death: PRMT5 steers p53, nature cell biology vol. 10 | No. 12 | Dec. 2008, pp. 1389-1390.
Gu, et al., Protein arginine methyltransferase 5 is essential for growth of lung cancer cells, Biochemical Journal Immediate Publication. Published on Jun. 18, 2012 as manuscript BJ20120768, pp. 1-20.
Chen, et al., Epigenetic changes during disease progression in a murine model of human chronic lymphocytic leukemia, PNAS, Aug. 11, 2009, vol. 106, No. 32, pp. 13433-13438.
Cho, et al., Arginine methylation controls growth regulation by E2F-1, The EMBO Journal vol. 31 | No. 7 | 2012, pp. 1785-1797.
Durant, et al., p53 methylation, Cell Cycle 8:6, Mar. 15, 2009, pp. 801-802.
He, et al., Induction of human fetal hemoglobin expression by adenosine-2',3'-dialdehyde, Journal of Translational Medicine 2013, 11:14, pp. 1-7.
Jansson, et al., Arginine methylation regulates the p53 response, nature cell biology vol. 10 | No. 12 | Dec. 2008, pp. 1431-1439.
Kanduri, et al., Differential genome-wide array—based methylation profiles in prognostic subsets of chronic lymphocytic leukemia, Blood, Jan. 14, 2010 vol. 115, No. 2, pp. 296-305.
Karkhanis, et al., Versatility of PRMT5-induced methylation in growth control and development, Cell Press, 2011, pp. 1-9.
Kim, et al., Identification of Gastric Cancer—Related Genes Using a cDNA Microarray Containing Novel Expressed Sequence Tags Expressed in Gastric Cancer Cells, Clinical Cancer Research, Jan. 15, 2005, vol. 11, 473-482.
Krause, et al., Protein arginine methyltransferases: Evolution and assessment of their pharmacological and therapeutic potential, Pharmacology & Therapeutics 113 (2007) 50-87.
Le Guezennec, et al., MBD2/NuRD and MBD3/NuRD, Two Distinct Complexes with Different Biochemical and Functional Properties, Molecular and Cellular Biology, Feb. 2006, p. 843-851.
Nicholas, et al., Abstract LB-254: PRMT5 is upregulated in malignant and metastatic melanoma, and regulates expression of the MITF transcription factor, Cancer Res Apr. 15, 2012 72; LB-254.
Pal, et al., mSin3A/Histone Deacetylase 2- and PRMT5-Containing Brg1 Complex Is Involved in Transcriptional Repression of the Myc Target Gene cad, Molecular and Cellular Biology, Nov. 2003, p. 7475-7487.
Pollack, et al., The Human Homologue of the Yeast Proteins Skb1 and Hsl7p Interacts with Jak Kinases and Contains Protein Methyltransferase Activity, J. Biol. Chem. 1999, 274:31531-31542.
Powers, et al., Protein Arginine Methyltransferase 5 Accelerates Tumor Growth by Arginine Methylation of the Tumor Suppressor Programmed Cell Death 4, Cancer Res Published OnlineFirst Jun. 23, 2011, pp. OF1-OF9.
Rank, et al., Identification of a PRMT5-dependent repressor complex linked to silencing of human fetal globin gene expression, Blood, Sep. 2, 2010 vol. 116, No. 9, pp. 1585-1592.
Scoumanne, et al., PRMT5 is required for cell-cycle progression and p53 tumor suppressor function, Nucleic Acids Research, 2009, vol. 37, No. 15 4965-4976.
Pal, et al., Low levels of miR-92b/96 induce PRMT5 translation and H3R8/H4R3 methylation in mantle cell lymphoma, The EMBO Journal (2007) 26, 3558-3569.
Wang, et al., Protein Arginine Methyltransferase 5 Suppresses the Transcription of the RB Family of Tumor Suppressors in Leukemia and Lymphoma Cells, Molecular and Cellular Biology, Oct. 2008, p. 6262-6277.
Gu, et al., Protein Arginine Methyltransferase 5 Functions in Opposite Ways in the Cytoplasm and Nucleus of Prostate Cancer Cells, PLOS ONE, Aug. 2012 | vol. 7 | Issue 8, pp. e44033, pp. 1-13.
Mach, et al., Development of Novel 1,2,3,4-Tetrahydroisoquinoline Derivatives and Closely Related Compounds as Potent and Selective Dopamine D3 Receptor Ligands; Chembiochem; 2004; 5; pp. 508-518.
Braun, et al., Ber Dtsch Chem Ges; 1926; pp. 2416-2425.
Zajdel, et al. Solid-Phase Synthesis of Aryl-Alkylamine Derivatives Using Protected Aminoalcohol Building Blocks on SynPhaseTM Lanterns; QSAR Comb. Sci. 26, 2007, No. 2, 215-219.

* cited by examiner

US 10,494,376 B2

TETRAHYDROISOQUINOLINE DERIVED PRMT5-INHIBITORS

CROSS REFERENCE TO RELATED APPLICATIONS

This application is a § 371 National State Application of PCT/EP2015/070149 filed Sep. 3, 2015 which claims priority to GB 1415571.7 filed Sep. 3, 2014 and GB 1508454.4 filed May 16, 2015.

The present invention related to C-alkyl bicyclic amines and their use as pharmaceuticals, and in particular, in treating cancer and hemoglobinopathies.

BACKGROUND TO THE INVENTION

Post-translational modification of proteins is a hallmark of signal transduction where cells are able to react quickly to changes or events in the cellular environment. Post-translational modification of proteins expands the structural and functional diversity of the proteome. The role of acetylation and phosphorylation of proteins has been extensively studied as highly reversible reactions for fine-tuning responses to external stimuli or changes in the environmental conditions. Recently, the importance of other types of protein modifications, including ubiquitination and methylation has begun to be recognized.

The methylation of proteins and the enzymes that carry out these reactions has increased the dimensions of gene regulation by marking genes that are transcriptionally active or silenced. Protein methylation can occur on amino acids such as lysine, arginine, histidine, or proline, and on carboxy groups.

Arginine methylation of mainly nuclear proteins is an important post-translational modification process involved in structural remodelling of chromatin, signal transduction, cellular proliferation, nucleocytoplasmic shuttling, translation, gene transcription, DNA repair, RNA processing, or mRNA splicing.

Methylation of proteins at arginine residues is catalysed by Protein Arginine Methyltransferase enzymes. The Protein Arginine Methyl Transferase (PRMT) family of enzymes are evolutionarily conserved between organisms but differ in the number of members in different organisms.

There are eleven members of the human PRMT family, eight of which have known enzymatic activity and target substrates. With the exception of PRMT2 and two recently identified putative PRMT genes (PRMT10 and PRMT11), all remaining proteins of the family possess enzymatic arginine methylation activity.

PRMTs are subdivided into two types based on the methylation that they catalyse at the guanidinium group of arginine residues of substrate proteins. There are three nitrogens in the guanidinium group, potentially all of which could be methylated; the two ψ-guanidino nitrogen atoms and the internal δ-guanidino nitrogen atom. Mono-methylation and dimethylation of arginine (MMA and DMA) is found in mammalian cells at one or both of the two ψ-guanidino nitrogen atoms; dimethylation may be either symmetric or asymmetric. The third methylated arginine is generated by monomethylation of the internal δ-guanidino nitrogen atom of arginine and has so far been documented only in yeast proteins. Type I PRMT enzymes catalyse the formation of MMA and asymmetric dimethylarginine by di-methylating the same nitrogen atom of the guanidinium group, whereas Type II PRMT enzymes catalyse the formation of MMA and symmetric di-methylarginine by mono-methylating each of the terminal nitrogen atoms. Type III enzymes methylate the internal δ-guanidino nitrogen atom. Of the eight well characterised human PRMTs, PRMT1, 3, 4, 6 and 8 are Type I enzymes, and PRMT5, 7 and 9 are Type II enzymes.

PRMTs catalyse the methylation of the guanidino nitrogen atoms of arginine residues through the transfer of a methyl group from S-adenosyl methionine (SAM). A by-product of the enzymatic methylation step is S-adenosyl-L-homocysteine (AdoHcy), which is hydrolyzed to adenosine and homocysteine by AdoHcy hydrolase (Krause et al., 2007).

PRMT5

PRMT5 (aka JBP1, SKB1, IBP72, SKB1his and HRM-TIL5) is a Type II arginine methyltransferase, and was first identified in a two-hybrid search for proteins interacting with the Janus tyrosine kinase (Jak2) (Pollack et al., 1999).

PRMT5 plays a significant role in control and modulation of gene transcription. Inter alia, PRMT5 is known to methylate histone H3 at Arg-8 (a site distinct from that methylated by PRMT4) and histone H4 at Arg-3 (the same site methylated by PRMT1) as part of a complex with human SWI/SNF chromatin remodelling components BRG1 and BRM.

In addition to direct repressive histone marks induced by PRMT5, the enzyme's role in gene silencing is also mediated through the formation of multiprotein repressor complexes that include NuRD components, HDACs, MDB proteins and DNA methyltransferases, (Rank et al., 2010; Le Guezennec et al., 2006; Pal et al., 2003).

PRMT5 is involved in the methylation and functional modulation of the tumour suppressor protein p53. See (Berger, 2008; Durant et al., 2009; Jansson et al., 2008; Scoumanne et al., 2009). Most of the physiological functions of p53 are attributable to its role as a transcriptional activator, responding to agents that damage DNA. p53 status is wild type in approximately half of human cancer cases. These include 94% in cervix, 87% in blood malignancies, 85% in bones and endocrine glands, and 75% of primary breast cancer. Restoration of p53 in cancer cells harbouring wild type p53, by way of inhibiting mechanisms that suppress its function leads to growth arrest and apoptosis, and is regarded as a potentially effective means of tumour suppression.

p53 target genes have two alternative downstream effects: either they pause the cell cycle, allowing the DNA to be repaired, or, if repair is not possible, they activate processes leading to apoptosis (programmed cell death). How p53 'chooses' between these distinct outcomes is a central question in the field of tumour biology.

p53 is replete with post-translational modifications. Phosphorylation was one of the first post-translational modifications to be clearly defined on p53. In the last decade it has become additionally clear that p53 is modified not only by phosphorylation, but that it is extensively modified by lysine acetylation and methylation, among other modifications. Indeed, besides histone proteins p53 is the most common protein substrate known for these post-translational modifications. However, despite the plethora of post-translational modifications, p53 has not been identified, until recently, as a substrate for arginine methylation.

Jansson et al (Jansson et al., 2008) discovered that PRMT5 is physically associated with a p53 cofactor called Strap. A co-factor complex that contains Strap et al binds to p53 in response to DNA damage. Jansson et al demonstrated that PRMT5 methylates p53 in vitro, and mapped the sites of methylation (R333, R335 and R337). They developed an antibody that specifically detects p53 methylated on these sites and confirmed that p53 is methylated in vivo. Jansson et al went on to show that p53 methylation requires PRMT5 and is increased in response to etoposide, a DNA damaging agent.

The role of PRMT5 and p53 arginine methylation on cell cycle regulation and DNA damage response have been explored by both Jansson et al and Scoumanne et al (Jansson et al., 2008; Scoumanne et al., 2009). Although some differences are evident between the results from the two groups in respect of cell cycle regulation in unperturbed cells (which may be ascribed to cell type specific effects and/or the actual nature of the experimental arrangements), both groups report similar results with respect to the DNA damage response.

In response to DNA damage, caused by a variety of agents, including doxorubicin, camptothecin and UV light, and also in response to treatment with Nutlin-3, knockdown of PRMT5 results in an increase in sub-G1 population and concomitant reduction in G1 cells and, in the presence of p53, a significant increase in apoptosis. Knockdown of PRMT5 also resulted in a reduced level of p21, a key p53 target gene that regulates cell cycle arrest during the p53 response and MDM2, a p53 E3 ubiquitin ligase, but not PUMA, NOXA, AIP1 & APAF1, p53 target genes linked to apoptosis.

Knockdown of PRMT5 (but not PRMT1 or CARM1/PRMT4) results in decreased p53 stabilisation, decreased basal p53 levels, and decreased p53 oligomerisation, and also decreased expression of eIF4E a major component of translational machinery involved in ribosome binding to mRNA. Indeed, eIF4E is a potent oncogene, which has been shown to promote malignant transformation in vitro and human cancer formation.

Knockdown of PRMT5 would be expected to lead to a reduction in the level of arginine methylated p53. Consistent with arginine methylation status of p53 influencing the p53 response (reduced arginine methylation biasing the response to proapoptotic), Jannson et al showed that a p53 mutant in which each of the three critical arginine residues were substituted with lysine (p53KKK) retained the ability to induce apoptosis but its cell cycle arrest activity was significantly compromised.

Moreover, pS3KKK also has a significantly reduced ability to induce transcription of p21, by contrast with APAF1. The promoter binding specificity of wild-type p53 to key target genes is also significantly affected by arginine methylating status: Knockdown of PRMT5 results in decreased p53 binding to the promoter regions of the p21 and (intriguingly) PUMA genes, but does not affect p53 binding to the promoter regions of NOXA or APAF1.

Taken together, it would seem that PRMT5 is a prosurvival factor, which regulates cell proliferation in unstressed conditions and modulates the p53 response during DNA damage. In particular, knockdown of PRMT5, leading to a reduction in the levels of arginine methylated p53, appears to bias the p53 DNA damage response to proapoptotic as opposed to cell cycle arrest.

PRMT5 is further linked to cancers in that it is aberrantly expressed in around half of human cancer cases. PRMT5 overexpression has been observed in patient tissue samples and cell lines of Prostate cancer (Gu et al., 2012), Lung cancer (Zhongping et al., 2012), Melanoma cancer (Nicholas et al., 2012), Breast cancer (Powers et al., 2011), Colorectal cancer (Cho et al., 2012), Gastric cancer (Kim et al., 2005), Esophagus and Lung carcinoma (Aggarwal et al., 2010) and B-Cell lymphomas and leukemia (Wang, 2008).

Moreover, elevated expression of PRMT5 in Melanoma, Breast and Colorectal cancers has been demonstrated to correlate with a poor prognosis.

Lymphoid malignancies including CLL are associated with over-expression of PRMT5. PRMT5 is over-expressed (at the protein level) in the nucleus and cytosol in a number of patient derived Burkitt's lymphoma; mantle cell lymphoma (MCL); in vitro EBV-transformed lymphoma; leukaemia cell lines; and B-CLL cell lines, relative to normal CD19+ B lymphocytes (Pal et al., 2007; Wang et al., 2008). Intriguingly, despite elevated levels of PRMT5 protein in these tumour cells, the levels of PRMT5 mRNA are reduced (by a factor of 2-5). Translation of PRMT5 mRNA is however, enhanced in lymphoma cells, resulting in increased levels of PRMT5 (Pal et al., 2007; Wang et al., 2008).

In addition to genomic changes, CLL, like almost all cancers, has aberrant epigenetic abnormalities characterised by global hypomethylation and hot-spots of repressive hypermethylation of promoters including tumour suppressor genes. While the role of epigenetics in the origin and progression of CLL remains unclear, epigenetic changes appear to occur early in the disease and specific patterns of DNA methylation are associated with worse prognosis (Chen et al., 2009; Kanduri et al., 2010). Global symmetric methylation of histones H3R8 and H4R3 is increased in transformed lymphoid cell lines and MCL clinical samples (Pal et al., 2007), correlating with the overexpression of PRMT5 observed in a wide variety of lymphoid cancer cell lines and MCL clinical samples.

PRMT5 is therefore a target for the identification of novel cancer therapeutics.

PRMT5 Function and Hemoglobinopathies

Hemoglobin is a major protein in red blood cells and is essential for the transport of oxygen from the lungs to the tissues. In adult humans, the most common hemoglobin type is a tetramer called hemoglobin A, consisting of two $\alpha$ and two $\beta$ subunits. In human infants, the hemoglobin molecule is made up of two $\alpha$ and two $\gamma$ chains. The gamma chains are gradually replaced by subunits as the infant grows. The developmental switch in human ß-like globin gene subtype from foetal ($\gamma$) to adult (ß) that begins at birth heralds the onset of the hemoglobinopathies ß-thalassemia and sickle cell disease (SCD). In ß-thalassemia the adult chains are not produced. In SCD a point mutation in the coding sequence in the ß globin gene leads to the production of a protein with altered polymerisation properties. The observation that increased adult $\gamma$-globin gene expression (in the setting of hereditary persistence of foetal hemoglobin (HPFH) mutations) significantly ameliorates the clinical severity of ß-thalassemia and SCD has prompted the search for therapeutic strategies to reverse $\gamma$-globin gene silencing. To date, this has been achieved through pharmacological induction, using compounds that broadly influence epigenetic modifications, including DNA methylation and histone deacetylation. The development of more targeted therapies is dependent on the identification of the molecular mechanisms underpinning foetal globin gene silencing. These mechanisms have remained elusive, despite exhaustive study of the HPFH mutations, and considerable progress in many other aspects of globin gene regulation.

PRMT5 plays a critical role in triggering coordinated repressive epigenetic events that initiate with dimethylation of histone H4 Arginine 3 (H4R3me2s), and culminate in DNA methylation and transcriptional silencing of the $\gamma$-genes (Rank et al., 2010). Integral to the synchronous establishment of the repressive markers is the assembly of a PRMT5-dependent complex containing the DNA methyltransferase DNMT3A, and other repressor proteins (Rank et al., 2010). DNMT3A is directly recruited to bind to the PRMT5-induced H4R3me2s mark, and loss of this mark through shRNA-mediated knock-down of PRMT5, or enforced expression of a mutant form of PRMT5 lacking methyltransferase activity leads to marked upregulation of γ-gene expression, and complete abrogation of DNA methylation at the γ-promoter. Treatment of human erythroid progenitors with non-specific methyltransferase inhibitors (Adox and MTA) also resulted in upregulation of γ-gene expression (He Y, 2013). Inhibitors of PRMT5 thus have potential as therapeutics for hemoglobinopathies such as ß-thalassemia and Sickle Cell Disease (SCD).

The present inventors have developed particular substituted β-hydroxy amides inhibit the activity of PRMT5 and therefore may be of use in treating conditions ameliorated by the inhibition of the activity of PRMT5.

SUMMARY OF THE INVENTION

A first aspect of the present invention provides a compound of formula I:

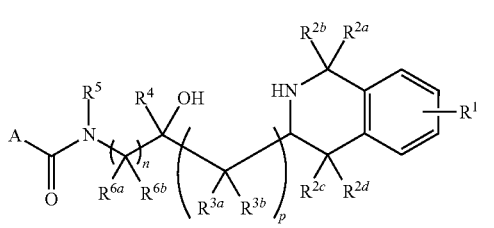

wherein:
n is 1 or 2;
p is 0 or 1;
$R^1$ is optionally one or more halo or methyl groups;
$R^{2a}$ and $R^{2b}$ are independently selected from the group consisting of:
  (i) F;
  (ii) H;
  (iii) Me; and
  (iv) $CH_2OH$;
$R^{2c}$ and $R^{2d}$ are independently selected from the group consisting of:
  (i) F;
  (ii) H;
  (iii) Me; and
  (iv) $CH_2OH$;
$R^{3a}$ and $R^{3b}$ are independently selected from H and Me;
$R^4$ is either H or Me;
$R^5$ is either H or Me;
$R^{6a}$ and $R^{6b}$ are independently selected from H and Me;
A is either
  (i) optionally substituted phenyl;
  (ii) optionally substituted naphthyl; or
  (iii) optionally substituted $C_{5-12}$ heteroaryl.

A second aspect of the present invention provides a compound of the first aspect for use in a method of therapy. The second aspect also provides a pharmaceutical composition comprising a compound of the first aspect and a pharmaceutically acceptable excipient.

A third aspect of the present invention provides a method of treatment of cancer, comprising administering to a patient in need of treatment, a compound of the first aspect of the invention or a pharmaceutical composition of the first aspect of the invention. The third aspect of the present invention also provides the use of a compound of the first aspect of the invention in the manufacture of a medicament for treating cancer, and a compound of the first aspect of the invention or pharmaceutical composition thereof for use in the treatment of cancer.

As described below, the compound of the first aspect may be administered simultaneously or sequentially with radiotherapy and/or chemotherapy in the treatment of cancer.

A fourth aspect of the present invention provides a method of treatment of hemoglobinopathies, comprising administering to a patient in need of treatment, a compound of the first aspect of the invention or a pharmaceutical composition of the first aspect of the invention. The fourth aspect of the present invention also provides the use of a compound of the first aspect of the invention in the manufacture of a medicament for treating hemoglobinopathies, and a compound of the first aspect of the invention or pharmaceutical composition of the first aspect of the invention for use in the treatment of hemoglobinopathies.

Definitions $C_{5-12}$ heteroaryl: The term "$C_{5-12}$ heteroaryl" as used herein, pertains to a monovalent moiety obtained by removing a hydrogen atom from an aromatic structure having from 5 to 12 rings atoms, of which from 1 to 3 are ring heteroatoms. The term 'aromatic structure' is used to denote a single ring or fused ring systems having aromatic properties, and the term 'ring heteroatom' refers to a nitrogen, oxygen or sulphur atom.

In this context, the prefixes (e.g. $C_{5-12}$, $C_{5-6}$, etc.) denote the number of atoms making up the aromatic structure, or range of number of atoms making up the aromatic structure, whether carbon atoms or heteroatoms.

Examples of $C_{5-12}$ heteroaryl structures include, but are not limited to, those derived from:

$N_1$: pyrrole (azole) ($C_5$), pyridine (azine) ($C_6$); pyridone ($C_6$); indole ($C_9$); quinoline ($C_{10}$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_1S_1$: thiazole ($C_5$), isothiazole ($C_5$);
$N_2S_1$: thiadiazole ($C_5$)
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$); benzimidazole ($C_9$)
$N_3$: triazole ($C_5$), triazine ($C_6$).

Optional Substituents

The optional substituents for the phenyl, naphthyl and $C_{5-12}$ heteroaryl groups in A may be selected from the following groups.

$C_{1-4}$ alkyl: The term "$C_{1-4}$ alkyl" as used herein, pertains to a monovalent moiety obtained by removing a hydrogen atom from a carbon atom of a saturated hydrocarbon compound having from 1 to 4 carbon atoms.

Examples of saturated alkyl groups include, but are not limited to, methyl ($C_1$), ethyl ($C_2$), propyl ($C_3$), and butyl ($C_4$).

Examples of saturated linear alkyl groups include, but are not limited to, methyl ($C_1$), ethyl ($C_2$), n-propyl ($C_3$), and n-butyl ($C_4$).

Examples of saturated branched alkyl groups include iso-propyl ($C_3$), iso-butyl ($C_4$), sec-butyl ($C_4$) and tert-butyl ($C_4$).

$C_{1-4}$ fluoroalkyl: The term "$C_{1-4}$ fluoroalkyl" refers to a $C_{1-4}$ alkyl group as defined above where one of more of the hydrogen atoms is replaced by a fluoro. Examples of $C_{1-4}$ fluoroalkyl include, but are not limited to, —$CF_3$, $CF_2H$, —$C_2F_5$, and —$C_2F_4H$.

$C_{3-6}$ cycloalkyl: the term '$C_{3-6}$ cycloalkyl' as used herein, pertains to a monovalent moiety obtained by removing a hydrogen atom from a carbon atom of a saturated cyclic core having 3, 4, 5 or 6 atom in the cyclic core all of which are carbon atoms. Examples of $C_{3-6}$ cycloalkyl include, but are not limited to, cyclopropyl, cyclohexyl and cyclopentyl.

$C_{5-6}$ heteroaryl: the term $C_{5-6}$ heteroaryl as used herein, pertains to a monovalent moiety obtained by removing a hydrogen atom from a ring atom of an aromatic structure having between one and three atoms that are not carbon forming part of said ring. Wherein, those atoms that are not carbon can be chosen independently from the list nitrogen, oxygen and sulphur. The group may be substituted by one or more $C_{1-4}$ alkyl groups.

Examples of $C_{5-6}$ heteroaryl groups include, but are not limited to, groups derived from:

$N_1$: pyridine ($C_6$);
$N_1O_1$: oxazole ($C_5$), isoxazole ($C_5$);
$N_2O_1$: oxadiazole (furazan) ($C_5$);
$N_2S_1$: thiadiazole ($C_5$)
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$).

$C_{5-6}$ heteroaryl methyl: —$CH_2$—($C_{5-6}$ heteroaryl), wherein $C_{5-6}$ heteroaryl is as defined above.

$C_{4-6}$ heterocyclyl: The term "$C_{4-6}$ heterocyclyl" as used herein, pertains to a monovalent moiety obtained by removing a hydrogen atom from a ring atom of a monocyclic heterocyclic compound, which moiety has from 4 to 6 ring atoms; of which from 1 to 2 atoms are heteroatoms, chosen from oxygen or nitrogen.

In this context, the prefixes (e.g. $C_4$-6) denote the number of ring atoms, or range of number of ring atoms, whether carbon atoms or heteroatoms.

Examples of $C_{4-6}$ heterocyclyl groups include, but are not limited to, those derived from:

$N_1$: azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);
$N_2$: diazetidine ($C_4$), imidazolidine ($C_5$), pyrazolidine (diazolidine) ($C_5$), imidazoline ($C_5$), pyrazoline (dihydropyrazole) ($C_5$), piperazine ($C_6$);
$O_1$: oxetane ($C_4$), tetrahydrofuran ($C_5$); oxane ($C_6$);
$O_2$: dioxetane ($C_4$), dioxolane ($C_5$); dioxane ($C_6$);
$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$).

Those $C_{4-6}$ heterocyclyl groups which include a N atom may be substituted on this atom by an acyl group, and in particular, by —C(=O)Me.

$C_{4-6}$ heterocyclyl methyl: —$CH_2$—($C_{4-6}$ heterocyclyl), wherein $C_{4-6}$ heterocyclyl is as defined above.

Phenyl: —$C_6H_5$, wherein the phenyl may itself be optionally substituted by one or more $C_{1-4}$ alkyl groups, one or more $C_{1-4}$ fluoroalkyl groups, one or more $C_{1-4}$ alkoxy groups, one or more halo substituents and one or more cyano substituents.

Benzyl: —$CH_2$-Phenyl, wherein phenyl is as defined above.

Halo: The term "halo" as used herein, refers to a group selected from fluoro, chloro, bromo and iodo.

Amido: —(C=O)NRR' wherein R and R' are independently selected from H, $C_{1-4}$ alkyl and $C_{4-6}$ heterocyclyl as defined above, or together form a group selected from (—$CH_2$—)$_n$ and —($CH_2$)$_m$—X—($CH_2$)$_p$—, where n=3-6, m and p=0-4, and X=O or NH. X may also be N—S(=O)$_2$, S or S(=O)$_2$. The cyclic amido groups may also be bridged by a further group selected from (—$CH_2$—)$_{n1}$ and —($CH_2$)$_{m1}$—X—($CH_2$)$_{p1}$—, where n1 is 1-3 and m1 and p1 are 1-3. The cyclic amido groups may also be further substituted by one, two or more hydroxy, oxo, $C_{1-2}$ alkyl, $C_{1-2}$ alkyl-$C_{1-2}$ alkoxy, $C_{1-2}$ alkyl-hydroxy and $C_{1-2}$ alkoxy groups or one spiro $C_{4-6}$ heteroaryl or spiro $C_{4-6}$ cycloalkyl group or be fused to an $C_{5-7}$ aromatic ring. Examples of amido groups include, but are not limited to, —C(=O)NH$_2$, —C(=O)NMe$_2$, —C(=O)NHMe, —C(=O)NHCH(CH$_3$)$_2$,

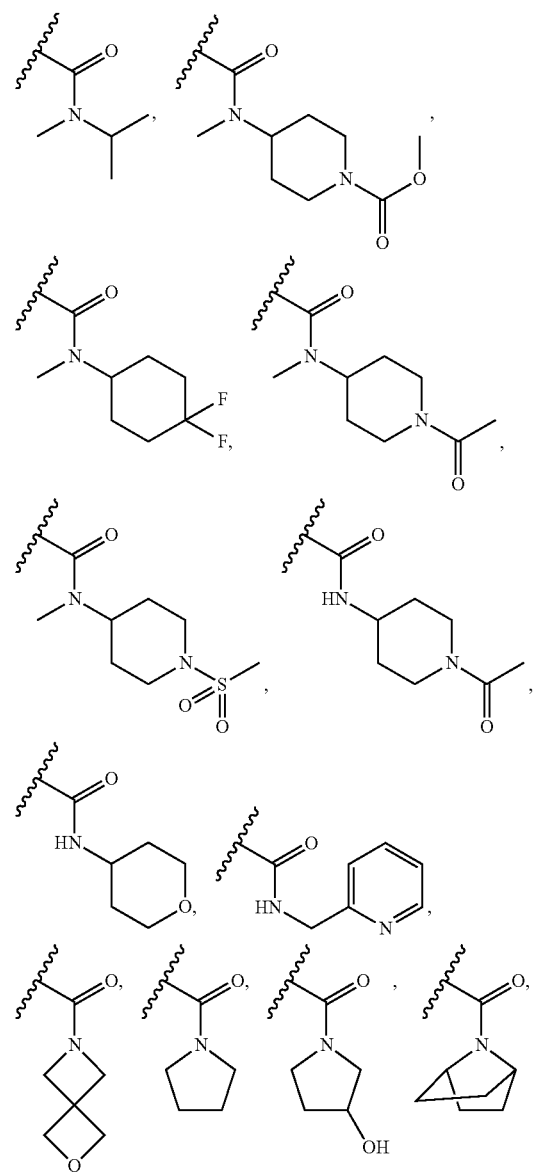

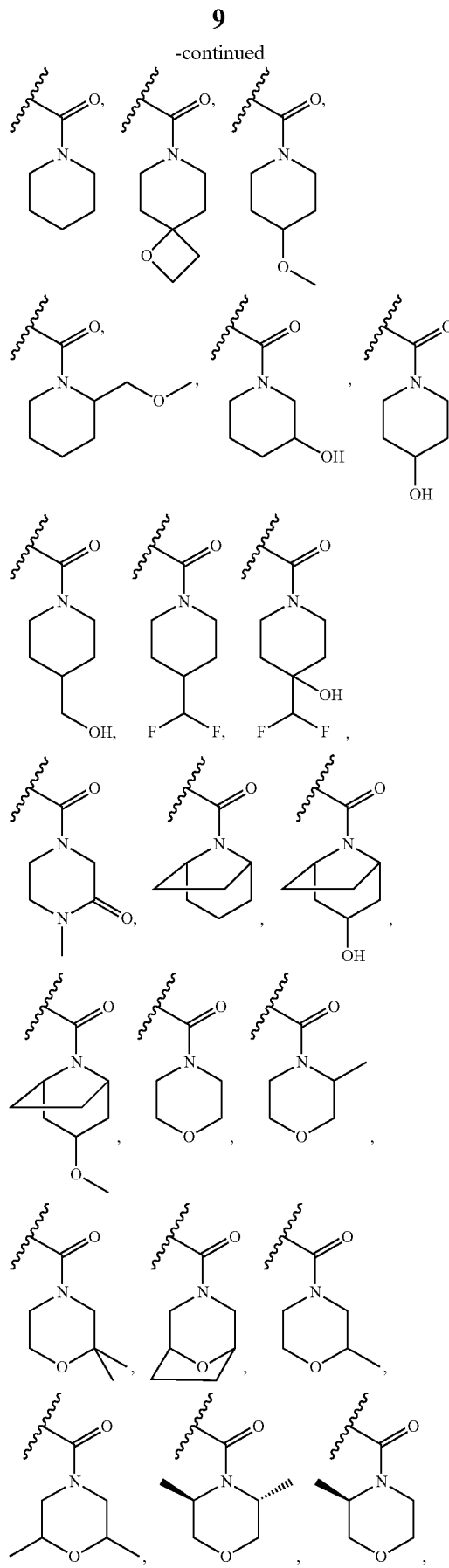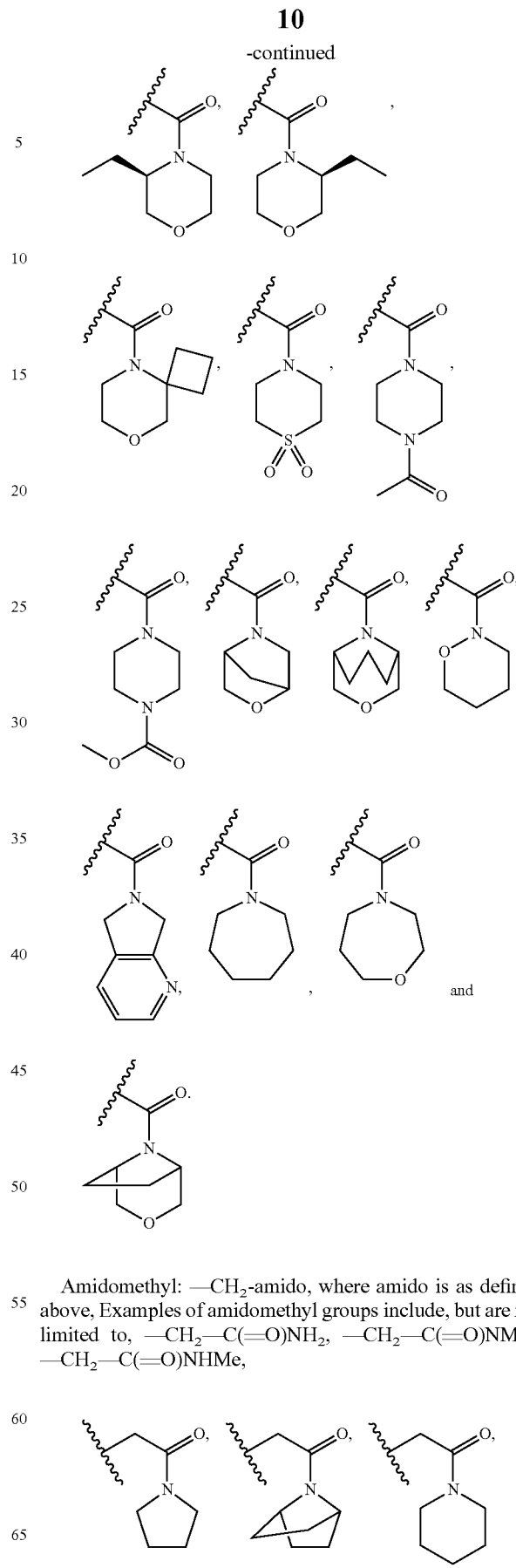
Amidomethyl: —$CH_2$-amido, where amido is as defined above, Examples of amidomethyl groups include, but are not limited to, —$CH_2$—C(=O)$NH_2$, —$CH_2$—C(=O)$NMe_2$, —$CH_2$—C(=O)NHMe,

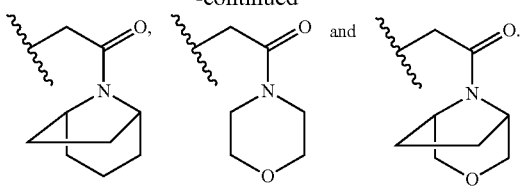

Acylamido: —NR(C═O)R' wherein R and R' are independently selected from H, $C_{1-4}$ alkyl and $C_{1-4}$ fluoro alkyl as defined above. R' may also be —$(CH_2)_n$—, where n is 3 or 4. Examples of an acylamido group include, but are not limited to, —N(H)C(═O)CF$_3$, —N(H)C(═O)Me, and:

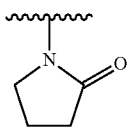

Acylamidomethyl: —CH$_2$-acylamido, where acylamido is as defined above, Examples of acylamidomethyl groups include, but are not limited to —CH$_2$—N(H)C(═O)Me and —CH$_2$—N(H)C(═O)CF$_3$.

$C_{1-4}$ alkyl ester: —C(═O)OR, wherein R is a $C_{1-4}$ alkyl group. Examples of $C_{1-4}$ alkyl ester groups include, but are not limited to, —C(═O)OCH$_3$, —C(═O)OCH$_2$CH$_3$, and —C(═O)OC(CH$_3$)$_3$.

$C_{1-4}$ alkyl ester methyl: —CH$_2$—($C_{1-4}$ alkyl ester), where $C_{1-4}$ alkyl ester is as defined above. Examples of $C_{1-4}$ alkyl ester methyl groups include, but are not limited to, —CH$_2$—C(═O)OCH$_3$, —CH$_2$—C(═O)OCH$_2$CH$_3$, and —CH$_2$—C(═O)OC(CH$_3$)$_3$.

$C_{1-4}$ alkyl carbamoyl: —NHC(═O)OR wherein R is a $C_{1-4}$ alkyl group as defined above. Examples of $C_{1-4}$ alkyl carbamoyl include, but are not limited to, —N(H)C(═O)OCH$_3$, —N(H)C(═O)OCH$_2$CH$_3$, and —N(H)C(═O)OC(CH$_3$)$_3$.

$C_{1-4}$ alkyl carbamoyl methyl: —CH$_2$—($C_{1-4}$ alkyl carbamoyl), where $C_{1-4}$ alkyl carbamoyl is as defined above. Examples of $C_{1-4}$ alkyl carbamoyl methyl include, but are not limited to, —CH$_2$—N(H)C(═O)OCH$_3$, —CH$_2$—N(H)C(═O)OCH$_2$CH$_3$, and —CH$_2$—N(H)C(═O)OC(CH$_3$)$_3$.

$C_{1-4}$ alkylacyl: —C(═O)R, wherein R is a $C_{1-4}$ alkyl group as defined above. Examples of $C_{1-4}$ alkylacyl groups include, but are not limited to, —C(═O)CH$_3$ (acetyl), —C(═O)CH$_2$CH$_3$ (propionyl) and —C(═O)C(CH$_3$)$_3$ (t-butyryl).

$C_{1-4}$ alkylacyl methyl: —CH$_2$—($C_{1-4}$ alkylacyl), where $C_{1-4}$ alkylacyl is as defined above. Examples of $C_{1-4}$ alkylacylmethyl groups include, but are not limited to, —CH$_2$—C(═O)CH$_3$, —CH$_2$—C(═O)CH$_2$CH$_3$, and —CH$_2$—C(═O)C(CH$_3$)$_3$.

Phenylcarbonyl: —C(═O)-phenyl, where phenyl is as defined above.

Carboxy (carboxylic acid): —C(═O)OH

Carboxymethyl: —CH$_2$—C(═O)OH.

Ether: —OP, wherein P is chosen from one of the following substituents: $C_{1-4}$ alkyl, benzyl, phenyl, $C_{1-4}$ fluoroalkyl, $C_{5-6}$ heteroaryl, —CH$_2$—$C_{5-6}$ heteroaryl, $C_{4-6}$ heterocyclyl, and —CH$_2$—$C_{4-6}$ heterocyclyl as defined above. Examples of an ether include, but are not limited to, —OPh, —OBn, —OCF$_3$, —OCH$_2$CF$_3$, —OCH(CH$_3$)$_2$, —OCH$_2$-cyclopropyl, —O—(N-acetyl)azetidinyl, e.g.

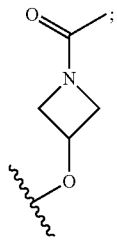

—O—(N-acetyl)piperidinyl, e.g.

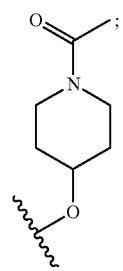

—O—oxetanyl, e.g.;    Piperidyloxy, e.g.

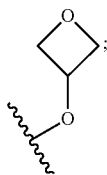 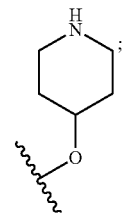

—O—(N-carboxylate)piperidinyl, e.g. where R is methyl, isopropyl, isobutyl;

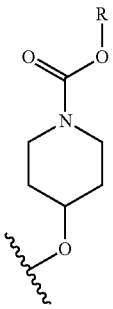

—O-tetrahydropyranyl, e.g.;    —O-tetrahydrofuranyl, e.g.;

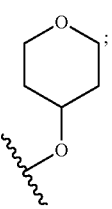 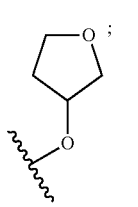

(8-methoxycarbonyl-8-
azabicyclo[3.2.1]
octan-3-yl)oxy:

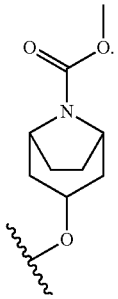

Amino: —NPP', wherein P and P' are independently chosen from H, $C_{1-4}$ alkyl, $C_{4-6}$ heterocyclyl, phenyl and $C_{5-6}$ heteroaryl as defined above. Examples of an amine include, but are not limited to, —$NH_2$—N(H)pyridazinyl,

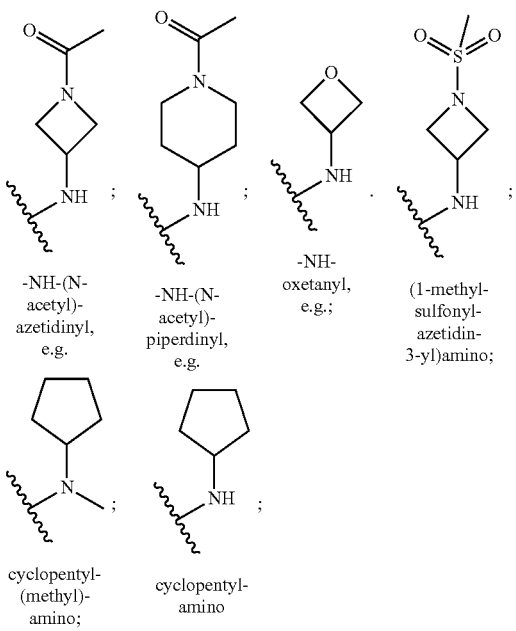

-NH-(N-acetyl)-azetidinyl, e.g.;  -NH-(N-acetyl)-piperdinyl, e.g.;  -NH-oxetanyl, e.g.;  (1-methyl-sulfonyl-azetidin-3-yl)amino;

cyclopentyl-(methyl)-amino;  cyclopentyl-amino

Aminomethyl: —$CH_2$-Amino, where amino is as defined above. Examples of aminomethyl include, but are not limited to, —$CH_2$—$NH_2$ and —$CH_2$—N(H)pyridazinyl.

Sulfonamido: —$SO_2$NRR' wherein R and R' are independently selected from H, $C_{1-4}$ alkyl, phenyl and $C_{5-6}$ heteroaryl as defined above. Examples of sulfonamido groups include, but are not limited to, —$SO_2$N(Me)$_2$ and —$SO_2$NPhMe.

Sulfonamino: —$NHSO_2$R wherein R is selected from $C_{1-4}$ alkyl, phenyl and $C_{5-6}$ heteroaryl as defined above. Examples of sulfonamino groups include, but are not limited, to —$NHSO_2$Me and —$NHSO_2$Ph Sulfone: —$SO_2$R, wherein R is selected from $C_{1-4}$ alkyl and $C_{1-4}$ fluoroalkyl as defined above. Example of sulfone groups includes but is not limited to $SO_2CF_3$.

Sulfoxide: —SOR, wherein R is selected from $C_{1-4}$ alkyl and $C_{1-4}$ fluoroalkyl as defined above. Example of sulfoxide groups includes but is not limited to $SOCF_3$.

Nitrile: —CN.
Nitrilemethyl: —$CH_2$—CN

Fused N-heterocyclic ring: where A is phenyl, it may have a $C_{5-6}$ $N_1$-containing heterocyclic ring fused to it as a substituent group. The $C_{5-6}$ $N_1$-containing heterocyclic ring may in particular be selected from:

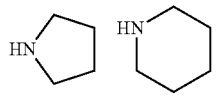

Which may be fused in any orientation, and wherein the N ring atom may be optionally substituted, for example by a $C_{1-4}$ alkylacyl group.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—$N^+HR^1R^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al, *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Isomers

Certain compounds of the invention may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Compounds of the present invention have at least two stereocentres, indicated by * in the formula below:

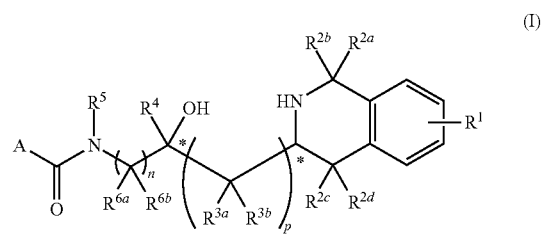

(I)

It may be preferred the compounds have the following stereochemistry:

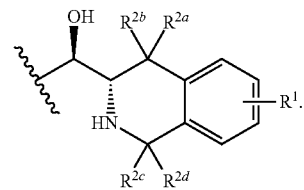

Alternatively, the compounds may have one of the following sterechemistries:

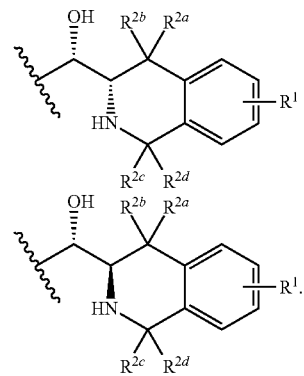

Assignment of the absolute configuration can be determined with X-ray crystallisation studies as described below.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

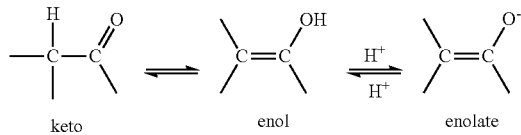

keto   enol   enolate

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Examples of isotopes that can be incorporated into compounds of the invention include isotopes of hydrogen, carbon, nitrogen, oxygen, phosphorous, fluorine, and chlorine, such as, but not limited to $^2H$ (deuterium, D), $^3H$ (tritium), $^{11}C$, $^{13}$, $^{14}C$, $^{15}N$, $^{18}F$, $^{31}P$, $^{32}P$, $^{35}S$, $^{36}Cl$, and $^{125}I$. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Therapeutic Indications

Compounds disclosed herein may provide a therapeutic benefit in a number of disorders, in particular, in the treatment or prevention of cancers and hemoglobinopathies.

Cancer

Modulators of PRMT5 mediated post-translational arginine methylation of p53 may regulate a pro-apoptotic p53 response, and may therefore be useful as therapeutic agents, for example in the treatment of cancer. Such agents may also be useful as therapeutic agents for the treatment of cancers which exhibit overexpression of PRMT5.

A "cancer" may be any form of cancer. In particular, a cancer can comprise any one or more of the following: leukemia, acute lymphocytic leukemia (ALL), acute myeloid leukemia (AML), chronic lymphocytic leukemia (CLL), chronic myeloid leukemia (CML), non-Hodgkin's lymphoma, Hodgkin's disease, prostate cancer, lung cancer, melanoma, breast cancer, colon and rectal cancer, colon cancer, squamous cell carcinoma and gastric cancer.

Alternatively, the cancer may comprise adrenocortical cancer, anal cancer, bladder cancer, blood cancer, bone cancer, brain tumor, cancer of the female genital system, cancer of the male genital system, central nervous system lymphoma, cervical cancer, childhood rhabdomyosarcoma, childhood sarcoma, endometrial cancer, endometrial sarcoma, esophageal cancer, eye cancer, gallbladder cancer, gastrointestinal tract cancer, hairy cell leukemia, head and neck cancer, hepatocellular cancer, hypopharyngeal cancer, Kaposi's sarcoma, kidney cancer, laryngeal cancer, liver cancer, malignant fibrous histiocytoma, malignant thymoma, mesothelioma, multiple myeloma, myeloma, nasal cavity and paranasal sinus cancer, nasopharyngeal cancer, nervous system cancer, neuroblastoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, rectal cancer, respiratory system, retinoblastoma, salivary gland cancer, skin cancer, small intestine cancer, soft tissue sarcoma, stomach cancer, stomach cancer, testicular cancer, thyroid cancer, urinary system cancer, uterine sarcoma, vaginal cancer, vascular system, Waldenstrom's macroglobulinemia and/or Wilms' tumor. Cancers may be of a particular type. Examples of types of cancer include lymphoma, melanoma, carcinoma (e.g. adenocarcinoma, hepatocellular carcinoma, medullary carcinoma, papillary carcinoma, squamous cell carcinoma), astrocytoma, glioma, medulloblastoma, myeloma, meningioma, neuroblastoma, sarcoma (e.g. angiosarcoma, chrondrosarcoma, osteosarcoma).

The cancer may be a PRMT5 overexpressing cancer. The cancer may over express PRMT5 protein relative to non-cancerous tissue. In some cases, the cancer overproduces PRMT5 mRNA relative to non-cancerous tissue.

Alternatively or additionally, the cancer may be a p53 overexpressing cancer. The cell may overexpress p53 protein relative to non-cancerous tissue. It may overproduce p53 mRNA as compared to non-cancerous tissue. In some cases, the level of p53 protein and/or mRNA in the cell is at a level approximately equivalent to that of a non-cancerous cell.

The agents described herein may be useful in combination with other anti-cancer therapies. They may act synergistically with chemo- or radiotherapy, and/or with p53 targeted drugs.

An inhibitor of PRMT5 would in all likelihood augment the effects of drugs (such as the nutlins) that restore p53. Inhibition of PRMT5, resulting in decreased arginine-methylated p53, may sensitize tumour cells to chemo- and radiotherapy by switching, or at least biasing, the cellular outcome to apoptosis.

Combination Therapies p53 is activated by DNA damage. PRMT5 is part of the complex of proteins that activate and modulate p53 activity in response to DNA damage. It is likely that inhibition of PRMT5, resulting in decreased arginine-methylated p53, would sensitize tumour cells to chemo- and radiotherapy by switching or at least biasing the cellular outcome to apoptosis. PRMT5 inhibition is likely to synergize well with low dose chemo- or radiotherapy, by stabilizing p53, and biasing the cellular outcome to apoptosis.

Biasing the p53 response towards apoptosis would in all likelihood be of benefit, and an agent that so biases the response would be expected to augment the effect of a p53 resurrecting drug. Thus, in some cases, a PRMT5 modulator disclosed herein may be administered in conjunction with a radiotherapeutic or chemotherapeutic regime. It may be administered in conjunction with a drug that resurrects cellular p53 activity, for example, a p53 agonist. The PRMT5 modulator may be administered simultaneously or sequentially with radio and/or chemotherapy. Suitable chemotherapeutic agents and radiotherapy protocols will be readily appreciable to the skilled person. In particular, the compound described herein may be combined with low dose chemo or radio therapy. Appropriate dosages for "low dose" chemo or radio therapy will be readily appreciable to the skilled practitioner.

Hemoglobinopathies

The compounds disclosed herein may be useful in the treatment or prevention of conditions that may benefit from the increased expression of γ-globin genes, for example, due to the release of repressive methylation of these genes. The compounds disclosed herein may be useful in the treatment or prevention of hemoglobinopathies. A hemoglobinopathy is a condition associated with the presence of abnormal hemoglobin in the blood of a subject. Such conditions include ß-thalassemia and Sickle Cell Disease, α-thalassemia and δ-thalassemia.

Hemoglobinopathies treatable by the compounds disclosed herein may be ameliorated by the re-activation of the subjects γ-globin genes (γ genes). In such cases, the subject is not a fetal mammal.

Methods of Treatment

The compounds of the present invention may be used in a method of therapy. Also provided is a method of treatment, comprising administering to a subject in need of treatment a therapeutically-effective amount of a compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

As described above, the anti cancer treatment defined herein may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and docetaxel (Taxotere) and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661 and 4-((2,4-dichloro-5-methoxyphenyl)amino)-6-methoxy-7-(3-(4-methylpiperazin-1-yl)propoxy)quinoline-3-carbonitrile (bosutinib, SKI-606; Cancer research (2003), 63(2), 375-81), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [HerceptinT], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic and antilymphangiogenic agents such as those which inhibit the effects of vascular endothelial growth factor, [for example the anti vascular endothelial cell growth factor A (VEGFA) antibody bevacizumab (AvastinT), the anti vascular endothelial cell growth factor A (VEGFA) antibody ranibizumab, the anti-VEGF aptamer pegaptanib, the anti vascular endothelial growth factor receptor 3 (VEGFR3) antibody IMC-3C5, the anti vascular endothelial cell growth factor C (VEGFC) antibody VGX-100, the anti vascular endothelial cell growth factor D (VEGFD) antibody VGX-200, the soluble form of the vascular endothelial growth factor receptor 3 (VEGFR3) VGX-300 and VEGF receptor tyrosine kinase inhibitors such as 4-(4-bromo-2-fluoroanilino)-6-methoxy-7-(1-methylpiperidin-4-ylmethoxy)quinazoline (vandetanib; ZD6474; Example 2 within WO 01/32651), 4-(4-fluoro-2-methylindol-5-yloxy)-6-methoxy-7-(3-pyrrolidin-1-ylpropoxy)quinazoline (cediranib; AZD2171; Example 240 within WO 00/47212), vatalanib (PTK787; WO 98/35985), pazopanib (GW786034), axitinib (AG013736), sorafenib and sunitinib (SU11248; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies Administration The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intravitreal and intrasternal; by implant of a depot, for example, subcutaneously, intravitreal or intramuscularly. The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences*, 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichlorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/mL to about 10 µg/mL, for example from about 10 ng/ml to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated by one of skill in the art that appropriate dosages of the compound, and compositions comprising the compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the active compound is administered to a human patient according to the following dosage regime: about 50 or about 75 mg, 3 or 4 times daily.

In one embodiment, the active compound is administered to a human patient according to the following dosage regime: about 100 or about 125 mg, 2 times daily.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

General Synthesis Methods

The compounds of the invention can be prepared employing the following general methods and using procedures described in detail in the examples. The reaction conditions referred to are illustrative and non-limiting, for example one skilled in the art may use a diverse range of synthetic methods to synthesis the desired compounds such as but not limited to methods described in literature (for example but not limited to March's Advanced Organic Chemistry: Reactions, Mechanisms, and Structure, 7th Edition or Larock's Comprehensive Organic Transformations: Comprehensive Organic Transformations: A Guide to Functional Group Preparations).

Compounds of formula I, as described above, can be prepared by synthetic strategies outlined below, wherein the definitions above apply.

General Synthesis 1

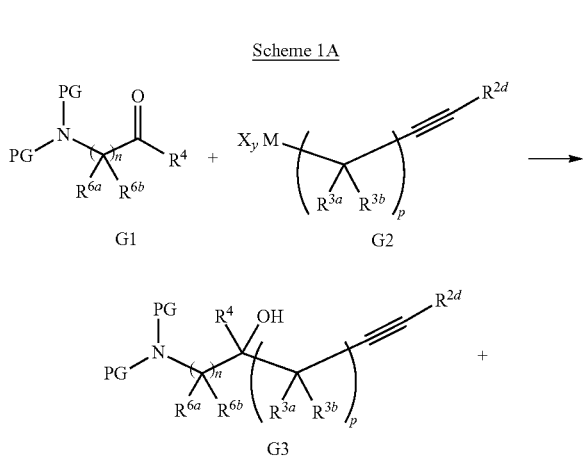

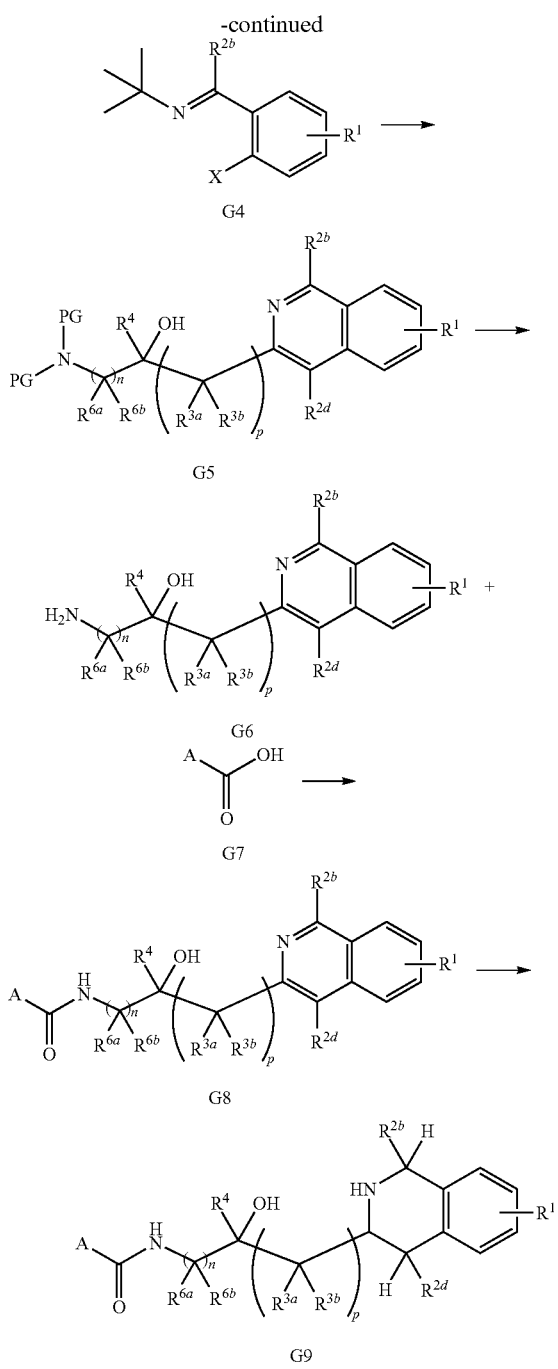

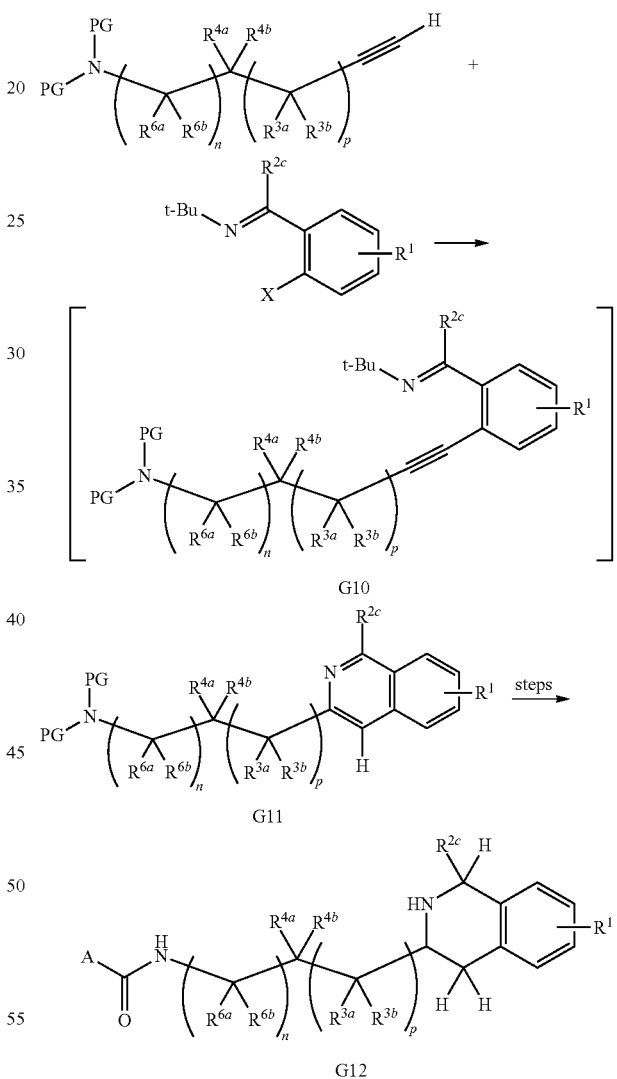

of a transition metal catalyst or combination of transition metal catalysts such as but not limited to bis(triphenylphosphine)nickel(II) chloride/Zn.

After removal of the protecting group, methods to synthesise amides G8 be apparent to those skilled in the art, but include for example the use of reagents such as HATU, HBTU, T3P and EDCl/HOBt, and the use of activated forms of the carboxylic acid G7 such as the corresponding acyl halide, carbamate or N-hydroxysuccinimide ester. Transformation of isoquinolines of structure G8 to give tetrahydroisoquinolines of structure G9 will be apparent to those skilled in the art and such methods include but are not limited to reduction in the presence of a transition metal catalyst.

Scheme 1A illustrates the synthesis of compounds with the structure G9. A coupling of a carbonyl compound of structure G3 with an organometallic compound of structure G2 to give a compound with structure G3 will be apparent to those skilled in the art. The group represented by (M) includes but is not limited to Mg, In, Zn and the group represented by (X) may be a halide where (Y) may be the number 1-3. Suitable protected amino groups represented by (PG) include but are not limited to phthalimide; and methods for the removal of said protecting groups will be known to those skilled in the art (for example Greene's Protective Groups in Organic Synthesis, 4th Edition). Synthesis of compounds with structure G5 is performed by reacting alkyne G3 with compounds of structure G4 in the presence Alternatively, for the synthesis of compounds with structure G12 where $R^{2a}$, $R^{2b}$, $R^{2d}$=H, a coupling of an alkyne and a aryl halide will be apparent to those skilled in the art and such methods include a coupling in the presence of a transition metal catalyst or catalyst combination such as but not limited to $PdCl_2(PPh_3)_2$/CuI and $Pd(OAc)_2$/$PPh_3$. This may be followed by cyclisation either in situ or as a separate step to give isoquinoline of structure G11. The synthetic steps to give compounds with general formula G12 will be similar to those used in Scheme 1A.

General Synthesis 2

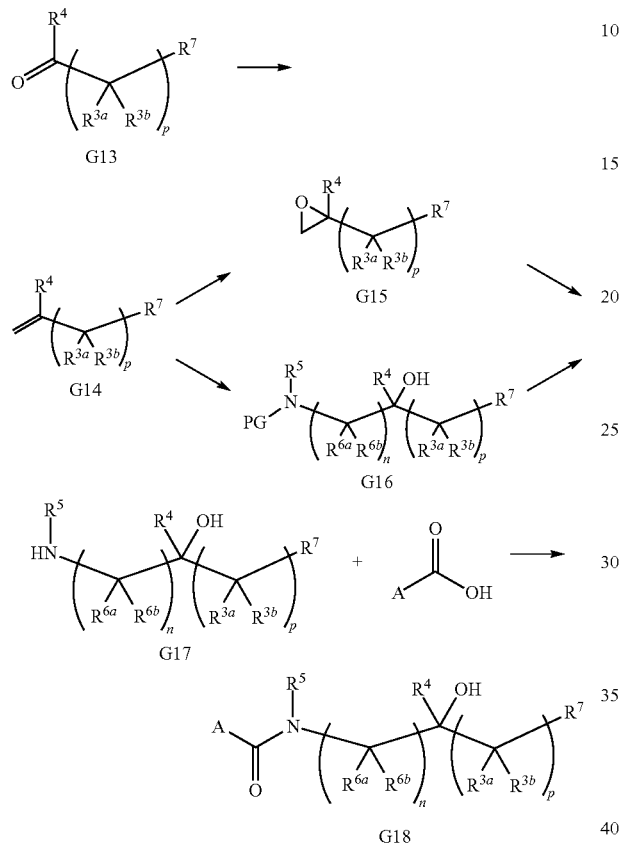

Where R⁷ represents the fused ring group.

Scheme 2A illustrates the synthesis of compounds G18 from aldehyde G13 (or ketone where R⁴=Me). Conversion of a carbonyl to an alkene will be apparent to those skilled in the art but methods include but are not limited to a Wittig reaction with [Ph₃PMe]⁺Br⁻ in the presence of a base such as KHMDS. The alkene G14 can be epoxidised with reagents such as mCPBA and then reacted with an amine to give intermediate G16. Alternatively, an aminohydroxylation can be performed by methods such as but not limited to reaction with (PG)NHOTs in the presence of potassium osmate dihydrate. Removal of the protecting group will be apparent to those skilled in the art (for example *Greene's Protective Groups in Organic Synthesis, 4th Edition*) and gives intermediate G17. Amide bond formation to give compounds G18 can be performed by methods previously described (General synthesis 1).

General Synthesis 3

Scheme 3A illustrates the synthesis of compounds G22 beginning with a Henry reaction between an aldehyde G19 (or ketone where R⁴=Me) and nitromethane in the presence or absence of a suitable base, such as but not limited to DBU, a KF, TBAF or sodium hydroxide, in the presence or absence of a chiral or achiral transition metal compound for example but not limited to complexes of copper, cobalt or zinc to furnish a nitro-alcohol G20 Reduction of the nitro group to the primary amine G21 will be apparent to those skilled in the art and include but are not limited to using reducing conditions such as a transition metal (Fe, In, Zn) in the presence of HCl, hydrogenation in the presence of a transition metal or transition metal catalyst. Amide bond formation to give compounds G22 can be performed by methods previously described (General synthesis 1). The method can also be carried out with nitroethane and other nitroalkanes, as appropriate.

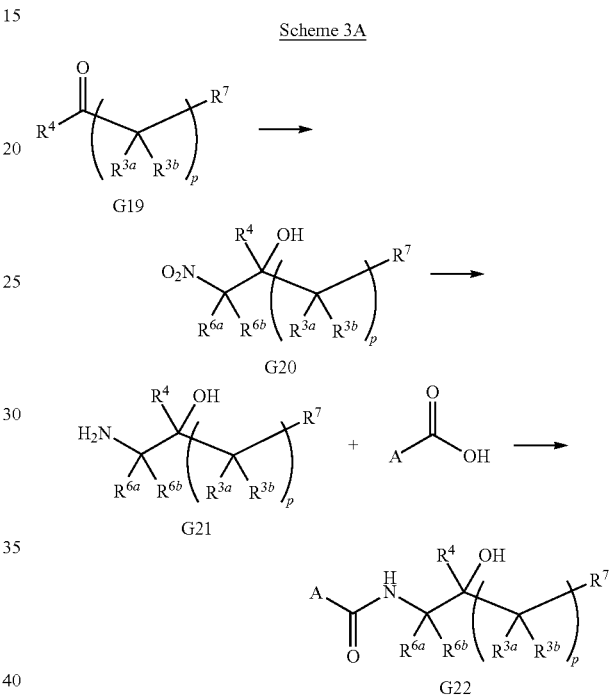

General Synthesis 4

Scheme 4A illustrates the addition of an amine (HNR⁸R⁹), as a substituent which is a part of A. This can be achieved by coupling a relevant carboxylic acid to a primary amine or a secondary amine, NHR⁸R⁹. Methods to form such amides will be apparent to those skilled in the art, but include for example the use of reagents such as HATU, HBTU, T3P and EDCl/HOBt, and the use of activated forms of the carboxylic acid such as the corresponding acyl halide, mixed anhydride or N-hydroxysuccinimide ester. The group denoted by (X) may be but not limited to halogen, tosylate or other suitable group. Conversion of (X) in G22 into an ester in G23 will be apparent to those skilled in the art, but include for example a carbonylation reaction which can be achieved by the use of carbon monoxide in the presence of an transition metal catalyst such as but not limited to PdCl₂dppf.DCM; and an alcoholic solvent such as but not limited to methanol, ethanol, isopropanol or tert-butyl alcohol. Formation of the carboxylic acid can be achieved by for example hydrolysis with a base such as an alkali metal hydroxide or an acid for example aqueous hydrochloric acid to form G24. The amide formation to form G25 can be achieved by the methods outline in Scheme 1A.

Scheme 4A

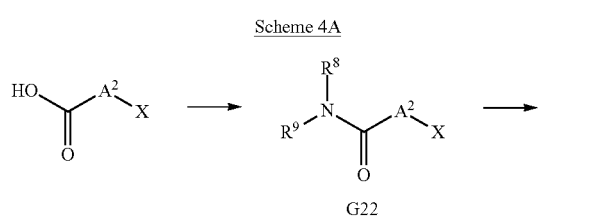

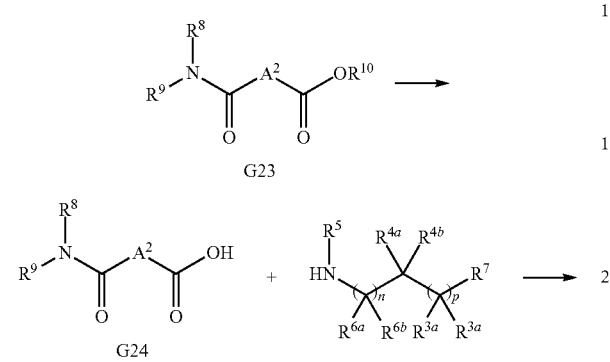

Alternatively, for the synthesis of ester G24 the order of steps can be reversed as described in Scheme 4B.

Scheme 4B

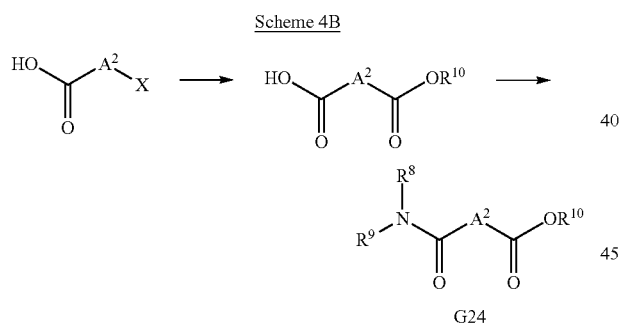

Alternatively for the synthesis of amide G25 the steps may be reordered such that the formation of the $R^8R^9N$ amide on the A substituent occurs after the coupling of A to the primary amine G21. This may be achieved by coupling a suitable amine with an intermediate where A bears a suitable functional group for coupling, for example but not limited to a carboxylic acid or alkali metal carboxylate salt, as shown in Scheme 4C.

Scheme 4C

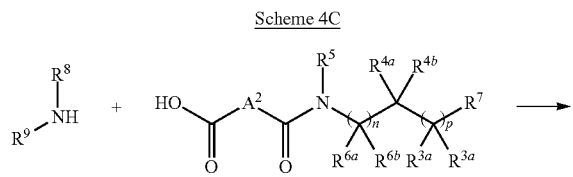

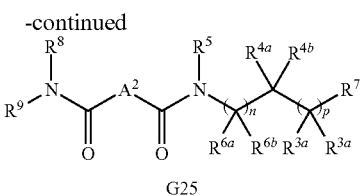

General Synthesis 5

Scheme 5A illustrates the addition of an $R^{11}$ group, as a substituent which is part of A. This can be achieved using any suitable coupling reaction known to the person skilled in the art, for example by Suzuki coupling. The groups denoted by $R^{11}X$ and $B^1$ are chosen to be suitable for the coupling reaction employed. For example, in the case of a Suzuki coupling reaction (X) may be a halogen, tosylate or other suitable group and $B^1$ represents a suitable boron compound including, but not limited to, a boronic acid or boronic ester.

Scheme 5A

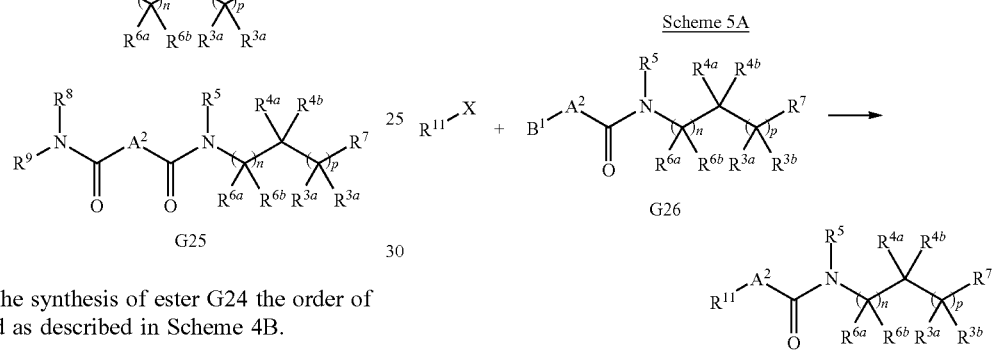

Examples of $B^1$ that can be used in the Suzuki coupling include, but are not limited to, those shown below.

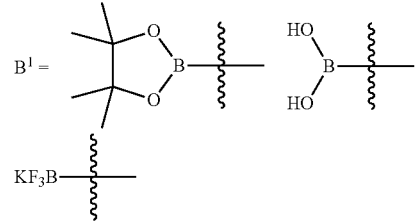

The types of $R^{11}X$ compounds that can be used in the Suzuki coupling include, but are not limited to, those shown in Table 1.

TABLE 1

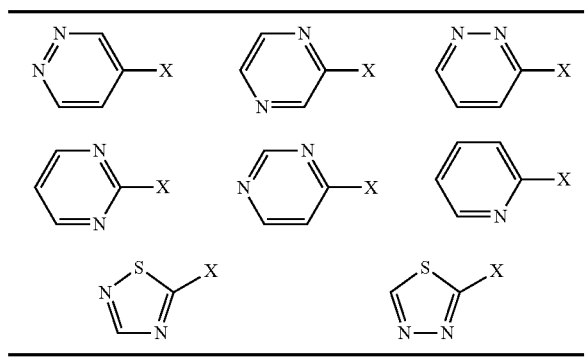

In addition to scheme 5A, the position of the (X) and (B¹) can be reversed as shown below in scheme 2B, to give the same final compound G27. Similarly to Scheme 2A, the groups denoted by R¹¹B¹ and (X) are chosen to be suitable for the coupling reaction employed. For example, in the case of a Suzuki coupling reaction (X) may be a halogen, tosylate or other suitable group and R¹¹B¹ represents a suitable boron compound including, but not limited to, a boronic acid or boronic ester.

Scheme 5C

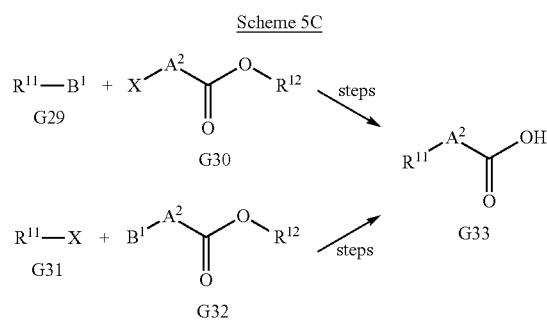

The types of R¹¹B¹ compounds that can be used in the Suzuki coupling include, but are not limited to, those shown in Table 2.

TABLE 2

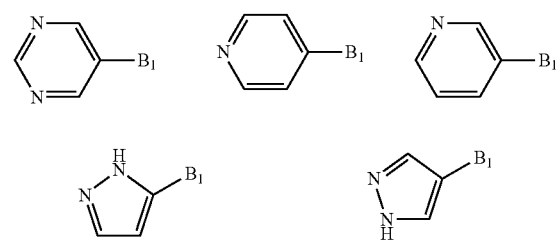

A variety of coupling reactions may be used to introduce the R¹¹ group other than Suzuki coupling, such as for example transition metal catalysed coupling reactions of for example tin (Stille type reaction) and zinc (Negishi type reaction) compounds. Substitution of the halogen by suitable nucleophiles in the presence or absence of other reagents such as for example transition metal compounds is also suitable.

Coupling reactions can also be used to prepare the carboxylic acids used in Scheme 1A for the amide formations, scheme 5C. In starting material G30 and G32, A as described herein, consists of -A²X and -A²B¹ respectively. In the product G33, A as described herein, consists of -A²R¹¹. The groups denoted by (X) and B¹ are chosen to be suitable for the coupling reaction employed. For example, in the case of a Suzuki coupling reaction (X) may be a halogen, tosylate or other suitable group and B¹ represents a suitable boron compound including, but not limited to, a boronic acid or boronic ester.

Scheme 5C

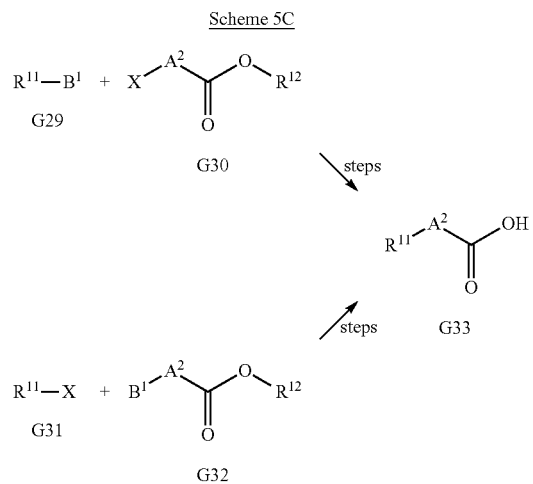

In G30 and G32 R¹² can be a H or a carbon group for example but not limited to Me, Et, Pr, iPr, Bu, t-Bu. In these instances where R¹² is carbon group it may be necessary to form the carboxylic acid before use in the amide coupling (Scheme 1A), generally this can be achieved by for example hydrolysis with a base such as an alkali metal hydroxide or an acid for example aqueous hydrochloric acid to form G33. The same method for converting an ester to a carboxylic acid is used in other general schemes.

General Synthesis 6

Scheme 6A illustrates the addition of an R¹³ group, as a substituent which is part of A. This can be achieved using any suitable coupling reaction known to the person skilled in the art, for example, by an SnAr displacement or Buchwald coupling. The group denoted by (X) may be but not limited to halogen and is chosen to be suitable for the coupling reaction employed.

Scheme 6A

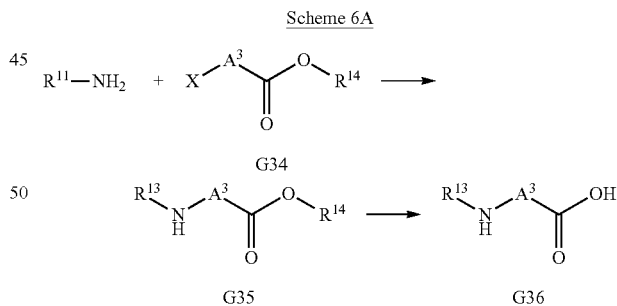

In G34 and G35 R¹⁴ can be a H or a carbon group for example but not limited to Me, Et, Pr, iPr, Bu, t-Bu. In these instances it may be necessary to form the carboxylic acid before use in an amide coupling (Scheme 1A), generally this can be achieved by, for example, hydrolysis with a base such as an alkali metal hydroxide or an acid, for example, aqueous hydrochloric acid to form G36. The same method for converting an ester to a carboxylic acid is used in other general schemes.

This method may also be extended to the addition of secondary amines.

Alternatively, to synthesise ether linked compounds, a similar strategy can be employed as shown in Scheme 6B. This can be achieved using any suitable coupling reaction known to a person skilled in the art, for example, by an SnAr displacement or an Ullman-type coupling to give compounds with structure G37. Upon hydrolysis using methods previously described, compounds with structure G38 may be obtained and used in an amide bond formation as shown in scheme 1A.

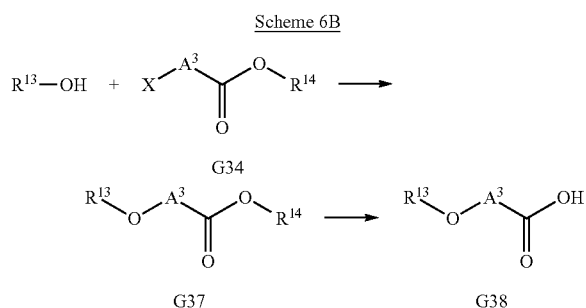

Scheme 6B

Both the above couplings may also be reversed, such that the group added is $R^{13}$—X.

Further Embodiments n

In some embodiments, n is 1. In some embodiments, n is 2.

p

In some embodiments, p is 0. In some embodiments, p is 1.

$R^1$

In some embodiments, there may be no $R^1$ substituents. In some embodiments, $R^1$ represents one to four Me or halo groups, preferably one to three Me or halo groups and more preferably one or two Me or halo groups. In some of these embodiments, $R^1$ may represent F. In others of these embodiments, $R^1$ may represent Me groups.

$R^2$ $R^{2a}$, $R^{2b}$, $R^{2c}$ and $R^{2d}$ are independently selected from H, F, $CH_2OH$ and Me. In some of these embodiments, $R^{2a}$, $R^{2b}$, $R^{2c}$ and $R^{2d}$ are independently selected from H, Me and $CH_2OH$. In further of these embodiments, $R^{2a}$, $R^{2b}$, $R^{2c}$ and $R^{2d}$ are independently selected from H and Me.

In some embodiments $R^{2a}$, $R^{2b}$, $R^{2c}$ and $R^{2d}$ are all H.

In some embodiments $R^{2a}$, $R^{2b}$, $R^{2c}$ and $R^{2d}$ are comprised of three H and one Me or $CH_2OH$ group. It may be preferred in these embodiments that $R^{2a}$ is Me and $R^{2b}$, $R^{2c}$ and $R^{2d}$ are H. It may be preferred in these embodiments that $R^{2c}$ is Me or $CH_2OH$ and $R^{2a}$, $R^{2b}$ and $R^{2d}$ are H.

In some embodiments $R^{2a}$, $R^{2b}$, $R^{2c}$ and $R^{2d}$ are comprised of two H and two Me groups. It may be preferred in these embodiments that $R^{2a}$ and $R^{2c}$ are Me and $R^{2b}$ and $R^{2d}$ are H. It may be preferred in these embodiments that $R^{2a}$ and $R^{2b}$ are Me and $R^{2c}$ and $R^{2d}$ are H. It may also be preferred in these embodiments that $R^{2c}$ and $R^{2d}$ are Me and $R^{2a}$ and $R^{2b}$ are H.

$R^3$ $R^{3a}$ and $R^{3b}$ are independently selected from H and Me. In some embodiments $R^{3a}$ is H and $R^{3b}$ is Me. In some embodiments $R^{3a}$ and $R^{3b}$ are both H. In some embodiments $R^{3a}$ and $R^{3b}$ are both Me.

$R^4$

In some embodiments $R^4$ is H. In some embodiments $R^4$ is Me.

$R^5$

In some embodiments $R^5$ is H. In some embodiments $R^5$ is Me.

$R^6$ $R^{6a}$ and $R^{6b}$ are independently selected from H and Me. In some embodiments $R^{6a}$ is H and $R^{6b}$ is Me. In some embodiments $R^{6a}$ and $R^{6b}$ are both H. In some embodiments $R^{6a}$ and $R^{6b}$ are both Me.

Stereoisomers

The carbon to which $R^4$ is attached is a chiral centre.

In some embodiments, the compound is a mixture of stereoisomers at this centre. In some embodiments, the compound is a single stereoisomer. In some of these embodiments, the compound is the (R)-stereoisomer. In others of these embodiments, the compound is the (S)-stereoisomer.

The compound may also include further chiral centres. The carbon in the THIQ moiety is chiral. In some embodiments, the compound is a mixture of stereoisomers at this centre. In other embodiments, the compound is a single stereoisomer at this centre. In some of these embodiments, the compound is the (R)-stereoisomer at this centre. In others of these embodiments, the compound is the (S)-stereoisomer at this centre.

Thus the compound may be a single diastereomer or a mixture of diastereomers.

It may be preferred the compounds have the following stereochemistry:

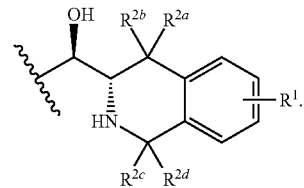

Alternatively, the compounds may have one of the following stereochemistries:

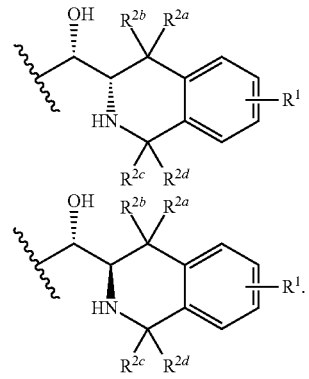

$R^1$-$R^5$, n & p

In some embodiments, $R^1$, $R^{2a}$, $R^{2b}$, $R^{2c}$, $R^{2d}$, $R^{3a}$, $R^{3b}$, $R^4$, $R^5$, $R^{6a}$ and $R^{6b}$ are all H, n is 1 and p is 0, and thus the compound of formula I is of formula Ia:

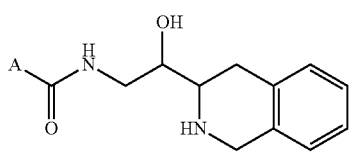

(Ia)

In some embodiments, $R^1$, $R^{2a}$, $R^{2b}$, $R^{2c}$, $R^{2d}$, $R^{3a}$, $R^{3b}$, $R^4$, $R^5$, $R^{6a}$ and $R^{6b}$ are all H, n is 1 and p is 1, and thus the compound of formula I is of formula Ib:

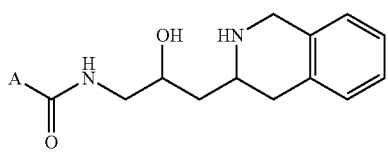

(Ib)

In some embodiments, $R^1$, $R^{2a}$, $R^{2b}$, $R^{2c}$, $R^{2d}$, $R^{3a}$, $R^{3b}$, $R^4$, $R^5$, $R^{6a}$ are all H, n is 1 and p is 0, and $R^{6b}$ is Me and thus the compound of formula I is of formula Ic:

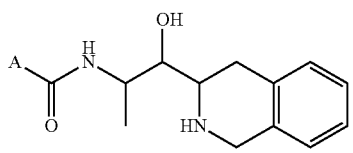

(Ic)

A

Optional Substituents

When the optional substituent on A is $C_{1-4}$ alkyl, it may be preferably selected from methyl, ethyl, i-Pr, t-Bu.

When the optional substituent on A is $C_{1-4}$ fluoroalkyl, it may preferably be selected from —$CF_3$ and —$CF_2H$.

When the optional substituent on A is $C_{5-6}$ heteroaryl, it may be substituted by one or more $C_{1-4}$ alkyl groups. These groups may preferably be on one or more of the nitrogen ring atoms (if present). These groups may also preferably be methyl.

When the optional substituent on A is $C_{5-6}$ heteroaryl, it may preferably be selected from pyridizinyl, pyrimidinyl, pyridinyl, pyrazolyl, pyrazinyl, oxadiazolyl, isoxazolyl, triazolyl, imidazolyl, benzimidazolyl and thiadiazolyl.

When the optional substituent on A is $C_{5-6}$ heteroaryl methyl, it may preferably be selected from —$CH_2$-imidazolyl and —$CH_2$-triazolyl.

When the optional substituent on A is $C_{5-6}$ heterocyclyl, it may preferably be morpholino.

When the optional substituent on A is $C_{5-6}$ heterocyclyl methyl, it may preferably be selected from —$CH_2$-morpholino and —$CH_2$-piperazinyl.

When the optional substituent on A is phenyl, it may be substituted by one or more $C_{1-4}$ alkyl groups. These groups may preferably be methyl.

When the optional substituent on A is phenyl, it may be substituted by one or more $C_{1-4}$ fluoroalkyl groups. These groups may preferably be trifluoromethyl.

When the optional substituent on A is phenyl, it may be substituted by one or more $C_{1-4}$ alkoxy groups. These groups may preferably be methoxy.

When the optional substituent on A is phenyl, it may be substituted by one or more halo substituents. These groups may preferably be fluoro or chloro, more preferably fluoro.

When the optional substituent on A is phenyl, it may be substituted by one or more cyano groups. It may be preferred that there is a single cyano substituent.

When the optional substituent on A is halo, it may preferably be selected from F, Cl and Br.

When the optional substituent on A is amido, the amido substituent groups R and R' may preferably form a ring, which ring may also be bridged or substituted. If the amido group is not cyclic, it may preferably be selected from —C(=O)$NH_2$, —C(=O)NMeH, —C(=O)$NMe_2$ and —C(=O)$N^i$PrH. If the amido group is cyclic, it may preferably be selected from —C(=O)-piperidinyl, —C(=O)-hydroxypiperidinyl, —C(=O)-methoxypiperidinyl, —C(=O)-pyrrolidinyl, —C(=O)-morpholino, —C(=O)-methylmorpholino, —C(=O)-dimethylmorpholino and —C(=O)-azetidinyl. Further cyclic amido groups include:

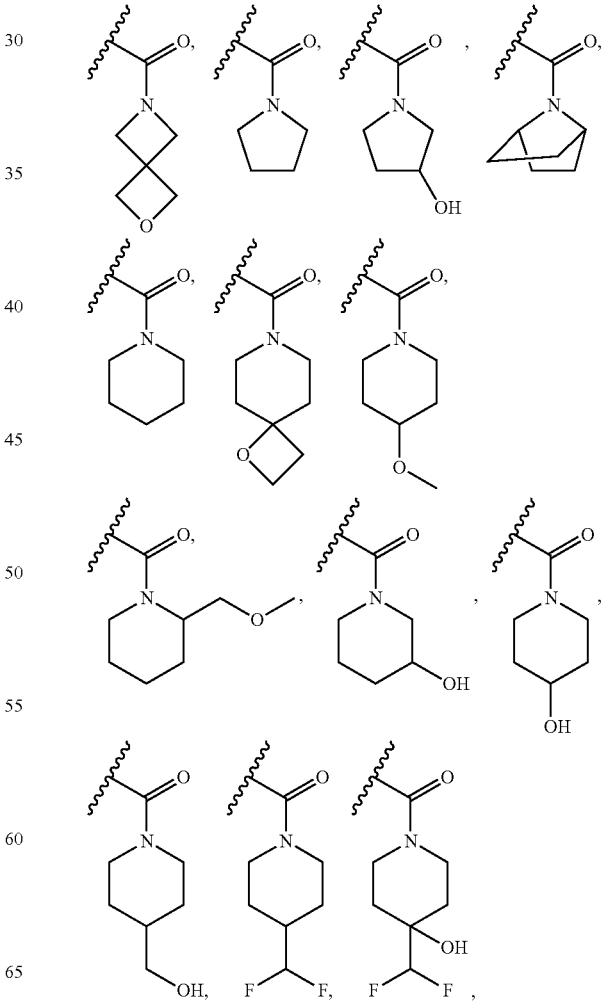

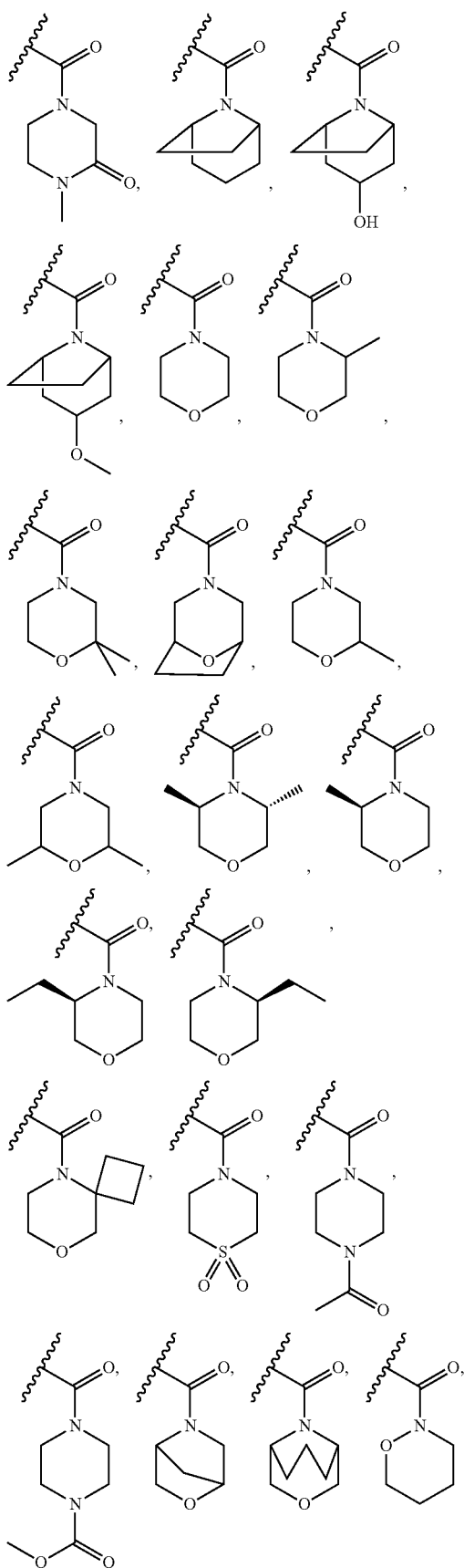

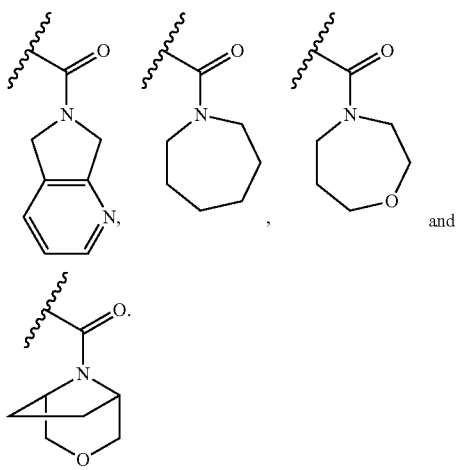

When the optional substituent on A is amidomethyl, the amido substituent groups R and R' may preferably form a ring, which ring may also be bridged or substituted. If the amido group is not cyclic, the amidomethyl group may preferably be selected from —CH$_2$C(=O)NH$_2$, —CH$_2$C(=O)NMeH and —CH$_2$C(=O)N$^i$PrH. If the amido group is cyclic, the amidomethyl group may preferably be selected from —CH$_2$C(=O)-pyrrolidinyl-CH$_2$C(=O)-morpholino, —C(=O)-hydroxypiperidinyl, —C(=O)-methoxypiperidinyl, —C(=O)-methylmorpholino and CH$_2$C(=O)-azetidinyl. Further cyclic amidomethyl groups include:

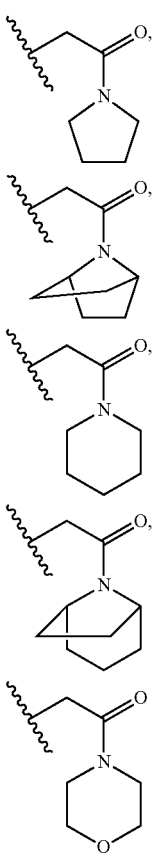

-continued

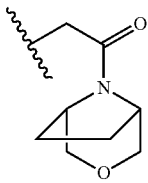

When the optional substituent on A is acylamido, it may preferably be γ-lactam.

When the optional substituent on A is acylamidomethyl, it may preferably be selected from —CH$_2$NHC(=O)Me, —CH$_2$NHC(=O)CF$_3$.

When the optional substituent on A is C$_{1-4}$ alkyl ester, it may preferably be —C(=O)—OMe.

When the optional substituent on A is C$_{1-4}$ alkyl ester methyl, it may preferably be —CH$_2$—C(=O)—OMe.

When the optional substituent on A is C$_{1-4}$ alkyl carbamoyl methyl, it may preferably be —CH$_2$NHC(=O)OMe.

When the optional substituent on A is C$_{1-4}$ alkylacyl, it may preferably be selected from —C(=O)Me and —C(=O)Et.

When the optional substituent on A is C$_{1-4}$ alkylacylmethyl, it may preferably be —CH$_2$C(=O)Me.

When the optional substituent on A is phenylcarbonyl, it may preferably be —C(=O)-Ph.

When the optional substituent on A is ether, it may preferably be selected from methoxy, ethoxy, —OBn, —OPh, —OCF$_3$, —OCF$_2$H, —O—(C$_6$H$_4$)—CN, —O-oxanyl, —OCH$_2$pyridinyl, —OCH$_2$-oxadiazolyl, —OCH$_2$-isoxazole, When the optional substituent on A is amino, the amino substituent may be a C$_{5-6}$ heteroaryl group, in which case the amino group may preferably be selected from —NH-pyrazinyl, —NH-pyrimidine. In other embodiments, the amino substituent may be a C$_{4-6}$ heterocyclyl group, such as optionally N-substituted azetidinyl, optionally N-substituted piperidinyl and oxetanyl. A further amino group may be:

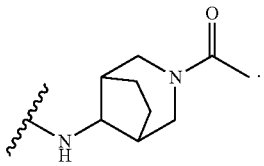 [SMILES: *NC1C2CCC1CN(C(C)=O)C2]

When the optional substituent on A is aminomethyl, it may preferably be —CH$_2$NH$_2$. Alternatively, the amino substituent may be as defined above When the optional substituent on A is sulfonamido it may preferably be selected from —SO$_2$NMePh, —SO$_2$NMe$_2$, and —SO$_2$NHEt.

When the optional substituent on A is sulfonamino, it may preferably be selected from —NHSO$_2$Ph and —NHSO$_2$Me.

When the optional substituent on A is sulfone, it may preferably be —SO$_2$CF$_3$.

Optionally Substituted Phenyl

In some embodiments A may be an optionally substituted phenyl.

In some of these embodiments, A is unsubstituted phenyl.

In some of these embodiments, the phenyl of A has 1, 2, 3, 4 or 5 substituents.

In some of these embodiments, the phenyl of A has 1 or 2 substituents.

It may be preferred that in some of these embodiments R$^1$, R$^{2a}$, R$^{2b}$, R$^{2c}$, R$^{2d}$, R$^{3a}$, R$^{3b}$, R$^4$ and R$^5$ are all hydrogen and n is 1. p may be 0 or 1.

It may be preferred in some of these embodiments that at least one of R$^1$, R$^{2a}$, R$^{2b}$, R$^{2c}$, R$^{2d}$, R$^{3a}$, R$^{3b}$, R$^4$ and R$^5$ is not hydrogen.

In the above embodiments, both R$^{6a}$ and R$^{6b}$ may be H.

It may be preferred in some of these some of these embodiments that R$^{1-6}$ and n and p are such that the compound is of formula Ia, Ib or Ic.

It may be preferred in these embodiments that the optional substituents are independently selected from the following: C$_{1-4}$ alkyl; C$_{1-4}$ fluoroalkyl; C$_{3-6}$ cycloalkyl; C$_{5-6}$ heteroaryl; C$_{5-6}$ heteroaryl methyl; C$_{4-6}$ heterocyclyl; C$_{4-6}$ heterocyclyl methyl; phenyl; benzyl; halo; amido; amidomethyl; acylamido; acylamidomethyl; C$_{1-4}$ alkyl ester; C$_{1-4}$ alkyl ester methyl; C$_{1-4}$ alkyl carbamoyl; C$_{1-4}$ alkyl carbamoyl methyl; C$_{1-4}$ alkylacyl; C$_{1-4}$ alkyl acyl methyl; phenylcarbonyl; carboxy; carboxymethyl; ether; amino; aminomethyl; sulfonamido; sulfonamino; sulfone; nitrile; and nitrilemethyl.

It may be preferred in these embodiments that the optional substituents are selected from: C$_{1-4}$ alkyl, fluoro, chloro, bromo, acetyl, methoxy, ethoxy, —C(=O)Me, —C(=O)Et, —CH$_2$C(=O)Me, phenyl, —CF$_3$, —CF$_2$H, —CN, —CH$_2$CN, —OBn, —OPh, —OCF$_3$, —OCF$_2$H, —O—(C$_6$H$_4$)—CN, —COOH, —CH$_2$COOH, —C(=O)OMe, —C(=O)NH$_2$, —C(=O)NMeH, —C(=O)NMe$_2$, —C(=O)N$^i$PrH, —C(=O)-piperidinyl, —C(=O)-pyrrolidinyl, —C(=O)-morpholino (which may be bridged or substituted by one of two methyl groups), —C(=O)-azetidinyl, —CH$_2$C(=O)NH$_2$, —CH$_2$C(=O)-azetidinyl, —CH$_2$C(=O)NMeH, —CH$_2$C(=O)N$^i$PrH, —CH$_2$C(=O)-pyrrolidinyl, —CH$_2$C(=O)-morpholino, —CH$_2$-morpholino, —CH$_2$-methylpiperazinyl, —OCH$_2$pyridinyl, —OCH$_2$-methyloxadiazolyl, —CH$_2$-imidazolyl, —O-tetrahydropyranyl, —CH$_2$-tetraydropyanyl, —NH-methylpyrazinyl, —CH$_2$-triazolyl, —NHSO$_2$Ph, —NHSO$_2$Me, —SO$_2$NMePh, —SO$_2$NMe$_2$, —SO$_2$NHEt, —SO$_2$CF$_3$, -γ-lactam, —CH$_2$NHC(=O)Me, —CH$_2$NHC(=O)OMe, —CH$_2$NHC(=O)CF$_3$, morpholino, —CH$_2$NH$_2$, —C(=O)Ph, —OCH$_2$-isoxazolyl, —NH-pyrimidinyl, pyridizinyl, pyrimidinyl, pyridinyl, pyrazolyl, methylpyrazolyl, dimethylpyrazolyl, pyrazinyl, pyridazinyl, methyloxadiazolyl, oxadiazolyl, dimethyloxadiazolyl, isoxazolyl, dimethyltriazolyl, imidazolyl, benzimidazolyl and thiadiazolyl.

It may be preferred in these embodiments that, when the optional substituent is a C$_{5-6}$ heteroaryl group, the heteroaryl ring itself is substituted with one or more C$_{1-4}$ alkyl groups.

It may be preferred in the above embodiments that 1 substituent is present. In may be preferred in the above embodiments that 2 substituents are present.

Halo and methoxy (including CF$_3$O) substituents may be preferred in the ortho position of the phenyl group. Ethoxy and alkyl (e.g. methyl, CF$_2$H and CF$_3$) substituents may also be preferred in the ortho position of the phenyl group. Alkyl and C$_{5-6}$ heteroaryl may be preferred in the meta position of the phenyl group. Amido and amidomethyl substituents may be preferred in the para position of the phenyl group. Particular favoured groups in the ortho position are ethoxy, methoxy, Cl, F and CF$_2$H.

In some embodiments, the phenyl group bears a halo or methoxy substituent in the ortho position, and an amido or amidomethyl substituent in the para position of the phenyl group.

In some embodiments, the phenyl group bears an amino substituent in the meta position.

Where the substituent on phenyl is a fused $C_{5-6}$ $N_1$-containing heterocyclic ring, A may have a core structure selected from:

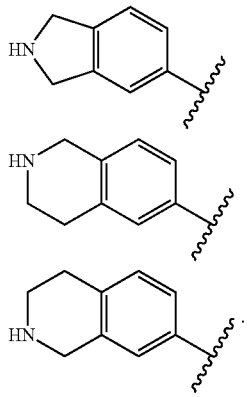

Particular A groups of interest include:

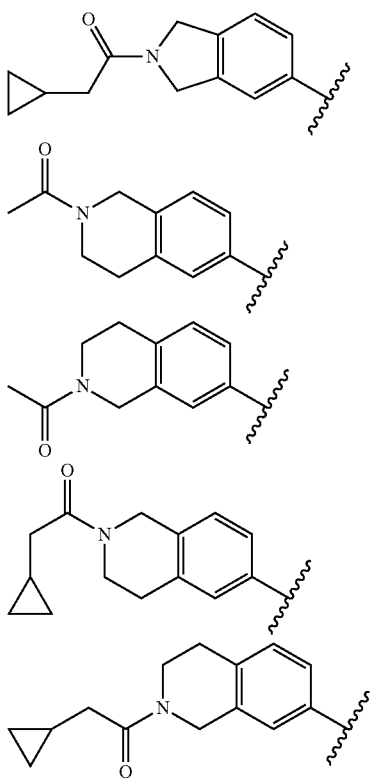

Optionally Substituted Naphthyl

When A is naphthyl, it may be in any orientation, e.g. naphth-1-yl, naphth-2-yl.

In some embodiments A may be optionally substituted naphthyl.

In some of these embodiments, A is unsubstituted naphthyl.

In some of these embodiments, the naphthyl ring of A has 1, 2, 3, 4 or 5 substituents.

In some of these embodiments, the naphthyl ring of A has 1 or 2 substituents.

It may be preferred that in some of these embodiments $R^1$, $R^{2a}$, $R^{2b}$, $R^{2c}$, $R^{2d}$, $R^{3a}$, $R^{3b}$, $R^4$ and $R^5$ are all hydrogen and n is 1. p may be 0 or 1.

It may be preferred in some of these embodiments that at least one of $R^1$, $R^{2a}$, $R^{2b}$, $R^{2c}$, $R^{2d}$, $R^{3a}$, $R^{3b}$, $R^4$ and $R^5$ is not hydrogen.

In the above embodiments, both $R^{6a}$ and $R^{6b}$ may be H.

It may be preferred in some of these some of these embodiments that $R^{1-6}$ and n and p are such that the compound is of formula Ia, Ib or Ic.

It may be preferred in these embodiments that the optional substituents refers to 0-2 substituents independently selected from the following: $C_{1-4}$ alkyl; $C_{1-4}$ fluoroalkyl; $C_{3-6}$ cycloalkyl; $C_{5-6}$ heteroaryl; $C_{5-6}$ heteroaryl methyl; $C_{4-6}$ heterocyclyl; $C_{4-6}$ heterocyclyl methyl; phenyl; benzyl; halo; amido; amidomethyl; acylamido; acylamidomethyl; $C_{1-4}$ alkyl ester; $C_{1-4}$ alkyl ester methyl; $C_{1-4}$ alkyl carbamoyl; $C_{1-4}$ alkyl carbamoyl methyl; $C_{1-4}$ alkylacyl; $C_{1-4}$ alkyl acyl methyl; phenylcarbonyl; carboxy; carboxymethyl; ether; amino; aminomethyl; sulfonamido; sulfonamino; sulfone; nitrile; and nitrilemethyl.

It may be preferred in these embodiments that 1 substituent is present. In may be preferred in these embodiments that 2 substituents are present.

Optionally Substituted $C_{5-12}$ Heteroaryl

In some embodiments A may be an optionally substituted $C_{5-12}$ heteroaryl group.

In some of these embodiments, A is unsubstituted $C_{5-12}$ heteroaryl group.

In some of these embodiments, the $C_{5-12}$ heteroaryl of A has 1, 2, 3, 4 or 5 substituents.

In some of these embodiments, the $C_{5-12}$ heteroaryl of A has 1 or 2 substituents.

It may be preferred in these embodiments that the $C_{5-12}$ heteroaryl ring is selected from one of the following: pyridinyl, pyrimidinyl, pyrazinyl, isoxazolyl, oxazolyl, thiophenyl, thiazolyl, thiadiazolyl, pyrazolyl, pyridonyl, imidazolyl, benzimidazolyl, imidazopyridinyl and quinolinyl. The heteroatoms may be in any location in the ring, which may be joined to the remainder of the molecule via a ring carbon atom. It may be further preferred that the $C_{5-12}$ heteroaryl ring is either pyridinyl or pyrimidinyl. It may also be further preferred that the $C_{5-12}$ heteroaryl is selected from pyridyl, pyrimidinyl, oxazolyl, oxadiazolyl, pyrazolyl and thiazolyl and in particular:

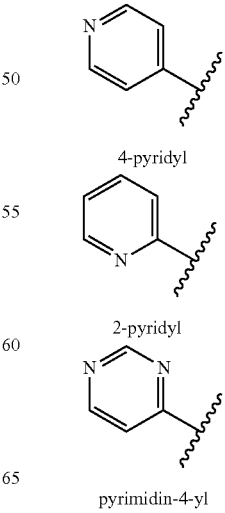

4-pyridyl 2-pyridyl pyrimidin-4-yl

-continued

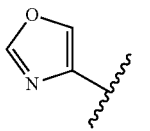

oxazol-4-yl

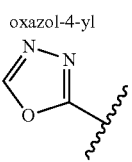

1,3,4-oxadiazol-2-yl

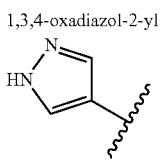

1H-pyrazol-4-yl

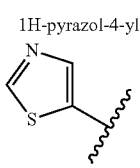

thiazol-5-yl

Further preferred groups may include benzothiazolyl and benzimidazolyl and in particular:

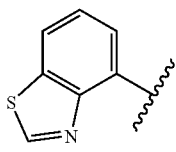

1,3-benzothiazol-4-yl

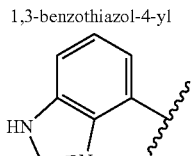

1H-benzimidazol-4-yl

It may be preferred that in some of these embodiments $R^1$, $R^{2a}$, $R^{2b}$, $R^{2c}$, $R^{2d}$, $R^{3a}$, $R^{3b}$, $R^4$ and $R^5$ are all hydrogen and n is 1. p may be 0 or 1.

It may be preferred in some of these embodiments that at least one of $R^1$, $R^{2a}$, $R^{2b}$, $R^{2c}$, $R^{2d}$, $R^{3a}$, $R^{3b}$, $R^4$ and $R^5$ is not hydrogen.

In the above embodiments, both $R^{6a}$ and $R^{6b}$ may be H.

It may be preferred in some of these some of these embodiments that $R^{1-6}$ and n and p are such that the compound is of formula Ia, Ib or Ic.

It may be preferred in these embodiments that the optional substituents are independently selected from the following: $C_{1-4}$ alkyl; $C_{1-4}$ fluoroalkyl; $C_{3-6}$ cycloalkyl; $C_{5-6}$ heteroaryl; $C_{5-6}$ heteroaryl methyl; $C_{4-6}$ heterocyclyl; $C_{4-6}$ heterocyclyl methyl; phenyl; benzyl; halo; amido; amidomethyl; acylamido; acylamidomethyl; $C_{1-4}$ alkyl ester; $C_{1-4}$ alkyl ester methyl; $C_{1-4}$ alkyl carbamoyl; $C_{1-4}$ alkyl carbamoyl methyl; $C_{1-4}$ alkylacyl; $C_{1-4}$ alkyl acyl methyl; phneylcarbonyl; carboxy; carboxymethyl; ether; amino; aminomethyl; sulfonamido; sulfonamino; sulfone; nitrile; and nitrilemethyl.

It may be preferred in these embodiments that the optional substituents are selected from: $C_{1-4}$ alkyl; $C_{1-4}$ fluoroalkyl; $C_{5-6}$ heteroaryl, $C_{4-6}$ heterocyclyl; phenyl; halo; and ether.

It may be preferred in these embodiments that the optional substituent are selected from; methyl, ethyl, butyl, chloro, bromo, fluoro, morpholino, pyrrolidinyl, —OBn, —OPh, phenyl, para-bromophenyl, pyrazolyl, pyrimidinyl, imidazolyl and —CF$_3$.

In may be preferred in these embodiments that 1 substituent is present. In may be preferred in these embodiments that 2 substituents are present.

Halo and methoxy substituents may be preferred in the ortho position of a $C_6$ heteroaryl group, or α-position of $C_5$ and $C_{7-12}$ heteroaryl group. Amido and amidomethyl substituents may be preferred in the para position of a $C_6$ heteroaryl group, or γ-position of $C_5$ and $C_{7-12}$ heteroaryl group.

In some embodiments, a $C_6$ heteroaryl group bears a halo or methoxy substituent in the ortho position, and an amido or amidomethyl substituent in the para position.

In some embodiments, a $C_6$ heteroaryl group bears an amino substituent in the meta position. In some embodiments, a $C_5$ or $C_{7-12}$ heteroaryl group bears an amino substituent in the β-position.

Where the $C_6$ heteroaryl group is 4-pyridyl, it may bear an ether substituent, for example in the 3-position. In some of these embodiments, the ether substituent may be —O—$C_{4-6}$ heterocyclyl, wherein the $C_{4-6}$ heterocyclyl may itself bear an ester group (e.g. methoxy ester).

Where the $C_6$ heteroaryl group is 2-pyridyl, it may bear an amido substituent, for example in the 4-position.

Where the $C_6$ heteroaryl group is 4-pyrimidinyl, it may bear an amino substituent, for example in the 3-position. In some of these embodiments, the amino substituent may be —NH—$C_{4-6}$ heterocyclyl, wherein the $C_{4-6}$ heterocyclyl may itself bear an acyl group (e.g. —C(═O)Me).

Where A is a $C_5$ heteroaryl group (e.g. oxazolyl, oxadiazolyl, pyrazolyl and thiazolyl), it may bear an amino, phenyl or $C_6$ heteroaryl substituent in the β-position.

In some embodiments A is selected from one of the following groups:

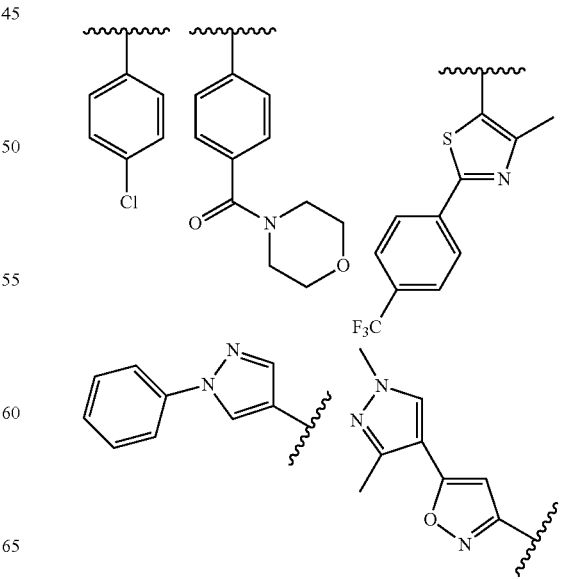

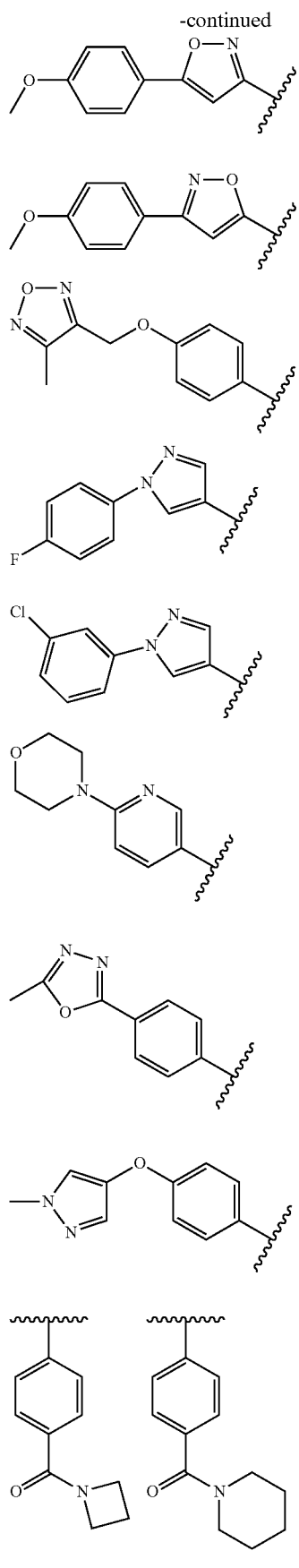
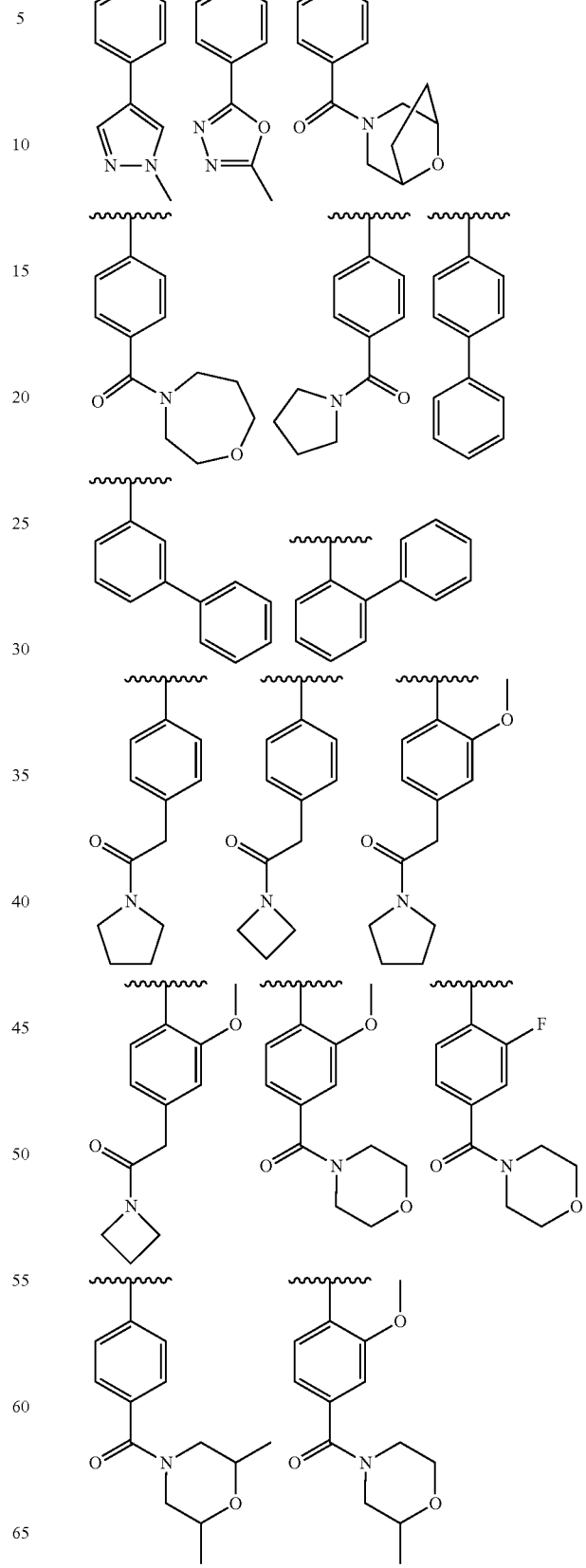

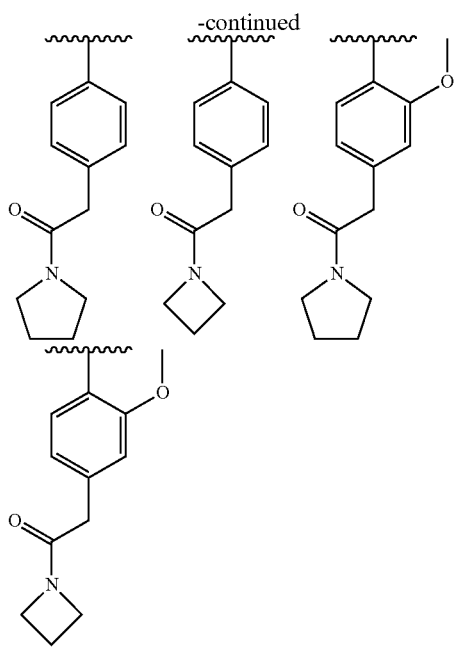
In some embodiments A may be selected from one of the following groups:
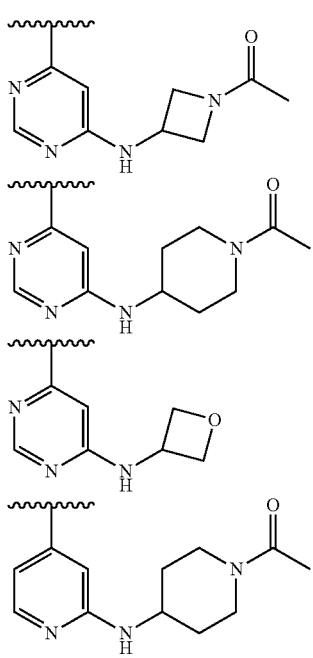
In further embodiments, it may be preferred that A is selected from one of the following groups:
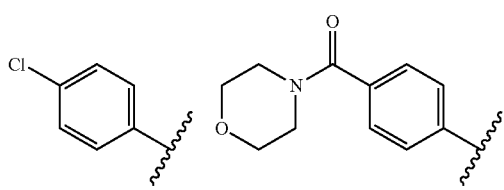
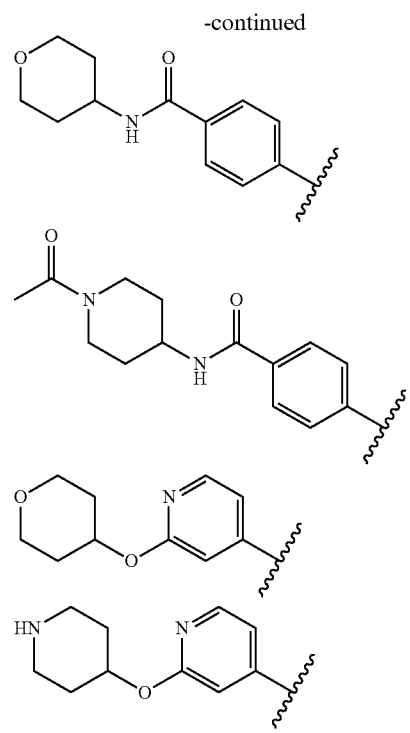
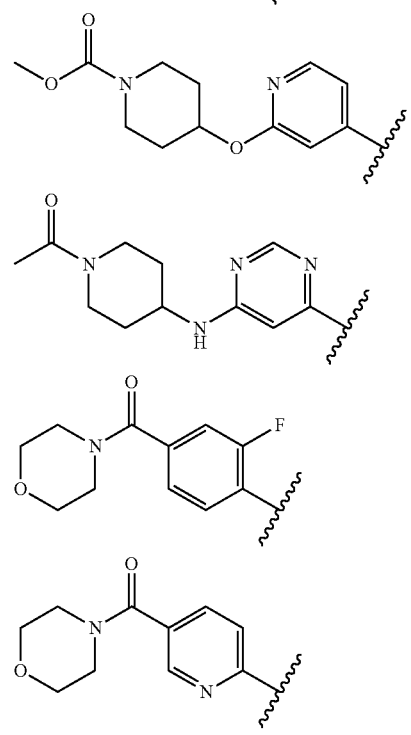
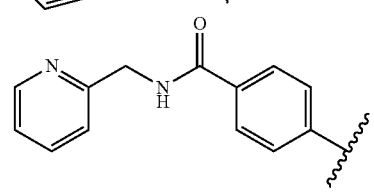

-continued
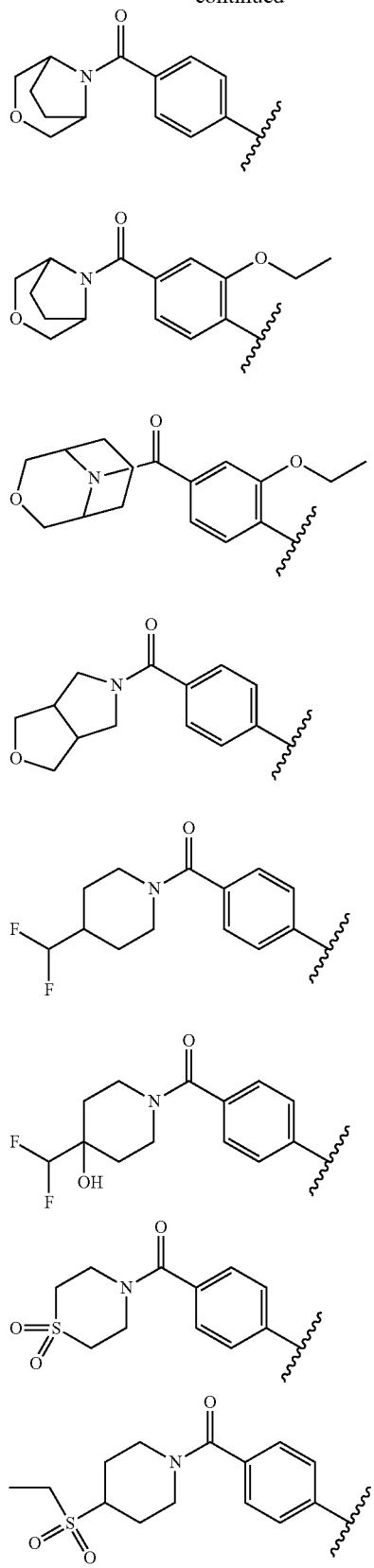
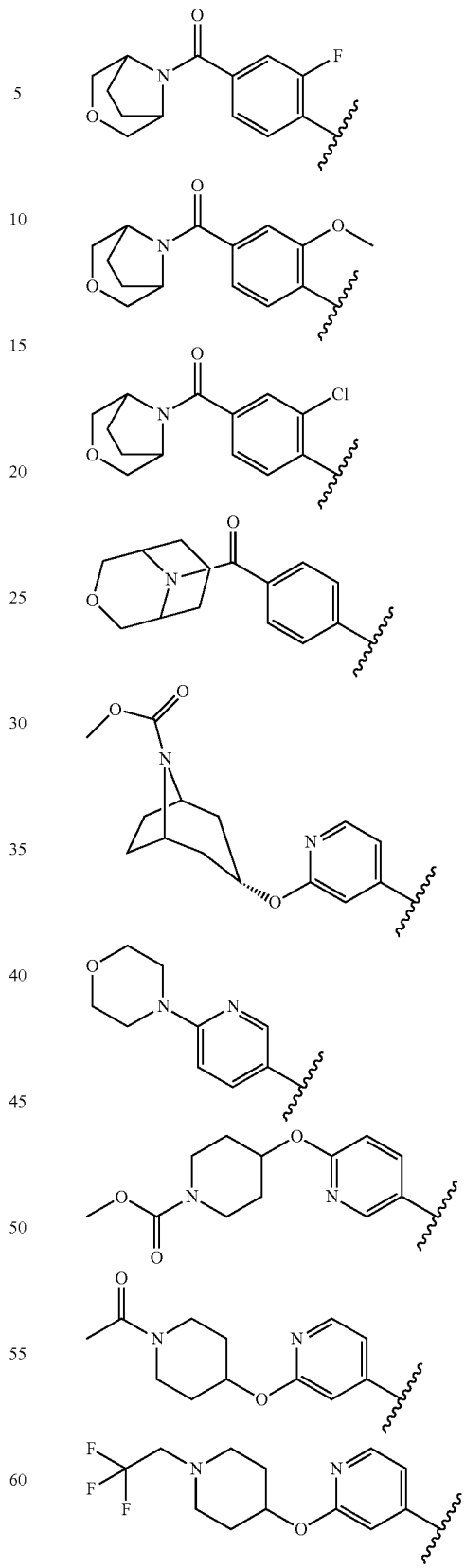
In further embodiments, it may be preferred that A is selected from one of the following groups:
In other further embodiments, the A group may be selected from:

phenyl with a para-amido substituent;

phenyl with a para-amido substituent, and an ortho-ethoxy group;

pyridyl with para ether or amino group, where the ether or amino substituent is a $C_{5-6}$ heterocyclic group—in these groups, the pyridyl N may be in the meta position; these groups may also have (in some embodiments) an ortho-ethoxy group; and pyridyl with a meta ether group, where the pyridyl N is in the para position.

It may be preferred that in some of these embodiments RN, $R^1$, $R^{2a}$, $R^{2b}$, $R^{2c}$, $R^{2d}$, $R^{3a}$, $R^{3b}$, $R^{4b}$, $R^5$, $R^{6a}$ and $R^{6b}$ are all hydrogen and that $R^{4a}$ is OH and n is 1.

p may be 0 or 1.

EXAMPLES

The following examples are provided solely to illustrate the present invention and are not intended to limit the scope of the invention, as described herein.

Acronyms

For convenience, many chemical moieties are represented using well known abbreviations, including but not limited to, methyl (Me), ethyl (Et), n-propyl (nPr), isopropyl (iPr), n-butyl (nBu), tert-butyl (tBu), phenyl (Ph), benzyl (Bn), methoxy (MeO), ethoxy (EtO), trimethylsilyl (TMS), and acetyl (Ac).

For convenience, many chemical compounds are represented using well known abbreviations, including but not limited to, methanol (MeOH), deuterated methanol ($d_4$-MeOD) ethanol (EtOH), isopropanol (i-PrOH), ether or diethyl ether ($Et_2O$), ethyl acetate (EtOAc), acetic acid (AcOH), acetonitrile (MeCN), dichloromethane (methylene chloride, DCM), trifluoroacetic acid (TFA), dimethylformamide (DMF), tetrahydrofuran (THF), dimethylsulfoxide (DMSO), deuterated chloroform ($CDCl_3$), diethylamine (DEA), deuterated dimethylsulfoxide ($d_6$-DMSO), N-ethyl-N'-(3-dimethylaminopropyl)carbodiimide hydrochloride (EDCl.HCl, EDCl), meta-chloroperoxybenzoic acid (mCPBA), 1,1'-bis(diphenylphosphino)ferrocene (dppf), tert-butyloxycarbonyl (Boc, BOC), 2-(trimethylsilyl)ethoxymethyl (SEM), triethylamine ($Et_3N$), 2-(1H-7-azabenzotriazol-1-yl)-1,1,3,3-tetramethyluronium hexafluorophosphate (HATU), 4-dimethylaminopyridine (DMAP), N,N-diisopropylethylamine (DIPEA), 1,1'-bis(diphenylphosphino)ferrocene dichloropalladium (II) ($PdCl_2$(dppf)), trans-dichlorobis(triphenylphosphine)palladium(II) ($PdCl_2(PPh_3)_2$), tris(dibenzylideneacetone) dipalladium(0) ($Pd_2(dba)_3$), tetrakis(triphenylphosphine)palladium(0) ($Pd(PPh_3)_4$), propylphosphonic anhydride (T3P), and 1-hydroxybenzotriazole (HOBt), hexamethylphosphoramide (HMPA), trimethylamine (TEA), dichloroethane (DCE), N-bromosuccinimide (NBS), N—N'-dicyclohexylcarbodiimide (DCC), p-toluenesulfonic acid (TsOH), 4-dimethylaminopyridine (DMAP), 1,1'-carbonyldiimidazole (CDI).

General Experimental Details

Unless otherwise stated the following generalisations apply. $^1$H NMR spectra were recorded on a Bruker Ultrashield Plus (400 MHz) or a Bruker AVANCE (400 MHz). The multiplicity of a signal is designated by the following abbreviations: s, singlet; d, doublet; t, triplet; q, quartet; dd, doublet of doublets; dt, doublet of triplets; tt, triplet of triplets; br, broad; m, multiplet. All observed coupling constants, J, are reported in Hertz.

LCMS data was generated using either an Agilent 6100 Series Single Quad LCMS (LCMS-A), an Agilent 1260 Infinity Series UPLC/MS (LCMS-B), an Agilent 1200 Series G6110A Quadrupole LCMS or Waters 2695 alliance (LCMS-C). Chlorine isotopes are reported as $^{35}$Cl, Bromine isotopes are reported as either $^{79}$Br Or $^{81}$Br or both $^{79}$Br/$^{81}$Br.

LCMS Method A (LCMS-A):
Instrument: Agilent 6100 Series Single Quad LC/MS
Agilent 1200 Series HPLC
Pump: 1200 Series G1311A Quaternary pump
Autosampler: 1200 Series G1329A Thermostatted Autosampler
Detector: 1200 Series G1314B Variable Wavelength Detector
LC Conditions:
Reverse Phase HPLC analysis
Column: Luna C8 (2) 5 μm 50×4.6 mm 100 Å
Column temperature: 30° C.
Injection Volume: 5 μL
Solvent A: Water 0.1% Formic Acid
Solvent B: MeCN 0.1% Formic Acid
Gradient: 5-100% solvent B over 10 min
Detection: 254 nm or 214 nm
MS conditions:
Ion Source: Quadrupole
Ion Mode: Multimode-ES
Drying gas temp: 300° C.
Vaporizer temperature: 200° C.
Capillary voltage (V): 2000 (positive)
Capillary voltage (V): 4000 (negative)
Scan Range: 100-1000
Step size: 0.1 sec
Acquisition time: 10 min
LCMS Method B (LCMS-B):
Instrument: Agilent 1260 Infinity Series UPLC/MS
Pump: 1260 Infinity G1312B Binary pump
Autosampler: 1260 Infinity G1367E 1260 HiP ALS
Detector: 1290 Infinity G4212A 1290 DAD
LC Conditions:
Reverse Phase HPLC analysis
Column: Poroshell 120 EC-C18 2.7 μm 50×3.0 mm
Column temperature: 35° C.
Injection Volume: 1 μL
Solvent A: Water 0.1% Formic Acid
Solvent B: MeCN 0.1% Formic Acid
Gradient: 5-100% solvent B over 3.8 min
Detection: monitored at 254 nm and 214 nm
MS Conditions:
Ion Source: Quadrupole
Ion Mode: API-ES
Drying gas temp: 350° C.
Capillary voltage (V): 3000 (positive)
Capillary voltage (V): 3000 (negative)
Scan Range: 100-1000
Step size: 0.1 sec
Acquisition time: 5 min
LCMS Method C (LCMS-C):
Instrument: Agilent 1200 Series G6110A Quadrupole
Pump: Binary pump
Detector: DAD
LC Conditions:
Reverse Phase HPLC analysis
Column: Xbridge-C18, 2.5 μm, 2.1×30 mm
Column temperature: 30° C.

Injection Volume: 1-10 µL
Solvent A: Water 0.07% Formic acid
Solvent B: Methanol
Gradient: 30-95% solvent B over 3.5 min (for medium polarity samples) or 10-95% solvent B over 3.7 min (for large polarity samples)
Detection: monitored at 254 nm and 214 nm
MS Conditions:
Ion Source: Quadrupole
Ion Mode: ES+
Drying gas temp: 350° C.
Drying gas flow: 10 L/min
Nebulizer pressure: 35 psi
Capillary voltage (V): 3500 (positive)
Scan Range: 50-900
Or
Instrument: Waters 2695 alliance
Pump: Quaternary Pump
Detector: 2996 Photodiode Array Detector
MS model: Micromass ZQ
LC Conditions:
Column: Xbridge-C18, 3.5 µm, 2.1×50 mm
Column temperature: 30° C.
Injection volume: 1-10 µL
Acquisition of wavelength: 214 nm, 254 nm
Solvent A: 0.07% HCOOH aqueous solution
Solvent B: MeOH
Run time: 8 min
Gradient: 20-95% solvent B over 5 min
Detection: 254 nm and 214 nm
MS Condition:
Ion source: ES+(or ES−) MS range: 50-900 m/z
Capillary: 3 kV Cone: 3 V Extractor: 3 V
Drying gas flow: 600 L/hr cone: 50 L/hr
Desolvation temperature: 300° C.
Source temperature: 100° C.
Sample Preparation:
The sample was dissolved in methanol, the concentration about 0.1-1.0 mg/mL, then filtered through the syringes filter with 0.22 µm.
Preparative RP-HPLC:
Agilent 1260 Infinity HPLC system
UV detection at 210 nm and 254 nm
Gradient or isocratic elution through a Phenomenex Luna C8 (2) column 100 Å Axia (250×21.2 mm; particle size 5 µm)
Flow rate: 10 mL/min
Gradients are as specified in the individual examples.
Analytical thin-layer chromatography was performed on Merck silica gel 60 F254 aluminium-backed plates which were visualised using fluorescence quenching under UV light or a basic $KMnO_4$ dip or Ninhydrin dip.
Preparative thin-layer chromatography (prep TLC) was performed using Tklst (China), grand grade: (HPTLC): 8±2 µm>80%; (TLC): 10-40 µm. Type: GF254. Compounds were visualised by UV (254 nm).
Flash chromatography was performed using a Biotage Isolera purification system using either Grace or RediSep® silica cartridges.
Column chromatography was performed using Tklst (China), grand grade, 100-200 meshes silica gel.
Microwave irradiation was achieved using a CEM Explorer SP Microwave Reactor.
Where necessary, anhydrous solvents were purchased from Sigma-Aldrich or dried using conventional methods. Solutions of inorganic acids or bases where made up as aqueous solutions unless stated otherwise.
Additional Cartridges used are as follows:
Phase Separator:
Manufacturer: Biotage
Product: ISOLUTE® Phase Separator (3 mL unless otherwise stated)
SCX and SCX-2 Cartridges:
Manufacturer: Biotage
Product: ISOLUTE® SCX 1 g, (6 mL SPE Column unless otherwise stated)
Manufacturer: Biotage
Product: ISOLUTE® SCX-2 1 g (6 mL Column)
Manufacturer: Silicycle
Product: SCX-2 500 mg or 5 g
Manufacturer: Agilent
Product: Bond Elut® SCX 10 g
Sample Extraction Cartridge:
Manufacturer: Waters
Product: Oasis® HLB 35 cc (6 g) LP extraction cartridge Intermediate Preparations (i) 2-(2-Hydroxy-3-(isoquinolin-3-yl)propyl)isoindoline-1,3-dione (I3)

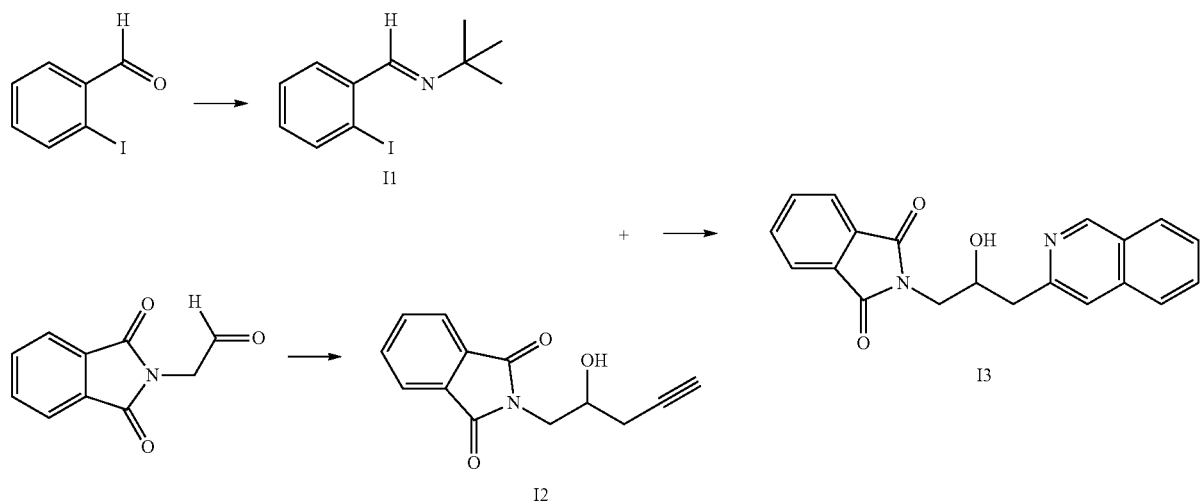

(a) (E)-N-tert-Butyl-1-(2-iodophenyl)methanimine (I1)

2-Iodobenzaldehyde (1.460 g, 6.29 mmol), water (3 mL) and tert-butylamine (1.98 mL, 18.9 mmol) were stirred at room temperature for 18 hours. The volatiles were removed in vacuo and the residue was extracted with diethyl ether (2×5 mL). The combined ether extracts were dried over sodium sulfate and concentrated to give the desired compound as a pale yellow oil (1.45 g, 80%)

(b) 2-(2-Hydroxypent-4-yn-1-yl)isoindoline-1,3-dione (I2)

2-(1,3-Dioxoisoindolin-2-yl)acetaldehyde (1.00 g, 5.29 mmol), indium powder (1.21 g, 10.6 mmol), THF (10 mL), water (10 mL) and propargyl bromide (80% in toluene, 1.38 mL, 10.6 mmol) were stirred vigorously at room temperature. After four hours, the volatile solvents were removed in vacuo and the aqueous residue diluted with water (100 mL). The aqueous mixture was extracted with DCM (3×100 mL) and the combined organic extracts were washed with brine (100 mL), dried over sodium sulfate and concentrated. Chromatography (40 g silica cartridge, 0-60% ethyl acetate in petroleum benzine 40-60° C.) gave the desired compound as a white solid (531 mg, 44%) $^1$H NMR (400 MHz, CDCl$_3$) δ 7.90-7.84 (m, 2H), 7.77-7.71 (m, 2H), 4.15-4.07 (m, 1H), 3.93-3.89 (m, 2H), 2.69 (br s, 1H), 2.58-2.43 (m, 2H), 2.09 (t, J=2.7 Hz, 1H); LCMS-B 3.39 min; m/z 212.1 [M–H$_2$O+H]$^+$; 230.1 [M+H]$^+$; 252.1 [M+Na]$^+$.

(c) 2-(2-Hydroxy-3-(isoquinolin-3-yl)propyl)isoindoline-1,3-dione (I3)

A Schlenk tube was loaded with zinc dust (86 mg, 1.3 mmol) and bis(triphenylphosphine)nickel(II) chloride (21 mg, 5 mol %) and purged with nitrogen. A solution of (E)-N-tert-butyl-1-(2-iodophenyl)methanimine I1 (188 mg, 0.65 mmol) and 2-(2-Hydroxypent-4-yn-1-yl)isoindoline-1,3-dione I2 (150 mg, 0.65 mmol) in dry acetonitrile (15 mL) was added via cannula and the mixture stirred at 80° C. under nitrogen. After 30 minutes, the mixture was cooled to room temperature, filtered through Celite and the Celite washed with acetonitrile (30 mL). The combined filtrates were concentrated in vacuo and the material was subjected to column chromatography (12 g silica cartridge, 0-10% methanol/DCM then 100% methanol). The mixture was loaded in methanol onto a 10 g SCX cartridge, the cartridge washed with methanol (60 mL) and eluted with 2.0 M ammonia in methanol (100 mL). The basic eluate was concentrated in vacuo to a yellow sticky solid. The yellow residue was slurried in ethyl acetate (2×2 mL) and the insoluble material dried in vacuo to give the desired compound (116 mg, 53% yield) as a white solid. $^1$H NMR (400 MHz, d$_6$-DMSO) δ 9.22-9.17 (m, 1H), 8.06-8.01 (m, 1H), 7.88-7.84 (m, 1H), 7.83-7.76 (m, 4H), 7.74-7.69 (m, 1H), 7.65 (s, 1H), 7.62-7.56 (m, 1H), 5.10 (d, J=5.5 Hz, 1H), 4.43-4.31 (m, 1H), 3.76-3.65 (m, 1H), 3.63-3.54 (m, 1H), 3.07-2.90 (m, 2H); LCMS-B: RT 3.26 min; m/z 333.2 [M+H]$^+$.

(ii) 2-(2-Hydroxy-2-(isoquinolin-3-yl)ethyl)isoindoline-1,3-dione (I5)

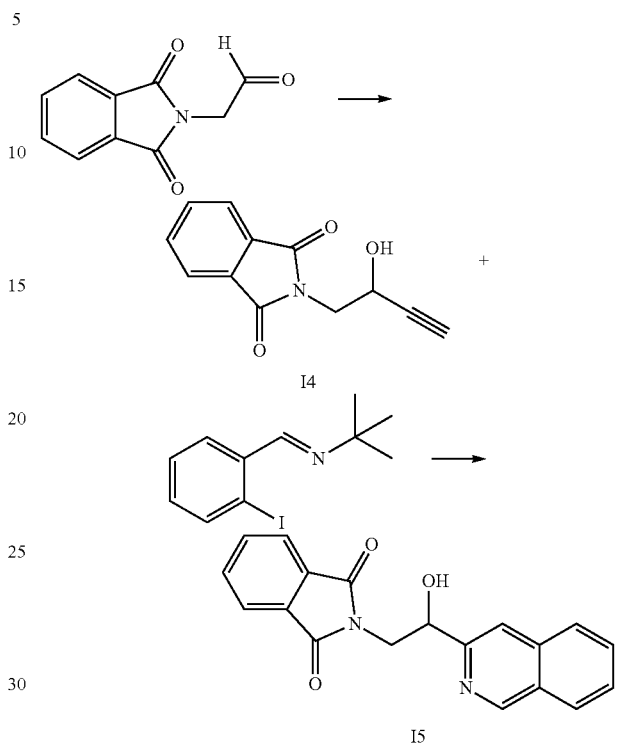

(a) 2-(2-Hydroxybut-3-yn-1-yl)isoindoline-1,3-dione (I4)

A 0.5 M THF solution of ethynyl magnesium bromide (3.33 mL, 1.67 mmol) was cooled to 0° C. under nitrogen. A solution of 2-(1,3-dioxoisoindolin-2-yl)acetaldehyde (300 mg, 1.59 mmol) in THF (3 mL) was added cannula and the mixture stirred at 0° C. under nitrogen. After 1.5 hours, the mixture was quenched with a saturated aqueous solution of ammonium chloride (3 mL) and the volatile solvents were removed in vacuo. The residue was diluted with water (10 mL) and DCM (15 mL), the aqueous phase was extracted with DCM (2×15 mL). The combined organic phases were dried over sodium sulfate and concentrated. Chromatography (12 g silica cartridge, 0-60% ethyl acetate in petroleum benzine 40-60° C.) gave the desired compound as a white solid (142 mg, 42%). $^1$H NMR (400 MHz, CDCl$_3$) δ 7.88 (dd, J=5.5, 3.1 Hz, 2H), 7.75 (dd, J=5.5, 3.1 Hz, 2H), 4.74-4.66 (m, 1H), 4.08 (dd, J=14.3, 8.0 Hz, 1H), 3.94 (dd, J=14.2, 3.9 Hz, 1H), 2.83 (d, J=7.7 Hz, 1H), 2.49 (d, J=2.1 Hz, 1H); LCMS-B: RT 3.37 min; no product ions detected.

(b) 2-(2-Hydroxy-2-(isoquinolin-3-yl)ethyl)isoindoline-1,3-dione (I5)

A Schlenk tube was loaded with zinc dust (84 mg, 1.3 mmol) and bis(triphenylphosphine)nickel(II) chloride (21 mg, 5 mol %) then flushed with nitrogen. A solution of N-tert-butyl-1-(2-iodophenyl)methanimine (184 mg, 0.641 mmol) and 2-(2-hydroxybut-3-yn-1-yl)isoindoline-1,3-dione I4 (138 mg, 0.641 mmol) in dry acetonitrile (15 mL) was added via cannula, and the mixture stirred at 80° C. under nitrogen. After 30 minutes, the mixture was cooled and filtered through Celite. The celite was washed with acetonitrile (2×20 mL) and the combined filtrates concentrated. Chromatography (12 g silica cartridge, 0-10% methanol/DCM) gave the desired compound as a pale yellow solid (174 mg, 85%). $^1$H NMR (400 MHz, d$_4$-DMSO) δ 9.20 (s, 1H), 8.15-8.07 (m, 1H), 8.02-7.97 (m, 1H), 7.96 (s, 1H), 7.91-7.80 (m, 5H), 7.80-7.73 (m, 1H), 7.68-7.61 (m, 1H), 5.91 (d, J=4.9 Hz, 1H), 5.18-5.07 (m, 1H), 4.04-3.95 (m, 1H), 3.92-3.79 (m, 1H); LCMS-B: RT 3.41 min; m/z 319.1 [M+H]$^+$.

(iii) 4-(Morpholine-4-carbonyl)benzoic acid (I7)

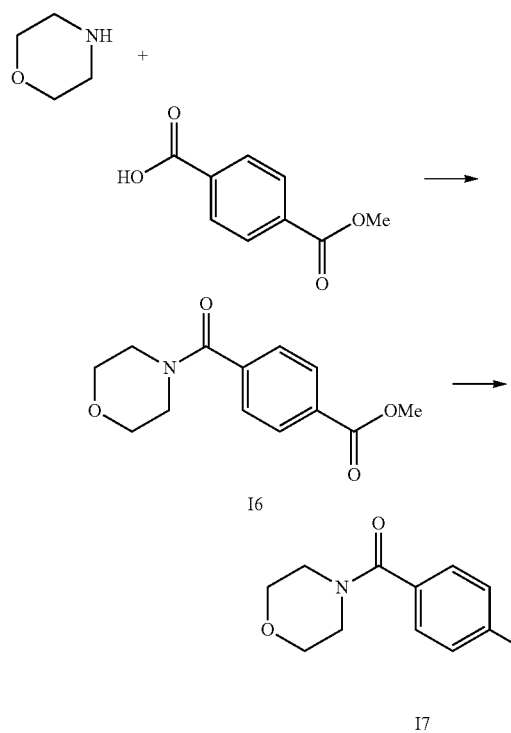

(a) Methyl 4-(morpholine-4-carbonyl)benzoate (I6)

To an ice-cooled (0° C.) solution of mono-methyl terephthalate (10.0 g, 55.5 mmol) in DCM (100 mL) was added oxalyl chloride (5.7 mL, 67 mmol) and a catalytic amount of DMF (10 drops). The mixture was stirred at 0° C. for 3 hours and the solvent was removed in vacuo. The residue was taken up in DCM (100 mL), cooled to 0° C. and morpholine (5.3 mL, 61 mmol) was added drop-wise followed by triethylamine (9.3 mL, 67 mmol). The reaction was stirred at room temperature for 16 hours. The reaction mixture was diluted with a saturated aqueous solution of NaHCO$_3$ (100 mL). The aqueous layer was extracted with DCM (3×100 mL) and the combined organic layers were washed with 1 M HCl (100 mL), water (100 mL) and brine (25 mL). The organic layer was dried (Na$_2$SO$_4$), filtered and concentrated in vacuo give the desired compound (14.0 g, quantitative) as a white solid: $^1$H NMR (400 MHz, CDCl$_3$) δ 8.09 (d, J=8.6 Hz, 2H), 7.47 (d, J=8.6 Hz, 2H), 3.93 (s, 3H), 3.87-3.71 (m, 4H), 3.69-3.52 (m, 2H), 3.50-3.25 (m, 2H) COOH peak not observed; LCMS-B: RT 3.35 min, m/z 250 [M+H]$^+$.

(b) 4-(Morpholine-4-carbonyl)benzoic acid (I7)

(i) A suspension of methyl 4-(morpholine-4-carbonyl)benzoate I6 (5.00 g, 20.1 mmol) and LiOH.H$_2$O (926 mg, 22.1 mmol) in THF (100 mL), MeOH (10 mL) and water (2 mL) was stirred at room temperature for 16 hours. The volatiles were concentrated under reduced pressure and the resulting gum suspended in a 0.5 M aqueous citric acid solution (100 mL). Et$_3$N (1 mL) was added and the water layer extracted with DCM (3×100 mL). The combined organic fractions were dried over MgSO$_4$ and the volatiles removed in vacuo to give the product as a white solid (3.55 g, 75%): $^1$H NMR (400 MHz, Chloroform-d) δ 8.17 (d, J=8.5, 2H), 7.53 (d, J=8.5, 2H), 3.95-3.58 (m, 6H), 3.44 (s, 2H); LCMS-B: RT 3.162 min; m/z 236.2 [M+H]$^+$.

(ii) Methyl 4-(morpholine-4-carbonyl)benzoate (I6) (6.95 g, 27.9 mmol) was dissolved in THF (100 mL) and a solution of lithium hydroxide monohydrate (1.65 g, 39.4 mmol) in water (50 mL) was added. The mixture was stirred at room temperature for 2 hours. The volatile solvents were removed in vacuo and the aqueous residue diluted with water (50 mL) and 10% w/v aqueous sodium hydrogen sulfate monohydrate (50 mL). The resulting slurry was filtered, the collected solid washed with water (20 mL) and dried under vacuum to give the desired compound (5.77 g, 88% yield) as a white powder. LCMS-B: RT 3.17 min; m/z 236.1 [M+H]$^+$, 258.2 [M+Na]; m/z 234.1 [M−H]$^-$ (iv) tert-Butyl (S)-3-((R)-2-amino-1-hydroxyethyl)-3,4-dihydroisoquinoline-2(1H)-carboxylate (I12)

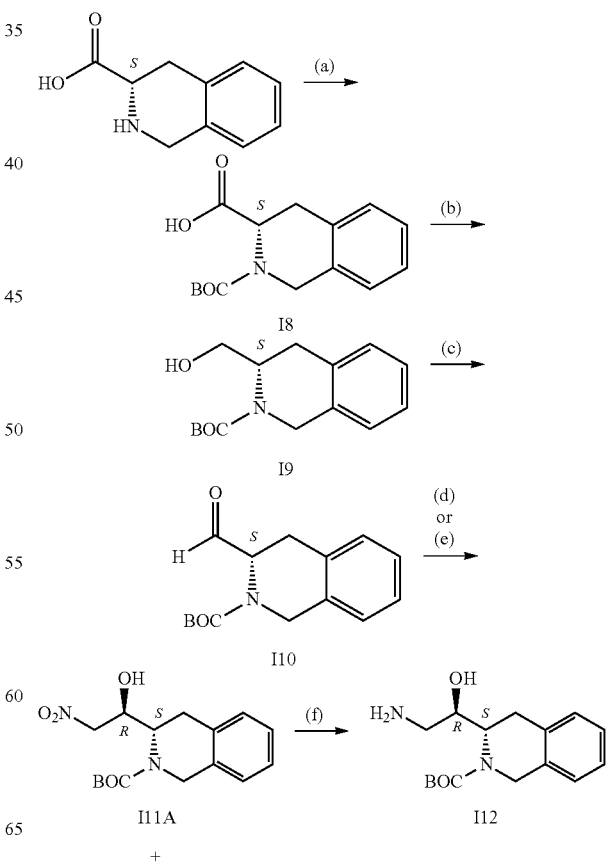

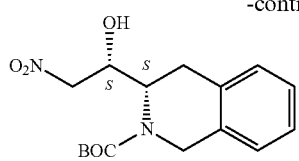

I11B minor isomer in method (d)

(a) (S)-2-(tert-Butoxycarbonyl)-1,2,3,4-tetrahydroisoquinoline-3-carboxylic acid (I8)

(S)-1,2,3,4-Tetrahydroisoquinoline-3-carboxylic acid (5.00 g, 28.2 mmol) was vigorously stirred in 1,4-dioxane (100 mL) and water (50 mL). Sodium bicarbonate (4.74 mg, 56.4 mmol) and Boc anhydride (6.77 g, 31.0 mmol) were added and the mixture was stirred vigorously at room temperature. After 17 hours the mixture was concentrated in vacuo and the residue dissolved in water (200 mL). A 30% w/v aqueous solution of sodium hydrogen sulfate monohydrate (30 mL) was added and the mixture extracted with chloroform (3×200 mL). The pooled organic extracts were washed with brine, dried over sodium sulfate and concentrated in vacuo to give the desired compound (7.50 g, 96% yield) as a thick syrup. LCMS-B: RT 3.64 min; m/z 178.1 [M-Boc+2H]$^+$; m/z 276.1 [M-H]$^-$ (b) tert-Butyl (S)-3-(hydroxymethyl)-3,4-dihydroisoquinoline-2(1H)-carboxylate (I9)

(S)-2-(tert-Butoxycarbonyl)-1,2,3,4-tetrahydroisoquinoline-3-carboxylic acid (I8) (7.50 g, 27.0 mmol) was dissolved in THF (150 mL) and CDI (8.77 g, 54.1 mmol) was added. The mixture was stirred for 30 minutes at room temperature then cooled to 0° C. A solution of sodium borohydride (1.16 g, 30.5 mmol) in water (15 mL) was added dropwise. After 40 minutes the mixture was quenched with acetone (25 mL) and concentrated in vacuo. The residue was partitioned between water (250 mL) and ethyl acetate (200 mL). The separated aqueous phase was extracted with ethyl acetate (2×250 mL), the combined organic extracts washed with 5% w/v aqueous NaHSO$_4$ (250 mL), brine (200 mL), dried over sodium sulfate and concentrated in vacuo. The residue was loaded in diethyl ether (50 mL) onto a plug of basic alumina and silica (50 mL each). The plug was eluted with diethyl ether (250 mL) and the eluate evaporated to give the desired compound (5.93 g, 83% yield) as a colourless syrup. $^1$H NMR (400 MHz, CDCl$_3$) δ 7.25-7.06 (m, 4H), 4.82-4.59 (m, 1H), 4.57-4.38 (m, 1H), 4.37-4.19 (m, 1H), 3.57-3.40 (m, overlaps with trace solvent), 3.03 (dd, J=16.1, 5.7 Hz, 1H), 2.80 (d, J=16.1 Hz, 1H), 1.50 (s, 9H). LCMS-B: RT 3.66 min; m/z 164.2 [M-Boc+2H]$^+$, 286.2 [M+Na]$^+$ (c) tert-Butyl (S)-3-formyl-3,4-dihydroisoquinoline-2(1H)-carboxylate (I10)

tert-Butyl (S)-3-(hydroxymethyl)-3,4-dihydroisoquinoline-2(1H)-carboxylate (I9) (1.50 g, 5.70 mmol), DCM (25 mL) and DMSO (5 mL) were cooled to 0° C. Triethylamine (2.38 mL, 17.1 mmol) was added, followed by pyridine-sulfur trioxide complex (2.72 g, 17.1 mmol). The mixture was stirred at 0° C. for 10 minutes then allowed to come to room temperature. After 2 hours, saturated sodium bicarbonate (75 mL) and water (75 mL) were added, and the mixture extracted with diethyl ether (3×150 mL). The pooled ether extracts were washed with 1:1 water: saturated aqueous NH$_4$Cl (200 mL), brine (200 mL), dried over sodium sulfate and concentrated in vacuo to give the desired compound as a colourless oil which was used without further purification.

(d) tert-Butyl (S)-3-((R)-1-hydroxy-2-nitroethyl)-3,4-dihydroisoquinoline-2(1H)-carboxylate (I11A) and tert-butyl (S)-3-((S)-1-hydroxy-2-nitroethyl)-3,4-dihydroisoquinoline-2(1H)-carboxylate (I11B)

A solution of tert-butyl (S)-3-formyl-3,4-dihydroisoquinoline-2(1H)-carboxylate (I10) (5.70 mmol @ 100% conversion) in i-propanol (50 mL) was cooled to 0° C. Nitromethane (1.22 mL, 22.8 mmol) and potassium fluoride (331 mg, 5.70 mmol) were added and the mixture stirred for 18 hours, allowing the temperature to come to room temperature as the ice bath thawed. The mixture was diluted with water (200 mL) and extracted with DCM (3×200 mL). The pooled DCM extracts were washed with brine, dried over sodium sulfate and concentrated in vacuo. Chromatography (40 g silica cartridge, 0-20% ethyl acetate/hexanes) gave two partly overlapping peaks, which were split into early (11A major, colourless syrup, 697 mg, 37% yield) and late (11B minor, colourless syrup, 170 mg, 9% yield) fractions. Overall: 867 mg, 47% yield.

Data for major isomer tert-butyl (S)-3-((R)-1-hydroxy-2-nitroethyl)-3,4-dihydroisoquinoline-2(1H)-carboxylate I11A:

$^1$H NMR (400 MHz, d$_4$-MeOD) δ 7.25-7.14 (m, 4H), 4.85-4.49 (m, 5H), 4.44 (dd, J=12.6, 9.3 Hz, 1H), 4.37-3.99 (m, overlaps with solvent), 3.19 (dd, J=15.9, 3.2 Hz, 1H), 2.92 (dd, J=15.8, 5.6 Hz, 1H), 1.51 (s, 9H). LCMS-B: RT 3.71 min; m/z 223.2 [M-Boc+2H]$^+$, 345.2 [M+Na]$^+$; m/z 321.2 [M-H]$^-$ Data for minor isomer tert-butyl (S)-3-((S)-1-hydroxy-2-nitroethyl)-3,4-dihydroisoquinoline-2(1H)-carboxylate I11B:

$^1$H NMR (400 MHz, d$_4$-MeOD) δ 7.25-7.11 (m, 4H), 4.75 (d, J=16.5 Hz, 1H), 4.68-4.48 (m, 4H), 4.42-4.23 (m, overlaps with residual nitromethane), 3.06 (dd, J=16.3, 6.1 Hz, 1H), 2.91 (d, J=16.1 Hz, 1H), 1.50 (s, 9H). LCMS-B: RT 3.70 min; m/z 223.2 [M-Boc+2H]$^+$, 345.2 [M+Na]*; m/z 321.2 [M-H]$^-$ (e) tert-Butyl (S)-3-((R)-1-hydroxy-2-nitroethyl)-3,4-dihydroisoquinoline-2(1H)-carboxylate (I11A)

Copper catalyst used:

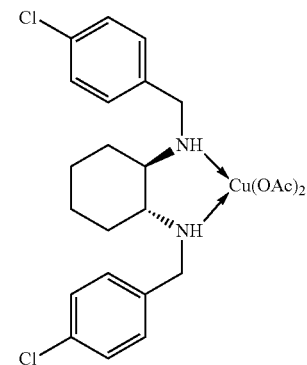

tert-Butyl (S)-3-formyl-3,4-dihydroisoquinoline-2(1H)-carboxylate (I10) (1.9 mmol @100% conversion), absolute ethanol (5 mL), nitromethane (1.02 mL, 19.0 mmol) and the copper catalyst (91 mg, 10 mol %) (see above FIGURE, prepared according to Tetrahedron: Asymmetry (2008) 2310-2315) were stirred at room temperature. After 90 hours the mixture was concentrated in vacuo, chromatography (40 g silica cartridge, 0-15% ethyl acetate/hexanes) gave the desired compound (352 mg, 58% yield over two steps). $^1$H NMR (400 MHz, d$_4$-MeOD) δ 7.25-7.13 (m, 4H), 4.85-4.68 (m, 1H), 4.65-4.49 (m, 1H), 4.49-4.39 (m, 1H), 4.36-3.96 (m, overlaps with trace solvent), 3.19 (dd, J=15.9, 3.2 Hz, 1H), 2.92 (dd, J=15.9, 5.6 Hz, 1H), 1.51 (s, 9H). LCMS-B: RT 3.25 min; m/z 321.1 [M−H]$^−$ (f) tert-Butyl (S)-3-((R)-2-amino-1-hydroxyethyl)-3,4-dihydroisoquinoline-2(1H)-carboxylate (I12)

tert-Butyl (S)-3-((R)-1-hydroxy-2-nitroethyl)-3,4-dihydroisoquinoline-2(1H)-carboxylate (I11A) (1.54 g, 4.78 mmol), absolute ethanol (75 mL) and 10% Pd/C (53% wetted with water, 1.5 g) were stirred under hydrogen (balloon). After 3 hours the mixture was filtered through celite, the celite was washed with absolute ethanol (100 mL) and the combined filtrates concentrated in vacuo to give the desired compound (1.34 g, 96% yield) as a pale grey-green syrup. LCMS-B: RT 3.27 min, m/z 293.2 [M+H]$^+$ Alternate Synthesis Method (a) (S)-2-(tert-Butoxycarbonyl)-1,2,3,4-tetrahydroisoquinoline-3-carboxylic acid (I8)

(S)-1,2,3,4-Tetrahydroisoquinoline-3-carboxylic acid (50.0 g, 282 mmol) was vigorously stirred in a mixture of 1,4-dioxane (1000 mL) and water (500 mL). Sodium bicarbonate (47.4 g, 564 mmol) and Boc anhydride (67.7 g, 310 mmol) were added and the reaction was stirred vigorously at room temperature for 6 days. The mixture was concentrated in vacuo and the residue dissolved in water (2000 mL). A 30% w/v aqueous solution of sodium hydrogen sulfate monohydrate (300 mL) was added and the mixture extracted with chloroform (3×1000 mL). The pooled organic extracts were washed with brine, dried over sodium sulfate and concentrated in vacuo to give the desired compound (90.0 g, quantitative) as a thick syrup. LCMS-B: RT 3.64 min; m/z 178.1 [M-Boc+2H]$^+$; m/z 276.1 [M−H]$^−$ (b) tert-Butyl (S)-3-(hydroxymethyl)-3,4-dihydroisoquinoline-2(1H)-carboxylate (I9)

(S)-2-(tert-Butoxycarbonyl)-1,2,3,4-tetrahydroisoquinoline-3-carboxylic acid (I8) (54.0 g, 195 mmol) was dissolved in THF (1000 mL) and CDI (63.2 g, 390 mmol) was added. The mixture was stirred for 2 hours at 30° C. then cooled to 0° C. A solution of sodium borohydride (14.7 g, 390 mmol) in water (120 mL) was added dropwise. After 3 hours the mixture was quenched with acetone (300 mL) and concentrated in vacuo. The residue was partitioned between water (1000 mL) and ethyl acetate (1000 mL). The separated aqueous phase was extracted with ethyl acetate (4×500 mL) and the combined organic extracts washed with 5% w/v aqueous NaHSO$_4$ (1000 mL), brine (500 mL), dried over sodium sulfate and concentrated in vacuo. The residue was purified by chromatography (5-20% ethyl acetate/petroleum ether) to give the desired compound (30.4 g, 59% yield) as a yellow syrup. $^1$H NMR (400 MHz, CDCl$_3$) δ 7.25-7.06 (m, 4H), 4.82-4.59 (m, 1H), 4.57-4.38 (m, 1H), 4.37-4.19 (m, 1H), 3.57-3.40 (m, overlaps with trace solvent), 3.03 (dd, J=16.1, 5.7 Hz, 1H), 2.80 (d, J=16.1 Hz, 1H), 1.50 (s, 9H). LCMS-B: RT 3.66 min; m/z 164.2 [M−Boc+2H]$^+$, 286.2 [M+Na]$^+$ (c) tert-Butyl (S)-3-formyl-3,4-dihydroisoquinoline-2(1H)-carboxylate (I10)

tert-Butyl (S)-3-(hydroxymethyl)-3,4-dihydroisoquinoline-2(1H)-carboxylate (I9) (16 g, 0.06 mol), DCM (250 mL) and DMSO (75 mL) were cooled to 0° C. Triethylamine (25.1 mL, 0.18 mol) was added, followed by pyridine-sulfur trioxide complex (28.6 g, 0.18 mol). The mixture was stirred at 0° C. for 30 minutes then allowed to come to room temperature and stirred at room temperature overnight. Saturated sodium bicarbonate (200 mL) and water (200 mL) were added, and the mixture extracted with diethyl ether (3×300 mL). The pooled ether extracts were washed with 1:1 water: saturated aqueous NH$_4$Cl (200 mL), dried over sodium sulfate and concentrated in vacuo to give the desired compound (16.0 g) as an orange oil which was used without further purification.

(e) tert-Butyl (S)-3-((R)-1-hydroxy-2-nitroethyl)-3,4-dihydroisoquinoline-2(1H)-carboxylate (I11A)

To a solution of tert-butyl (S)-3-formyl-3,4-dihydroisoquinoline-2(1H)-carboxylate (I10) (0.06 mol @100% conversion) in absolute ethanol (50 mL) was added a solution of the copper catalyst (6.8 g, 20 mol %) (see above FIGURE, prepared according to Tetrahedron: Asymmetry (2008) 2310-2315) in absolute ethanol (10 mL). The mixture was cooled to 0° C. and nitromethane (36.0 g, 0.6 mol) was added. The reaction was stirred at 0° C. for 3 days, the mixture was concentrated in vacuo and purified by chromatography (5% ethyl acetate/petroleum ether) to give the desired compound (7.5 g, 39% yield over two steps). $^1$H NMR (400 MHz, d$_4$-MeOD) δ 7.25-7.13 (m, 4H), 4.85-4.68 (m, 1H), 4.65-4.49 (m, 1H), 4.49-4.39 (m, 1H), 4.36-3.96 (m, overlaps with trace solvent), 3.19 (dd, J=15.9, 3.2 Hz, 1H), 2.92 (dd, J=15.9, 5.6 Hz, 1H), 1.51 (s, 9H). LCMS-B: RT 3.25 min; m/z 321.1 [M−H]$^−$ (f) tert-Butyl (S)-3-((R)-2-amino-1-hydroxyethyl)-3,4-dihydroisoquinoline-2(1H)-carboxylate (I12)

To a solution of tert-butyl (S)-3-((R)-1-hydroxy-2-nitroethyl)-3,4-dihydroisoquinoline-2(1H)-carboxylate (I11A) (7.5 g, 23.3 mmol) in absolute ethanol (100 mL) was added 10% Pd/C (7.5 g) and the reaction was stirred under an atmosphere of hydrogen. After 3 hours, the mixture was filtered through Celite, the Celite was washed with absolute ethanol (200 mL) and the combined filtrates concentrated in vacuo to give the desired compound (5.3 g, 78% yield) as a pale grey solid. LCMS-B: RT 3.27 min, m/z 293.2 [M+H]$^+$ (v) 2-Methylbenzoic acid (I13)

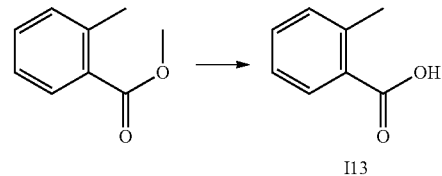

I13

(a) 2-Methylbenzoic acid (I13)

Methyl 2-methylbenzoate (0.19 mL, 1.33 mmol) was dissolved in THF (4 mL) and water (0.6 mL) and lithium hydroxide monohydrate (0.34 g, 7.99 mmol) was added. The reaction was then stirred at room temperature for 24 hours. The volatiles were removed in vacuo and the resulting residue diluted with EtOAc (50 mL) followed by 2 M aqueous NaOH (50 mL). The layers were separated and the aqueous layer was acidified with 1 M aqueous HCl (checked by pH paper), then extracted with EtOAc (2×70 mL), washed with brine, dried ($Na_2SO_4$), filtered and concentrated in vacuo to give the desired compound (0.010 g, 6% yield) as an off-white solid. $^1$H NMR (400 MHz, $CDCl_3$) δ 8.05 (dd, J=8.1, 1.5 Hz, 1H), 7.46 (td, J=7.5, 1.5 Hz, 1H), 7.32-7.26 (m, 2H), 2.66 (s, 3H), OH not observed. LCMS-A: RT 5.627 min; mass ion not detected

(vi) 3-(Pyridazin-4-yl)benzoic acid (I15)

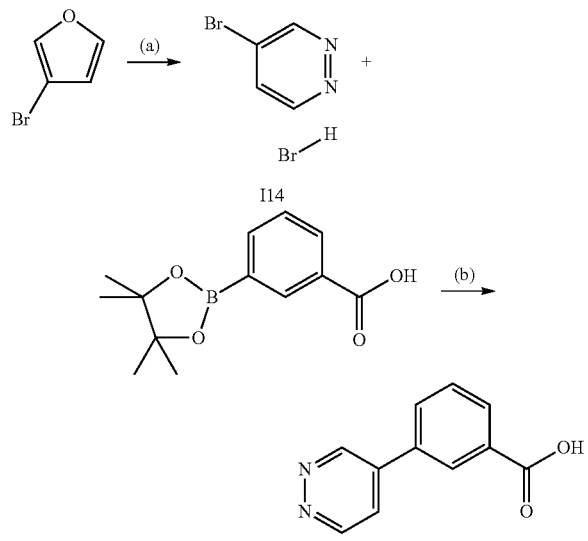

(a) 4-Bromopyridazine hydrobromide (I14)

Potassium acetate (7.4 g, 75 mmol) and 3-bromofuran (4.0 g, 27 mmol) were stirred in acetic acid (20 mL) and a solution of bromine (1.4 mL, 27 mmol) in acetic acid (10 mL) was added dropwise. After one hour the mixture was filtered, the solids washed with acetic acid (10 mL) and the filtrate concentrated. The mixture was dissolved in ethanol (40 mL) and hydrazine hydrate (4 mL) added. After 3 hours the mixture was added to ethyl acetate (100 mL) and brine (100 mL). The aqueous phase was extracted with further ethyl acetate (100 mL), and the aqueous phases discarded. The pooled ethyl acetate phases were washed with brine (100 mL), and the brine extracted with ethyl acetate (100 mL). The pooled ethyl acetate phases were dried over sodium sulfate and evaporated. The residue was diluted with 1,4-dioxane (20 mL) and treated with 33% HBr in acetic acid (4 mL) dropwise. The dark suspension was filtered, the collected solids washed with 1,4-dioxane (2×20 mL), acetone (20 mL) and air dried to give the desired compound (4.41 g, 68% yield) as a brown solid. $^1$H NMR (400 MHz, $d_6$-DMSO) δ 9.51 (dd, J=2.5, 1.1 Hz, 1H), 9.15 (dd, J=5.7, 1.0 Hz, 1H), 8.16 (dd, J=5.6, 2.5 Hz, 1H). LCMS-B: RT 2.80 min; m/z 159.0 $[M+H]^+$ for $^{79}$Br (free base)

(b) 3-(Pyridazin-4-yl)benzoic acid (I15)

3-(4,4,5,5-Tetramethyl-1,3,2-dioxaborolan-2-yl)benzoic acid (0.50 g, 2.0 mmol), 4-bromopyridazine hydrobromide (I14) (0.58 g, 2.4 mmol), $PdCl_2$(dppf) DCM complex (83 mg, 5 mol %) and 1,4-dioxane (10 mL) were loaded into a microwave tube. A solution of potassium carbonate (0.83 g, 6.0 mmol) in water (5 mL) was added, the mixture degassed with a stream of nitrogen bubbles then heated in the microwave (120° C./30 minutes). The mixture was cooled, and the volatile solvents removed in vacuo. The aqueous residue was diluted with water to 75 mL, and shaken with DCM (75 mL). The mixture was filtered through celite, the aqueous layer separated and washed with further DCM (75 mL). The DCM extracts were discarded, the aqueous phase was diluted with water (25 mL) and treated with 5% w/v citric acid until pH 3 to pH paper. The resulting precipitate was collected by filtration, washed with water and dried under vacuum to give the desired compound (312 mg, 78% yield) as a pale brown solid. $^1$H NMR (400 MHz, $d_6$-DMSO) δ 9.70-9.65 (m, 1H), 9.33-9.28 (m, 1H), 8.38 (s, 1H), 8.17 (d, J=7.8 Hz, 1H), 8.12-8.05 (m, 2H), 7.71 (t, J=7.8 Hz, 1H). Acyl proton not observed. LCMS-B: RT 3.15 min, m/z 201.1 $[M+H]^+$; m/z 199.1 $[M-H]^-$

(vii) 4-(5-Morpholino-1,3,4-oxadiazol-2-yl)benzoic acid (I17)

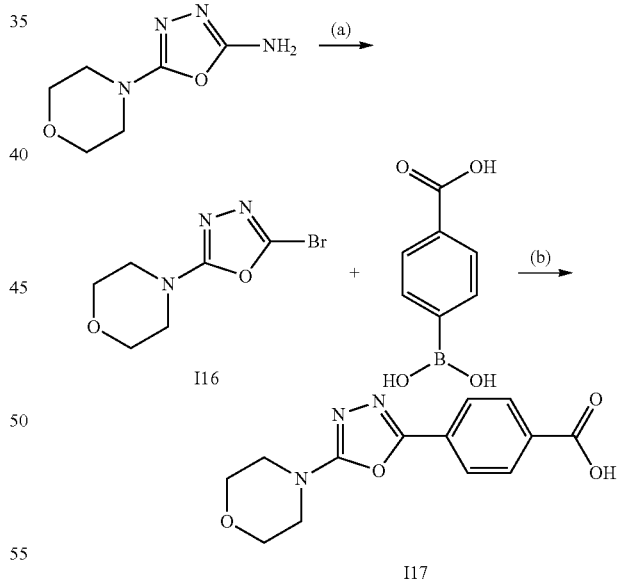

(a) 4-(5-Bromo-1,3,4-oxadiazol-2-yl)morpholine (I16)

5-Morpholino-1,3,4-oxadiazol-2-amine (250 mg, 1.47 mmol) and copper(II) bromide (492 mg, 2.20 mmol) were stirred in acetonitrile (15 mL) under nitrogen for 5 minutes. tert-Butyl nitrite (0.349 mL, 2.94 mmol) was added and the mixture stirred at room temperature for 17 hours. The mixture was diluted with 0.5M HCl (25 mL) and ethyl acetate (25 mL). The organic phase was separated, and the aqueous phase extracted with further ethyl acetate (2×25 mL). The combined organic phases were washed with brine (30 mL), dried over sodium sulfate and evaporated. Chromatography (12 g silica cartridge, 0-60% ethyl acetate/hexanes) gave the desired compound (104 mg, 30% yield) as a yellow solid. $^1$H NMR (400 MHz, CDCl$_3$) δ 3.82-3.77 (m, 4H), 3.52-3.48 (m, 4H). LCMS-B: RT 3.22 min; m/z 236.1 [M+H]$^+$ for $^{81}$Br (b) 4-(5-Morpholino-1,3,4-oxadiazol-2-yl)benzoic acid (I17)

4-(5-Bromo-1,3,4-oxadiazol-2-yl)morpholine (I16) (102 mg, 0.436 mmol), 4-boronobenzoic acid (108 mg, 0.654 mmol), PdCl$_2$(dppf) DCM complex (18 mg, 5 mol %), and 1,4-dioxane (3 mL) were degassed with a stream of nitrogen bubbles. A 1.0M aqueous solution of cesium carbonate (1.5 mL, 1.5 mmol) was added, the mixture again degassed with a stream of nitrogen bubbles, then heated in a microwave (120° C./30 minutes). The mixture was diluted with water (20 mL) and diethyl ether (20 mL), filtered through celite, the organic phase was discarded and the aqueous phase was concentrated in vacuo. The residue was dissolved in water (10 mL) and the pH adjusted to 1 with 6M HCl. The precipitate was collected by filtration, the supernatant discarded, the solid resuspended in water (5 mL) and again collected by filtration. The collected solid was repeatedly suspended in absolute ethanol (20 mL) and the solvents removed in vacuo (three times) to give the desired compound (115 mg, 96% yield) as a brown solid of approximately 80% purity. $^1$H NMR (400 MHz, d$_6$-DMSO) δ 8.10-8.05 (m, 2H), 8.02-7.97 (m, 2H), 3.76-3.71 (m, 4H), 3.53 (m, overlaps with solvent). LCMS-B: RT 3.25 min; m/z 276.2 [M+H]$^+$; m/z 274.1 [M−H]$^-$ (viii) 2-Fluoro-4-(morpholine-4-carbonyl)benzoic acid (I20)

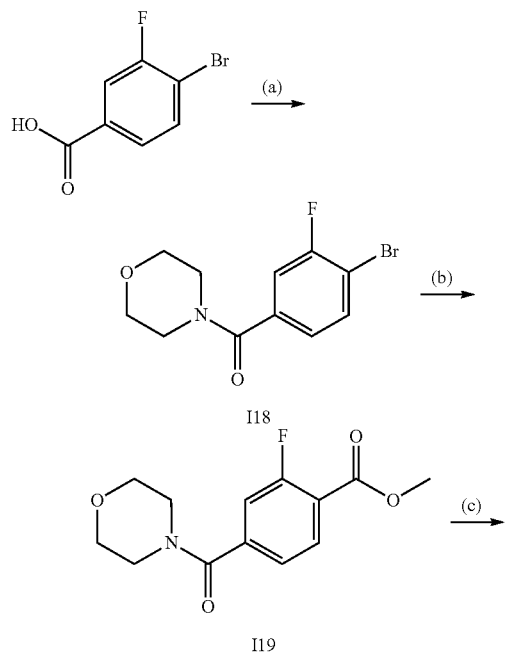

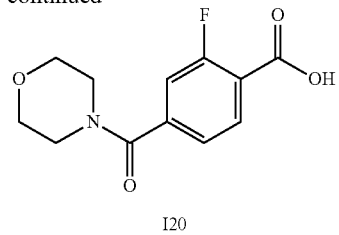

(a) (4-Bromo-3-fluorophenyl)(morpholino)methanone (I18)

4-Bromo-3-fluorobenzoic acid (2.19 g, 10.0 mmol), DCM (100 mL), morpholine (2.59 mL, 30.0 mmol), DMAP (122 mg, 10 mol %) and EDCl.HCl (2.876 g, 15.0 mmol) were stirred at room temperature. After 17 hours the mixture was added to 2% w/v sodium hydroxide (100 mL). The separated aqueous phase was extracted with DCM (2×50 mL), the pooled DCM extracts washed with 1 M HCl (75 mL), brine (50 mL), dried over sodium sulfate and evaporated. Chromatography (40 g silica cartridge, 0-60% ethyl acetate/hexanes) gave the desired compound (2.63 g, 91% yield) as a colourless syrup. $^1$H NMR (400 MHz, CDCl$_3$) δ 7.61 (dd, J=8.1, 6.8 Hz, 1H), 7.19 (dd, J=8.5, 1.9 Hz, 1H), 7.08 (ddd, J=8.1, 1.9, 0.7 Hz, 1H), 3.70 (br s, 6H), 3.45 (br s, 2H). LCMS-B: RT 3.49 min; m/z 290.0, 288.1 [M+H]$^+$ (b) Methyl 2-fluoro-4-(morpholine-4-carbonyl)benzoate (I19)

(4-Bromo-3-fluorophenyl)(morpholino)methanone (I18) (2.62 g, 9.09 mmol), dry methanol (20 mL), PdCl$_2$(dppf) DCM complex (376 mg, 5 mol %) and triethylamine (2.54 mL, 18.2 mmol) were loaded into a Schlenk tube and flushed with nitrogen. The tube was flushed with carbon monoxide and the mixture brought to reflux under carbon monoxide (balloon). After 18 hours the mixture was cooled to room temperature, filtered through celite and the celite washed with methanol (40 mL). The combined filtrates were evaporated, chromatography (40 g silica cartridge, 20-60% ethyl acetate/hexanes) gave the desired compound (2.25 g, 93% yield) as a pale orange solid. $^1$H NMR (400 MHz, CDCl$_3$) δ 7.99 (t, J=7.3 Hz, 1H), 7.25-7.17 (m, 2H), 3.94 (s, 3H), 3.78 (br s, 4H), 3.63 (br s, 2H), 3.40 (br s, 2H). LCMS-A: RT 5.30 min; m/z 268.1 [M+H]$^+$ (c) 2-Fluoro-4-(morpholine-4-carbonyl)benzoic acid (I20)

Methyl 2-fluoro-4-(morpholine-4-carbonyl)benzoate (I19) (1.00 g, 3.74 mmol) was dissolved in THF (20 mL) and a solution of lithium hydroxide monohydrate (188 mg, 4.49 mmol) in water (10 mL) was added and the mixture was stirred vigorously at room temperature. After 2 hours, the volatile solvents were removed in vacuo and the aqueous residue cooled to 4° C. Cold 3.0 M aqueous HCl (5 mL) was added, the resulting slurry diluted with water (5 mL), filtered, the collected solids washed with water (5 mL) and air dried to give the desired compound (817 mg, 86% yield) as a white solid. $^1$H NMR (400 MHz, d$_4$-MeOD) δ 8.05-7.99 (m, 1H), 7.32 (s, 1H), 7.30 (dd, J=3.7, 1.4 Hz, 1H), 3.76 (br s, 4H), 3.63 (br s, 2H), 3.42 (br s, 2H). LCMS-B: RT 3.20 min; m/z 254.2 [M+H]$^+$; 276.2 [M+Na]$^+$

(ix) 3-(Pyrimidin-5-yl)benzoic acid (I21)

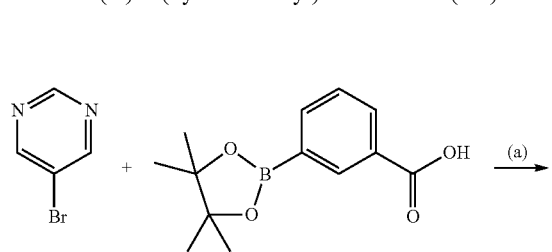

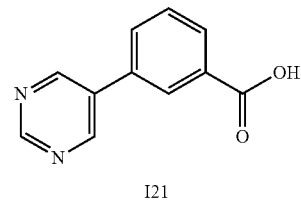

I21

(a) 3-(Pyrimidin-5-yl)benzoic acid (I21)

3-(4,4,5,5-Tetramethyl-1,3,2-dioxaborolan-2-yl)benzoic acid (496 mg, 2.00 mmol), 5-bromopyrimidine (382 mg, 2.40 mmol), PdCl$_2$(dppf) DCM complex (82 mg, 5 mol %) were stirred in 1,4-dioxane (10 mL) under nitrogen and a solution of potassium carbonate (829 mg, 6.00 mmol) in water (5 mL) was added. The mixture was degassed with a stream of nitrogen bubbles and heated in the microwave (120° C./30 minutes). The volatiles were removed in vacuo and the aqueous residue diluted with water (50 mL) and DCM (50 mL). The mixture was filtered through celite, the DCM phase discarded and the aqueous phase extracted with further DCM (2×50 mL). The DCM extracts were again discarded, the aqueous phase was adjusted to pH 3 with 30% w/v aqueous NaHSO$_4$ and the precipitate collected by filtration and dried under vacuum (40° C./3 hours over P$_2$O$_5$) to give the desired compound (137 mg, 34% yield) as a grey solid. LCMS-B: RT 3.25 min; m/z 201.1 [M+H]$^+$

(x) Lithium 4-((1-acetylpiperidin-4-yl)(methyl)carbamoyl)benzoate (I26)

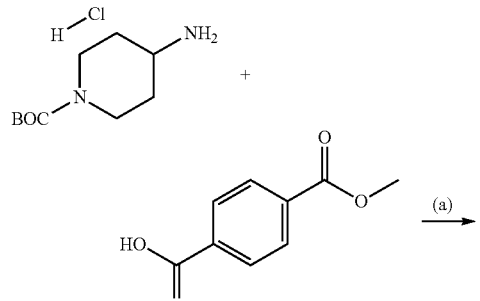

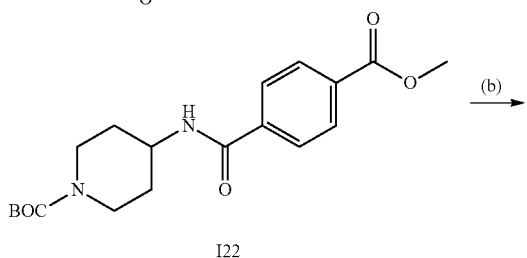

I22

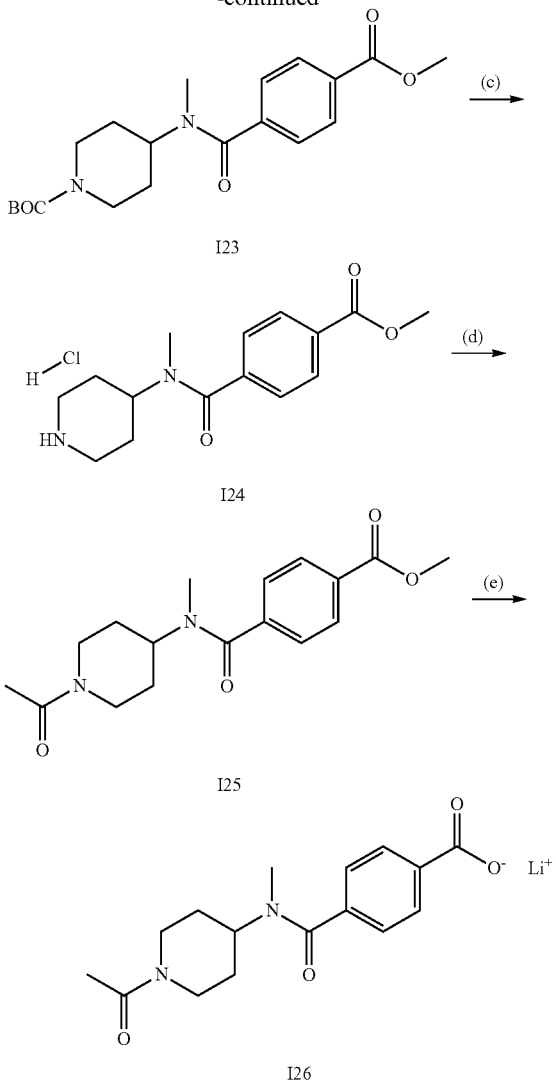

(a) tert-Butyl 4-(4-(methoxycarbonyl)benzamido)piperidine-1-carboxylate (I22)

4-(Methoxycarbonyl)benzoic acid (1.00 g, 5.55 mmol), DCM (25 mL), DMAP (34 mg, 5 mol %), tert-butyl 4-aminopiperidine-1-carboxylate hydrochloride salt (1.45 g, 6.11 mmol) and EDCl.HCl (1.28 g, 6.66 mmol) were stirred at room temperature. After 18 hours the mixture was diluted with 10% w/v NaHSO$_4$ (50 mL) and DCM (50 mL). The aqueous phase was extracted with further DCM (2×50 mL), the pooled DCM extracts were washed with 1:1 saturated aqueous NaHCO$_3$: water (50 mL), dried over sodium sulfate and concentrated in vacuo to give the desired compound (1.82 g, 91% yield) as a white solid. $^1$H NMR (400 MHz, CDCl$_3$) δ 8.10-8.06 (m, 2H), 7.83-7.78 (m, 2H), 6.11 (d, J=7.9 Hz, 1H), 4.19-4.04 (m, 3H), 3.94 (s, 3H), 2.98-2.81 (m, 2H), 2.07-1.97 (m, 2H), 1.51-1.35 (m, 11H). LCMS-B: RT 3.63 min; m/z 307.1 [M-$^t$Bu+2H]$^+$, 385.2 [M+Na]$^+$, 263.1 [M-Boc+2H]$^+$, m/z 361.2 [M−H]$^-$ (b) tert-Butyl 4-(4-(methoxycarbonyl)-N-methylbenzamido)piperidine-1-carboxylate (I23)

tert-Butyl 4-(4-(methoxycarbonyl)benzamido)piperidine-1-carboxylate (I22) (1.00 g, 2.76 mmol) was dissolved in DMF (10 mL) and cooled to 0° C. A 60% dispersion (in mineral oil) of sodium hydride (331 mg, 8.28 mmol) and methyl iodide (0.344 mL, 5.52 mmol) were added and the mixture stirred at room temperature. After one hour saturated ammonium chloride (10 mL) was added and the mixture added to water (200 mL). The suspension was extracted with diethyl ether (3×100 mL), the pooled ether phases washed with brine (100 mL), dried over sodium sulfate and concentrated in vacuo. Chromatography (24 g silica cartridge, 0-60% ethyl acetate/hexanes) gave the desired compound (602 mg, 58% yield) as a white solid. LCMS-B: RT 3.67 min; m/z 321.1 [M-$^t$Bu+2H]$^+$, 277.1 [M-Boc+2H]$^+$, 399.1 [M+Na]$^+$ (c) Methyl 4-(methyl(piperidin-4-yl)carbamoyl) benzoate hydrochloride salt (I24)

tert-Butyl 4-(4-(methoxycarbonyl)-N-methylbenzamido) piperidine-1-carboxylate (I23) (600 mg, 1.59 mmol), 1,4-dioxane (6 mL) and 4.0M HCl in 1,4-dioxane (6 mL) were stirred at room temperature. After 5 hours the resulting precipitate was filtered, washed with further 1,4-dioxane (2×5 mL) and air dried to give the desired compound (444 mg, 89% yield) as a white solid. LCMS-B: RT 3.09 min; m/z 277.1 [M+H]$^+$ (free base)

(d) Methyl 4-((1-acetylpiperidin-4-yl)(methyl)carbamoyl)benzoate (I25)

Methyl 4-(methyl(piperidin-4-yl)carbamoyl)benzoate hydrochloride salt (I24) (200 mg, 0.639 mmol), DCM (5 mL), triethylamine (0.267 mL, 1.92 mmol), DMAP (8 mg, 10 mol %) and acetyl chloride (0.068 mL, 0.96 mmol) were stirred at room temperature. After 17 hours the mixture was diluted with water (5 mL) and DCM (5 mL). The mixture was passed through a phase separation cartridge and the DCM phase concentrated in vacuo. Chromatography (12 g silica cartridge, 0-100% ethyl acetate/hexanes) gave the desired compound (176 mg, 87% yield) as a pale yellow solid. LCMS-B: RT 3.27 min; m/z 319.1 [M+H]$^+$ (e) Lithium 4-((1-acetylpiperidin-4-yl)(methyl)carbamoyl)benzoate (I26)

Methyl 4-((1-acetylpiperidin-4-yl)(methyl)carbamoyl) benzoate (I25) (170 mg, 0.53 mmol) was dissolved in THF (1 mL) and methanol (0.5 mL). A solution of lithium hydroxide monohydrate (25 mg, 0.59 mmol) in water (0.5 mL) was added and the mixture stirred at room temperature. After 3 hours the mixture was concentrated in vacuo, the residue was dried under vacuum over P$_2$O$_5$ to give the desired compound (153 mg, 92% yield) as an off-white solid. LCMS-B: 3.13 min; m/z 305.1 [M-Li+2H]$^+$, m/z 303.1 [M-Li]$^-$ (xi) Lithium 4-((1-(methoxycarbonyl)piperidin-4-yl) (methyl)carbamoyl)benzoate (I28)

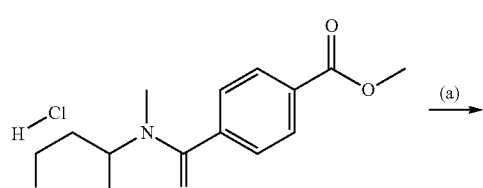

I24

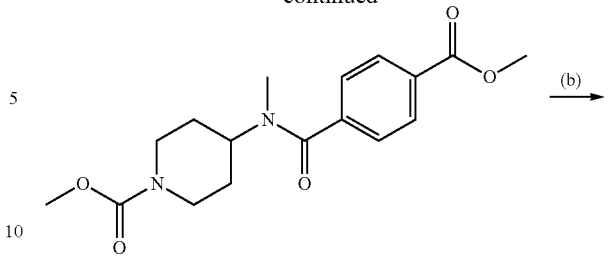

I27

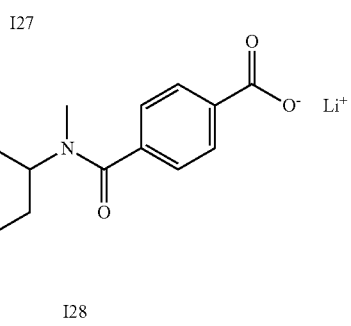

I28

(a) Methyl 4-(4-(methoxycarbonyl)-N-methylbenzamido)piperidine-1-carboxylate (I27)

Methyl 4-(methyl(piperidin-4-yl)carbamoyl)benzoate hydrochloride salt (I24) (200 mg, 0.639 mmol), DCM (5 mL), triethylamine (0.267 mL, 1.92 mmol), DMAP (8 mg, 10 mol %) and methyl chloroformate (0.074 mL, 0.96 mmol) were stirred at room temperature. After 17 hours the mixture was diluted with water (5 mL) and DCM (5 mL). The mixture was passed through a phase separation cartridge and the DCM phase concentrated in vacuo. Chromatography (12 g silica cartridge, 0-100% ethyl acetate/hexanes) gave the desired compound (135 mg, 63% yield) as a white solid. LCMS-B: RT 3.40 min; m/z 335.1 [M+H]$^+$ (b) Lithium 4-((1-(methoxycarbonyl)piperidin-4-yl) (methyl)carbamoyl)benzoate (I28)

Methyl 4-(4-(methoxycarbonyl)-N-methylbenzamido)piperidine-1-carboxylate (I27) was dissolved in THF (1 mL) and methanol (0.5 mL). A solution of lithium hydroxide monohydrate (18 mg, 0.43 mmol) in water (0.5 mL) was added and the mixture stirred at room temperature. After 3 hours the mixture was concentrated in vacuo, the residue was dried under vacuum over P$_2$O$_5$ to give the desired compound (127 mg, quant yield) as an off-white solid. LCMS-B: RT 3.26 min; m/z 321.3 [M-Li+2H]$^+$; m/z 319.1 [M-Li]$^-$ (xii) 2-((Tetrahydro-2H-pyran-4-yl)oxy)isonicotinic acid (I29)

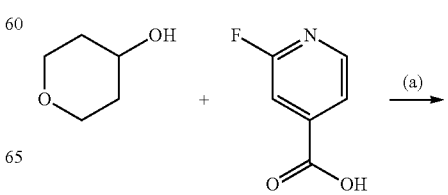

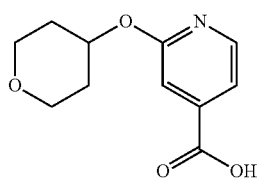

I29

(a) 2-((Tetrahydro-2H-pyran-4-yl)oxy)isonicotinic acid (I29)

A solution of tetrahydro-2H-pyran-4-ol (0.462 g, 4.52 mmol, 2 equiv) in anhydrous DMF (5 mL) was added to a stirring suspension of sodium hydride (60% dispersion in oil, 0.362 g, 9.04 mmol, 4 equiv) in anhydrous DMF (5 mL) under an atmosphere of nitrogen. The mixture was stirred at room temperature for 10 minutes before a solution of 2-fluoroisonicotinic acid (0.319 g, 2.26 mmol, 1 equiv) in DMF (5 mL) was added. The mixture was stirred for a further 16 hours at room temperature. $H_2O$ (~20 mL) was carefully added and the pH of the aqueous mixture was adjusted to ~2 with aqueous HCl (~2 M). The aqueous was extracted with EtOAc (3×30 mL), the organics were combined, washed with brine, dried ($Na_2SO_4$) and the solvent removed in vacuo. The resultant residue was purified by column chromatography (Biotage Isolera, 40 g $SiO_2$ cartridge, 0-100% EtOAc in petroleum benzine 40-60° C.) to give the desired compound (383 mg, 76% yield) as a white solid. $^1H$ NMR (400 MHz, $d_6$-DMSO) δ 8.31 (dd, J=5.2, 0.8 Hz, 1H), 7.36 (dd, J=5.2, 1.4 Hz, 1H), 7.15 (dd, J=1.3, 0.7 Hz, 1H), 5.21 (tt, J=8.7, 4.1 Hz, 1H), 3.86 (dt, J=11.3, 4.3 Hz, 2H), 3.58-3.45 (m, 2H), 2.06-1.93 (m, 2H), 1.74-1.55 (m, 2H), OH not observed. LCMS-B: RT 3.36 min, m/z 224 [M+H]⁻.

(xiii) 2-((1-(Methoxycarbonyl)piperidin-4-yl)oxy)isonicotinic acid (I32)

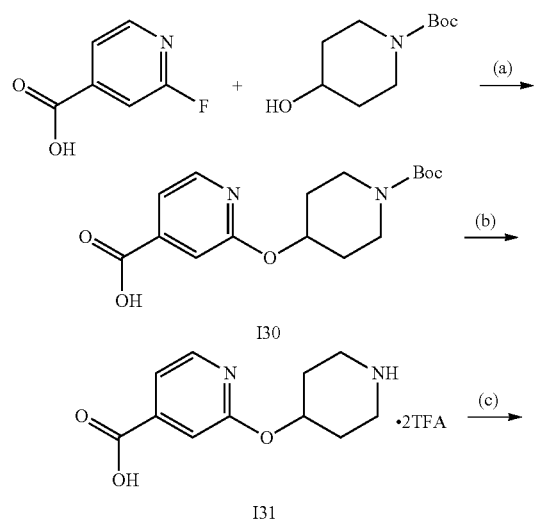

(a) 2-((1-(tert-Butoxycarbonyl)piperidin-4-yl)oxy)isonicotinic acid (I30)

A solution of tert-butyl 4-hydroxypiperidine-1-carboxylate (0.500 g, 2.48 mmol) in anhydrous DMF (5 mL) was added to a stirring suspension of sodium hydride (60% dispersion in mineral oil, 0.238 g, 5.95 mmol) in anhydrous DMF (5 mL) under an atmosphere of nitrogen. The mixture was stirred at room temperature for 10 minutes before a solution of 2-fluoroisonicotinic acid (0.319 g, 2.26 mmol) in DMF (5 mL) was added. The mixture was stirred for a further 16 hours at room temperature and 4 hours at 60° C. After returning to room temperature, water (~20 mL) was carefully added and the pH of the aqueous mixture was adjusted to ~2 with aqueous HCl (~2 M). The aqueous was extracted with EtOAc (3×30 mL), the organics were combined, washed with brine, dried ($MgSO_4$) and the solvent removed in vacuo. The resultant residue was purified by column chromatography (Biotage Isolera, 40 g $SiO_2$ cartridge, 0-100% EtOAc in petroleum benzine 40-60° C.) to give a white solid. Analysis by $^1H$ NMR showed an approximate 1:1 mixture of the desired product and the isonicotinic acid starting material. This material was reacted with another equivalent of the Boc-protected hydroxypiperidine anion: A solution of tert-butyl 4-hydroxypiperidine-1-carboxylate (0.500 g, 2.48 mmol) in anhydrous DMF (5 mL) was added to a stirring suspension of sodium hydride (60% dispersion in mineral oil, 0.238 g, 5.95 mmol) in anhydrous DMF (5 mL) under an atmosphere of nitrogen. The mixture was stirred at room temperature for 10 minutes before a solution of the 1:1 product/starting material mixture in DMF (5 mL) was added and stirring was continued for 16 hours. Water (~20 mL) was carefully added and the pH of the aqueous mixture was adjusted to ~2 with aqueous HCl (~2 M). The aqueous was extracted with DCM (3×30 mL), the organics were combined, dried ($MgSO_4$) and the solvent removed in vacuo. The resultant residue was purified by column chromatography (Biotage Isolera, 40 g $SiO_2$ cartridge, 0-100% EtOAc in petroleum benzine 40-60° C.) to give the desired compound (0.419 g, 58% yield) as a white solid. $^1H$ NMR (400 MHz, $d_6$-DMSO) δ 8.34-8.27 (m, 1H), 7.39-7.34 (m, 1H), 7.17-7.13 (m, 1H), 5.27-5.15 (m, 1H), 3.74-3.62 (m, 2H), 3.23-3.11 (m, 2H), 2.00-1.88 (m, 2H), 1.63-1.49 (m, 2H), 1.40 (s, 9H). LCMS-B: RT 3.65 min; m/z 321.2 [M−H]⁻

(b) 2-(Piperidin-4-yloxy)isonicotinic acid bis(2,2,2-trifluoroacetic acid) salt (I31)

To a solution of 2-((1-(tert-butoxycarbonyl)piperidin-4-yl)oxy)isonicotinic acid I30 (141 mg, 0.439 mmol, 1 equiv) in DCM (10 mL) was added TFA (0.5 mL, 6.5 mmol, 15 equiv). The reaction was stirred at room temperature for 16 hours and then dried in vacuo to give a colourless oil. The residue was taken up in diethyl ether:methanol (10 mL, 1:1)

and dried in vacuo to give the desired compound (196 mg, quantitative yield) as a white solid. LCMS-B: RT 1.74 min, m/z 223 [M+H]+ (free base)

(c) 2-((1-(Methoxycarbonyl)piperidin-4-yl)oxy) isonicotinic acid (I32)

Methylchloroformate (68 μL, 0.87 mmol, 2 equiv) was added drop-wise to a mixture of 2-(piperidin-4-yloxy)isonicotinic acid.bis(2,2,2-trifluoroacetic acid) salt I31 (196 mg, 0.437 mmol, 1 equiv) and sodium hydroxide (73 mg, 1.8 mmol) in water (10 mL). The reaction was stirred at ambient temperature overnight. The aqueous phase was separated and adjusted to pH 1 with a 1M aqueous solution of HCl. The aqueous phase was extracted with EtOAc (3×20 mL), and the combined organic layers were dried over $Na_2SO_4$, filtered, and the filtrate concentrated in vacuo. The resultant oil was purified by column chromatography (12 g $SiO_2$ cartridge, 0-100% EtOAc in petroleum benzine 40-60° C.) to give the desired compound (103 mg, 84% yield) as a glassy solid. $^1$H NMR (400 MHz, $CDCl_3$) δ 8.29 (dd, J=5.3, 0.8 Hz, 1H), 7.45 (dd, J=5.3, 1.4 Hz, 1H), 7.36 (dd, J=1.4, 0.8 Hz, 1H), 6.98 (br s, 1H), 5.27 (tt, J=7.4, 3.6 Hz, 1H), 3.86-3.75 (m, 2H), 3.73 (s, 3H), 3.49-3.34 (m, 2H), 2.06-1.95 (m, 2H), 1.86-1.70 (m, 2H)

(xiv) Lithium 5-(morpholine-4-carbonyl)picolinate (I34)

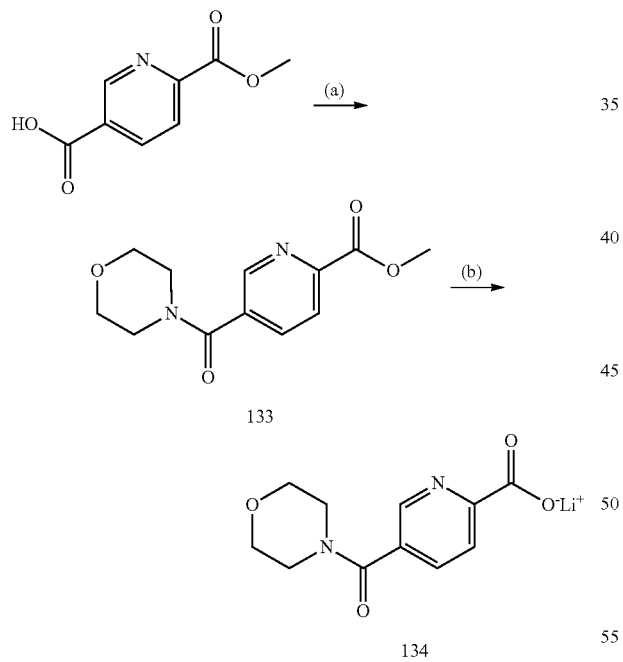

(a) Methyl 5-(morpholine-4-carbonyl)picolinate (I33)

6-(Methoxycarbonyl)nicotinic acid (1.00 g, 5.52 mmol), DCM (30 mL), DMAP (67 mg, 10 mol %), morpholine (1.43 mL, 16.6 mmol) and EDCl.HCl (1.59 g, 8.28 mmol) were stirred together at room temperature. After 18 hours the mixture was diluted with water, the organic phase separated and the aqueous phase extracted with DCM (2×30 mL). The pooled organic extracts were washed with brine and concentrated in vacuo. Chromatography (40 g silica cartridge, 0-100% ethyl acetate/hexanes) gave the desired compound (1.108 g, 80% yield) as a colourless oil that became solid on standing. LCMS-B: RT 3.12 min; m/z 251.2 [M+H]+, (b) Lithium 5-(morpholine-4-carbonyl)picolinate (I34)

Methyl 5-(morpholine-4-carbonyl)picolinate (I33) (1.11 g, 4.43 mmol) was dissolved in THF (10 mL) and a solution of lithium hydroxide monohydrate (204 mg, 4.87 mmol) in water (5 mL) was added. After 2 hours the mixture was concentrated in vacuo, the residue was dried by evaporation with absolute ethanol (3×100 mL), washed with diethyl ether (100 mL) and dried in vacuo to give the desired compound (0.995 g, 89% yield) as a white solid. LCMS-A: RT 4.01 min; m/z 237.6 [M-Li+2H]+; m/z 235.6 [M-Li]−

(xv) Lithium 4-(((R)-2-((S)-2-(tert-butoxycarbonyl)-1,2,3,4-tetrahydroisoquinolin-3-yl)-2-hydroxyethyl) carbamoyl)benzoate (I36)

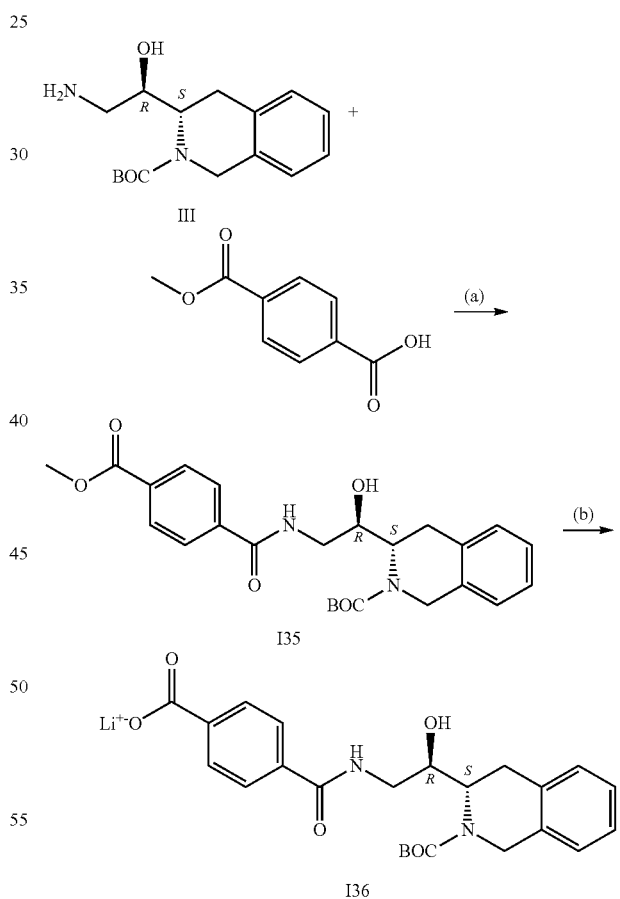

(a) tert-Butyl (S)-3-((R)-1-hydroxy-2-(4-(methoxycarbonyl)benzamido)ethyl)-3,4-dihydroisoquinoline-2(1H)-carboxylate (I35)

tert-Butyl (S)-3-((R)-2-amino-1-hydroxyethyl)-3,4-dihydroisoquinoline-2(1H)-carboxylate (I12) (400 mg, 1.37 mmol), MeCN (10 mL), triethylamine (0.381 mL, 2.74 mmol), 4-(methoxycarbonyl)benzoic acid (246 mg, 1.37 mmol) and HATU (780 mg, 2.05 mmol) were stirred together at room temperature. After 18 hours the mixture was concentrated in vacuo, chromatography (12 g silica cartridge, 0-60% ethyl acetate/hexanes) gave the desired compound (309 mg, 50% yield) as a colourless oil. $^1$H NMR (400 MHz, d$_4$-MeOD) δ 8.11-8.03 (m, 2H), 7.94-7.84 (m, 2H), 7.22-7.10 (m, 4H), 4.48-4.23 (m, 2H), 3.92 (s, 3H), 3.85-3.70 (m, 1H), 3.68-3.57 (m, 1H), 3.22 (dd, J=16.1, 2.8 Hz, 1H), 2.95 (dd, J=15.9, 5.3 Hz, 1H), 1.56-1.45 (m, 9H). LCMS-B: RT 3.80 min; m/z 355.3 [M-Boc+2H]$^+$; m/z 453.2 [M-H]$^-$ (b) Lithium 4-(((R)-2-((S)-2-(tert-butoxycarbonyl)-1,2,3,4-tetrahydroisoquinolin-3-yl)-2-hydroxyethyl)carbamoyl)benzoate (I36)

tert-Butyl (S)-3-((R)-1-hydroxy-2-(4-(methoxycarbonyl)benzamido)ethyl)-3,4-dihydroisoquinoline-2(1H)-carboxylate (I35) (307 mg, 0.675 mmol) was dissolved in THF (2 mL) and a solution of lithium hydroxide monohydrate (31 mg, 0.74 mmol) in water (1 mL) was added. After 18 hours the mixture was concentrated in vacuo, the residue was dried by evaporation with absolute ethanol (3×20 mL) to give the crude desired compound (308 mg) as a pale yellow solid. LCMS-B: RT 3.58 min; m/z 439.2 [M-Li+2H]$^-$ (xvi) 4-(3-Oxa-8-azabicyclo[3.2.1]octane-8-carbonyl)benzoic acid (I38)

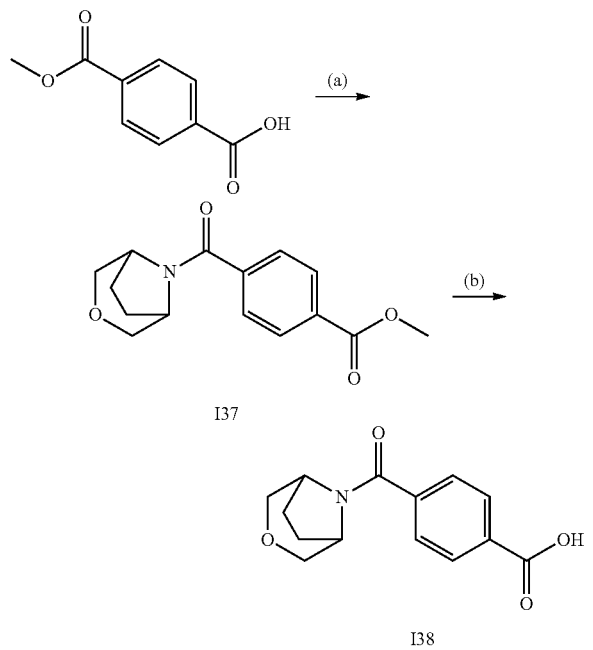

(a) Methyl 4-(3-oxa-8-azabicyclo[3.2.1]octane-8-carbonyl)benzoate (I37)

To a solution of 4-(methoxycarbonyl)benzoic acid (0.66 g, 3.7 mmol) in DCM (20 mL) was added, 3-oxa-8-azabicyclo[3.2.1]octane hydrochloride (0.50 g, 3.4 mmol), DIPEA (0.87 g, 6.7 mmol), HOBt (45 mg, 0.3 mmol) and EDCl (0.77 g, 4.0 mmol). The resulting mixture was stirred at room temperature overnight. The mixture was partitioned against saturated aqueous NaHCO$_3$ (20 mL×2) and the aqueous layer extracted with DCM (5 mL×2). The combined organic layers were washed with brine (20 mL×2), dried (Na$_2$SO$_4$) and concentrated. The crude residue obtained was purified by column chromatography (1% methanol/DCM) to give the desired compound (0.79 g, 85% yield) as a white solid. LCMS-C: RT 0.61 min; m/z 276.1 [M+H]$^+$ (b) 4-(3-Oxa-8-azabicyclo[3.2.1]octane-8-carbonyl)benzoic acid (I38)

To a solution of methyl 4-(3-oxa-8-azabicyclo[3.2.1]octane-8-carbonyl)benzoate I37 (0.77 g, 2.8 mmol) in a mixture of THF (20 mL), methanol (2 mL) and water (2 mL) was added LiOH.H$_2$O (0.59 g, 14 mmol). The resulting mixture was stirred at room temperature overnight, then the solvent was removed and the residue obtained diluted with water (20 mL). The pH of the aqueous solution was adjusted to 6 by addition of 2 M HCl. The aqueous layer was extracted with DCM (20 mL×3) and the combined organic layers washed with brine (20 mL×2), dried (Na$_2$SO$_4$) and concentrated to give the desired compound (0.46 g, 63% yield) as a white solid. LCMS-C: RT 0.83 min; m/z 262.1 [M+H]$^+$ (xvii) 4-(3-Oxa-8-azabicyclo[3.2.1]octane-8-carbonyl)-2-ethoxybenzoic acid (I42)

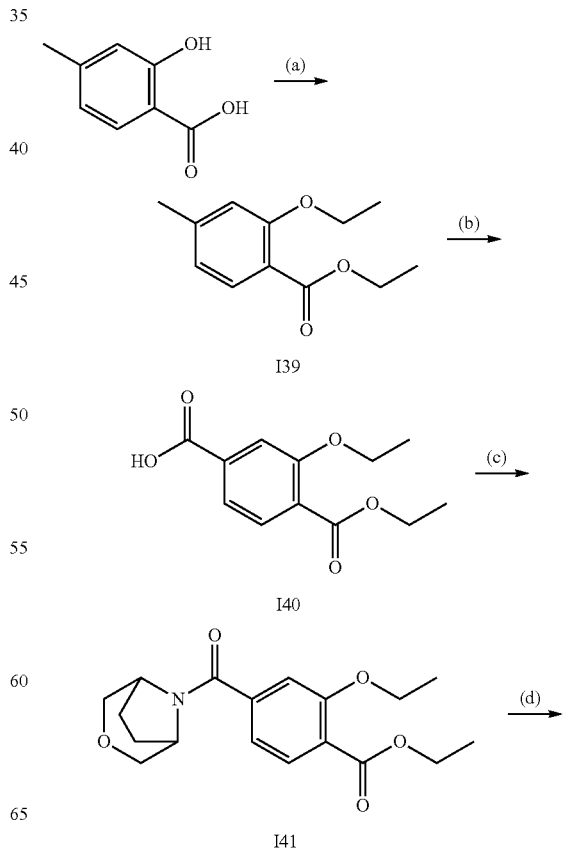

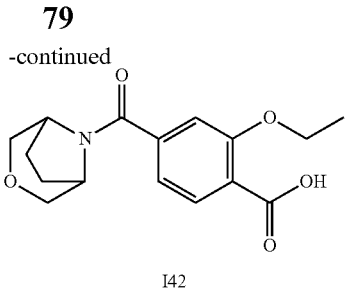

I42

(a) Ethyl-2-ethoxy-4-methylbenzoate (I39)

To a mixture of 2-hydroxy-4-methylbenzoic acid (8.2 g, 54 mmol) and $K_2CO_3$ (22.4 g, 162 mmol) in DMSO (70 mL) at 40° C. was added ethyl iodide (12.6 g, 80.8 mmol) drop-wise over a period of 30 minutes. The reaction was stirred for 2 hours then further ethyl iodide (12.6 g, 80.8 mmol) was added over 30 minutes. The resulting mixture was stirred for another 8 hours at 40° C., then diluted with DCM (150 mL) and filtered. The filtrate was washed with water (200 mL×10) and brine (200 mL×2), dried ($Na_2SO_4$) and concentrated to give the desired compound (10.1 g, 90% yield) as a yellow liquid. LCMS-C: RT 2.70 min; m/z 209.1 [M+H]$^+$

(b) 3-Ethoxy-4-(ethoxycarbonyl)-benzoic acid (I40)

To a solution of ethyl 2-ethoxy-4-methylbenzoate I39 (10.0 g, 48.1 mmol) in a mixture of pyridine (25 mL) and water (75 mL) was added $KMnO_4$ (22.8 g, 144 mmol). The resulting mixture was heated at 50° C. for 48 hours, then cooled and allowed to stir at room temperature 24 hours. The mixture was filtered and the filter cake washed with hot water. The combined aqueous filtrates were washed with EtOAc (75 mL×3) and acidified with 2M HCl solution. The mixture was extracted with DCM (150 mL×3), the combined DCM layers were washed with brine, dried ($Na_2SO_4$) and concentrated to give the desired compound (5.0 g, 44% yield) as a white solid. LCMS-C: RT 0.25 min; m/z 239.0 [M+H]$^+$

(c) Ethyl-4-(3-oxa-8-azabicyclo[3.2.1]octane-8-carbonyl)-2-ethoxybenzoate (I41)

To a solution of 3-ethoxy-4-(ethoxycarbonyl)benzoic acid I40 (2.5 g, 10.4 mmol) in DCM (20 mL) was added 3-oxa-8-azabicyclo[3.2.1]octane hydrochloride (1.4 g, 9.5 mmol), HOBt (135.1 mg, 1.0 mmol), DIPEA (2.5 g, 19.0 mmol) and EDCl (2.2 g, 11.4 mmol). The resulting mixture was stirred at room temperature overnight. The mixture was partitioned against saturated aqueous $NaHCO_3$, and extracted with DCM (20 mL×2). The combined organic layers were washed with brine, dried ($Na_2SO_4$) and concentrated. The residue was purified by column chromatography (1% methanol/dichloromethane) to give the desired compound (2.5 g, 80% yield) as a yellow oil. LCMS-C: RT 2.40 min; m/z 334.1 [M+H]$^+$

(d) 4-(3-Oxa-8-azabicyclo[3.2.1]octane-8-carbonyl)-2-ethoxybenzoic acid (I42)

To a solution of ethyl-4-(3-oxa-8-azabicyclo-[3.2.1]-octane-8-carbonyl)-2-ethoxybenzoate I41 (2.4 g, 7.2 mmol) in a mixture of THF (20 mL), methanol (2 mL) and water (2 mL) was added $LiOH.H_2O$ (1.5 g, 36 mmol). The resulting mixture was stirred at room temperature for 24 hours. The solvent was removed and the residue obtained diluted with water (20 mL), the pH of the aqueous mixture was adjusted to 6 by addition of 2 M HCl. The mixture was extracted with DCM (20 mL×3) and the combined organic layers washed with brine (10 mL×2), dried ($Na_2SO_4$) and concentrated to give the desired compound (1.7 g, 79% yield) as a yellow oil. $^1$H NMR (400 MHz, $d_4$-MeOD) δ 7.83 (d, J=7.8 Hz, 1H), 7.19 (d, J=1.0 Hz, 1H), 7.10 (dd, J=7.8, 1.3 Hz, 1H), 4.65 (br s, 1H), 4.20 (q, J=7.0 Hz, 2H), 3.97 (br s, 1H), 3.82 (d, J=10.8 Hz, 1H), 3.72 (d, J=11.0 Hz, 2H), 3.59 (d, J=10.9 Hz, 1H), 2.13-1.94 (m, 4H), 1.45 (t, J=7.0 Hz, 3H). LCMS-C: RT 1.20 min; m/z 306.1 [M+H].

Alternate Synthesis Method

(a) Ethyl-2-ethoxy-4-methylbenzoate (I39)

To a mixture of 2-hydroxy-4-methylbenzoic acid (20 g, 131.5 mmol) and $K_2CO_3$ (54.5 g, 394.5 mmol) in DMSO (50 mL) was added ethyl iodide (21.5 g, 197.2 mmol) drop-wise over a period of 30 minutes. The reaction was stirred for 2 hours then further ethyl iodide (21.5 g, 197.3 mmol) was added over 30 minutes. The resulting mixture was stirred for another 8 hours at 40° C., then diluted with DCM (150 mL) and filtered. The filtrate was washed with water (150 mL×15) and brine (100 mL×2), dried ($Na_2SO_4$) and concentrated to give the desired compound as a yellow oil (27 g, 98%). LCMS-C: RT 2.70 min; m/z 209.1 [M+H]$^+$

(b) 3-Ethoxy-4-(ethoxycarbonyl)-benzoic acid (I40)

To a solution of ethyl 2-ethoxy-4-methylbenzoate I39 (10.0 g, 48.1 mmol) in a mixture of pyridine (25 mL) and water (75 mL) was added $KMnO_4$ (22.8 g, 144 mmol). The resulting mixture was heated at 50° C. for 48 hours, then cooled and allowed to stir at room temperature for 24 hours. The mixture was filtered and the filter cake washed with hot water, the combined aqueous filtrates were washed with EtOAc (75 mL×3) and acidified with 2M HCl solution. The aqueous was extracted with DCM (150 mL×3), the combined organic layers were washed with brine, dried ($Na_2SO_4$) and concentrated to give the desired compound (5.0 g, 44% yield) as a white solid. LCMS-C: RT 0.25 min; m/z 239.0 [M+H]$^+$

(c) Ethyl-4-(3-oxa-8-azabicyclo[3.2.1]octane-8-carbonyl)-2-ethoxybenzoate (I41)

To a solution of 3-ethoxy-4-(ethoxycarbonyl)benzoic acid I40 (10.0 g, 42 mmol) in DCM (20 mL) was added 3-oxa-8-azabicyclo[3.2.1]octane hydrochloride (5.7 g, 38.2 mmol), HOBt (0.52 g, 3.8 mmol), DIPEA (9.8 g, 76.2 mmol) and EDCl (8.8 g, 45.7 mmol). The resulting mixture was stirred at room temperature overnight. The above reaction was repeated from 8.5 g of 3-ethoxy-4-(ethoxycarbonyl) benzoic acid and the two batches combined and worked up together. The reaction was partitioned against saturated aqueous $NaHCO_3$, and extracted with DCM (200 mL×2). The combined organic layers were washed with brine, dried ($Na_2SO_4$) and concentrated. The residue was purified by column chromatography (50% ethyl acetate/petroleum ether) to give the desired compound (20.5 g, 87%) as a yellow oil. LCMS-C: RT 2.40 min; m/z 334.1 [M+H]$^+$

(d) 4-(3-Oxa-8-azabicyclo[3.2.1]octane-8-carbonyl)-2-ethoxybenzoic acid (I42)

To a solution of ethyl-4-(3-oxa-8-azabicyclo-[3.2.1]-octane-8-carbonyl)-2-ethoxybenzoate I41 (20.4 g, 61.2 mmol)

in a mixture of THF (150 mL), methanol (15 mL) and water (15 mL) was added LiOH.H$_2$O (12.9 g, 306.1 mmol). The resulting mixture was stirred at room temperature for 48 hours. The solvent was removed and the residue obtained diluted with water (50 mL), the pH of the aqueous mixture was adjusted to 4 by addition of 2 M HCl. The mixture was extracted with DCM (150 mL×3) and the combined organic layers washed with brine (200 mL×2), dried (Na$_2$SO$_4$) and concentrated to give the desired compound (16.8 g, 90%) as a white solid. $^1$H NMR (400 MHz, d$_4$-MeOD) δ 7.83 (d, J=7.8 Hz, 1H), 7.19 (d, J=1.0 Hz, 1H), 7.10 (dd, J=7.8, 1.3 Hz, 1H), 4.65 (br s, 1H), 4.20 (q, J=7.0 Hz, 2H), 3.97 (br s, 1H), 3.82 (d, J=10.8 Hz, 1H), 3.72 (d, J=11.0 Hz, 2H), 3.59 (d, J=10.9 Hz, 1H), 2.13-1.94 (m, 4H), 1.45 (t, J=7.0 Hz, 3H). LCMS-C: RT 1.20 min; m/z 306.1 [M+H]$^+$.

(xviii) 6-((1-Acetylpiperidin-4-yl)amino)pyrimidine-4-carboxylic acid (I47)

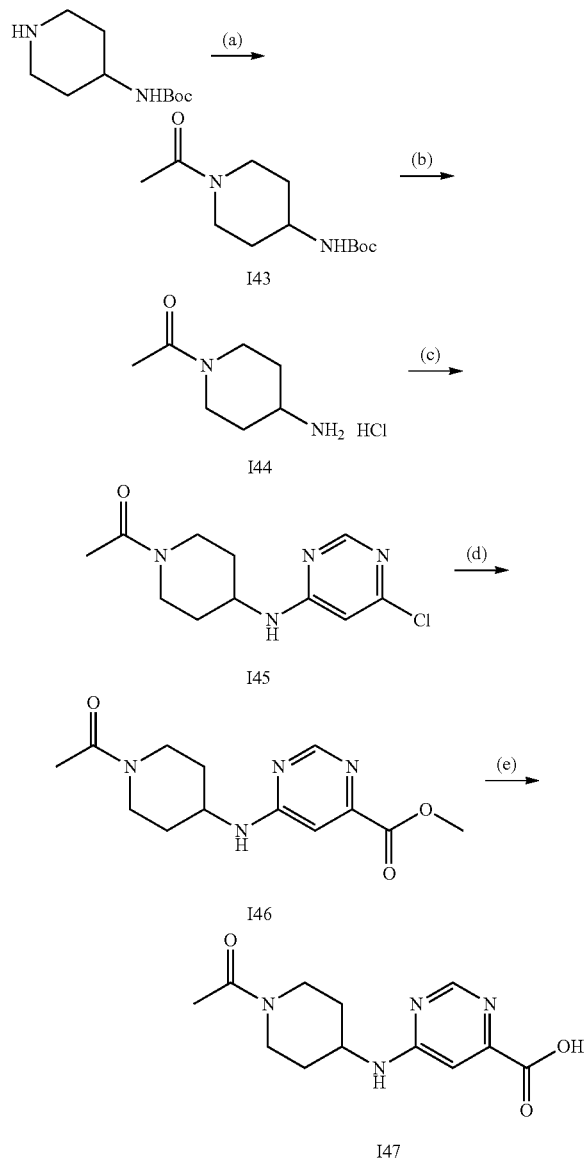

(a) tert-Butyl (1-acetylpiperidin-4-yl)carbamate (I43)

To a solution of tert-butyl piperidin-4-ylcarbamate (5.0 g, 25 mmol) in DCM (80 mL) at 0° C. were added Et$_3$N (3.8 g, 38 mmol) and Ac$_2$O (2.6 g, 25 mmol). The resulting mixture was stirred at 0° C. for 2 hours. The reaction was quenched with water (30 mL), separated and the organic layer was washed with saturated NaHCO$_3$ (30 mL), dried over Na$_2$SO$_4$ and concentrated to give the desired compound (5.6 g, 93% yield) as a pale yellow solid. LCMS-C: RT 1.88 min; m/z 265.1[M+Na]$^+$ (b) 1-(4-Aminopiperidin-1-yl)ethanone hydrochloride (I44)

To a solution of tert-butyl (1-acetylpiperidin-4-yl)carbamate I43 (2.5 g, 10 mmol) in MeOH (10 mL) was added HCl/EtOAc (2 M, 10 mL). The mixture was stirred at room temperature overnight. The solvent was removed to give the desired compound (1.6 g, 89% yield) as a white solid. LCMS-C: RT 0.25 min; m/z 143.1[M+H]$^+$ (free base)

(c) 1-(4-((6-Chloropyrimidin-4-yl)amino)piperidin-1-yl)ethanone (I45)

To a solution of 1-(4-aminopiperidin-1-yl)ethanone hydrochloride I44 (1.0 g, 5.6 mmol) in i-PrOH (10 mL) were added DIPEA (2.17 g, 16.8 mmol) and 4,6-dichloropyrimidine (0.83 g, 5.6 mmol). The resulting mixture was stirred at 100° C. in a sealed tube overnight. The solvent was removed under reduced pressure, the residue was diluted with water (50 mL) and the pH adjusted to 12 by addition of 1 M NaOH. The aqueous layer was extracted with DCM (4×50 mL), the combined organic layers were washed with brine (100 mL), dried over Na$_2$SO$_4$ and concentrated. The residue was purified by column chromatography (100% EtOAc) to give the desired compound (1.3 g, 92% yield) as a yellow oil. $^1$H NMR (400 MHz, d$_4$-MeOD) δ 8.24 (s, 1H), 6.50 (s, 1H), 4.44-4.41 (m, 1H), 4.17 (m, 1H), 3.94-3.90 (m, 1H), 3.28-3.20 (m, 1H), 2.91-2.84 (m, 1H), 2.12-2.05 (m, 5H), 1.52-1.40 (m, 2H). LCMS-C: RT 0.73 min; m/z 255.1[M+H]$^+$ (d) Methyl 6-((1-acetylpiperidin-4-yl)amino)pyrimidine-4-carboxylate (I46)

To a solution of 1-(4-((6-chloropyrimidin-4-yl)amino)piperidin-1-yl)ethanone I45 (1.7 g, 6.7 mmol) in MeOH (25 mL) were added Et$_3$N (2.0 g, 20 mmol) and PdCl$_2$(dppf) (0.24 g, 0.33 mmol). The reaction was then heated at reflux overnight under an atmosphere of carbon monoxide (balloon). The solvent was removed under reduced pressure, the residue was diluted with water (50 mL) and the aqueous layer extracted with DCM (3×50 mL). The combined organic layers were washed with brine (100 mL), dried over Na$_2$SO$_4$ and concentrated. The residue was purified by column chromatography (0-5% MeOH/DCM) to give the desired compound (1.2 g, 65% yield) as a red solid. LCMS-C: RT 0.49 min; m/z 279.1 [M+H]$^+$

(e) 6-((1-Acetylpiperidin-4-yl)amino)pyrimidine-4-carboxylic acid (I47)

To a solution of methyl 6-((1-acetylpiperidin-4-yl)amino)pyrimidine-4-carboxylate I46 (100 mg, 0.34 mmol) in MeOH (3 mL) was added a solution of NaOH (27 mg, 0.68 mmol) in water (1 mL). The resulting mixture was stirred at room temperature overnight. The pH of the solution was adjusted to pH 6 by addition of 3 M HCl and concentrated. The residue was lyophilized to give the crude desired compound (110 mg) as a yellow solid. LCMS-C: RT 0.28 min; m/z 265.1[M+H]$^+$

(xix) 3-((1-(Methoxycarbonyl)piperidin-4-yl)oxy)benzoic acid (I48)

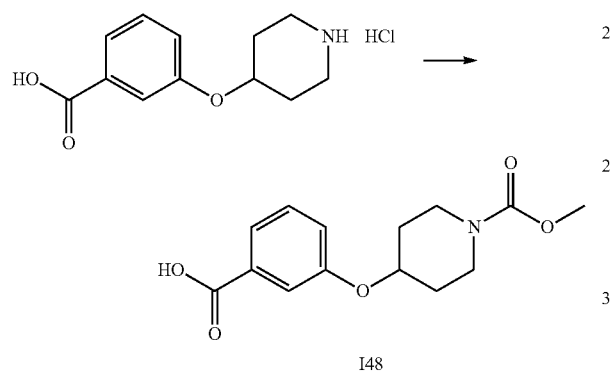

I48

Methyl chloroformate (240 μL, 3.10 mmol, 2 equiv) was added drop-wise to a mixture of 3-(piperidin-4-yloxy)benzoic acid hydrochloride (400 mg, 1.55 mmol, 1 equiv) and sodium hydroxide (261 mg, 6.52 mmol, 4.2 equiv) in water (10 mL). The reaction was stirred at ambient temperature overnight, acidified to pH=3 with a 0.5 M aqueous solution of citric acid and extracted with EtOAc (3×20 mL). The combined organic layers were dried over Na$_2$SO$_4$, filtered, and the filtrate concentrated in vacuo. The crude product was purified by column chromatography (12 g SiO$_2$ cartridge, 0-60% EtOAc in petroleum benzine 40-60° C.) to give the title compound (201 mg, 46% yield) as a colourless oil. $^1$H NMR (400 MHz, CDCl$_3$) δ 9.47 (s, 1H), 7.72-7.68 (m, 1H), 7.61 (dd, J=2.6, 1.5 Hz, 1H), 7.36 (t, J=7.9 Hz, 1H), 7.16-7.10 (m, 1H), 4.56 (tt, J=6.9, 3.4 Hz, 1H), 3.77-3.65 (m, 5H), 3.54-3.38 (m, 2H), 1.99-1.87 (m, 2H), 1.84-1.71 (m, 2H). LCMS-B: RT 3.09 min, m/z 280.1 [M+H]$^+$, 278.1 [M–H]$^-$.

(xx) 2-(Piperidin-4-lox)isonicotinic acid dihydrochloride (I49)

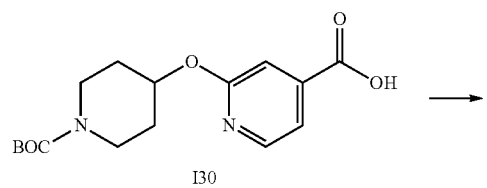

I30

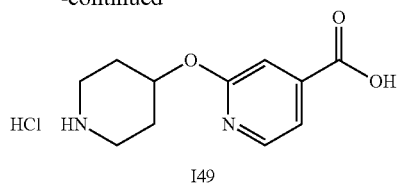

I49

To 2-((1-(tert-butoxycarbonyl)piperidin-4-yl)oxy)isonicotinic acid I30 (1.76 g, 4.15 mmol, 1 equiv) in 1,4-dioxane (10 mL) was added a 4M solution of HCl in 1,4-dioxane (1.35 mL, 5.39 mmol, 1.3 equiv). The reaction was stirred at room temperature for 16 hours then dried in vacuo to give a white solid. The solid was re-suspended in 1,4-dioxane (10 mL) and a 4M solution of HCl in 1,4-dioxane (4 mL, 16 mmol, 3.9 equiv) was added. The reaction was stirred at room temperature for an additional 2 days, and then the solvent was evaporated to give the title compound (1.23 g @ 100% conversion) as a white solid. LCMS-B (hydrophilic method): RT 0.56 min, m/z 221.1 [M–H]$^-$ for the free base.

(xxi) 2-((1-(Isopropoxycarbonyl)piperidin-4-yl)oxy)isonicotinic acid (I50 and 2-((1-(Isobutoxycarbonyl)piperidin-4-yl)oxy)isonicotinic acid (I51)

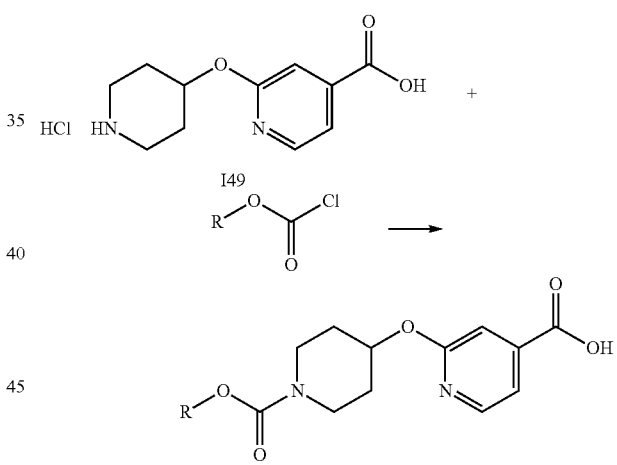

General Method

The desired chloroformate (0.87 mmol, 2 equiv) was added drop-wise to a mixture of 2-(piperidin-4-yloxy)isonicotinic acid dihydrochloride I49 (129 mg, 0.437 mmol, 1 equiv) and sodium hydroxide (73 mg, 1.8 mmol, 4.2 equiv) in water (10 mL). The reaction was stirred at ambient temperature overnight. The pH was adjusted to pH=3 with a 0.5 M aqueous solution of citric acid and the aqueous phase was extracted with EtOAc (3×20 mL). The combined organic layers were washed with water (20 mL), brine (20 mL), dried over Na$_2$SO$_4$ and concentrated in vacuo. The resultant oil was purified by column chromatography (12 g SiO$_2$ cartridge, 0-65% EtOAc in petroleum benzine 40-60° C.) to give the title compound.

| Intermediate | Name and Structure | Yield and Analytical data |
|---|---|---|
| I50 | 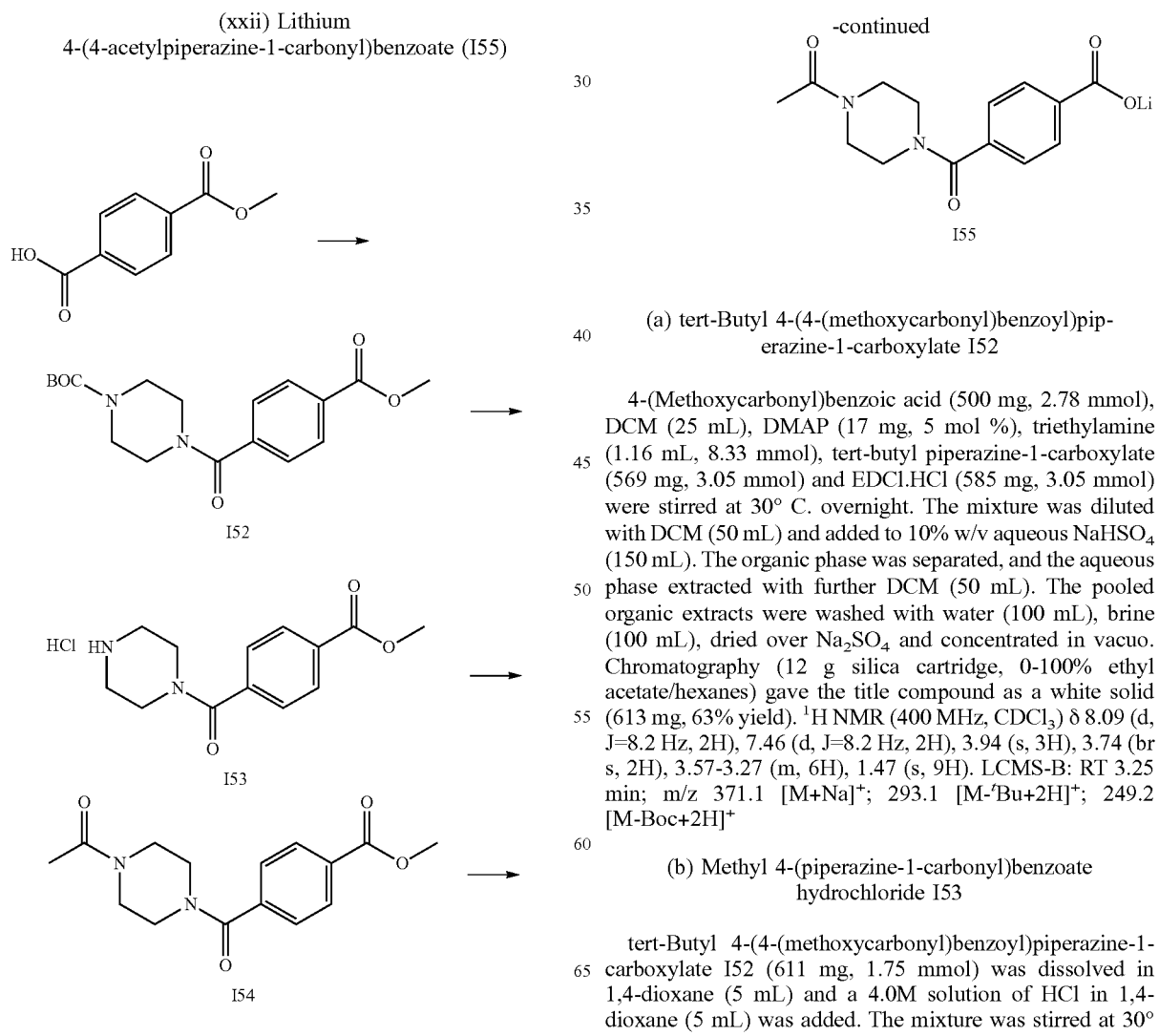

2-((1-Isopropoxycarbonyl)piperidin-4-yl)oxy)isonicotinic acid | 114 mg, 85% yield LCMS-B: RT 3.21 min, m/z 309.1 [M + H]$^+$, 331.1 [M + Na]$^+$. |
| I51 | 2-((1-(1-Isobutoxycarbonyl)piperidin-4-yl)oxy)isonicotinic acid | 46 mg, 16% yield LCMS-B: RT 3.31 min, m/z 323.1 [M + H]$^+$, 345.1 [M + Na]$^+$. |

(xxii) Lithium 4-(4-acetylpiperazine-1-carbonyl)benzoate (I55)

(a) tert-Butyl 4-(4-(methoxycarbonyl)benzoyl)piperazine-1-carboxylate I52

4-(Methoxycarbonyl)benzoic acid (500 mg, 2.78 mmol), DCM (25 mL), DMAP (17 mg, 5 mol %), triethylamine (1.16 mL, 8.33 mmol), tert-butyl piperazine-1-carboxylate (569 mg, 3.05 mmol) and EDCl.HCl (585 mg, 3.05 mmol) were stirred at 30° C. overnight. The mixture was diluted with DCM (50 mL) and added to 10% w/v aqueous NaHSO$_4$ (150 mL). The organic phase was separated, and the aqueous phase extracted with further DCM (50 mL). The pooled organic extracts were washed with water (100 mL), brine (100 mL), dried over Na$_2$SO$_4$ and concentrated in vacuo. Chromatography (12 g silica cartridge, 0-100% ethyl acetate/hexanes) gave the title compound as a white solid (613 mg, 63% yield). $^1$H NMR (400 MHz, CDCl$_3$) δ 8.09 (d, J=8.2 Hz, 2H), 7.46 (d, J=8.2 Hz, 2H), 3.94 (s, 3H), 3.74 (br s, 2H), 3.57-3.27 (m, 6H), 1.47 (s, 9H). LCMS-B: RT 3.25 min; m/z 371.1 [M+Na]$^+$; 293.1 [M-$^t$Bu+2H]$^+$; 249.2 [M-Boc+2H]$^+$ (b) Methyl 4-(piperazine-1-carbonyl)benzoate hydrochloride I53 tert-Butyl 4-(4-(methoxycarbonyl)benzoyl)piperazine-1-carboxylate I52 (611 mg, 1.75 mmol) was dissolved in 1,4-dioxane (5 mL) and a 4.0M solution of HCl in 1,4-dioxane (5 mL) was added. The mixture was stirred at 30°

C. for 2 hours then concentrated in vacuo to give the title compound as a white solid (511 mg). LCMS-B: RT 0.95 min; m/z 249.1 [M+H]⁺ for free base.

(c) Methyl 4-(4-acetylpiperazine-1-carbonyl)benzoate I54

Methyl 4-(piperazine-1-carbonyl)benzoate hydrochloride I53 (100 mg, 0.35 mmol), DCM (1.5 mL), triethylamine (0.147 mL, 1.05 mmol), DMAP (0.4 mg, 1 mol %) and acetyl chloride (0.050 mL, 0.70 mmol) were stirred at 30° C. After 17 hours, the mixture was quenched with 10% w/v aqueous NaHSO₄ (1 mL), the organic phase separated and loaded onto a 4 g silica cartridge. Chromatography (0-100% ethyl acetate/hexanes) gave the title compound as a white solid (54 mg, 53% yield). LCMS-B: RT 2.92 min; m/z 291.1 [M+H]⁺

(d) Lithium 4-(4-acetylpiperazine-1-carbonyl)benzoate I55

Methyl 4-(4-acetylpiperazine-1-carbonyl)benzoate I54 (54 mg, 0.19 mmol) and lithium hydroxide monohydrate (8.6 mg, 0.21 mmol) were stirred in THF (1 mL), water (0.5 mL) and methanol (0.5 mL). After 4 hours, the mixture was concentrated in vacuo, the residue diluted with absolute ethanol (5 mL) and again concentrated in vacuo to give the title compound as a white solid (54 mg). The solid was used without further characterisation or purification.

(xxiii) Lithium 4-(4-(methoxycarbonyl)piperazine-1-carbonyl)benzoate I57

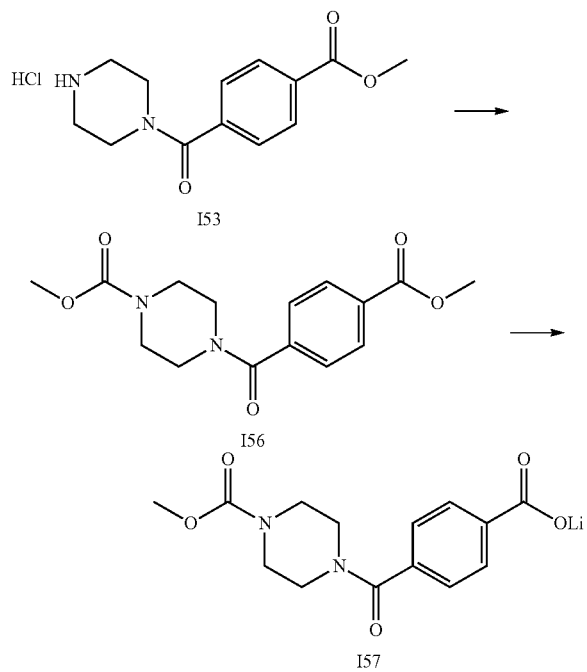

(a) Methyl 4-(4-(methoxycarbonyl)benzoyl)piperazine-1-carboxylate I56

Methyl 4-(piperazine-1-carbonyl)benzoate hydrochloride I53 (100 mg, 0.35 mmol), DCM (1.5 mL), triethylamine (0.147 mL, 1.05 mmol), DMAP (0.4 mg, 1 mol %) and methyl chloroformate (0.054 mL, 0.70 mmol) were stirred at 30° C. After 17 hours the mixture was quenched with 10% w/v aqueous NaHSO₄ (1 mL), the organic phase separated and loaded onto a 4 g silica cartridge. Chromatography (0-100% ethyl acetate/hexanes) gave the title compound as a white solid (58 mg, 54% yield). LCMS-B: RT 3.03 min; m/z 307.1 [M+H]⁺

(b) Lithium 4-(4-(methoxycarbonyl)piperazine-1-carbonyl)benzoate I57

Methyl 4-(4-(methoxycarbonyl)benzoyl)piperazine-1-carboxylate I56 (58 mg, 0.19 mmol) and lithium hydroxide monohydrate (8.7 mg, 0.21 mmol) were stirred in THF (1 mL), water (0.5 mL) and methanol (0.5 mL). After 4 hours, the mixture was concentrated in vacuo, the residue diluted with absolute ethanol (5 mL) and again concentrated in vacuo to give the title compound as a white solid (56 mg). The solid was used without further characterisation or purification.

(xxiv) 2-(1-Acetylpiperidin-4-yl)oxy)benzoic acid I58

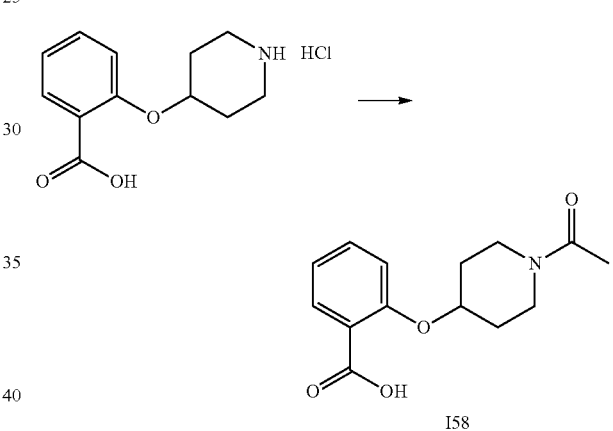

2-(Piperidin-4-yloxy)benzoic acid hydrochloride (200 mg, 0.78 mmol), DCM (5 mL), triethylamine (0.541 mL, 3.88 mmol) and acetyl chloride (0.221 mL, 3.10 mmol) were stirred at 30° C. After 3 hours, DCM (5 mL) and water (10 mL) were added and the mixture adjusted to pH 1 with 3M aqueous HCl. The organic layer was separated (phase separator cartridge) and concentrated in vacuo. Chromatography (12 g silica cartridge, 0-100% ethyl acetate/hexanes, then 0-20% methanol/ethyl acetate) gave the title compound as pale yellow solid (173 mg, 85% yield). LCMS-A: RT 5.24 min; m/z 264.2 [M+H], (xxv) Lithium 4-(3-oxa-8-azabicyclo[3.2.1]octane-8-carbonyl)-2-ethoxy-5-fluorobenzoate I61

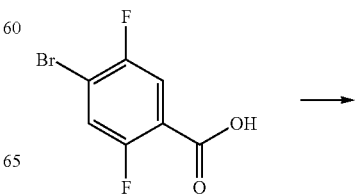

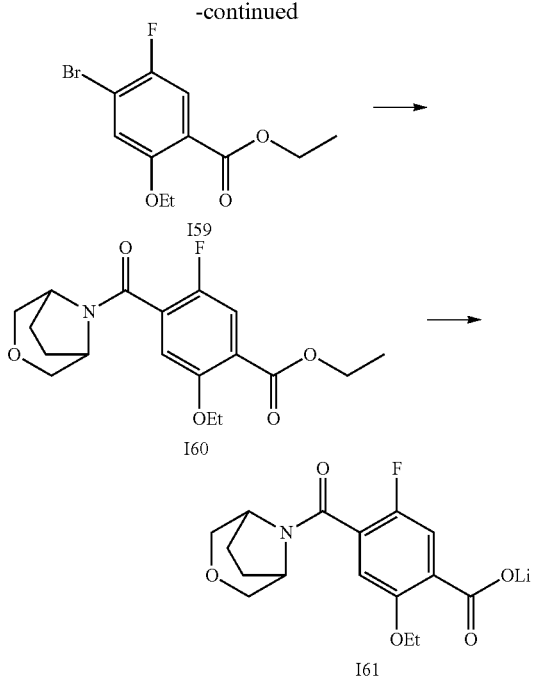

(a) Ethyl 4-bromo-2-ethoxy-5-fluorobenzoate I59

4-Bromo-2,5-difluorobenzoic acid (1.00 g, 4.22 mmol) was suspended in DCM (20 mL) and cooled to 0° C. Oxalyl chloride (0.543 mL, 6.33 mmol) and DMF (1 drop) were added and the mixture stirred at room temperature. After one hour, the mixture was concentrated in vacuo, the residue dissolved in DCM (10 mL) and cooled to 0° C. Absolute ethanol (10 mL) was added and the mixture stirred at room temperature. After 15 minutes, the mixture was concentrated in vacuo and the residue taken up in absolute ethanol. Sodium metal (146 mg, 6.33 mmol) was dissolved in absolute ethanol (30 mL) and the solution added to the solution of the ester. After 2 hours, the reaction had a thick precipitate, the mixture was diluted with dry THF (50 mL) and the stir bar replaced with an oversized stir bar. After 19 hours, the mixture was concentrated in vacuo, the residue slurried in ethyl acetate (75 mL) and filtered. The filtrate was concentrated in vacuo and purified by chromatography (12 g silica cartridge, 0-10% ethyl acetate/hexanes) to give the title compound (216 mg, 18% yield) as a white solid. $^1$H NMR (400 MHz, CDCl$_3$) δ 7.57 (d, J=8.6 Hz, 1H), 7.13 (d, J=5.5 Hz, 1H), 4.35 (q, J=7.2 Hz, 2H), 4.07 (q, J=7.0 Hz, 2H), 1.46 (t, J=7.0 Hz, 3H), 1.37 (t, J=7.1 Hz, 3H). LCMS-B: RT 3.53 min, m/z 245.0 [M-OEt]$^+$ for $^{79}$Br (b) Ethyl 4-(3-oxa-8-azabicyclo[3.2.1]octane-8-carbonyl)-2-ethoxy-5-fluorobenzoate I60

Palladium(II) acetate (8 mg, 5 mol %), xantphos (21 mg, 5 mol %), sodium carbonate (232 mg, 2.19 mmol), 3-oxa-8-azabicyclo[3.2.1]octane hydrochloride salt (163 mg, 1.09 mmol) and ethyl 4-bromo-2-ethoxy-5-fluorobenzoate I59 (212 mg, 0.728 mmol) were stirred in toluene (2 mL) in a schlenk tube under nitrogen. The tube was flushed with carbon monoxide, and heated to 80° C. under carbon monoxide atmosphere. After 18 hours, the mixture was cooled to room temperature and diluted with ethyl acetate (20 mL). The mixture was filtered through Celite and the filtrate concentrated in vacuo. Chromatography (12 g silica cartridge, 0-60% ethyl acetate/hexanes) gave the title compound (41 mg, 16% yield) as a pale yellow film. $^1$H NMR (400 MHz, CDCl$_3$) δ 7.51 (d, J=9.2 Hz, 1H), 7.01 (d, J=5.1 Hz, 1H), 4.75 (d, J=5.8 Hz, 1H), 4.36 (q, J=7.1 Hz, 2H), 4.10 (q, J=7.0 Hz, 2H), 3.84 (d, J=11.0 Hz, 1H), 3.73-3.68 (m, 2H), 3.64 (d, J=10.9 Hz, 1H), 3.56 (dd, J=11.0, 1.6 Hz, 1H), 2.13-1.90 (m, 4H), 1.45 (t, J=7.0 Hz, 3H), 1.38 (t, J=7.1 Hz, 3H). LCMS-B: RT 3.23 min; m/z 352.1 [M+H]$^+$ (c) Lithium 4-(3-oxa-8-azabicyclo[3.2.1]octane-8-carbonyl)-2-ethoxy-5-fluorobenzoate I61

A solution of ethyl 4-(3-oxa-8-azabicyclo[3.2.1]octane-8-carbonyl)-2-ethoxy-5-fluorobenzoate 160 (41 mg, 0.12 mmol) in THF (1 mL) was stirred vigorously, and a solution of lithium hydroxide monohydrate (7.3 mg, 0.18 mmol) in water (0.5 mL) was added. After 4.5 hours, the mixture was concentrated in vacuo, the residue dissolved in absolute ethanol and the mixture again concentrated in vacuo to give the title compound. LCMS-B: RT 2.96 min; m/z 324.1 [M-Li+2H]$^+$; m/z 322.1 [M-Li]$^-$ (xxvi) 6-(3-Oxa-8-azabicyclo[3.2.1]octane-8-carbonyl)-2-ethoxynicotinic acid I65

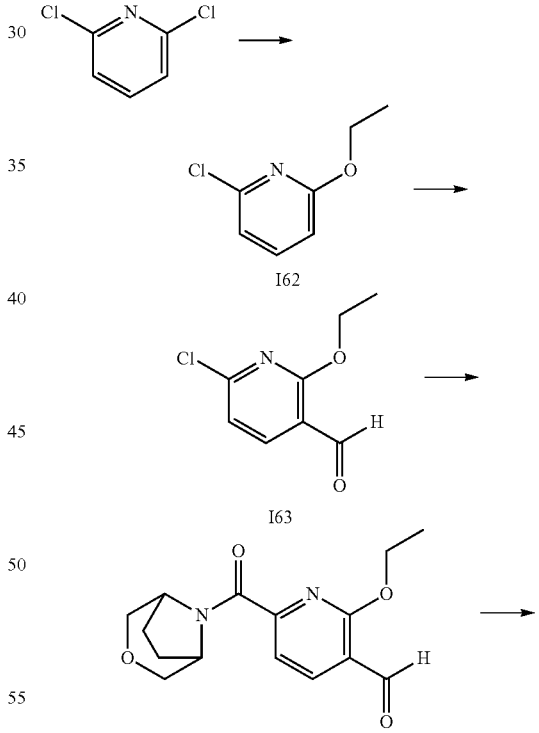

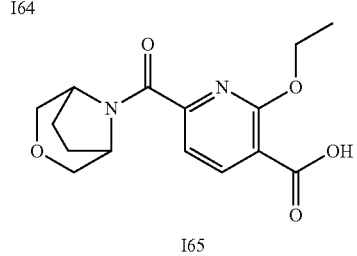

(a) 2-Chloro-6-ethoxypyridine I62

To a solution of 2,6-dichloropyridine (5.0 g, 33.8 mmol) in EtOH (50 mL) was added EtONa (9.2 g, 0.14 mol). The mixture was stirred at 60° C. for 24 hours. The solvent was removed and the residue obtained was dissolved in water (100 mL). The aqueous layer was acidified to pH 7 with 2 M HCl, then extracted with DCM (100 mL×2). The combined organic layers were washed with water (100 mL) and brine (100 mL), dried ($Na_2SO_4$) and concentrated to give the title compound as yellow oil (4.2 g, 79%). LCMS-C: RT 2.64 min; m/z 158.1 $[M+H]^+$.

(b) 6-Chloro-2-ethoxynicotinaldehyde I63

To a solution of 2-chloro-6-ethoxypyridine I62 (2.0 g, 12.7 mmol) in THF (40 mL) at −78° C. was added t-BuLi (1.6 M in pentane, 8.8 mL, 14.0 mmol) dropwise under $N_2$. After stirring at the same temperature for 1 hour, DMF (2.8 g, 38.1 mmol) was added dropwise and the reaction mixture was stirred at −78° C. for 30 minutes then warmed to room temperature and stirred for 30 minutes. The reaction mixture was quenched with 2M HCl (5 mL) and extracted with EtOAc (50 mL×2). The combined organic layers were washed with water (50 mL×3) and brine (50 mL), dried ($Na_2SO_4$) and concentrated to give the title compound as yellow oil (2.0 g, 87%). $^1$H NMR (400 MHz, DMSO-$d_6$) δ 10.17 (s, 1H), 8.09 (d, J=8.0 Hz, 1H), 7.23 (d, J=8.0 Hz, 1H), 4.44 (q, J=14.0, 7.2 Hz, 2H), 1.38 (t, J=7.2 Hz, 3H). LCMS-C: RT 2.64 min; m/z 186 $[M+H]^+$; 218.1 $[M+MeOH+H]^+$.

(c) 6-(3-Oxa-8-azabicyclo[3.2.1]octane-8-carbonyl)-2-ethoxynicotinaldehyde I64

To a solution of 3-oxa-8-azabicyclo[3.2.1]octane hydrochloride (1.5 g, 10.3 mmol) in toluene (80 mL) was added $Et_3N$ (2.6 g, 25.8 mmol), Xantphos (0.2 g, 0.34 mmol) and $Pd(OAc)_2$ (40 mg, 0.17 mmol). The mixture was degassed three times under $N_2$ followed by addition of 6-chloro-2-ethoxynicotinaldehyde I63 (1.6 g, 8.6 mmol). The mixture was degassed three times under $N_2$ and then three times under CO. The reaction was then stirred at 90° C. overnight. Water (80 mL) was added and the mixture was extracted with EtOAc (80 mL×2), the combined organic layers were washed with water (80 mL), brine (80 mL), dried ($Na_2SO_4$) and concentrated. The residue was purified by column chromatography (100% petroleum ether to 50% EtOAc in petroleum ether) to give the title compound as a yellow solid (1.1 g, 44%): LCMS-C: RT 2.22 min; m/z 291.1 $[M+H]^+$.

(d) 6-(3-Oxa-8-azabicyclo[3.2.1]octane-8-carbonyl)-2-ethoxynicotinic acid I65

To a mixture of 6-(3-oxa-8-azabicyclo[3.2.1]octane-8-carbonyl)-2-ethoxynicotinaldehyde I64 (100 mg, 0.34 mmol) in a mixture of t-BuOH (5 mL) and 2-methylbut-2-ene (2 mL) was added a solution of $NaH_2PO_4 \cdot 2H_2O$ (376 mg, 2.4 mmol) and $NaClO_2$ (300 mg, 3.3 mmol) in water (5 mL). The resulting mixture was stirred at room temperature for 2 hours after which the solvent was removed under reduced pressure. The residue obtained was dissolved in water and the aqueous layer was acidified to pH 5 with 2 M HCl and extracted with EtOAc (20 mL×4). The combined organic layers were dried ($Na_2SO_4$) and concentrated to give the title compound as a white solid (80 mg, 76%). LCMS-C: RT 1.74 min; m/z 307.1 $[M+H]^+$.

(xxvii) 6-(2-Oxo-2-(piperidin-1-yl)ethyl)nicotinic acid I70

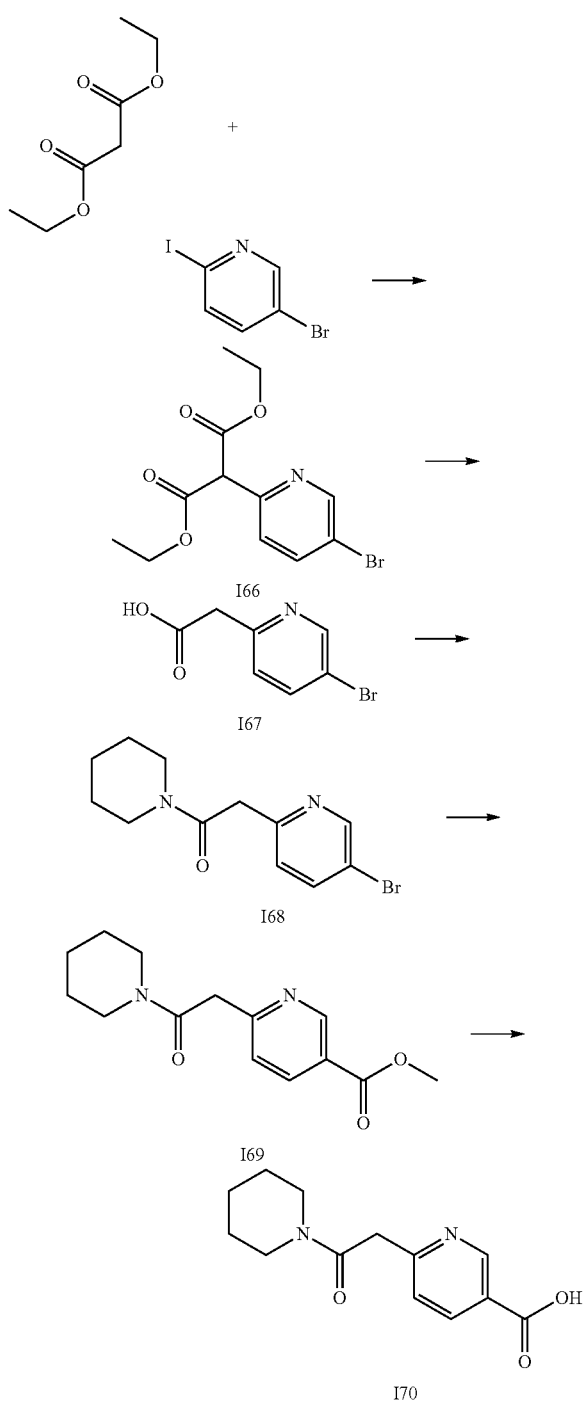

(a) Diethyl 2-(5-bromopyridin-2-yl)malonate 166

To a solution of 5-bromo-2-iodopyridine (18.0 g, 63.4 mmol) in 1,4-dioxane (100 mL) was added diethyl malonate (20.3 g, 126.8 mmol), Cs$_2$CO$_3$ (62.0 g, 190.2 mmol), CuI (1.2 g, 6.3 mmol) and picolinic acid (1.6 g, 12.7 mmol). The resulting mixture was heated to 70° C. and stirred overnight. Water (100 mL) and EtOAc (100 mL) were added and the aqueous layer extracted with EtOAc (3×50 mL). The combined organic extracts were washed with water (3×50 mL) and brine (3×50 mL), dried (Na$_2$SO$_4$) and concentrated. The crude product was purified by silica gel chromatography (ethyl acetate/petroleum ether=1/20) to give the title compound as yellow oil (19.6 g, 97%). LCMS-C: RT 2.49 min; m/z 316.0, 318.0 [M+H]$^+$.

(b) 2-(5-Bromopyridin-2-yl)acetic acid I67

To a solution of diethyl 2-(5-bromopyridin-2-yl)malonate I66 (2.1 g, 6.6 mmol) in MeOH (30 mL) was added 2 M NaOH aqueous solution (14 mL, 28 mmol). The resulting mixture was stirred at room temperature for 3 hours. The solution was concentrated under reduced pressure and the residue was dissolved in water (20 mL). The pH of the solution was adjusted to 3-4 by addition of 6 M HCl. The white precipitate formed was collected by filtration, washed with water and dried at 50° C. to give the title compound as a white solid (1.0 g, 70%). LCMS-C: RT 0.78 min; m/z 216.0 [M+H]$^+$.

(c) 2-(5-Bromopyridin-2-yl)-1-(piperidin-1-yl)ethanone I68

To a solution of 2-(5-bromopyridin-2-yl)acetic acid I67 (890 mg, 4.1 mmol) in DCM (5 mL) was added HATU (2.4 g, 6.2 mmol) followed by a solution of piperidine (526 mg, 6.2 mmol) in DCM (5 mL) and DIPEA (1.9 mL, 14.4 mmol). The resulting mixture was stirred at room temperature overnight. Water (15 mL) and DCM (15 mL) were then added, the layers were separated and the aqueous layer extracted with DCM (3×15 mL). The combined organic extracts were washed with saturated NaHCO$_3$ (3×10 mL) and brine (3×10 mL), dried (Na$_2$SO$_4$) and concentrated in vacuo. The residue was purified by silica gel chromatography (ethyl acetate/petroleum ether=1/10) to give the title compound as a white solid (960 mg, 82%). $^1$HNMR (400 MHz, DMSO-d$_6$) δ 8.59 (d, J=2.4 Hz, 1H), 7.97 (dd, J=8.4, 2.4 Hz, 1H), 7.28 (d, J=8.4 Hz, 1H), 3.83 (s, 2H), 3.45-3.40 (m, 4H), 1.58-1.52 (m, 2H), 1.43-1.37 (m, 4H); LCMS-C: RT 2.22 min; m/z 283.1 [M+H]$^+$.

(d) Methyl 6-(2-oxo-2-(piperidin-1-yl)ethyl)nicotinate I69

To a solution of 2-(5-bromopyridin-2-yl)-1-(piperidin-1-yl)ethanone I68 (500 mg, 1.8 mmol) in MeOH (20 mL) was added Pd(dppf)C$_2$ (65 mg, 0.1 mmol) and triethylamine (394 mg, 3.9 mmol). The resulting mixture was heated at reflux under a carbon monoxide atmosphere overnight. The mixture was concentrated and the residue was purified by silica gel chromatography (ethyl acetate/petroleum ether=1/1) to give the title compound as a yellow solid (417 mg, 90%). LCMS-C: RT 1.62 min; m/z 263.1 [M+H]$^+$.

(e) 6-(2-Oxo-2-(piperidin-1-yl)ethyl)nicotinic acid I70

To a solution of methyl 6-(2-oxo-2-(piperidin-1-yl)ethyl)nicotinate I69 (390 mg, 1.5 mmol) in a mixture of THF (5 mL), MeOH (2 mL) and water (2 mL) was added lithium hydroxide monohydrate (313 mg, 7.4 mmol). The resulting mixture was stirred at room temperature overnight. The organic solvent was removed and the aqueous layer neutralized with 4 M HCl aqueous solution to a pH of 5-6. The water was removed to give the title crude product which was dissolved in a mixed solution of MeOH/DCM (1/20) and filtered. The filtrate was concentrated in vacuo to give the title compound as a yellow oil (338 mg, 91%). The material was carried forward without further purification. LCMS-C: RT 0.55 min; m/z 249.1 [M+H]$^+$.

(xxviii) 2-(3,6-Dihydro-2H-pyran-4-yl)-4,4,5,5-tetramethyl-1,3,2-dioxaborolane I71

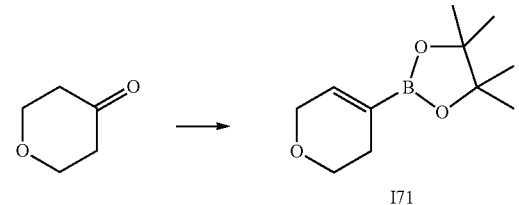

To a solution of diisopropylamine (1.41 g, 13.98 mmol) in THF (10 mL) at −20° C. under N$_2$ was added dropwise n-BuLi (5.82 mL, 13.98 mmol). The mixture was stirred for 30 minutes at −20° C. then cooled to −70° C. and a solution of dihydro-2H-pyran-4(3H)-one (2.0 g, 9.99 mmol) in THF (5 mL) was added. The reaction was then stirred at −70° C. for 30 minutes. A solution of 1,1,1-trifluoro-N-phenylmethanesulfonamide (3.57 g, 9.99 mmol) in THF (5 mL) was added dropwise, the resulting mixture was allowed to warm to room temperature and stirred for 18 hours. The reaction mixture was concentrated under reduced pressure and the residue obtained diluted with water (20 mL). The mixture was extracted with ethyl acetate (3×20 mL) and the combined organic layers dried (Na$_2$SO$_4$), filtered and concentrated. The residue obtained was purified by silica gel chromatography (ethyl acetate/petroleum ether=1/20) to give the triflate intermediate.

To a solution of 4,4,4',4',5,5,5',5'-octamethyl-2,2'-bi(1,3,2-dioxaborolane) (993 mg, 3.91 mmol) in DMSO (5 mL) under N$_2$ was added KOAc (959.8 mg, 9.78 mmol) and Pd(dppf)Cl$_2$ (71.7 mg, 0.097 mmol). A solution of the triflate intermediate (750 mg) in DMSO (1 mL) was added and the reaction heated at 80° C. overnight. The mixture was diluted with water (20 mL) and extracted with DCM (3×20 mL). The combined organic layers were washed with saturated NaHCO$_3$ (3×10 mL) and brine (3×10 mL), dried (Na$_2$SO$_4$) and concentrated. The residue obtained was purified by silica gel chromatography (ethyl acetate/petroleum ether=1/2) to give the title compound (300 mg) as a white solid which was used without further purification or analysis.

(xxix) 2-(Tetrahydro-2H-pyran-4-yl)isonicotinic acid I75

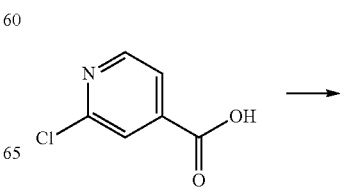

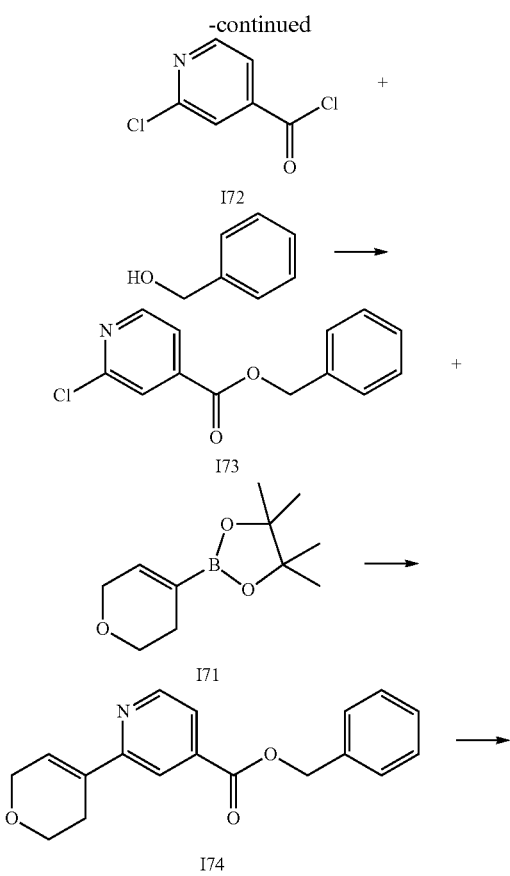

(a) 2-Chloroisonicotinoyl chloride I72

A solution of 2-chloroisonicotinic acid (2.0 g, 12.69 mmol) in thionyl chloride (15 mL) was heated at 80° C. for 3 hours. The mixture was concentrated in vacuo and the residue resuspended in DCM (3×10 mL) and concentrated to remove the excess thionyl chloride to give the title compound as yellow oil (2.2 g, 100%). LCMS-C: (MeOH quench) RT 1.79 min; m/z 172.1 [M+H].

(b) Benzyl 2-chloroisonicotinate I73

To a solution of benzyl alcohol (1.37 g, 12.69 mmol) in DCM (80 mL) was added triethylamine (5.07 g, 50.76 mmol) followed by dropwise addition of 2-chloroisonicotinoyl chloride I72 (2.2 g, 12.69 mmol) and the reaction was stirred at room temperature overnight. The mixture was diluted with water (50 mL) and extracted with DCM (3×50 mL). The combined organic layers were washed with saturated NaHCO₃ (3×10 mL), brine (3×10 mL), dried (Na₂SO₄) and concentrated to give the title compound (3.1 g, 99%) as brown oil. LCMS-C: RT 2.88 min; m/z 248.1 [M+H]⁺.

(c) Benzyl 2-(3,6-dihydro-2H-pyran-4-yl)isonicotinate I74

To a solution of benzyl 2-chloroisonicotinate I73 (319 mg, 1.29 mmol) in a mixture of toluene (2 mL) and THF (10 mL) was added 2-(3,6-dihydro-2H-pyran-4-yl)-4,4,5,5-tetramethyl-1,3,2-dioxaborolane I71 (300 mg, 1.42 mmol) and 2M Na₂CO₃ aqueous solution (1.29 mL). Pd(dppf)Cl₂ (38 mg, 0.05 mmol) was added and the reaction heated at 100° C. for 3 hours. The mixture was diluted with 1M HCl (20 mL) and extracted with DCM (3×20 mL), the combined organic layers were washed with saturated NaHCO₃ (3×10 mL), brine (3×10 mL), dried (Na₂SO₄) and concentrated. The residue was purified by silica gel chromatography (ethyl acetate/petroleum ether=1/5) to give the title compound (60 mg, 6%) as a yellow oil. LCMS-C: RT 2.88 min; m/z 296.2 [M+H]⁺.

(d) 2-(Tetrahydro-2H-pyran-4-yl)isonicotinic acid I75

To a solution of benzyl 2-(3,6-dihydro-2H-pyran-4-yl) isonicotinate I74 (60 mg, 0.20 mmol) in MeOH (5 mL) was added 10% Pd/C (20 mg). The mixture was stirred under H₂ at room temperature for 1 day. The mixture was filtered and the filtrate concentrated to give the title compound as a yellow oil (30 mg, 71%). LCMS-C: RT 0.52 min; m/z 208.2 [M+H]⁺.

(xxx) 4-(2-(3-Oxa-8-azabicyclo[3.2.1]octan-8-yl)-2-oxoethyl)-2-ethoxybenzoic acid I79

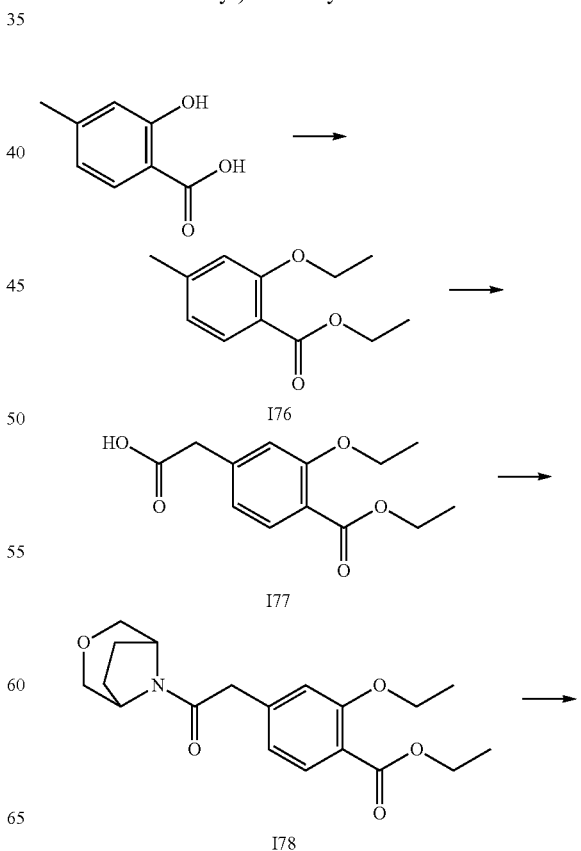

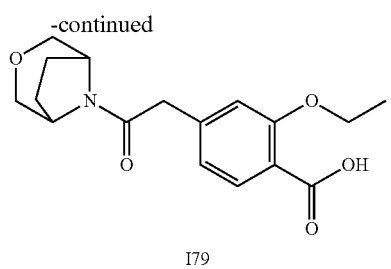

I79

(a) Ethyl 2-ethoxy-4-methylbenzoate I76

To a mixture of 2-hydroxy-4-methylbenzoic acid (20.0 g, 131.5 mmol) and K$_2$CO$_3$ (54.5 g, 394.5 mmol) in DMSO (50 mL) at 40° C. was added bromoethane (21.5 g, 197.2 mmol) over 30 minutes. The reaction was then stirred at 40° C. for 2 hours. Further bromoethane (21.5 g, 197.2 mmol) was then added dropwise and the reaction stirred at 40° C. for 8 hours. DCM (200 mL) was added and the mixture was filtered. The organic layer was washed with water (4×150 mL), dried (Na$_2$SO$_4$) and concentrated to give the title compound (24.1 g, 88%) as a clear oil. LCMS-C: RT 2.77 min; m/z 209.1 [M+H]$^+$.

(b) 2-(3-Ethoxy-4-(ethoxycarbonyl)phenyl)acetic acid I77

To a solution of diisopropylamine (1.46 g, 14.4 mmol) in anhydrous THF (20 mL) at –30° C. was added n-BuLi (2.4M in hexane, 5.8 mL, 14.4 mmol) slowly under a nitrogen atmosphere. The mixture was stirred at –30° C. for 30 minutes then cooled to –78° C. and HMPA (4.0 g) was added. A solution of ethyl 2-ethoxy-4-methylbenzoate I76 (2.0 g, 9.6 mmol) in anhydrous THF (5 mL) was then added dropwise and the resulting mixture stirred at –78° C. for 2 hours. CO$_2$ (g) was bubbled through the mixture until the colour of the anion discharged then for a further 30 minutes. The reaction was allowed to warm to 10° C., then diluted with water (20 mL) and extracted with diethyl ether (2×20 mL). The aqueous layer was acidified to pH 2 by addition of 10% aqueous H$_2$SO$_4$ and extracted with DCM (2×20 mL). The combined DCM layers were washed with water and brine, dried (Na$_2$SO$_4$) and concentrated to give the title compound (550 mg, 23%) as yellow oil. LCMS-C: RT 2.36 min; m/z 253.1 [M+H]$^+$.

(c) Ethyl 4-(2-(3-oxa-8-azabicyclo[3.2.1]octan-8-yl)-2-oxoethyl)-2-ethoxybenzoate I78

A mixture of 2-(3-ethoxy-4-(ethoxycarbonyl)phenyl)acetic acid I77 (550 mg, 2.2 mmol), 3-oxa-8-azabicyclo[3.2.1]octane hydrochloride salt (320 mg, 2.1 mmol), EDCl (500 mg, 2.6 mmol), HOBt (30 mg, 0.22 mmol) and DIPEA (710 mg, 5.5 mmol) in DCM (10 mL) was stirred at room temperature overnight. Water (20 mL) was added and the reaction mixture extracted with DCM (3×10 mL), the organic layers were combined and washed with saturated aqueous NaHCO$_3$, water and brine, dried (Na$_2$SO$_4$) and concentrated to give the title product (710 mg, 93%) as a yellow oil. LCMS-C: RT 2.38 min; m/z 348.2 [M+H]$^+$.

(d) 4-(2-(3-Oxa-8-azabicyclo[3.2.1]octan-8-yl)-2-oxoethyl)-2-ethoxybenzoic acid I79

To a solution of ethyl 4-(2-(3-oxa-8-azabicyclo[3.2.1]octan-8-yl)-2-oxoethyl)-2-ethoxybenzoate I78 (710 mg, 2.0 mmol) in a mixture of THF (5 mL), MeOH (10 mL) and water (5 mL) was added LiOH.H$_2$O (429 mg, 10.2 mmol). The reaction was stirred at room temperature overnight then the solvent was removed in vacuo. The residue obtained was re-dissolved in water (10 mL) then acidified to pH 2 by addition of 10% aqueous H$_2$SO$_4$ solution. The resulting mixture was extracted with DCM (3×10 mL) and the combined organic layers dried (Na$_2$SO$_4$) and concentrated to give the title compound (540 mg, 85%) as a yellow solid. LCMS-C: RT 1.20 min; m/z 320.2 [M+H]$^+$.

(xxxi) 5-Chloro-2-((tetrahydro-2H-pyran-4-yl)oxoisonicotinic acid I81

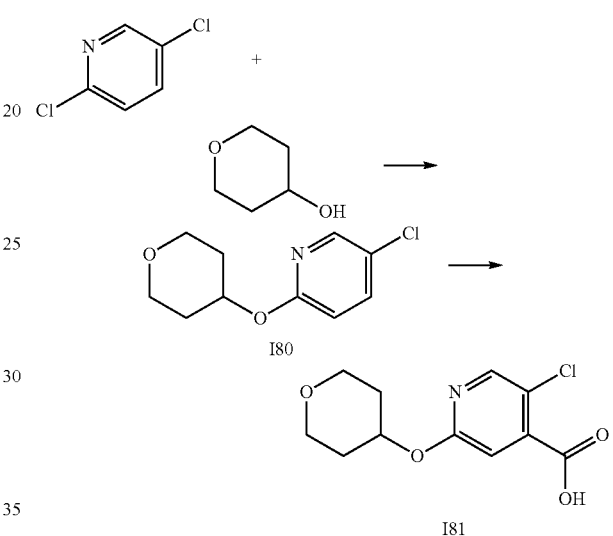

I81

(a) 5-Chloro-2-((tetrahydro-2H-pyran-4-yl)oxy)pyridine I80

To a solution of tetrahydro-2H-pyran-4-ol (1.0 g, 10 mmol) in DMF (25 mL) at 0° C. was added NaH in mineral oil (60% wt, 1.2 g, 30 mmol) and the mixture was stirred at 0° C. for 30 minutes. 2,5-Dichloropyridine (1.8 g, 12 mmol) was added and the resulting mixture was heated at 60° C. for 2 hours, then cooled to room temperature and allowed to stir overnight. The reaction was partitioned between EtOAc (50 mL) and water and the organic fraction washed with water (3×50 mL) and brine, dried (Na$_2$SO$_4$) and concentrated. The crude material obtained was purified by silica gel chromatography (2% EtOAc in petroleum ether) to give the title compound (1.3 g, 62%). LCMS-C: RT 2.65 min; m/z 214.1 [M+H]$^+$.

(b) 5-Chloro-2-((tetrahydro-2H-pyran-4-yl)oxy)isonicotinic acid I81

To a solution of diisopropylamine (284 mg, 2.81 mmol) in anhydrous THF (20 mL) at –5° C. was added n-BuLi (2.4M in hexane, 1.2 mL, 2.81 mmol) slowly under a nitrogen atmosphere. The mixture was then stirred at –15° C. to –5° C. for 30 minutes, then cooled to –78° C. and a solution of 5-chloro-2-((tetrahydro-2H-pyran-4-yl)oxy)pyridine I80 (500 mg, 2.34 mmol) in anhydrous THF (5 mL) was added dropwise. The resulting mixture was stirred at –78° C. for 2 hours and then CO$_2$ (g) was bubbled through the mixture for 15 minutes. Water (10 mL) was added and the mixture extracted with diethyl ether (×2). The aqueous layer was separated and acidified to pH 3 by addition of 10% aqueous $H_2SO_4$, the aqueous layer was extracted with DCM (×2) and the combined organic layers washed with water and brine, dried ($Na_2SO_4$) and concentrated to give the title compound (240 mg, 40%) as a white solid. LCMS-C: RT 1.77 min; m/z 258.2[M+H]$^+$.

(xxxii) Lithium 6-((1-(methoxycarbonyl)piperidin-4-yl)oxy)pyrimidine-4-carboxylate I86

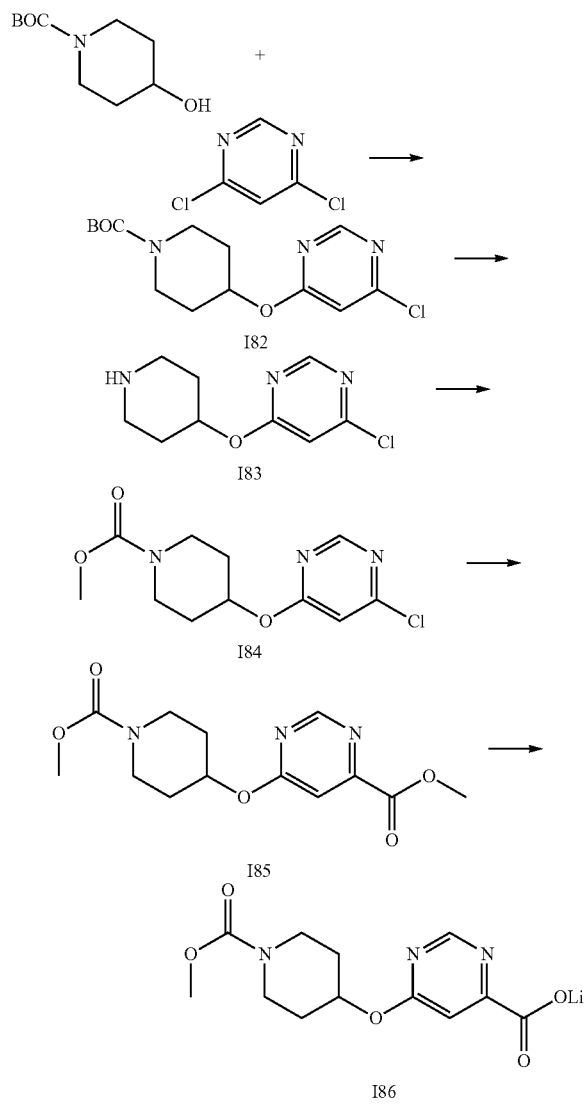

(a) tert-Butyl 4-((6-chloropyrimidin-4-yl)oxy)piperidine-1-carboxylate I82

To a solution of tert-butyl 4-hydroxypiperidine-1-carboxylate (3.2 g, 16.1 mmol) in THF (45 mL) was added NaH in mineral oil (60% wt, 0.97 g, 24.2 mmol) and the mixture was stirred at 60° C. for 1 hour, then cooled to room temperature and a solution of 4,6-dichloropyrimidine (2.0 g, 13.4 mmol) in THF (15 mL) was added. The resulting mixture was then stirred at room temperature for 2 hours. Water (50 mL) was added and the reaction mixture was extracted with EtOAc (×2). The combined organic layers were washed with brine, dried ($Na_2SO_4$) and concentrated to give the title compound (4.3 g, 100%) as a yellow oil. LCMS-C: RT 2.95 min; m/z 314.1 [M+H]$^+$.

(b) 4-Chloro-6-(piperidin-4-yloxy)pyrimidine dihydrochloride I83

A solution of tert-butyl 4-((6-chloropyrimidin-4-yl)oxy)piperidine-1-carboxylate I82 (4.3 g, 13.4 mmol) in HCl/EtOAc (4 M, 40 mL) was stirred at room temperature for 2 hours. The reaction mixture was concentrated and the residue was washed with diethyl ether and dried to give the title compound (3.3 g, 86%) as a yellow solid. LCMS-C: RT 0.31 min; m/z 214.1 [M+H]$^+$ for free base.

(c) Methyl 4-((6-chloropyrimidin-4-yl)oxy)piperidine-1-carboxylate I84

To a solution of 4-chloro-6-(piperidin-4-yloxy)pyrimidine dihydrochloride I83 (3.3 g, 11.5 mmol) and $Et_3N$ (5.8 g, 57.6 mmol) in DCM (40 mL) was added methyl chloroformate (1.3 g, 13.8 mmol). The reaction was then stirred at room temperature for 2 hours. Water (100 mL) was added and the aqueous extracted with DCM (×2). The combined organic layers were washed with saturated aqueous $NaHCO_3$, water, and brine, dried ($Na_2SO_4$) and concentrated to give the title compound (2.6 g, 83%) as a yellow oil. LCMS-C: RT 2.47 min; m/z 272.1 [M+H]$^+$.

(d) Methyl 6-((1-(methoxycarbonyl)piperidin-4-yl)oxy)pyrimidine-4-carboxylate I85

A mixture of methyl 4-((6-chloropyrimidin-4-yl)oxy)piperidine-1-carboxylate I84 (500 mg, 1.84 mmol), $PdCl_2$ (dppf) (67 mg, 0.09 mmol) and $Et_3N$ (372 mg, 3.68 mmol) in MeOH (10 mL) under an atmosphere of CO (g) was heated at 50° C. for 6 hours. The reaction mixture was concentrated in vacuo and the residue obtained purified by silica gel chromatography (33% EtOAc in petroleum ether) to give the title compound (330 mg, 61%) as a yellow oil. LCMS-C: RT 2.35 min; m/z 296.3 [M+H]$^+$.

(e) Lithium 6-((1-(methoxycarbonyl)piperidin-4-yl)oxy)pyrimidine-4-carboxylate I86

To a solution of methyl 6-((1-(methoxycarbonyl)piperidin-4-yl)oxy)pyrimidine-4-carboxylate 185 (100 mg, 0.34 mmol) in a mixture of THF (1 mL), MeOH (2 mL) and water (1 mL) was added $LiOH.H_2O$ (30 mg, 0.68 mmol). The reaction was stirred at room temperature overnight, then concentrated and the residue was lyophilized to give a crude product (110 mg) as yellow solid which was used in the next step without further purification. LCMS-C: RT 1.21 min; m/z 282.1 [M-Li+2H]$^+$.

(xxxiii) 2-Ethoxy-4-(2-oxo-2-(pyrrolidin-1-yl)ethyl)benzoic acid I88

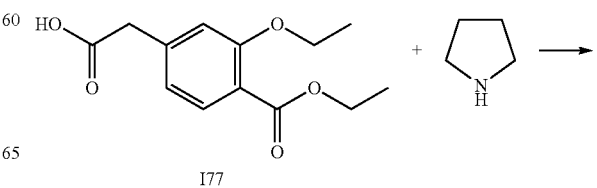

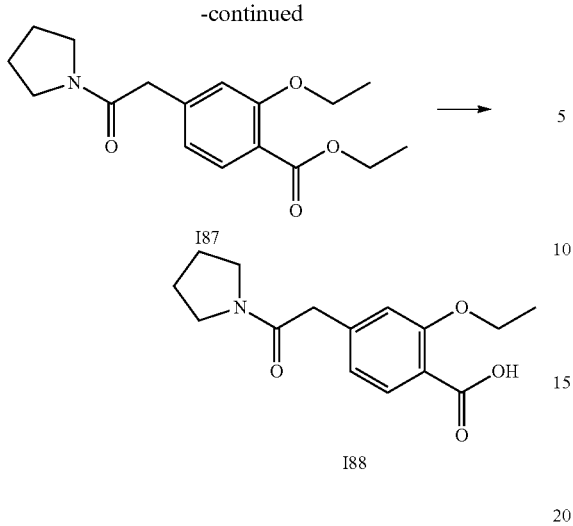

(a) Ethyl 2-ethoxy-4-(2-oxo-2-(pyrrolidin-1-yl)ethyl)benzoate I87

A solution of 2-(3-ethoxy-4-(ethoxycarbonyl)phenyl)acetic acid (170 mg, 0.67 mmol), pyrrolidine (47.9 mg, 0.67 mmol), EDCl (154 mg, 0.8 mmol), HOBt (9.5 mg, 0.07 mmol) and DIPEA (173 mg, 1.34 mmol) in DCM (5 mL) was stirred at room temperature overnight. Water (5 mL) was added and the reaction mixture was extracted with DCM (3×5 mL). The combined organic layers were washed with saturated aqueous NaHCO$_3$, water and brine, dried (Na$_2$SO$_4$) and concentrated to give the title compound (170 mg, 83%) as a yellow oil. LCMS-C: RT 2.47 min; m/z 306.1 [M+H]$^+$.

(b) 2-Ethoxy-4-(2-oxo-2-(pyrrolidin-1-yl)ethyl)benzoic acid I88

To a solution of ethyl 2-ethoxy-4-(2-oxo-2-(pyrrolidin-1-yl)ethyl)benzoate I87 (170 mg, 0.56 mmol) in a mixture of THF (2 mL), MeOH (4 mL) and water (2 mL) was added LiOH.H$_2$O (47 mg, 1.1 mmol) and the mixture was stirred at room temperature overnight. The reaction mixture was concentrated in vacuo and the residue re-dissolved in water (5 mL) and acidified to pH 2 with 10% aqueous H$_2$SO$_4$. The aqueous layer was extracted with DCM (3×5 mL) and the combined organic fractions dried (Na$_2$SO$_4$) and concentrated to give the title compound (120 mg, 77%) as a yellow solid. LCMS-C: RT 1.76 min; m/z 278.1 [M+H]$^+$.

(xxxiv) 2-Ethoxy-3-methyl-4-(morpholine-4-carbonyl)benzoic acid I95

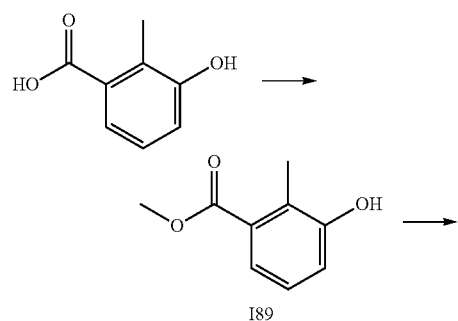

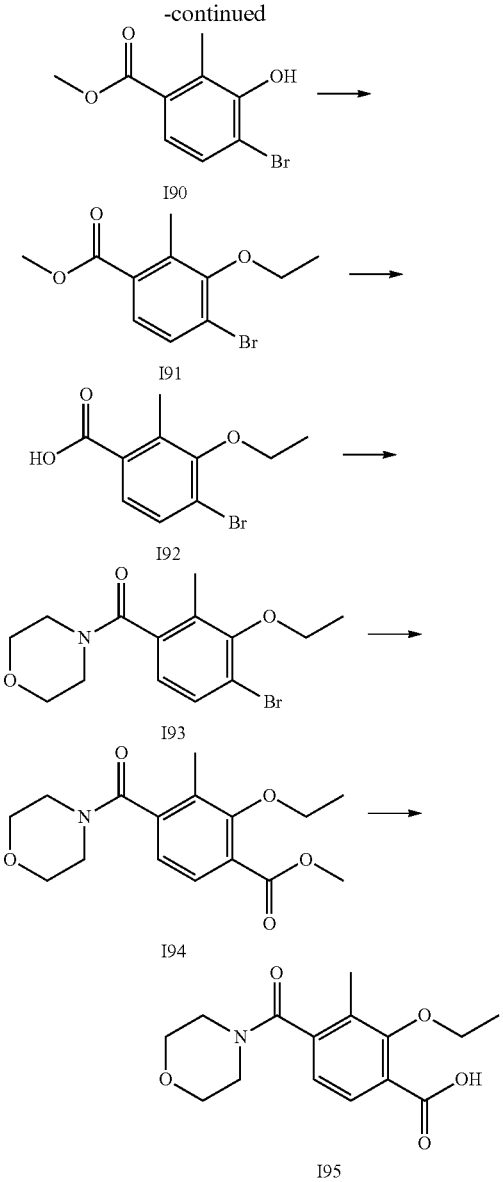

(a) Methyl 3-hydroxy-2-methylbenzoate I89

To a solution of 3-hydroxy-2-methylbenzoic acid (10.0 g, 65.7 mmol) in MeOH (100 mL) was added SOCl$_2$ (15.6 g, 131.5 mmol) slowly and the mixture was stirred at 50° C. overnight. The reaction mixture was concentrated and the residue dissolved in DCM (100 mL). The organic solution was washed with saturated aqueous NaHCO$_3$, dried (Na$_2$SO$_4$) and concentrated to give the title compound (10.7 g, 98%) as a white solid. LCMS-C: RT 1.98 min; m/z 167.1 [M+H]$^+$.

(b) Methyl 4-bromo-3-hydroxy-2-methylbenzoate I90

To a solution of tert-butylamine (2.0 g, 27.1 mmol) in DCM (180 mL) at −70° C. was added a solution of Br$_2$ (4.2 g, 27.1 mmol) in DCM (10 mL) dropwise and the mixture was stirred at −70° C. for 1 hour. A solution of methyl 3-hydroxy-2-methylbenzoate I89 (4.5 g, 27.1 mmol) in DCM (10 mL) was then added dropwise and the resulting mixture allowed to warm to room temperature and stirred overnight. The reaction was quenched by addition of water (30 mL) and the aqueous layer extracted with DCM (3×50 mL). The combined organic layers were washed with brine, dried ($Na_2SO_4$) and concentrated. The crude residue obtained was purified by silica gel chromatography (2% EtOAc in petroleum ether) to give the title compound (2.2 g, 33%) as a white solid. LCMS-C: RT 2.46 min; m/z 245.0, 247.0 [M+H]$^+$. $^1$H NMR (400 MHz, DMSO-$d_6$) δ 9.38 (s, 1H), 7.46 (d, J=8.4 Hz, 1H), 7.17 (d, J=8.4 Hz, 1H), 3.80 (s, 3H), 2.38 (s, 3H).

(c) Methyl 4-bromo-3-ethoxy-2-methylbenzoate I91

To a solution of methyl 4-bromo-3-hydroxy-2-methylbenzoate I90 (2.1 g, 8.6 mmol) in DMSO (10 mL) was added $K_2CO_3$ (3.5 g, 25.8 mmol) and ethyl bromide (1.4 g, 12.9 mmol). The reaction was then stirred at 40° C. overnight. Water (30 mL) was added and the aqueous extracted with DCM (3×20 mL). The organic layer was washed with water (10×30 mL), dried ($Na_2SO_4$), and concentrated to give the title compound (2.2 g, 95%) as a yellow solid. LCMS-C: RT 3.08 min; m/z 273.0, 275.0 [M+H]$^+$.

(d) 4-Bromo-3-ethoxy-2-methylbenzoic acid I92

To a solution of methyl 4-bromo-3-ethoxy-2-methylbenzoate I91 (2.1 g, 10.0 mmol) in a mixture of MeOH (10 mL) and water (0.2 mL) was added NaOH (0.4 g, 20.0 mmol). The reaction was stirred at room temperature overnight then the solvent was removed under reduced pressure. The residue obtained was re-dissolved in water (20 mL) and acidified with 1M HCl to pH 2. The aqueous layer was extracted with DCM (4×20 mL) and the combined organic layers dried ($Na_2SO_4$) and concentrated to give the title compound (2.4 g, 92%) as a white solid. LCMS-C: RT 2.75 min; m/z 281.0, 283.0 [M+Na]$^+$.

(e) (4-Bromo-3-ethoxy-2-methylphenyl)(morpholino)methanone I93

To a solution of 4-bromo-3-ethoxy-2-methylbenzoic acid I92 (2.4 g, 9.3 mmol) in DCM (500 mL) at 0° C. was added oxalyl chloride (3.5 g, 27.9 mmol) and DMF (0.2 mL). The reaction was stirred for 3 hours then morpholine (1.6 g, 18.6 mmol) and triethylamine (4.1 g, 40.9 mmol) were added and stirring was continued overnight at 0° C. Water (100 mL) was added and the mixture was extracted with DCM (2×100 mL), the combined organic layers were washed with brine, dried ($Na_2SO_4$) and concentrated. The residue obtained was purified by silica gel chromatography (1% MeOH in DCM) to give the title compound (720 mg, 24%) as a white solid. LCMS-C: RT 2.48 min; m/z 328.1, 330.1 [M+H]$^+$.

(f) Methyl 2-ethoxy-3-methyl-4-(morpholine-4-carbonyl)benzoate I94

To a solution of (4-bromo-3-ethoxy-2-methylphenyl)(morpholino)methanone I93 (720 mg, 2.2 mmol) in MeOH (10 mL) was added $PdCl_2$(dppf) (81 mg, 0.11 mmol) and TEA (489 mg, 4.8 mmol). The reaction was then heated at reflux overnight under a CO atmosphere. The mixture was concentrated and the residue obtained dissolved in DCM (20 mL), washed with water and brine, dried ($Na_2SO_4$) and concentrated. The residue obtained was purified by silica gel chromatography (1% MeOH in DCM) to give the title compound (670 mg) as a yellow oil. LCMS-C: RT 2.02 min; m/z 308.2 [M+H]$^+$.

(g) 2-Ethoxy-3-methyl-4-(morpholine-4-carbonyl)benzoic acid I95

To a solution of methyl 2-ethoxy-3-methyl-4-(morpholine-4-carbonyl)benzoate I94 (670 mg, 2.2 mmol) in a mixture of THF (1 mL), MeOH (10 mL) and water (0.1 mL) was added LiOH.$H_2O$ (275 mg, 6.5 mmol) The reaction was stirred at room temperature overnight, then concentrated under reduced pressure. The residue obtained was re-dissolved in water (20 mL) then acidified with 1M HCl to pH 2. The aqueous mixture was extracted with DCM (10 mL×3) and the combined organic layers were dried ($Na_2SO_4$) and concentrated to give the title compound (310 mg, 48%) as a brown oil. LCMS-C: RT 0.89 min; m/z 294.1 [M+H]$^+$.

(xxxv) 2-Fluoro-4-(3-oxa-8-aza-bicyclo[3.2.1]octane-8-carbonyl)-benzoic acid I97

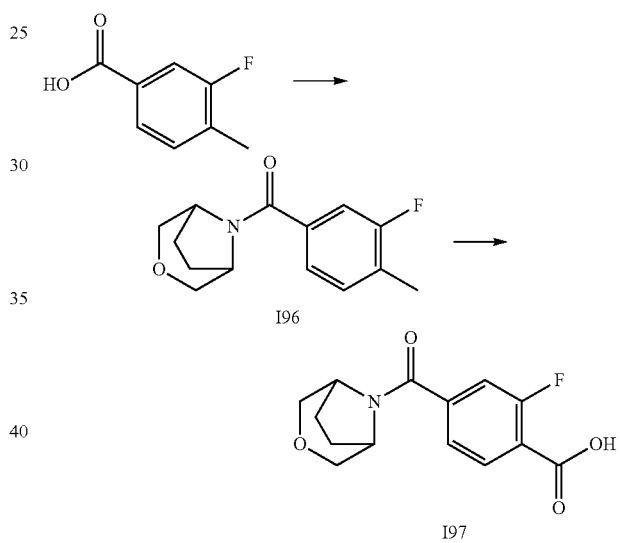

(a) (3-Fluoro-4-methyl-phenyl)-(3-oxa-8-aza-bicyclo[3.2.1]oct-8-yl)-methanone I96

To a solution of 3-fluoro-4-methylbenzoic acid (2.0 g, 13.0 mmol) and 3-oxa-8-azabicyclo[3.2.1]octane hydrochloride (1.8 g, 11.8 mmol) in DCM (10 mL) were added DIPEA (6.3 mL, 35.4 mmol), EDCl (2.72 g, 14.2 mmol) and HOBt (162.1 g, 1.2 mmol). The mixture was then stirred at room temperature overnight. Saturated aqueous $NaHCO_3$ (50 mL) was added and the mixture was extracted with DCM (3×50 mL). The combined organic extracts were dried ($Na_2SO_4$) and concentrated and the residue was purified by chromatography (5% EtOAc/petroleum ether) to give the title compound as a yellow solid (1.7 g, 58%). LCMS-C: RT 2.30 min; m/z 250.1 [M+H]$^+$.

(b) 2-Fluoro-4-(3-oxa-8-aza-bicyclo[3.2.1]octane-8-carbonyl)-benzoic acid I97

To a solution of (3-fluoro-4-methyl-phenyl)-(3-oxa-8-aza-bicyclo[3.2.1]oct-8-yl)-methanone 196 (800 mg, 3.2 mmol) in a mixture of pyridine (6 mL) and H$_2$O (12 mL) was added KMnO$_4$ (5.1 g, 32 mmol) and the mixture was stirred at room temperature for 2 days. The resulting suspension was filtered through Celite and the filtrate washed with DCM (3×50 mL). The remaining aqueous layer was acidified to pH 3 by addition of 2M HCl, and extracted with DCM (4×60 mL). The combined organic layers were dried (Na$_2$SO$_4$) and concentrated to give the title compound as an off-white solid (500 mg, 56%). LCMS-C: RT 2.89 min; m/z 280.1 [M+H]$^+$.

(xxxvi) 6-(3-Oxa-8-azabicyclo[3.2.1]octane-8-carbonyl)-4-ethoxynicotinic acid I103

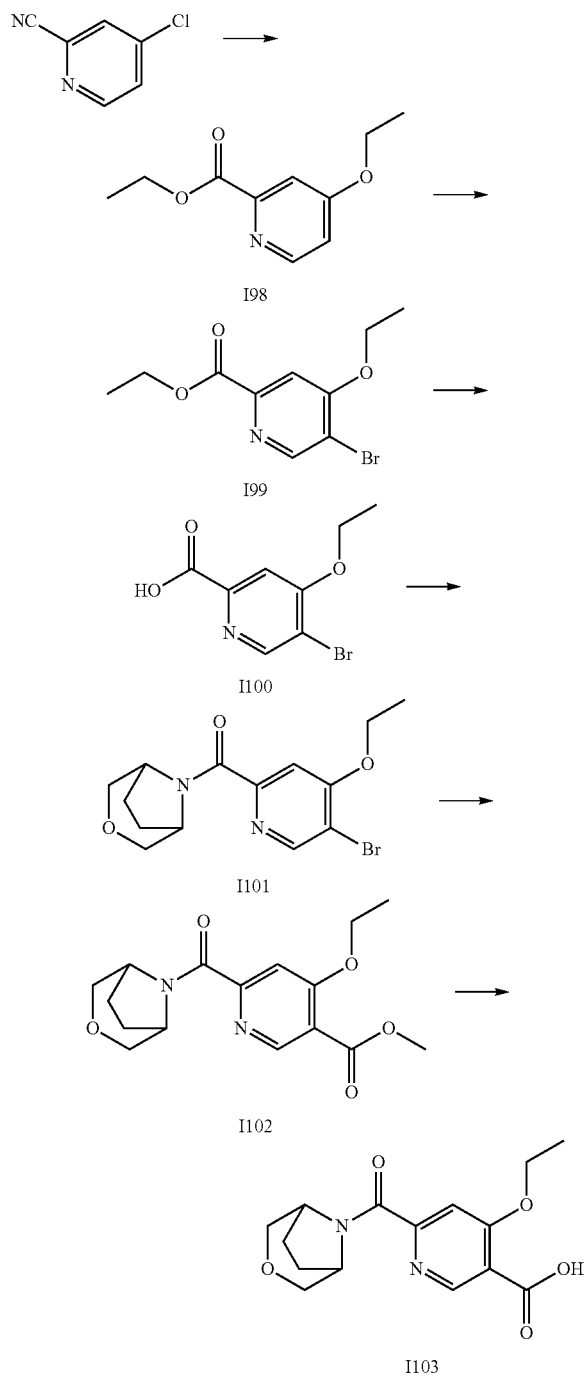

(a) Ethyl 4-ethoxypicolinate I98

A solution of 4-chloropicolinonitrile (5.5 g, 39.7 mmol) in saturated HCl/EtOH solution (80 mL) was stirred at 80° C. for 2 days. The solvent was removed under reduced pressure, saturated aqueous NaHCO$_3$ (200 mL) was added and the aqueous layer extracted with DCM (3×200 mL). The pooled organic extracts were dried (Na$_2$SO$_4$) and concentrated to give the title compound as a white solid (2.6 g, 34%). $^1$H NMR (400 MHz, CDCl$_3$) δ 8.52 (d, J=5.6 Hz, 1H), 7.63 (d, J=2.4 Hz, 1H), 6.93-6.91 (m, 1H), 4.80-4.43 (m, 2H), 4.16-4.11 (m, 2H), 1.46-1.41 (m, 6H). LCMS-C: RT 1.35 min; m/z 196.1[M+H]$^+$.

(b) Ethyl 5-bromo-4-ethoxypicolinate I99

To a solution of ethyl 4-ethoxypicolinate I98 (1.6 g, 8.2 mmol) in concentrated H$_2$SO$_4$ (80 mL) was added NBS (2.7 g, 14.8 mmol). The reaction was stirred at room temperature overnight then quenched by addition of saturated aqueous NaHCO$_3$ (150 mL). The aqueous layer was extracted with DCM (3×130 mL) and the combined organic layers dried (Na$_2$SO$_4$) and concentrated to give the title compound as a yellow solid (2.0 g, 91%). $^1$H NMR (400 MHz, CDCl$_3$) δ 8.67 (s, 1H), 7.63 (s, 1H), 4.94-4.40 (m, 2H), 4.29-4.23 (m, 2H), 1.54-1.51 (m, 3H), 1.46-1.42 (m, 3H); LCMS-C: RT 2.59 min; m/z 274.0, 276.0 [M+H]$^+$.

(c) 5-Bromo-4-ethoxypicolinic acid I100

To a solution of ethyl 5-bromo-4-ethoxypicolinate I99 (1.6 g, 6.0 mmol) in a mixture of THF (20 mL), MeOH (2 mL) and H$_2$O (0.2 mL) was added LiOH.H$_2$O (1.0 g, 24.0 mmol). The reaction was then stirred at room temperature for 2 days. The solvent was removed under reduced pressure and the residue obtained dissolved in water (10 mL) and acidified to pH 3 with 1 M HCl. The aqueous phase was extracted with DCM (4×50 mL) and the pooled organic extracts dried (Na$_2$SO$_4$) and concentrated to give the title compound as a yellow solid (800 mg, 54%). LCMS-C: RT 0.86 min; m/z 246.0, 248.0 [M+H]$^+$ (d) 3-Oxa-8-azabicyclo[3.2.1]octan-8-yl(5-bromo-4-ethoxypyridin-2-yl)methanone I101

To a solution of 5-bromo-4-ethoxypicolinic acid I100 (300 mg, 1.2 mmol) and 3-oxa-8-azabicyclo[3.2.1]octane hydrochloride (153 mg, 1.0 mmol) in DCM (5 mL) were added DIPEA (0.72 mL, 4.1 mmol), EDCl (393 mg, 2.0 mmol) and HOBt (15 mg, 0.1 mmol). The mixture was stirred at room temperature overnight, then quenched by addition of saturated aqueous NaHCO$_3$ (50 mL) and the mixture was extracted with DCM (3×50 mL). The combined organic layers were dried (Na$_2$SO$_4$) and concentrated and the residue obtained purified by chromatography (20% EtOAc/petroleum ether) to give the title compound as a yellow solid (262 mg, 75%). LCMS-C: RT 5.56 min; m/z 340.9, 342.9 [M+H]$^+$ (e) Methyl 6-(3-oxa-8-azabicyclo[3.2.1]octane-8-carbonyl)-4-ethoxynicotinate I102

To a solution of 3-oxa-8-azabicyclo[3.2.1]octan-8-yl(5-bromo-4-ethoxypyridin-2-yl)methanone I101 (650 mg, 1.9 mmol) in MeOH (50 mL) was added Et$_3$N (577 mg, 5.7 mmol) and PdCl$_2$(dppf) (73 mg, 0.05 mmol). The reaction was then heated at reflux for 2 days under an atmosphere of CO. The solvent was removed under reduced pressure and the residue obtained taken up in water (100 mL) and extracted with DCM (3×100 mL). The combined organic layers were dried over (Na$_2$SO$_4$) and concentrated. The residue obtained was purified by chromatography (33% EtOAc/petroleum ether) to give the title compound as a brown solid (400 mg, 66%). LCMS-C: RT 4.94 min; m/z 320.8 [M+H]$^+$.

(f) 6-(3-Oxa-8-azabicyclo[3.2.1]octane-8-carbonyl)-4-ethoxynicotinic acid I103

To a solution of methyl 6-(3-oxa-8-azabicyclo[3.2.1]octane-8-carbonyl)-4-ethoxynicotinate I102 (350 mg, 1.1 mmol) in MeOH (20 mL) was added 1 M aqueous NaOH (2.2 mL) and the mixture was stirred at room temperature overnight. The solvent was removed under reduced pressure and the residue obtained taken up in water (15 mL). The aqueous was acidified to pH 4 by addition of 1M HCl, then extracted with DCM (4×60 mL) and the pooled extracts dried (Na$_2$SO$_4$) and concentrated to give the title compound as a yellow solid (320 mg, 95%). LCMS-C: RT 0.61 min; m/z 307.1 [M+H]$^+$.

(xxxvii) 4-(3-Oxa-8-azabicyclo[3.2.1]octane-8-carbonyl)-2-chlorobenzoic acid 105

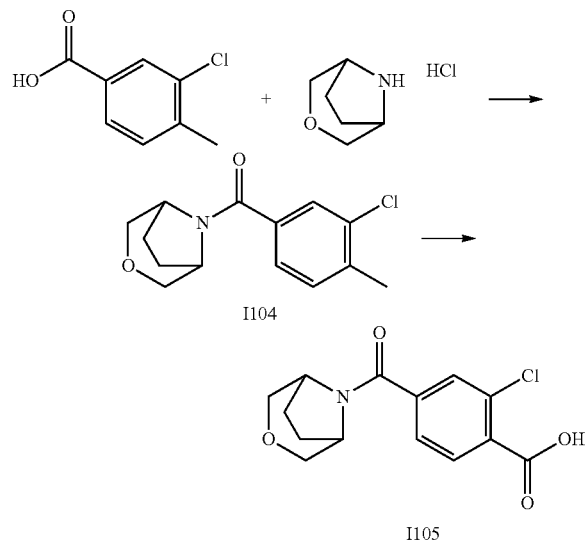

(a) 3-Oxa-8-azabicyclo[3.2.1]octan-8-yl(3-chloro-4-methylphenyl)methanone I104

To a solution of 3-chloro-4-methylbenzoic acid (2.26 g, 13.24 mmol) in DCM (20 mL) was added DIPEA (4.7 g, 36.10 mmol), EDCl (3.5 g, 18.05 mmol), HOBt (190 mg, 1.40 mmol) and 3-oxa-8-azabicyclo[3.2.1]octane hydrochloride (1.8 g, 12.03 mmol). The resulting mixture was stirred at room temperature overnight, then diluted with water (10 mL) and partitioned against DCM (10 mL). The aqueous layer was extracted with DCM (3×5 mL) and the combined organic extracts washed with saturated NaHCO$_3$ (3×5 mL) and brine (3×5 mL), dried (Na$_2$SO$_4$), filtered and concentrated. The crude product was purified by silica gel chromatography (ethyl acetate/petroleum ether=1/10) to give the title compound (3.0 g, 92%) as a white solid. $^1$HNMR (400 MHz, Methanol-d$_4$) δ 7.50 (d, J=1.6 Hz, 1H), 7.40 (d, J=7.6 Hz, 1H), 7.33 (dd, J=7.6, 1.6 Hz, 1H), 4.61-4.56 (m, 1H), 3.99 (s, 1H), 3.78-3.59 (m, 4H), 2.41 (s, 3H), 2.00-1.99 (m, 4H); LCMS-C: RT 2.51 min; m/z 266.1 [M+H]$^+$ (b) 4-(3-oxa-8-azabicyclo[3.2.1]octane-8-carbonyl)-2-chlorobenzoic acid I105

To a solution of 3-oxa-8-azabicyclo[3.2.1]octan-8-yl(3-chloro-4-methylphenyl)methanone I104 (500 mg, 1.88 mmol) in a mixture of pyridine (5 mL) and water (15 mL) was added KMnO$_4$ (1.78 g, 11.28 mmol) in portions. The resulting mixture was heated to 50° C. and stirred for 48 hours. The mixture was filtered and the filtrate was extracted with ethyl acetate (3×5 mL). The pH of the aqueous phase was adjusted to pH 1-2 by addition of concentrated HCl, then extracted with DCM (8×5 mL). The combined organic extracts were dried (Na$_2$SO$_4$), filtered and concentrated to give the title compound (340 mg, 61%) as a white solid. LCMS RT 0.88 min; m/z 296.1 [M+H]$^+$.

(xxxviii) 2-(Trifluoromethyl)-1H-benzo[d]imidazole-6-carboxylic acid I106

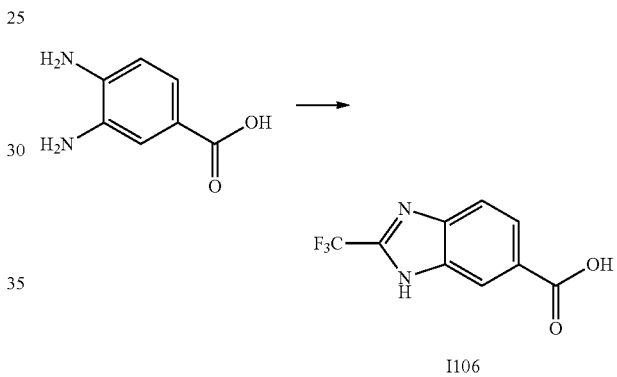

A solution of 3,4-diaminobenzoic acid (1.0 g, 6.6 mmol) in TFA (15 mL) was stirred at 70° C. for 16 hours. The reaction mixture was concentrated, the crude material was purified by column chromatography (DCM:methanol=50:1) to give the title compound as an off-white solid (1.3 g, 86%). LCMS-C: RT 1.76 min; m/z 231.1 [M+H]$^+$.

(xxxix) 4-(3-Oxa-8-azabicyclo[3.2.1]octane-8-carbonyl)-3-(difluoromethyl)benzoic acid I110

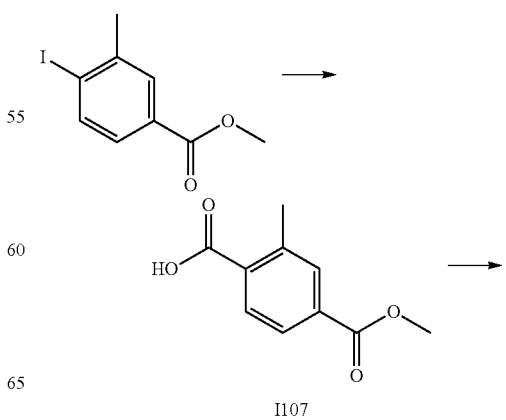

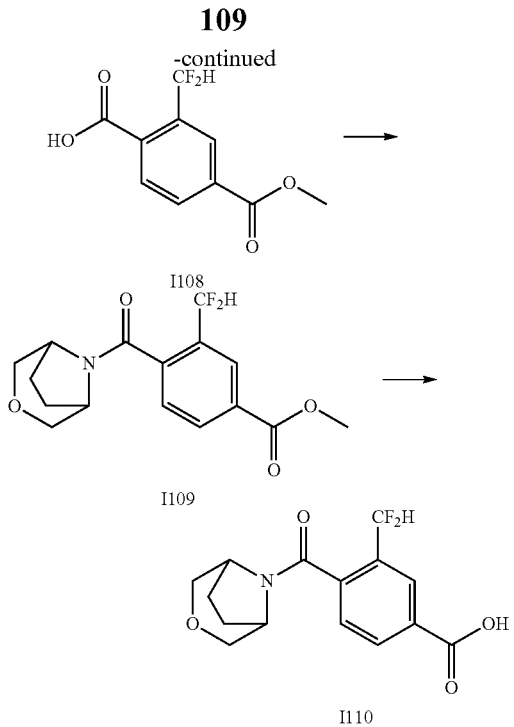

(a) 4-(Methoxycarbonyl)-2-methylbenzoic acid I107

A solution of methyl 4-iodo-3-methylbenzoate (2.0 g, 7.2 mmol) in THF (30 mL) under $N_2$ was cooled to −20° C., a solution of iso-propylmagnesium chloride (2 M in THF, 4 mL, 8.0 mmol) was added dropwise and the suspension stirred at −20° C. for 1 hour. $CO_2$ (g) was bubbled through the mixture, and the reaction stirred at room temperature for 1 hour. The solvent was evaporated and water was added, the aqueous layer was washed with DCM (15 mL×3) and the pH adjusted to 3 by addition of 3M HCl. The mixture was extracted with DCM (15 mL×3) and the combined organic layers dried ($Na_2SO_4$) and concentrated to give the title compound as a white solid (870 mg, 88%). LCMS-C: RT 2.26 min; m/z 195.1 [M+H]$^+$.

(b) 2-(Difluoromethyl)-4-(methoxycarbonyl)benzoic acid I108

To a solution of 4-(methoxycarbonyl)-2-methylbenzoic acid I107 (450 mg, 2.3 mmol) in MeCN (20 mL) and water (20 mL) was added $AgNO_3$ (79 mg, 0.5 mmol), $Na_2S_2O_8$ (552 mg, 2.3 mmol) and Selectfluor® (4.6 g, 13.9 mmol). The resulting mixture was stirred at 80° C. for 6 hours. Further $AgNO_3$ (19 mg, 0.003 mmol), $Na_2S_2O_8$ (138 mg, 0.6 mmol) and Selectfluor® (1.2 g, 3.5 mmol) were added and the resulting mixture was stirred at 80° C. for 3 hours. The pH of the reaction mixture was adjusted to pH 9 by addition of saturated aqueous $NaHCO_3$ solution and washed with DCM (20 mL×2). The pH of the aqueous fraction that remained was adjusted to 3-4 by addition of 2M HCl solution and extracted with DCM (20 mL×3). The combined organic layers were washed with brine (10 mL×2), dried ($Na_2SO_4$) and concentrated to give the title compound (180 mg, 41%) as a yellow solid. LCMS-C: RT 2.30 min; m/z 229.1 [M−H]$^+$.

(c) Methyl4-(3-oxa-8-azabicyclo[3.2.1]octane-8-carbonyl)-3-(difluoromethyl)benzoate I109

To a solution of 3-oxa-8-azabicyclo[3.2.1]octane hydrochloride (59 mg, 0.4 mmol) in DCM (5 mL) was added 2-(difluoromethyl)-4-(methoxycarbonyl)benzoic acid I108 (100 mg, 0.4 mmol), HOBt (5.3 mg, 0.04 mmol), DIPEA (102 mg, 0.79 mmol) and EDCl (91 mg, 0.5 mmol). The resulting mixture was stirred at room temperature overnight. The reaction mixture was partitioned against saturated aqueous $NaHCO_3$, the organic layer was washed with brine (4 mL×2), dried ($Na_2SO_4$) and concentrated. The residue was purified by prep TLC (DCM:methanol=20:1) to give the title compound as a white solid (45 mg, 35%). LCMS-C: RT 2.40 min; m/z 326.1 [M+H]$^+$.

(d) 4-(3-Oxa-8-azabicyclo[3.2.1]octane-8-carbonyl)-3-(difluoromethyl)benzoic acid I110

To a solution of methyl 4-(3-oxa-8-azabicyclo[3.2.1]octane-8-carbonyl)-3-(difluoromethyl) benzoate I109 (42 mg, 0.13 mmol) in a mixture of THF (5 mL), methanol (0.5 mL) and water (0.5 mL) was added LiOH.$H_2O$ (27 mg, 0.65 mmol). The resulting mixture was stirred at room temperature overnight. The reaction mixture was filtered and concentrated under reduced pressure. The residue obtained was diluted with water (3 mL) and the pH of the aqueous mixture was adjusted to 6 by addition of 2 M HCl. The aqueous solution was extracted with DCM (3 mL×2) and the combined organic layers washed with brine (2 mL×2), dried ($Na_2SO_4$) and concentrated to give the title compound as a white solid (49 mg, quantitative yield). LCMS-C: RT 1.95 min; m/z 312.1 [M+H]$^+$.

(xl) 4-(3-Oxa-8-azabicyclo[3.2.1]octane-8-carbonyl)-2-ethoxybenzoic acid I112

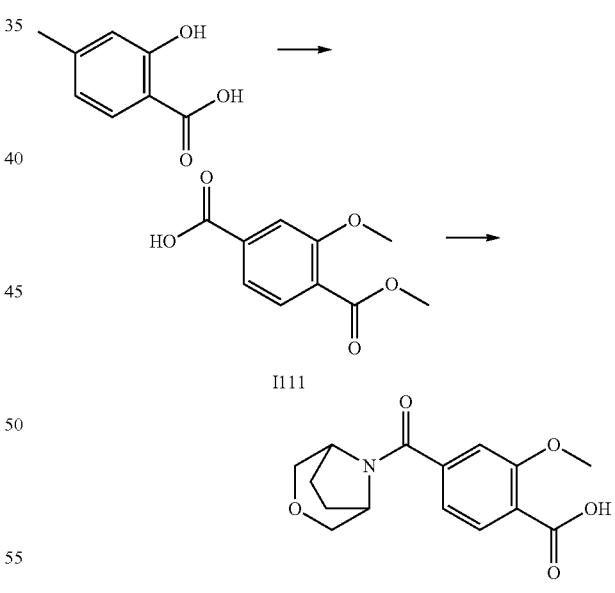

(a) 3-Methoxy-4-(methoxycarbonyl)benzoic acid I111

To a mixture of 2-hydroxy-4-methylbenzoic acid (10.0 g, 65.7 mmol) and $K_2CO_3$ (22.7 g, 164.3 mmol) in DMF (200 mL) at room temperature was added methyl iodide (20.5 g, 144.5 mmol) over a period of 10 minutes. The resulting mixture was stirred at room temperature overnight, then diluted with DCM (150 mL) and filtered. The filtrate was washed with water (200 mL×10) and brine (200 mL×2), dried (Na$_2$SO$_4$) and concentrated to give the intermediate as a yellow liquid (11.0 g).

To a solution of the intermediate in a mixture of pyridine (30 mL) and water (90 mL) was added KMnO$_4$ (30.37 g, 192.2 mmol). The resulting mixture was heated at 50° C. for 48 hours, then cooled and allowed to stir at room temperature for 24 hours. The mixture was filtered and the filter cake washed with hot water. The combined aqueous filtrates were washed with EtOAc (75 mL×3) and acidified to pH 2 with 2M aqueous HCl solution. The mixture was extracted with DCM (150 mL×3) and the combined organic layers were washed with brine, dried (Na$_2$SO$_4$) and concentrated to give the title compound as a white solid (7.0 g, 51% yield over 2 steps): LCMS-C: RT 1.24 min; m/z 211.0 [M+H]$^+$.

(b) 4-(3-Oxa-8-azabicyclo[3.2.1]octane-8-carbonyl)-2-methoxybenzoic acid I112

To a solution of 3-methoxy-4-(methoxycarbonyl)benzoic acid I111 (0.5 g, 2.4 mmol) in DCM (20 mL) was added 3-oxa-8-azabicyclo[3.2.1]octane hydrochloride (0.38 g, 2.5 mmol), HOBt (0.43 g, 3.2 mmol), triethylamine (0.85 g, 8.4 mmol) and EDCl (0.60 g, 3.2 mmol). The resulting mixture was stirred at room temperature overnight. Saturated aqueous NaHCO$_3$ was added, the organic layer was separated and the aqueous extracted with DCM (20 mL×2). The combined organic layers were washed with brine, dried (Na$_2$SO$_4$) and concentrated. The residue was purified by column chromatography (5% methanol in dichloromethane) to give the intermediate as a white solid.

To a solution of the intermediate in a mixture of THF (4 mL) and methanol (4 mL) was added aqueous NaOH (2 M, 4 mL). The resulting mixture was then stirred at room temperature for 14 hours. The solvent was removed, and the residue obtained was diluted with water (20 mL). The pH of the aqueous mixture was adjusted to 6 by addition of 2 M aqueous HCl solution. The mixture was extracted with DCM (20 mL×3) and the combined organic layers washed with brine (10 mL×2), dried (Na$_2$SO$_4$) and concentrated to give the title compound as a white solid (0.7 g, quantitative yield over 2 steps). LCMS-C: RT 0.55 min; m/z 292.1 [M+H]$^+$.

(xli) 2-(1-Acetylpiperidin-4-yl)-1H-benzo[d]imidazole-5-carboxylic acid I117

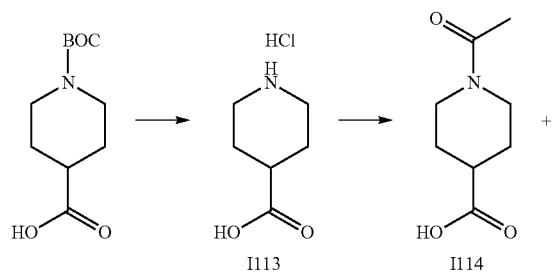

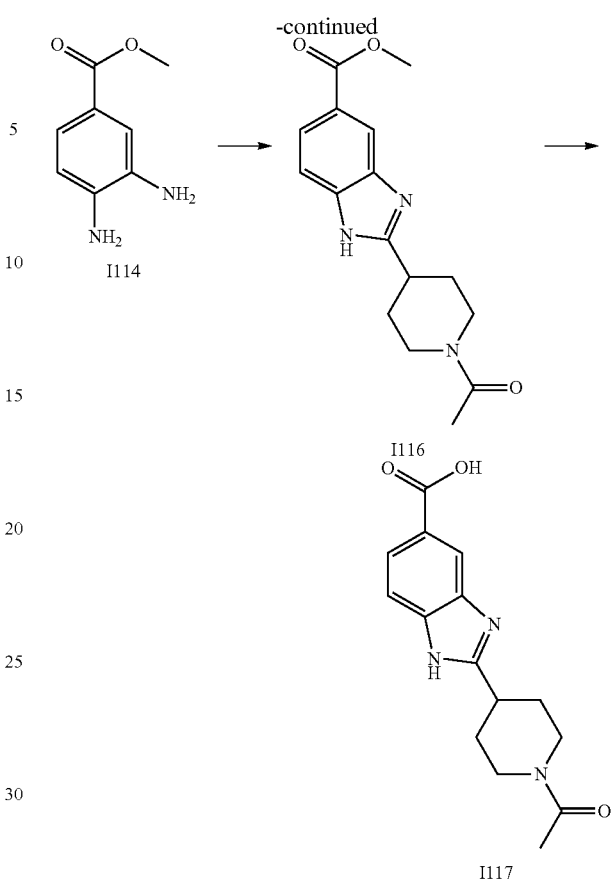

(a) Piperidine-4-carboxylic acid hydrochloride I113

A mixture of 1-(tert-butoxycarbonyl)piperidine-4-carboxylic acid (1.0 g, 4.4 mmol) in saturated EtOAc/HCl solution (10 mL) was stirred at room temperature for 2 hours. The mixture was concentrated to give the title compound (720 mg, 99%) as a white solid. LCMS-C: RT 0.72 min; m/z 130.1 [M+H]$^+$ for free base.

(b) 1-Acetylpiperidine-4-carboxylic acid I114

To a mixture of piperidine-4-carboxylic acid hydrochloride I113 (720 mg, 4.3 mmol) and Et$_3$N (528 mg, 5.2 mmol) in DCM (10 mL) was added Ac$_2$O (488 mg, 4.8 mmol). The reaction was stirred at room temperature overnight then concentrated and the residue obtained recrystallized from EtOH to give the title compound (400 mg, 54%) as a white solid. LCMS-C: RT 0.73 min; m/z 172.1 [M+H]$^+$.

(c) Methyl 2-(1-acetylpiperidin-4-yl)-1H-benzo[d]imidazole-5-carboxylate I16

A mixture of 1-acetylpiperidine-4-carboxylic acid I114 (200 mg, 1.2 mmol), methyl 3,4-diaminobenzoate (194 mg, 1.2 mmol), EDCl (269 mg, 1.4 mmol), HOBt (16 mg, 0.12 mmol) and DIPEA (302 mg, 2.3 mmol) in DCM (5 mL) was stirred at room temperature overnight. The precipitate was collected by filtration and the filter cake dried to give an intermediate compound (182 mg, 49%) as a yellow oil. LCMS-C: RT 4.27 min; m/z 319.9 [M+H]$^+$.

A mixture of the intermediate compound (130 mg, 0.41 mmol) in AcOH (5 mL) was heated at 65° C. for 3 hours to form a clear solution. The reaction mixture was neutralised with saturated aqueous NaHCO₃ to pH 6-7 and extracted with DCM (3×10 mL). The combined organic layers were washed with brine and dried (Na₂SO₄). The chemistry was repeated with a further 50 mg of starting material and the product from the two batches combined to give the title compound (110 mg, 65%). LCMS-C: RT 4.28 min; m/z 301.9 [M+H]⁺.

(d) 2-(1-Acetylpiperidin-4-yl)-1H-benzo[d]imidazole-5-carboxylic acid I117

To a mixture of methyl 2-(1-acetylpiperidin-4-yl)-1H-benzo[d]imidazole-5-carboxylate I116 (110 mg, 0.36 mmol) in a mixture of THF (1 mL), MeOH (2 mL) and water (1 mL) was added LiOH.H₂O (136 mg, 3.2 mmol) and the mixture was stirred at room temperature overnight. The reaction mixture was concentrated and the residue obtained re-dissolved in water (3 mL) then neutralised by addition of 10% aqueous H₂SO₄ to pH 6. The aqueous solution was lyophilized to give the crude title compound (300 mg) as yellow solid containing some Li₂SO₄ which was used in the next step without purification. LCMS-C: RT 0.30 min; m/z 288.1 [M+H]⁺.

(xlii) 2-Ethoxy-4-(5-methyl-1,3,4-oxadiazol-2-yl)benzoic acid I120

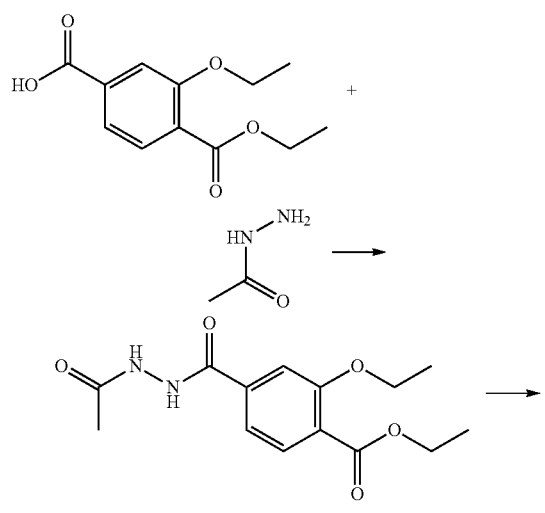

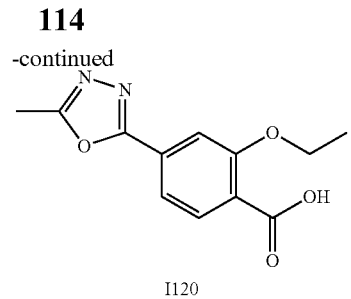

(a) Ethyl 4-(2-acetylhydrazinecarbonyl)-2-ethoxybenzoate I118

To a solution of 3-ethoxy-4-(ethoxycarbonyl)benzoic acid I40 (500 mg, 2.1 mmol) in DCM (20 mL) was added DIPEA (960 mg, 7.4 mmol), HOBt (30 mg, 0.2 mmol), EDCl (800 mg, 4.2 mmol) and acetohydrazide (156 mg, 2.1 mmol). The mixture was stirred at room temperature overnight then diluted with DCM (50 mL). The organic layer was washed with water (50 mL) and brine (50 mL), dried (Na₂SO₄) and concentrated. The residue was purified by column chromatography (100% DCM to 4% MeOH in DCM) to give the title compound as an off-white solid (350 mg, 57%). LCMS-C: RT 4.79 min; m/z 294.9 [M+H]⁺.

(b) Ethyl 2-ethoxy-4-(5-methyl-1,3,4-oxadiazol-2-yl)benzoate I119

A mixture of ethyl 4-(2-acetylhydrazinecarbonyl)-2-ethoxybenzoate I118 (330 mg, 1.1 mmol) in POCl₃ (3 mL) was heated at reflux for 1.5 hours. The mixture was poured into ice-water (20 mL) and the aqueous layer extracted with DCM (20 mL×2). The combined organic layers were washed with saturated NaHCO₃ (40 mL×3) and brine (40 mL), dried (Na₂SO₄) and concentrated to give the crude product as a yellow solid (290 mg, 94%). The crude product was used for the next step without purification. LCMS-C: RT 5.40 min; m/z 277.0 [M+H]⁺.

(c) 2-Ethoxy-4-(5-methyl-1,3,4-oxadiazol-2-yl)benzoic acid I120

To a solution of ethyl 2-ethoxy-4-(5-methyl-1,3,4-oxadiazol-2-yl)benzoate I119 (270 mg, 1.0 mmol) in MeOH (10 mL) was added a solution of NaOH (193 mg, 4.8 mmol) in water (2 mL). The resulting mixture was stirred at room temperature overnight. The solvent was removed and the residue obtained suspended in water (5 mL). The pH of the aqueous solution was adjusted to pH 4-5 by addition of 1 M aqueous HCl solution. The solid which precipitated was collected by filtration, washed with water (5 mL) and dried to give the title compound as a yellow solid (110 mg, 45%). LCMS-C: RT 4.77 min, m/z 249.0 [M+H],

(xliii) 2-Chloro-6-(oxetan-3-yloxy)isonicotinic acid I121

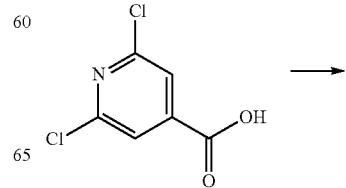

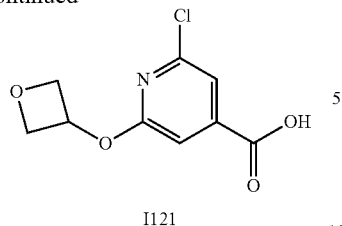

I121

To a mixture of oxetan-3-ol (1.1 g 15.6 mmol) in dry DMF (20 mL) was added NaH (60% in mineral oil, 832 mg, 20.8 mmol) at 0° C. under nitrogen atmosphere and the mixture was stirred for 30 minutes, then 2,6-dichloroisonicotinic acid (2.0 g, 10.4 mmol) was added. The resulting mixture was heated to 50° C. overnight. Water (20 mL) was added and the mixture was acidified with 1 M HCl to form a white suspension. The solid was collected by filtration to give the title compound (2.0 g, 83%) as a white solid. LCMS-C: RT 2.24 min; m/z 230.0, 232.0 [M+H]$^+$ (xliv) 6-((1-Acetylpiperidin-4-yl)oxy)pyridazine-4-carboxylic acid I124

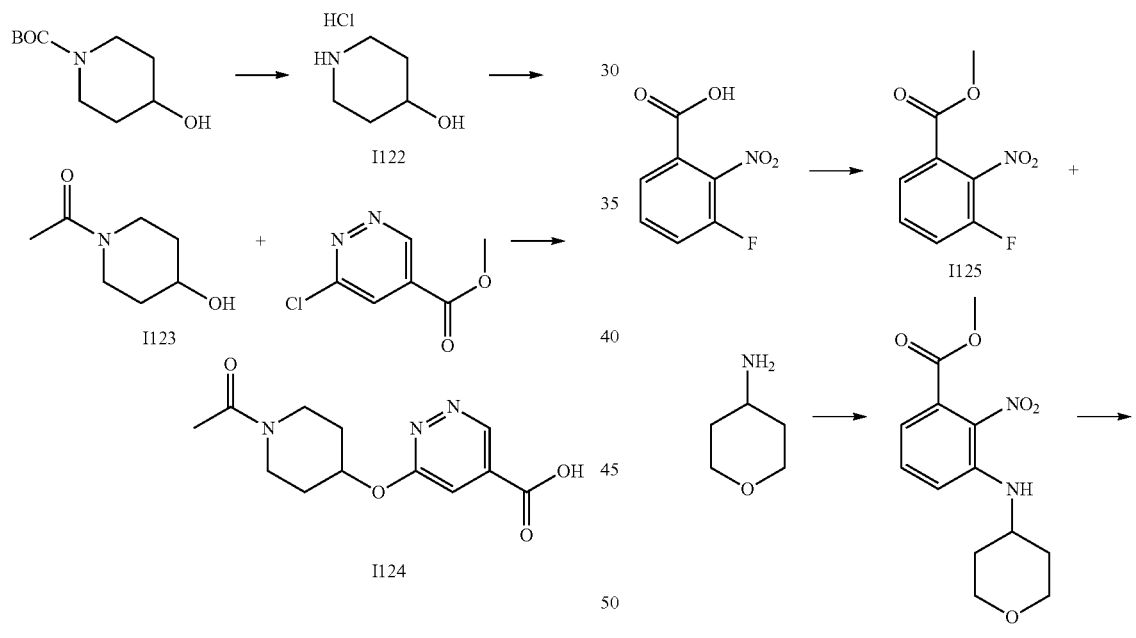

(a) Piperidin-4-ol hydrochloride I122

To a solution of tert-butyl 4-hydroxypiperidine-1-carboxylate (10.9 g, 49.7 mmol, 1.0 eq) in EtOAc (40 mL) was added a saturated solution of HCl in EtOAc (10 mL), and the resulting mixture was stirred at room temperature overnight. The mixture was concentrated to give the title compound (7.0 g) as a white solid.

(b) 1-(4-hydroxypiperidin-1-yl) ethanone I123

A mixture of piperidin-4-ol hydrochloride salt I122 (1.63 g, 11.9 mmol), acetic anhydride (1.82 g, 17.8 mmol) and K$_2$CO$_3$ (4.11 g, 29.7 mmol) in acetone (25 mL) was stirred at room temperature overnight. The reaction mixture was filtered and the filtrate was concentrated to give the crude title compound (1.6 g) as yellow oil which was used for the next step without further purification. LCMS-C: RT 0.29 min; m/z 144.1 [M+H]$^+$ (c) 6-((1-Acetylpiperidin-4-yl)oxy)pyridazine-4-carboxylic acid I124

To a solution of 1-(4-hydroxypiperidin-1-yl)ethanone I123 (166 mg, 1.16 mmol, 2.0 eq) in DMF (5 mL) at 0° C. was added NaH (60% in mineral oil, 58 mg, 1.45 mmol, 2.5 eq). Methyl 6-chloropyridazine-4-carboxylate (100 mg, 0.58 mmol, 1.0 eq) was added and the reaction was allowed to warm slowly to room temperature and stirred overnight. The reaction was quenched by addition of saturated aqueous NaHCO$_3$ (15 mL) and the aqueous washed with DCM (15 mL×3). The aqueous layer was acidified to pH 5 with 1M HCl and extracted with DCM (15 mL×3), the combined organic fractions were dried (MgSO$_4$) and concentrated to give the crude title compound (130 mg) as a brown oil. LCMS-C: RT 2.19 min, m/z 266.1 [M+H]$^+$ (xlv) 1-(Tetrahydro-2H-pyran-4-yl)-1H-benzo[d]imidazole-4-carboxylic acid I129

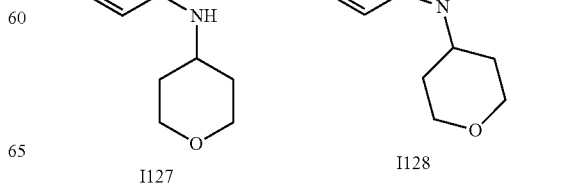

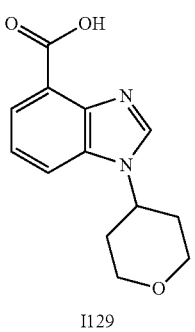

I129

(a) Methyl 3-fluoro-2-nitrobenzoate I125

To a solution of 3-fluoro-2-nitrobenzoic acid (1.0 g, 5.4 mmol) in DCM (15 mL) and DMF (1 drop) was added (COCl)$_2$ (1.4 g, 10.8 mmol) dropwise. The mixture was stirred at room temperature for 2 hours. Methanol (5 mL) was added dropwise to the mixture and stirring was continued for 1 hour. The solvent was removed and the residue was dissolved in DCM (50 mL), the organic layer was washed with saturated NaHCO$_3$ (50 mL), water (50 mL) and brine (50 mL), dried (Na$_2$SO$_4$) and concentrated to give the title compound as a colourless solid (1.0 g, 93%). LCMS-C: RT 2.30 min; m/z 222.0 [M+Na]$^+$.

(b) Methyl 2-nitro-3-((tetrahydro-2H-pyran-4-yl)amino)benzoate I126

To a solution of methyl 3-fluoro-2-nitrobenzoate I125 (100 mg, 0.5 mmol) in MeCN (5 mL) were added tetrahydro-2H-pyran-4-amine (50 mg, 0.5 mmol) and DIPEA (97 mg, 0.75 mmol). The mixture was heated at 50° C. overnight. The solvent was removed and the residue diluted with EtOAc (30 mL). The organic layer was washed with water (30 mL×2) and brine (30 mL), dried (Na$_2$SO$_4$) and concentrated to give the title compound as a brown solid (130 mg, 93%). LCMS-C: RT 2.28 min; m/z 281.1 [M+H]$^+$.

(c) Methyl 2-amino-3-((tetrahydro-2H-pyran-4-yl)amino)benzoate I127

To a solution of methyl 2-nitro-3-((tetrahydro-2H-pyran-4-yl)amino)benzoate I126 (130 mg, 0.46 mmol) in EtOH (4 mL) was added 10% Pd/C (20 mg). The mixture was stirred under a hydrogen atmosphere at room temperature overnight. The catalyst was removed by filtration through Celite and the filtrate concentrated to give the title compound as a yellow solid (100 mg, 86%). LCMS-C: RT 2.32 min; m/z 251.1 [M+H]f.

(d) Methyl 1-(tetrahydro-2H-pyran-4-yl)-1H-benzo[d]imidazole-4-carboxylate I128

To a solution of methyl 2-amino-3-((tetrahydro-2H-pyran-4-yl)amino)benzoate I127 (100 mg, 0.4 mmol) in trimethyl orthoformate (1 mL) was added TsOH.H$_2$O (8 mg, 0.04 mmol). The reaction was heated at 100° C. for 2.5 hours then cooled to room temperature and poured into water (10 mL). The aqueous layer was extracted with EtOAc (10 mL×2), the combined organic fractions were dried (Na$_2$SO$_4$) and concentrated. The residue was purified by preparative TLC (6% MeOH/DCM) to give the title compound as a grey solid (45 mg, 43%). LCMS-C: RT 0.33 min; m/z 261.1 [M+H]$^+$.

(e) 1-(Tetrahydro-2H-pyran-4-yl)-1H-benzo[d]imidazole-4-carboxylic acid I129

To a solution of methyl 1-(tetrahydro-2H-pyran-4-yl)-1H-benzo[d]imidazole-4-carboxylate I128 (300 mg, 1.1 mmol) in MeOH (5 mL) was added a solution of NaOH (90 mg, 2.2 mmol) in water (1 mL). The resulting mixture was stirred at room temperature overnight. The solvent was removed and the residue re-suspended in water (5 mL). The pH of the aqueous solution was adjusted to 4-5 by addition of 1 M aqueous HCl solution. The precipitate was collected by filtration, washed with water (5 mL) and dried in air to give the title compound as a grey solid (150 mg, 53%). LCMS-C: RT 0.66 min, m/z 247.1 [M+H]$^+$ (xlvi) 2-Methyl-1-(tetrahydro-2H-pyran-4-yl)-1H-benzo[d]imidazole-4-carboxylic acid I131

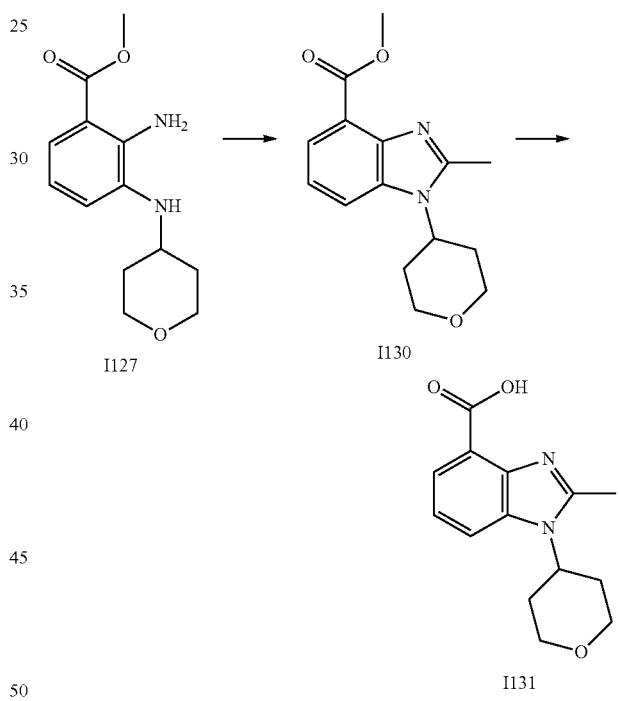

(a) Methyl 2-methyl-1-(tetrahydro-2H-pyran-4-yl)-1H-benzo[d]imidazole-4-carboxylate I130

To a solution of methyl 2-amino-3-((tetrahydro-2H-pyran-4-yl)amino)benzoate I127 (300 mg, 1.2 mmol) in triethyl orthoacetate (5 mL) was added TsOH.H$_2$O (23 mg, 0.12 mmol). The mixture was heated at 100° C. for 3 hours then cooled to room temperature and poured into water (50 mL). The aqueous layer was extracted with EtOAc (50 mL×2) and the combined organic fractions washed with brine (100 mL), dried (Na$_2$SO$_4$) and concentrated. The residue was purified by column chromatography (2% MeOH/DCM) to give the title compound as a solid (200 mg, 52%). LCMS-C: RT 0.34 min, m/z 275.1 [M+H]$^+$. $^1$H NMR (400 MHz, Methanol-d$_4$) δ 7.96 (d, J=8.4 Hz, 1H), 7.86 (d, J=8.4 Hz, 1H), 7.33 (t, J=8.4 Hz, 1H), 4.83-4.66 (m, 1H), 4.16-4.12 (m, 2H), 3.97 (s, 3H), 3.69-3.63 (m, 2H), 2.72 (s, 3H), 2.62-2.51 (m, 2H), 1.90-1.86 (m, 2H).

(b) 2-Methyl-1-(tetrahydro-2H-pyran-4-yl)-1H-benzo[d]imidazole-4-carboxylic acid I131

To a solution of methyl 2-methyl-1-(tetrahydro-2H-pyran-4-yl)-1H-benzo[d]imidazole-4-carboxylate I130 (200 mg, 0.73 mmol) in MeOH (5 mL) was added a solution of NaOH (60 mg, 1.46 mmol) in water (1 mL). The resulting mixture was stirred at room temperature overnight. The solvent was removed and the residue suspended in water (2 mL). The pH of the aqueous solution was adjusted to 4-5 by addition of 1 M aqueous HCl solution. The aqueous layer was washed with DCM (3 mL×2) and lyophilized to give the title compound as a brown solid (220 mg). The crude product was used in the next step without further purification. LCMS-C: RT 0.31 min, m/z 261.1 [M+H]$^+$ (xlvii) Lithium 5-((1-(methoxycarbonyl)piperidin-4-yl)oxy)nicotinate I135

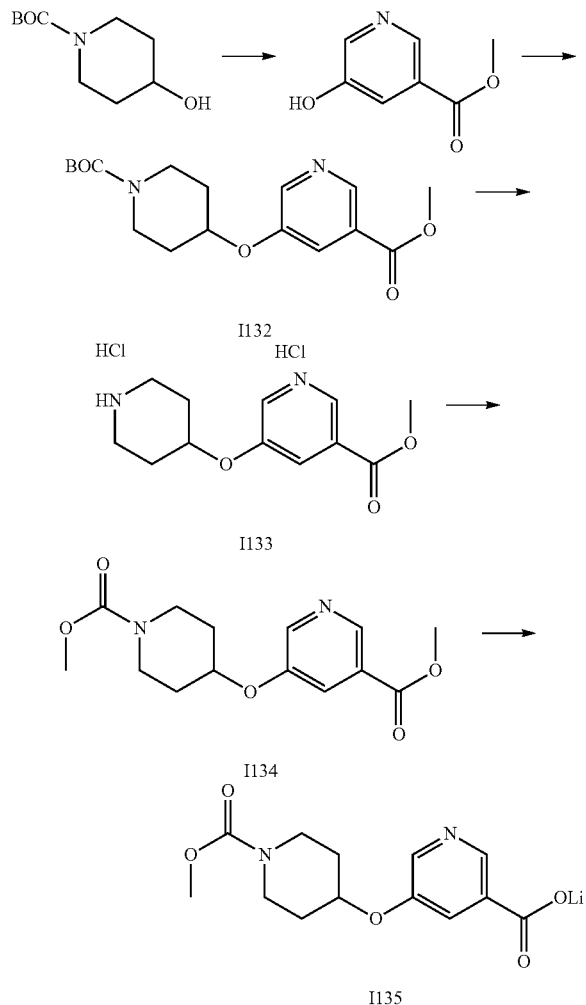

(a) Methyl 5-((1-(tert-butoxycarbonyl)piperidin-4-yl)oxy)nicotinate I132

To a solution of methyl 5-hydroxynicotinate (500 mg, 3.3 mmol) in dry THF (10 mL) at 0° C. were added tert-butyl 4-hydroxypiperidine-1-carboxylate (660 mg, 3.3 mmol), DIAD (870 mg, 4.3 mmol) and PPh$_3$ (950 mg, 3.6 mmol). The mixture was stirred at 0° C. for 1 hour then allowed to warm slowly to room temperature and stirred overnight. The mixture was diluted with EtOAc (100 mL) and washed with water (100 mL) and brine (100 mL), dried (Na$_2$SO$_4$) and concentrated. The residue obtained was purified by column chromatography (20% EtOAc/petroleum ether) to give the title compound as yellow oil (580 mg, 58%). LCMS-C: RT 2.77 min, m/z 337.2 [M+H]$^+$ (b) Methyl 5-(piperidin-4-yloxy)nicotinate dihydrochloride I133

A mixture of methyl 5-((1-(tert-butoxycarbonyl)piperidin-4-yl)oxy)nicotinate I132 (570 mg, 1.7 mmol) in HCl in diethyl ether (2.0 M, 5 mL) was stirred at room temperature for 3 hours. The solvent was removed to give the title compound as an off-white solid (500 mg, 96%). LCMS-C: RT 0.31 min, m/z 237.1 [M+H]$^+$ (c) Methyl 5-((1-(methoxycarbonyl)piperidin-4-yl)oxy)nicotinate I134

To a solution of methyl 5-(piperidin-4-yloxy)nicotinate dihydrochloride I133 (500 mg, 1.6 mmol) in DCM (10 mL) was added Et$_3$N (520 mg, 5.1 mmol). Methyl chloroformate (185 mg, 1.9 mmol) was then added dropwise and the mixture stirred at room temperature for 1 hour. The mixture was diluted with DCM (50 mL) and washed with water (50 mL) and brine (50 mL), dried (Na$_2$SO$_4$) and concentrated. The residue was purified by column chromatography (5% methanol/DCM) to give the title compound as a yellow oil (390 mg, 82%). $^1$H NMR (400 MHz, Methanol-d$_4$) δ 8.71 (d, J=1.6 Hz, 1H), 8.47 (d, J=2.8 Hz, 1H), 7.92 (dd, J=2.8, 1.6 Hz, 1H), 4.80-4.74 (m, 1H), 3.95 (s, 3H), 3.80-3.74 (m, 2H), 3.70 (s, 3H), 3.46-3.40 (m, 2H), 2.04-1.98 (m, 2H), 1.78-1.70 (m, 2H). LCMS-C: RT 2.34 min, m/z 295.1 [M+H]$^+$ (d) Lithium 5-((1-(methoxycarbonyl)piperidin-4-yl)oxy)nicotinate I135

To a solution of methyl 5-((1-(methoxycarbonyl)piperidin-4-yl)oxy)nicotinate I134 (350 mg, 1.2 mmol) in a mixture of THF (3 mL), MeOH (6 mL) and water (1.5 mL) was added LiOH.H$_2$O (50 mg, 2.4 mmol). The reaction was stirred at room temperature overnight then concentrated under reduced pressure. The residue obtained was re-dissolved in water (3 mL) and lyophilized to give the title compound as a white solid (420 mg). LCMS-C: RT 1.31 min; m/z 281.1 [M-Li+2H]$^+$.

(xlviii) 5-Methoxynicotinic acid I137

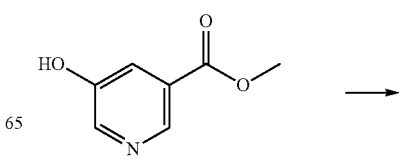

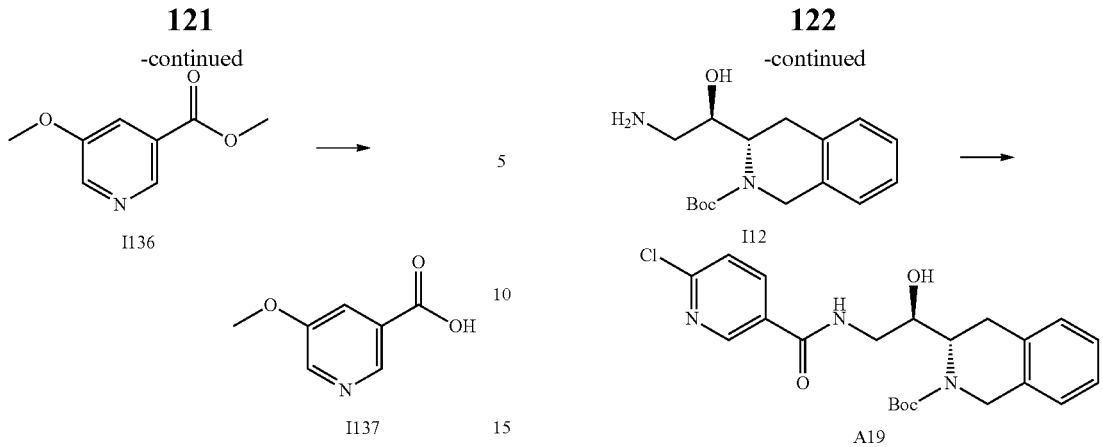

(a) Methyl 5-methoxynicotinate I136

To a suspension of NaH (60% in mineral oil, 1.46 g, 0.03 mol, washed three times with hexane) in DMF (50 mL) was added methyl-5-hydroxynicotinate (4.0 g, 0.04 mol) portion-wise, keeping the temperature below 10° C. After 30 minutes, methyl iodide (3.87 g, 0.03 mol) was added dropwise over 20 minutes. The mixture was stirred at room temperature for 3 hours, then quenched with MeOH and concentrated in vacuo. The residue was dissolved in chloroform and partitioned against saturated NaHCO₃ and brine. The organic layer was separated and the aqueous layer was extracted with chloroform, the combined organic fractions were dried (Na₂SO₄) and concentrated in vacuo. The residue obtained was purified by flash silica gel chromatography (petroleum ether/EtOAc=5/1 then 3/1) to give the title compound (1.0 g, 23%) as a white solid. LCMS-C: RT 1.16 min; m/z 168.1 [M+H].

(b) 5-Methoxynicotinic acid I137

To a solution of methyl 5-methoxynicotinate I136 (300 mg, 1.79 mmol) in a mixture of THF (4 mL) and methanol (4 mL) was added NaOH (2 M aqueous solution, 3 mL). The resulting mixture was stirred at room temperature for 14 hours. The solvent was removed and the residue obtained diluted with water (20 mL). The pH of the aqueous mixture was adjusted to 6 by addition of a 2 M aqueous HCl solution. The mixture was extracted with DCM (20 mL×3) and the combined organic layers washed with brine (10 mL×2), dried (Na₂SO₄) and concentrated to give the title compound as a white solid (230 mg, 84%). LCMS-C: RT 0.36 min; m/z 154.1 [M+H]$^+$.

(ii) Alternate synthesis of (S)-tert-Butyl 3-((R)-2-(6-chloronicotinamido)-1-hydroxyethyl)-3,4-dihydroisoquinoline-2(1H)-carboxylate A19

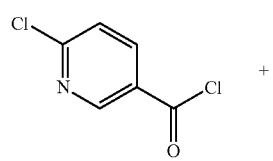

To a solution of (S)-tert-butyl 3-((R)-2-amino-1-hydroxy-ethyl)-3,4-dihydroisoquinoline-2(1H)-carboxylate I12 (500 mg, 1.71 mmol, 1.0 eq) in DCM (10 mL) at 0° C. was added Et₃N (520 mg, 5.13 mmol, 3.0 eq) and 6-chloronicotinoyl chloride (301 mg, 1.71 mmol, 1.0 eq). The reaction was stirred at room temperature under a nitrogen atmosphere overnight. Saturated aqueous NaHCO₃ (50 mL) was added and the resulting mixture extracted with DCM (3×50 mL). The combined organic fractions were dried (Na₂SO₄) and concentrated and the crude residue purified by chromatography (25% EtOAc/petroleum ether) to give the title compound (510 mg, 69%) as a white solid. LCMS-C: RT 2.87 min; m/z 454.2 [M+Na]$^+$.

(l) 5-Isopropoxynicotinic acid I39

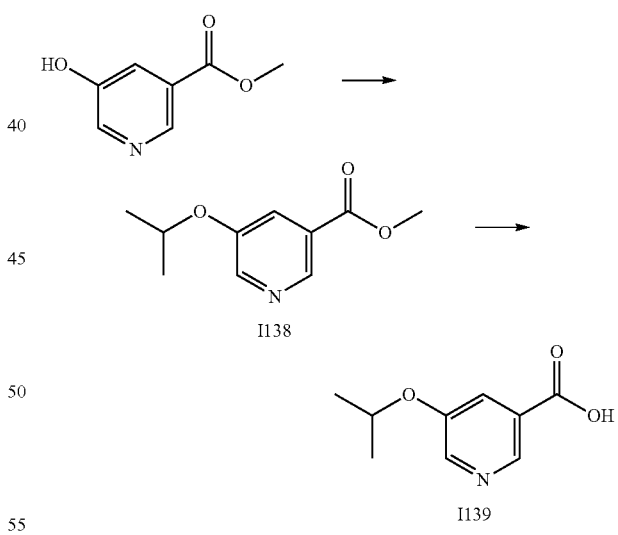

(a) Methyl 5-isopropoxynicotinate I38

A mixture of DCC (1.62 g, 7.84 mmol) and CuCl (129 mg, 1.31 mmol) in isopropanol (20 mL) was heated at 60° C. After 13 hours, 5-hydroxynicotinic acid methyl ester (1.0 g, 6.53 mmol) and benzene (20 mL) were added and the reaction heated at 105° C. for 24 hours. The mixture was diluted with chloroform and filtered. The organic filtrate was washed with saturated NaHCO₃ (15 mL), water and brine, dried (Na₂SO₄) and concentrated. Purification by flash silica gel chromatography (EtOAc/petroleum ether=1/6) gave the title compound (300 mg, 24%) as a white solid. LCMS-C: RT 2.32 min; m/z 196.1 [M+H]+.

(b) 5-Isopropoxynicotinic acid I39

To a solution of methyl 5-isopropoxynicotinate I38 (300 mg, 1.54 mmol) in a mixture of THF (2 mL) and methanol (4 mL) was added NaOH (2M aqueous solution, 2 mL). The resulting mixture was stirred at room temperature for 14 hours. The solvent was removed, and the residue diluted with water (20 mL). The pH of the aqueous mixture was adjusted to 6 by addition of a 2 M aqueous HCl solution. The mixture was extracted with DCM (20 mL×3) and the combined organic layers washed with brine (10 mL×2), dried (Na$_2$SO$_4$) and concentrated to give the title compound (250 mg, 90%) as a white solid. LCMS-C: RT 0.88 min; m/z 182.1 [M+H]+.

Example 1: N-(2-Hydroxy-3-(1,2,3,4-tetrahydroisoquinolin-3-yl)propyl)-4-(morpholine-4-carbonyl)benzamide (1)

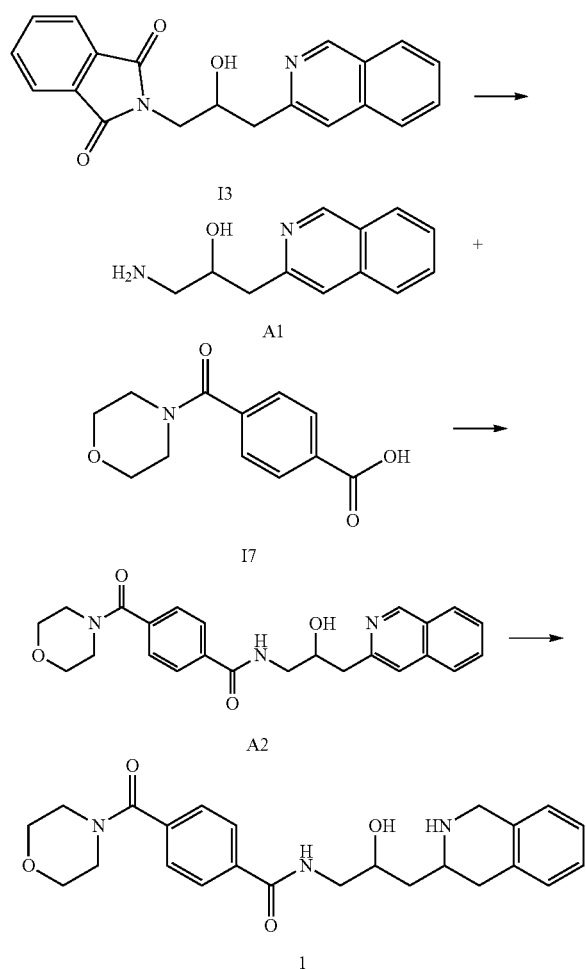

(a) 1-Amino-3-(isoquinolin-3-yl)propan-2-ol (A1)

2-(2-Hydroxy-3-(isoquinolin-3-yl)propyl)isoindoline-1,3-dione I3 (114 mg, 0.343 mmol) and absolute ethanol (5 mL) were brought to 80° C. Hydrazine hydrate (0.25 mL, 8.0 mmol) was added and the mixture stirred at 80° C. After two hours, the heterogeneous mixture was cooled to room temperature, diluted with cold absolute ethanol (5 mL) and filtered. The collected solids were washed with cold ethanol (2 mL) and the combined filtrates were concentrated. The residue was dissolved in absolute ethanol and concentrated in vacuo three times to give the desired compound as a pale yellow syrup (70 mg, quant.). The material was taken onto the next step without further purification. $^1$H NMR (400 MHz, d$_4$-methanol) δ 9.19 (s, 1H), 8.22-8.16 (m, OH), 8.08-8.02 (m, 1H), 7.89-7.83 (m, 1H), 7.79-7.73 (m, 1H), 7.71 (s, 1H), 7.66-7.59 (m, 1H), 4.11-4.03 (m, 1H), 3.12-2.97 (m, 2H), 2.85-2.77 (m, 1H), 2.73-2.64 (m, 1H). LCMS-B: RT 1.55 min; m/z 203.2 [M+H]+.

(b) N-(2-Hydroxy-3-(isoquinolin-3-yl)propyl)-4-(morpholine-4-carbonyl)benzamide A2

1-Amino-3-(isoquinolin-3-yl)propan-2-ol A1 (70 mg, 0.35 mmol), DMF (2.5 mL), DIPEA (0.121 mL, 0.69 mmol), 4-(morpholine-4-carbonyl)benzoic acid I7 (90 mg, 0.38 mmol) and HATU (197 mg, 0.52 mmol) were stirred at room temperature. After 3 hours, the mixture was added to 2% w/v sodium hydroxide (50 mL) and extracted with DCM (3×30 mL). The combined organic extracts were washed with brine (50 mL), dried over sodium sulfate and concentrated in vacuo. Chromatography (12 g silica cartridge, 0-10% methanol/DCM) gave the desired compound as a white solid (88 mg, 61%). $^1$H NMR (400 MHz, d$_4$-methanol) δ 9.18 (s, 1H), 8.09-8.02 (m, 1H), 7.93-7.85 (m, 3H), 7.78-7.72 (m, 2H), 7.66-7.58 (m, 1H), 7.53-7.46 (m, 2H), 4.35-4.27 (m, 1H), 3.77 (br s, 3H), 3.66-3.57 (m, 3H), 3.55-3.47 (m, 2H), 3.22-3.14 (m, 1H), 3.11-3.04 (m, 1H); LCMS-B: RT 3.16 min; m/z 420.3 [M+H]+; m/z 418.1 [M−H]−.

(c) N-(2-Hydroxy-3-(1,2,3,4-tetrahydroisoquinolin-3-yl)propyl)-4-(morpholine-4-carbonyl)benzamide (1)

N-(2-Hydroxy-3-(isoquinolin-3-yl)propyl)-4-(morpholine-4-carbonyl)benzamide A2 (20 mg, 0.048 mmol) and nickel(II) chloride hexahydrate (14 mg, 0.057 mmol) were dissolved in methanol (2 mL). The mixture was stirred at room temperature and sodium borohydride (22 mg, 0.57 mmol) was added in one portion. After 30 minutes, the mixture was quenched with 3M HCl (0.5 mL) and concentrated in vacuo. The residue was suspended in methanol and applied to a 1 g SCX cartridge. The cartridge was washed with methanol (15 mL) and eluted with 2M ammonia in methanol (15 mL). The basic eluate was concentrated in vacuo. The residue and nickel(II) chloride hexahydrate (14 mg, 0.057 mmol) were dissolved in methanol (2 mL). The mixture was stirred at room temperature and sodium borohydride (22 mg, 0.57 mmol) was added in one portion. After one hour the mixture was quenched with 3M HCl (0.5 mL) and concentrated in vacuo. The residue was suspended in methanol and applied to 2×1 g SCX cartridges. The cartridges were each washed with methanol (15 mL) and eluted with 2M ammonia in methanol (15 mL). The combined basic eluate was concentrated in vacuo to give the desired compound as a colourless syrup (8 mg, 41%). LCMS-B: RT 3.18 min; m/z 424.3 [M+H]+.

Example 2: N-(2-hydroxy-2-(1,2,3,4-tetrahydroiso-quinolin-3-yl)ethyl)-4-(morpholine-4-carbonyl)benzamide (2)

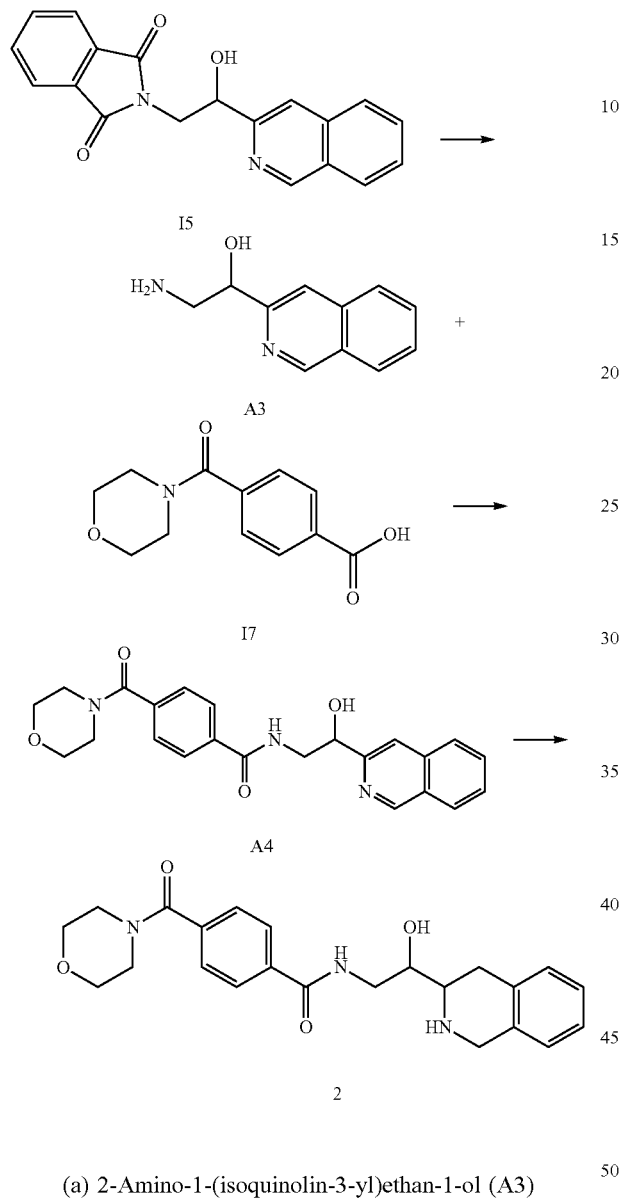

(a) 2-Amino-1-(isoquinolin-3-yl)ethan-1-ol (A3)

2-(2-Hydroxy-2-(isoquinolin-3-yl)ethyl)isoindoline-1,3-dione I5 (50 mg, 0.16 mmol) was dissolved in ethanol (1 mL) and hydrazine hydrate (0.050 mL, 0.79 mmol) was added. The mixture was heated at 80° C. for 3 hours and allowed to cool. The mixture was filtered and the solid was washed with further ethanol (2 mL). The combined filtrates were concentrated to give the desired compound as a yellow syrup (32 mg, >100% yield). The material was carried forward without further purification: LCMS-B: RT 2.06 min; m/z 189.2 [M+H]+.

(b) N-(2-Hydroxy-2-(isoquinolin-3-yl)ethyl)-4-(morpholine-4-carbonyl)benzamide (A4)

2-Amino-1-(isoquinolin-3-yl)ethan-1-ol A3 (32 mg, 0.16 mmol), DMF (1 mL), 4-(Morpholine-4-carbonyl)benzoic acid I7 (48 mg, 0.20 mmol), DIPEA (0.059 mL, 0.34 mmol) and HATU (97 mg, 0.26 mmol) were stood at room temperature. After 3 hours, the mixture was diluted with 2% w/v aqueous sodium hydroxide (10 mL) and extracted with chloroform (3×10 mL). The combined organic extracts were washed with brine, dried over sodium sulfate and concentrated. Chromatography (4 g silica cartridge, 0-10% methanol/chloroform) gave the desired compound as an off-white solid (29 mg, 45% yield over two steps): $^1$H NMR (400 MHz, d$_4$-methanol) δ 9.23 (s, 1H), 8.12-8.06 (m, 1H), 7.97-7.89 (m, 2H), 7.88-7.82 (m, 2H), 7.80-7.73 (m, 1H), 7.70-7.62 (m, 1H), 7.53-7.44 (m, 2H), 5.17-5.08 (m, 1H), 3.93-3.86 (m, 1H), 3.84-3.71 (m, 5H), 3.62 (br s, 2H), 3.42 (br s, 2H); LCMS-B: RT 3.15 min, m/z 406.2 [M+H]+

(c) N-(2-Hydroxy-2-(1,2,3,4-tetrahydroisoquinolin-3-yl)ethyl)-4-(morpholine-4-carbonyl)benzamide (2)

N-(2-Hydroxy-2-(isoquinolin-3-yl)ethyl)-4-(morpholine-4-carbonyl)benzamide A4 (10 mg, 0.025 mmol) and nickel (II) chloride hexahydrate (7.0 mg, 0.030 mmol) were dissolved in methanol (1 mL) and sodium borohydride (12 mg, 0.30 mmol) was added. The black suspension was stirred at room temperature. The reaction was quenched with 1.25 M HCl in methanol (0.5 mL) and concentrated in vacuo. The residue was suspended in methanol (1 mL) and loaded onto a 1 g SCX cartridge. The cartridge was washed with methanol (10 mL) then eluted with 2.0 M ammonia in methanol (10 mL). The basic eluate was concentrated and the material was dissolved in methanol (1 mL. Nickel(II) chloride hexahydrate (7.0 mg, 0.030 mmol) and sodium borohydride (12 mg, 0.30 mmol) were added and the mixture stirred for 1.5 hours. The reaction was quenched with 1.25 M HCl in methanol (0.5 mL) and concentrated in vacuo. The residue was suspended in methanol (1 mL) and loaded onto a 1 g SCX cartridge. The cartridge was washed with methanol (10 mL) then eluted with 2.0 M ammonia in methanol (10 mL). The basic eluate was concentrated to give the desired compound as a white solid (6.1 mg, 60%). LCMS-B: RT 3.16 min; m/z 410.3 [M+H]+.

Examples 3-29, 57-89, 111-120 and 126 (Table A)

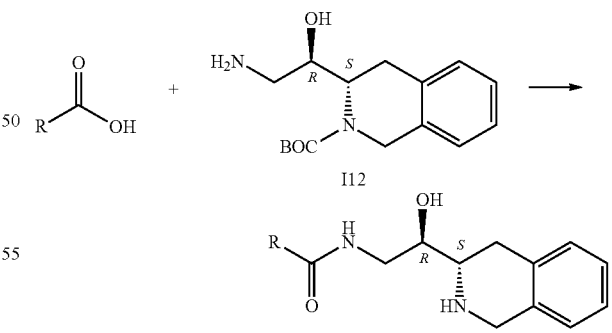

Method AA:

The respective carboxylic acid (0.070 mmol), triethylamine (0.019 mL, 0.14 mmol), tert-butyl (S)-3-((R)-2-amino-1-hydroxyethyl)-3,4-dihydroisoquinoline-2(1H)-carboxylate (I12) (20 mg, 0.068 mmol), DMF (0.5 mL) and HATU (39 mg, 0.10 mmol) were stood at room temperature. After 17 hours, water (1.5 mL) and DCM (1 mL) were added, the mixture agitated then passed through a phase separation cartridge. The collected DCM phase was diluted with 4.0 M HCl in 1,4-dioxane (1 mL), stood for 2 hours then loaded onto a 0.5 g SCX cartridge. The cartridge was washed with methanol (10 mL) then eluted with 2M ammonia in methanol (10 mL). The basic eluate was concentrated to afford the amide product.

Method AB:

To a solution of the respective acid (0.17 mmol, 1 equiv) in DMF (2 mL) and MeCN (2 mL) were added DIPEA (89 µL, 0.51 mmol, 3 equiv), HATU (97 mg, 0.26 mmol, 1.5 equiv) and a solution of tert-butyl (S)-3-((R)-2-amino-1-hydroxyethyl)-3,4-dihydroisoquinoline-2(1H)-carboxylate (I12) (50 mg, 0.17 mmol, 1 equiv) in DMF (2 mL). The reaction was stirred at room temperature for 16 hours, then quenched with a saturated aqueous solution of $NaHCO_3$ (5 mL). DCM was added and the mixture stirred and then passed through a phase separation cartridge (aqueous phase extracted×3 with DCM). The combined organic filtrates were dried in vacuo to give a yellow oil which was taken up in 4.0 M HCl in 1,4-dioxane (1 mL) and stirred at room temperature for 2 days. The reaction was dried in vacuo and then purified by solid-phase extraction (1 g SCX-2 cartridge, 3 column volumes of methanol followed by 3 column volumes of 0.2 M methanolic ammonia). The basic eluate was concentrated to afford the amide product.

Method AC:

To a solution of the respective acid (0.17 mmol, 1 equiv) in DMF (2 mL) and MeCN (5 mL) was added DIPEA (89 µL, 0.51 mmol, 3 equiv), HATU (98 mg, 0.26 mmol, 1.5 equiv) and tert-butyl (S)-3-((R)-2-amino-1-hydroxyethyl)-3,4-dihydroisoquinoline-2(1H)-carboxylate (I12) (50 mg, 0.17 mmol, 1 equiv). The reaction was stirred for 16 hours at room temperature, then quenched with a saturated aqueous solution of $NaHCO_3$ (5 mL) and extracted with DCM (3×5 mL) utilizing a phase separation cartridge. The organic filtrates were dried in vacuo to give a yellow oil which was taken up in 4.0 M HCl in 1,4-dioxane and stirred at room temperature for 16 hours. The reaction was dried in vacuo and then purified by solid-phase extraction (1 g SCX-2 cartridge, 3 column volumes of methanol followed by 3 column volumes of 0.2 M methanolic ammonia). The basic eluate was concentrated to afford the amide product.

Method AD:

To a solution of the respective acid (0.17 mmol, 1 equiv), DIPEA (89 µL, 0.51 mmol, 3 equiv) and HATU (98 mg, 0.26 mmol, 1.5 equiv) was added a solution of tert-butyl (S)-3-((R)-2-amino-1-hydroxyethyl)-3,4-dihydroisoquinoline-2(1H)-carboxylate (I12) (50 mg, 0.17 mmol, 1 equiv) in DMF (2 mL). The reaction was stood at room temperature for 16 hours, quenched with a saturated aqueous solution of $NaHCO_3$ (5 mL) and extracted with DCM (×3) utilizing a phase separation cartridge. The organic filtrates were reduced under a stream of air, DCM:TFA (2 mL, 1:1) was added and the reaction stood at room temperature for the specified time. The reaction mixture was concentrated under a stream of air and then purified by solid-phase extraction (1 g SCX-2 cartridge, 3 column volumes of methanol followed by 3 column volumes of 0.2 M methanolic ammonia) to give the crude product which was further purified by column chromatography (12 g $SiO_2$ cartridge, 50-100% EtOAc (modified by the addition of 1% v/v of 3.5 M methanolic ammonia) in petroleum benzine 40-60° C. followed by 0-50% MeOH in EtOAc modified by the addition of 1% v/v of 2.0 M methanolic ammonia) and then by preparative reversed phase HPLC (5-100% acetonitrile in water, 0.1% TFA). The product fractions were combined and dried in vacuo to give the amide product as a TFA salt.

Method AE:

To a solution of the respective acid (33 mg, 0.17 mmol, 1 equiv) in DMF (2 mL) was added DIPEA (104 µL, 0.595 mmol, 3 equiv), HATU (113 mg, 0.297 mmol, 1.5 equiv) and a solution of tert-butyl (S)-3-((R)-2-amino-1-hydroxyethyl)-3,4-dihydroisoquinoline-2(1H)-carboxylate (I12) (0.17 mmol, 1 equiv) in DMF (2 mL). The reaction was stirred at room temperature for 16 hours then quenched with a saturated aqueous solution of $NaHCO_3$ (5 mL) and extracted with DCM (×3) utilizing a phase separation cartridge. The organic filtrates were dried in vacuo to give a yellow oil which was taken up in DCM (5 mL), TFA (1 mL) was subsequently added and the reaction was stirred at room temperature for 2 hours. The mixture was dried in vacuo and purified by solid-phase extraction (1 g SCX-2 cartridge, 3 column volumes of methanol followed by 3 column volumes of 0.2 M methanolic ammonia) to give the crude amide product as a brown oil. This material was further purified by column chromatography (12 g silica cartridge, 50-100% EtOAc (modified by the addition of 1% v/v of 3.5 M methanolic ammonia) in petroleum benzine 40-60° C. followed by 0-50% MeOH in EtOAc modified by the addition of 1% v/v of 2.0 M methanolic ammonia). The product-containing fractions were combined and stirred in EtOAc and a 1 M aqueous solution of NaOH (4 mL) for 2 hours. DCM was added and the mixture stirred and then passed through a phase separation cartridge (3 repeats). The organic filtrates were dried in vacuo and the residue purified by solid-phase extraction (1 g SCX-2 cartridge, 3 column volumes of methanol followed by 3 column volumes of 0.2 M methanolic ammonia) to give a yellow oil. The oil was further purified by preparative reversed phase HPLC (5-85% acetonitrile in water, 0.1% TFA). The product fractions were combined and dried in vacuo to give the amide product as a TFA salt.

Method AF:

tert-Butyl (S)-3-((R)-2-amino-1-hydroxyethyl)-3,4-dihydroisoquinoline-2(1H)-carboxylate (I12) (60 mg, 0.21 mmol), MeCN (2 mL), DIPEA (0.071 mL, 0.41 mmol), the respective acid (48 mg, 0.21 mmol) and HATU (117 mg, 0.31 mmol) were stirred at room temperature. After 18 hours the mixture was concentrated in vacuo, chromatography (4 g silica cartridge, 0-100% ethyl acetate/hexanes then 100% ethyl hexanes) gave the intermediate as a colourless syrup. This intermediate was dissolved in 1,4-dioxane (2.5 mL) and 4.0 M HCl in 1,4-dioxane (2.5 mL) was added. After 2 hours the mixture was diluted with diethyl ether (50 mL), the solvent decanted, the fine precipitate washed with diethyl ether (2×50 mL) and dried in vacuo to give the amide product.

Method AG:

tert-Butyl (S)-3-((R)-2-amino-1-hydroxyethyl)-3,4-dihydroisoquinoline-2(1H)-carboxylate (I12) (50 mg, 0.17 mmol), MeCN (1.5 mL), DMF (0.5 mL), DIPEA (0.060 mL, 0.34 mmol), the respective acid (41 mg, 0.17 mmol) and BOP (113 mg, 0.26 mmol) were stirred at room temperature. After 18 hours the mixture was added to water (50 mL) and extracted with ethyl acetate (3×25 mL). The pooled ethyl acetate phases were washed with brine (2×30 mL), dried over sodium sulfate and concentrated in vacuo. Chromatography (4 g silica cartridge, 0-10% methanol/DCM) gave the intermediate as a pale yellow oil. This intermediate was dissolved in 1,4-dioxane (2 mL), and a solution of 4.0 M HCl in 1,4-dioxane (2 mL) was added. The mixture was stirred at room temperature for 3 hours, the solvent removed from the precipitate by decantation and the solid washed with diethyl ether (3×5 mL). The solid was dried in vacuo to give the amide product.

Method AH:

The respective carboxylic acid (0.068 mmol), triethylamine (0.019 mL, 0.14 mmol), tert-butyl (S)-3-((R)-2-amino-1-hydroxyethyl)-3,4-dihydroisoquinoline-2(1H)-carboxylate I12 (20 mg, 0.068 mmol), DMF (0.5 mL) and HATU (39 mg, 0.10 mmol) were stood at room temperature. After 17 hours, water (1.5 mL) and DCM (1 mL) were added, the mixture agitated then passed through a phase separation cartridge. The collected DCM phase was diluted with 4.0 M HCl in 1,4-dioxane (1 mL), stood for 17 hours, then loaded onto a 1 g SCX cartridge. The cartridge was washed with methanol (6 mL) then eluted with 7 M ammonia in methanol (6 mL). The basic eluate was concentrated to afford the desired compound.

Method AI:

To a solution of the respective acid (0.17 mmol, 1 equiv), DIPEA (89 µL, 0.51 mmol, 3 equiv) and HATU (98 mg, 0.26 mmol, 1.5 equiv) was added a solution of tert-butyl (S)-3-((R)-2-amino-1-hydroxyethyl)-3,4-dihydroisoquinoline-2(1H)-carboxylate I12 (50 mg, 0.17 mmol, 1 equiv) in DMF (2 mL). The reaction was stood at room temperature for 16 hours, quenched with a saturated aqueous solution of $NaHCO_3$ (5 mL) and extracted with DCM (×3) utilizing a phase separation cartridge. The organic filtrates were reduced under a stream of air, DCM:TFA (2-4 mL, 1:1) was added and the reaction stood at room temperature for the specified time (see Table A). The reaction mixture was concentrated under a stream of air and then purified by solid-phase extraction (1 g SCX-2 cartridge, 3 column volumes of methanol followed by 3 column volumes of 0.2 M methanolic ammonia) to give the desired compound.

Method AJ:

The respective acid or lithium salt (0.068 mmol), triethylamine (0.019 mL, 0.14 mmol), tert-butyl (S)-3-((R)-2-amino-1-hydroxyethyl)-3,4-dihydroisoquinoline-2(1H)-carboxylate I12 (20 mg, 0.068 mmol), DMF (0.5 mL) and HATU (39 mg, 0.10 mmol) were stood at room temperature. After 17 hours, water (1.5 mL) and DCM (1.5 mL) were added, the mixture agitated then passed through a phase separation cartridge. The collected DCM phase was treated with 0.1 g Dowex 50×8 resin, H$^+$-form, the mixture filtered and the filtrate diluted with 4.0 M HCl in 1,4-dioxane (2 mL). The mixture was stood for 3 hours then loaded onto a 1 g SCX cartridge. The cartridge was washed with methanol (15 mL) then eluted with 2 M ammonia in methanol (15 mL). The basic eluates were concentrated to afford the desired compound.

Method AK:

The crude lithium salt (0.059 mmol @ 100% conversion), triethylamine (0.016 mL, 0.12 mmol) and HATU in DMF (0.5 mL) were stood for two minutes then tert-butyl (S)-3-((R)-2-amino-1-hydroxyethyl)-3,4-dihydroisoquinoline-2(1H)-carboxylate I12 (17 mg, 0.059 mmol) was added. After 17 hours, the mixture was diluted with water and DCM (1.5 mL each), the DCM phase separated with a phase separation cartridge and treated with Dowex 50W×8 resin (H$^+$-form, 200-400 mesh, 100 mg). The suspension was filtered and the collected beads washed with DCM (0.5 mL). The DCM filtrate was diluted with 4.0 M HCl/1,4-dioxane (2 mL) and stood at room temperature. After one hour, the mixture was diluted with methanol (2 mL) and loaded onto a 1 g SCX cartridge. The cartridge was washed with methanol (15 mL) and eluted with 2 M ammonia in methanol (10 mL). The basic eluate was concentrated to afford the desired compound.

Method AL:

To a solution of the respective acid (1.0 eq) or lithium salt and tert-butyl (S)-3-((R)-2-amino-1-hydroxyethyl)-3,4-dihydroisoquinoline-2(1H)-carboxylate I12 (1.0 eq) in DCM were added DIPEA (3.0 eq), HOBt (0.1 eq), and EDCl.HCl (2.0 eq). The resulting mixture was stirred at room temperature overnight. Water was added to the reaction mixture and the mixture was extracted with DCM (3 times). The combined organic layers were washed with brine, dried ($Na_2SO_4$) and concentrated to give the crude product which was purified by prep TLC (DCM:MeOH=20:1) to give the Boc protected intermediate. A solution of the Boc protected intermediate (1.0 eq) in saturated HCl/EtOAc solution or saturated HCl/diethyl ether solution was stirred at room temperature for 2-3 hours. The mixture was concentrated and the residue washed with diethyl ether to give the desired product. In some cases, the HCl salt is not pure enough, in such cases the crude product was added to aqueous saturated $NaHCO_3$ solution. The resulting mixture was extracted with DCM (3 times). The organic layers were combined, dried ($Na_2SO_4$) and concentrated to give the residue which was purified by prep TLC (DCM:MeOH=15:1) to give the desired product.

Method AM:

To a solution of the respective lithium salt (1.0 eq) and tert-butyl (S)-3-((R)-2-amino-1-hydroxyethyl)-3,4-dihydroisoquinoline-2(1H)-carboxylate I12 (1.2 eq) in DMF were added $Et_3N$ (10.0 eq), T3P® (2.0 eq), and DMAP (0.5 eq). The resulting mixture was then stirred at room temperature for 1 hour. Water was added to the reaction mixture and the aqueous layer extracted with EtOAc (×3). The combined organic layers were washed with water, brine, dried ($Na_2SO_4$) and concentrated to give the crude product which was purified by prep TLC (DCM:MeOH=20:1) to give the Boc protected intermediate.

A solution of the Boc protected intermediate (1.0 eq) in saturated HCl/EtOAc solution or saturated HCl/diethyl ether solution was stirred at room temperature for 2-3 hours. The mixture was concentrated and the residue was washed with diethyl ether to give the desired product.

TABLE A

| Ex | Name and Structure | Analytical data | Method |
| --- | --- | --- | --- |
| 3 | 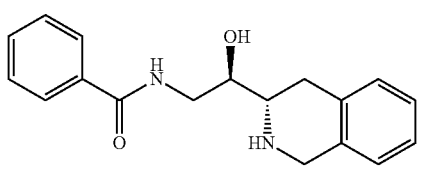 [SMILES: O=C(NC[C@@H](O)[C@@H]1Cc2ccccc2CN1)c1ccccc1]<br>N-((R)-2-Hydroxy-2-((S)-1,2,3,4-tetrahydroisoquinolin-3-yl)ethyl)benzamide | LCMS-A: RT 4.468 min; m/z 297.2 [M + H]$^+$ | AA<br>Stirred for 3 hours with HCl/1,4-dioxane.<br>Elution with 7M ammonia in methanol. |

TABLE A-continued

| Ex | Name and Structure | Analytical data | Method |
|---|---|---|---|
| 4 | 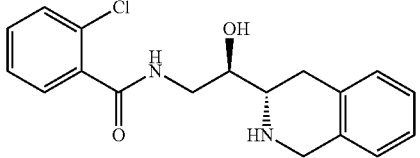 [SMILES: O=C(NC[C@@H](O)[C@@H]1Cc2ccccc2CN1)c1ccccc1Cl]<br>2-Chloro-N-((R)-2-hydroxy-2-((S)-1,2,3,4-tetrahydroisoquinolin-3-yl)ethyl)benzamide | LCMS-A: RT 4.484 min; m/z 331.1 [M + H]$^+$ | AA<br>Stirred for 3 hours with HCl/1,4-dioxane.<br>Elution with 7M ammonia in methanol. |
| 5 | 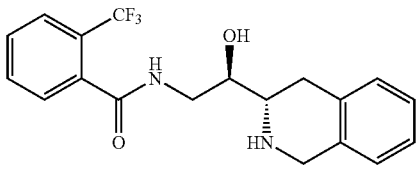 [SMILES: O=C(NC[C@@H](O)[C@@H]1Cc2ccccc2CN1)c1ccccc1C(F)(F)F]<br>N-((R)-2-Hydroxy-2-((S)-1,2,3,4-tetrahydroisoquinolin-3-yl)ethyl)-2-(trifluoromethyl)benzamide | LCMS-A: RT 4.600 min; m/z 365.2 [M + H]$^+$ | AA<br>Stirred for 3 hours with HCl/1,4-dioxane.<br>Elution with 7M ammonia in methanol. |
| 6 | 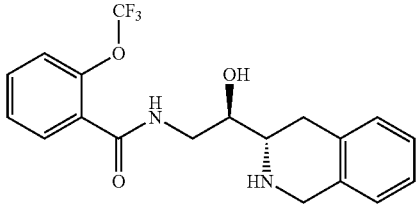 [SMILES: O=C(NC[C@@H](O)[C@@H]1Cc2ccccc2CN1)c1ccccc1OC(F)(F)F]<br>N-((R)-2-Hydroxy-2-((S)-1,2,3,4-tetrahydroisoquinolin-3-yl)ethyl)-2-(trifluoromethoxy)benzamide | LCMS-A: RT 4.681 min; m/z 381.2 [M + H]$^+$ | AA<br>Stirred for 3 hours with HCl/1,4-dioxane.<br>Elution with 7M ammonia in methanol. |
| 7 | 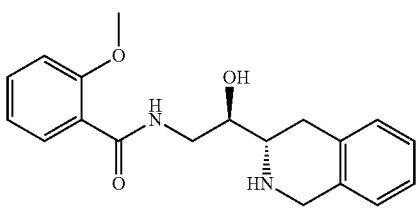 [SMILES: COc1ccccc1C(=O)NC[C@@H](O)[C@@H]1Cc2ccccc2CN1]<br>N-((R)-2-Hydroxy-2-((S)-1,2,3,4-tetrahydroisoquinolin-3-yl)ethyl)-2-methoxybenzamide | LCMS-A: RT 4.546 min; m/z 327.2 [M + H]$^+$ | AA<br>Stirred for 3 hours with HCl/1,4-dioxane. Elution with 7M ammonia in methanol. |
| 8 | 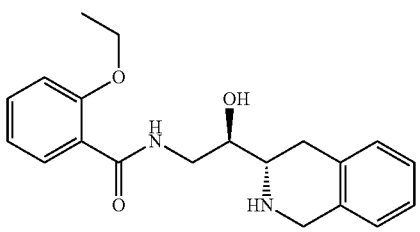 [SMILES: CCOc1ccccc1C(=O)NC[C@@H](O)[C@@H]1Cc2ccccc2CN1]<br>2-Ethoxy-N-((R)-2-hydroxy-2-((S)-1,2,3,4-tetrahydroisoquinolin-3-yl)ethyl)benzamide | LCMS-A: RT 4.649 min; m/z 341.2 [M + H]$^+$ | AA<br>Stirred for 3 hours with HCl/1,4-dioxane.<br>Elution with 7M ammonia in methanol. |

TABLE A-continued

| Ex | Name and Structure | Analytical data | Method |
|---|---|---|---|
| 9 | 2-Fluoro-N-((R)-2-hydroxy-2-((S)-1,2,3,4-tetrahydroisoquinolin-3-yl)ethyl)benzamide | LCMS-A: RT 4.463 min; m/z 315.2 [M + H]$^+$ | Stirred for 3 hours with HCl/1,4-dioxane. Elution with 7M ammonia in methanol. |
| 10 | N-((R)-2-Hydroxy-2-((S)-1,2,3,4-tetrahydroisoquinolin-3-yl)ethyl)-2-methylbenzamide | LCMS-A: RT 4.519 min; m/z 311.2 [M + H]$^+$ | Stirred for 3 hours with HCl/1,4-dioxane. Elution with 7M ammonia in methanol. Carboxylic acid: I13 |
| 12 | N-((R)-2-Hydroxy-2-((S)-1,2,3,4-tetrahydroisoquinolin-3-yl)ethyl)-3-(pyridazin-4-yl)benzamide | LCMS-B: RT 3.12 min; m/z 375.2 [M + H]$^+$ | AA Carboxylic acid: I15 |
| 13 | N-((R)-2-Hydroxy-2-((S)-1,2,3,4-tetrahydroisoquinolin-3-yl)ethyl)-4-(5-morpholino-1,3,4-oxadiazol-2-yl)benzamide | LCMS-B: RT 3.18 min; m/z 450.2 [M + H]$^+$ | AA Carboxylic acid: I17 |
| 14 | N-((R)-2-Hydroxy-2-((S)-1,2,3,4-tetrahydroisoquinolin-3-yl)ethyl)-2-phenyloxazole-4-carboxamide | LCMS-B: RT 3.36 min; m/z 364.2 [M + H]$^+$ | AA |

TABLE A-continued

| Ex | Name and Structure | Analytical data | Method |
|---|---|---|---|
| 15 | 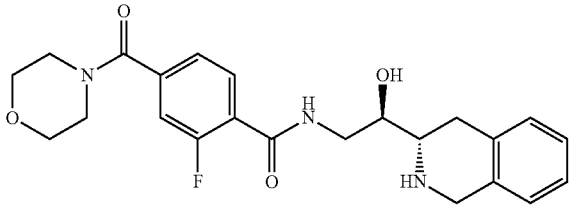 [SMILES: O=C(NC[C@@H](O)[C@@H]1Cc2ccccc2CN1)c1ccc(C(=O)N2CCOCC2)cc1F]<br>2-Fluoro-N-((R)-2-hydroxy-2-((S)-1,2,3,4-tetrahydroisoquinolin-3-yl)ethyl)-4-(morpholine-4-carbonyl)benzamide | LCMS-B: RT 3.14 min; m/z 428.3 [M + H]$^+$ | AA<br>Carboxylic acid: I20 |
| 16 | 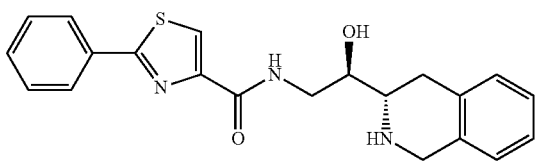 [SMILES: O=C(NC[C@@H](O)[C@@H]1Cc2ccccc2CN1)c1csc(-c2ccccc2)n1]<br>N-((R)-2-Hydroxy-2-((S)-1,2,3,4-tetrahydroisoquinolin-3-yl)ethyl)-2-phenylthiazole-4-carboxamide | LCMS-B: RT 3.39 min; m/z 380.2 [M + H]$^+$ | AA |
| 17 | 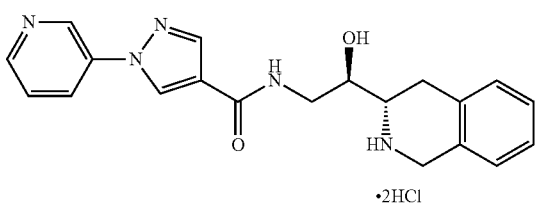 [SMILES: O=C(NC[C@@H](O)[C@@H]1Cc2ccccc2CN1)c1cnn(-c2cccnc2)c1 ; "·2HCl"]<br>•2HCl<br>N-((R)-2-Hydroxy-2-((S)-1,2,3,4-tetrahydroisoquinolin-3-yl)ethyl)-1-(pyridin-3-yl)-1H-pyrazole-4-carboxamide dihydrochloride salt | LCMS-B: RT 3.10 min; m/z 364.2 [M + H]$^+$ (free base) | AA<br>Precipitated from HCl/1,4-dioxane, collected, washed with MeOH and dried to give the title compound. |
| 18 | 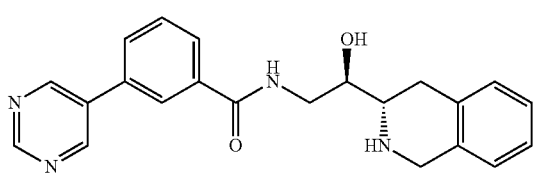 [SMILES: O=C(NC[C@@H](O)[C@@H]1Cc2ccccc2CN1)c1cccc(-c2cncnc2)c1]<br>N-((R)-2-Hydroxy-2-((S)-1,2,3,4-tetrahydroisoquinolin-3-yl)ethyl)-3-(pyrimidin-5-yl)benzamide | LCMS-B: RT 3.20 min; m/z 375.1 [M + H]$^+$ | AA<br>Carboxylic acid: I21 |
| 19 | 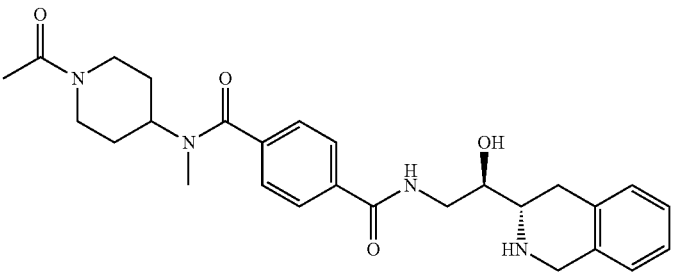 [SMILES: CC(=O)N1CCC(N(C)C(=O)c2ccc(C(=O)NC[C@@H](O)[C@@H]3Cc4ccccc4CN3)cc2)CC1]<br>N$^1$-(1-Acetylpiperidin-4-yl)-N$^4$-((R)-2-hydroxy-2-((S)-1,2,3,4-tetrahydroisoquinolin-3-yl)ethyl)-N$^1$-methylterephthalamide | LCMS-B: RT 3.19 min; m/z 479.2 [M + H]$^+$ | AA<br>Carboxylic acid (as lithium salt): I26 |

TABLE A-continued

| Ex | Name and Structure | Analytical data | Method |
|---|---|---|---|
| 20 | 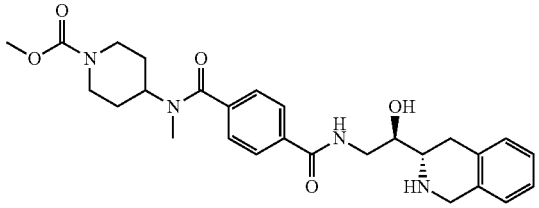<br>Methyl 4-(4-(((R)-2-hydroxy-2-((S)-1,2,3,4-tetrahydroisoquinolin-3-yl)ethyl)carbamoyl)-N-methylbenzamido)piperidine-1-carboxylate | LCMS-B: RT 3.15 min; m/z 450.2 $[M - CO_2]^+$ | AA<br>Carboxylic acid (as lithium salt): I28 |
| 21 | 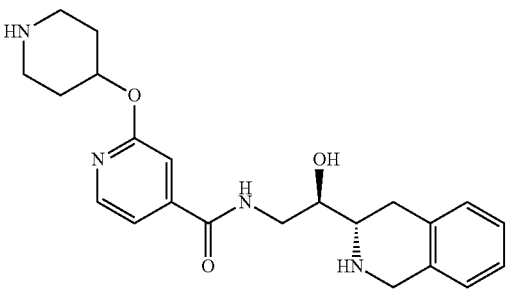 [SMILES: O=C(NC[C@@H](O)[C@@H]1Cc2ccccc2CN1)c1ccnc(OC2CCNCC2)c1]<br>N-((R)-2-Hydroxy-2-((S)-1,2,3,4-tetrahydroisoquinolin-3-yl)ethyl)-2-(piperidin-4-yloxy)isonicotinamide | LCMS-B: RT 3.19 min, m/z 397 $[M + H]^+$ | AB<br>Carboxylic acid: I30 |
| 22 | 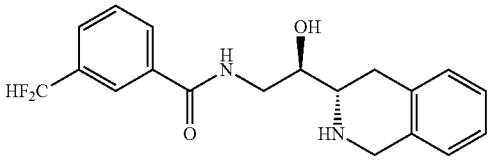<br>3-(Difluoromethyl)-N-((R)-2-hydroxy-2-((S)-1,2,3,4-tetrahydroisoquinolin-3-yl)ethyl)benzamide | LCMS-B: RT 3.30 min, m/z 347 $[M + H]^+$ | AC<br>Reaction carried out on 0.14 mmol scale of amine |
| 23 | 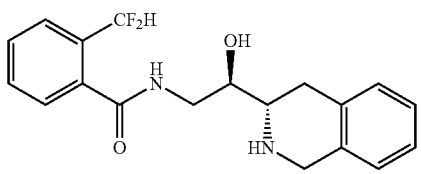 [SMILES: O=C(NC[C@@H](O)[C@@H]1Cc2ccccc2CN1)c1ccccc1C(F)F]<br>2-(Difluoromethyl)-N-((R)-2-hydroxy-2-((S)-1,2,3,4-tetrahydroisoquinolin-3-yl)ethyl)benzamide | LCMS-B: RT 3.23 min, m/z 347 $[M + H]^+$ | AC<br>Reaction carried out on 0.14 mmol scale of amine |
| 24 | 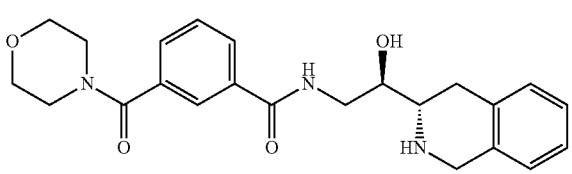 [SMILES: O=C(NC[C@@H](O)[C@@H]1Cc2ccccc2CN1)c1cccc(C(=O)N2CCOCC2)c1]<br>N-((R)-2-Hydroxy-2-((S)-1,2,3,4-tetrahydroisoquinolin-3-yl)ethyl)-3-(morpholine-4-carbonyl)benzamide | LCMS-B: RT 3.07 min, m/z 410 $[M + H]^+$ | AC |

TABLE A-continued

| Ex | Name and Structure | Analytical data | Method |
|----|---|---|---|
| 25 | 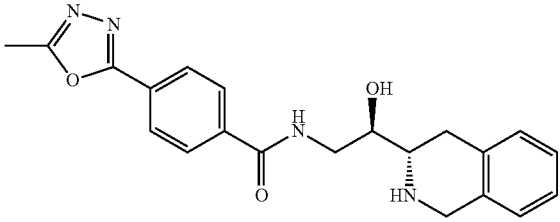 [SMILES: Cc1nnc(-c2ccc(C(=O)NC[C@@H](O)[C@@H]3Cc4ccccc4CN3)cc2)o1]<br>N-((R)-2-Hydroxy-2-((S)-1,2,3,4-tetrahydroisoquinolin-3-yl)ethyl)-4-(5-methyl-1,3,4-oxadiazol-2-yl)benzamide | LCMS-B: RT 3.19 min, m/z 379 [M + H]$^+$ | AC |
| 26 | 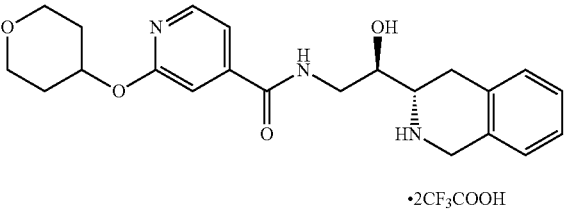 [SMILES: O=C(NC[C@@H](O)[C@@H]1Cc2ccccc2CN1)c1ccnc(OC2CCOCC2)c1]<br>N-((R)-2-Hydroxy-2-((S)-1,2,3,4-tetrahydroisoquinolin-3-yl)ethyl)-2-((tetrahydro-2H-pyran-4-yl)oxy)isonicotinamide bis(2,2,2-trifluoroacetic acid) salt | $^1$H NMR (400 MHz, d$_4$-MeOD) δ 8.23 (dd, J = 5.3, 0.8 Hz, 1H), 7.36-7.14 (m, 6H), 5.25 (tt, J = 8.3, 4.0 Hz, 1H), 4.54-4.32 (m, 2H), 4.29-4.20 (m, 1H), 3.95 (dt, J = 11.5, 4.6 Hz, 2H), 3.71-3.50 (m, 5H), 3.30-3.15 (m, 2H), 2.13-2.02 (m, 2H), 1.80-1.68 (m, 2H). LCMS-B: RT 2.80 min, m/z 398 [M + H]$^+$ (free base), 396 [M − H]$^−$ (free base) | AD<br>Carboxylic acid: I29<br>Treatment with TFA for 24 hours. |
| 27 | 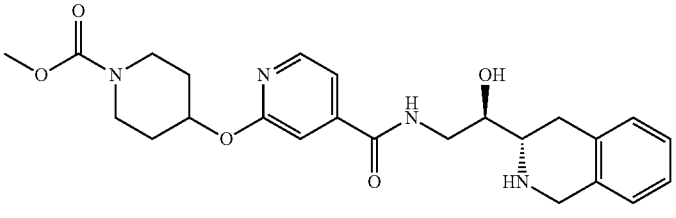<br>Methyl 4-((4-(((R)-2-hydroxy-2-((S)-1,2,3,4-tetrahydroisoquinolin-3-yl)ethyl)carbamoyl)pyridin-2-yl)oxy)piperidine-1-carboxylate bis(2,2,2-trifluoroacetic acid) salt | $^1$H NMR (400 MHz, d$_4$-MeOD) δ 8.23 (dd, J = 5.3, 0.7 Hz, 1H), 7.35-7.15 (m, 6H), 5.27 (tt, J = 7.5, 3.6 Hz, 1H), 4.57-4.32 (m, 2H), 4.29-4.21 (m, 1H), 3.84-3.72 (m, 2H), 3.68-3.50 (m, 3H), 3.46-3.34 (m, 2H), 3.29-3.15 (m, 2H), 2.06-1.95 (m, 2H), 1.80-1.66 (m, 2H). LCMS-B: RT 2.83 min, m/z 455 [M + H]$^+$ (free base) | AE<br>Carboxylic acid: I32 |
| 28 | 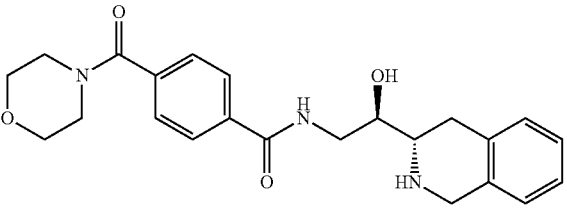<br>N-((R)-2-Hydroxy-2-((S)-1,2,3,4-tetrahydroisoquinolin-3-yl)ethyl)-4-(morpholine-4-carbonyl)benzamide hydrochloride | $^1$H NMR (400 MHz, d$_6$-DMSO) δ 9.42 (d, J = 10.7 Hz, 1H), 9.01-8.90 (m, 1H), 8.81 (t, J = 5.9 Hz, 1H), 7.95-7.89 (m, 2H), 7.51-7.46 (m, 2H), 7.30-7.18 (m, 4H), 5.98 (s, 1H), 4.44-4.34 (m, 1H), 4.24-4.15 (m, 2H), 3.76-3.23 (m, overlaps with solvent), 3.19-3.04 (m, 3H). LCMS-A: RT 1.67 min; m/z 410.2 [M + H]$^+$ (free base) | AF<br>Carboxylic acid: I7 |

TABLE A-continued

| Ex | Name and Structure | Analytical data | Method |
|---|---|---|---|
| 29 | 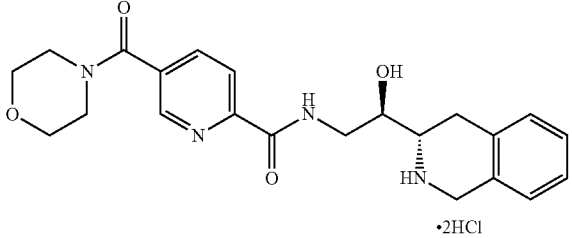 [SMILES: O=C(NC[C@@H](O)[C@@H]1Cc2ccccc2CN1)c1ccc(C(=O)N2CCOCC2)cn1 ; "·2HCl"]<br>N-((R)-2-Hydroxy-2-((S)-1,2,3,4-tetrahydroisoquinolin-3-yl)ethyl)-5-(morpholine-4-carbonyl)picolinamide dihydrochloride salt | LCMS-B: RT 3.11 min; m/z 411.3 [M + H]⁺ (free base) | AG<br>Carboxylic acid (as lithium salt): I34 |
| 57 | 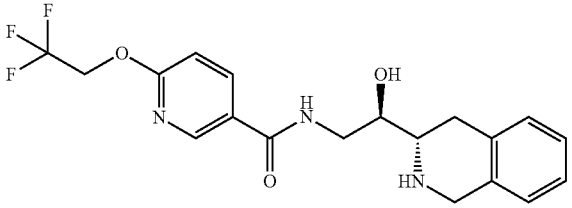 [SMILES: O=C(NC[C@@H](O)[C@@H]1Cc2ccccc2CN1)c1ccc(OCC(F)(F)F)nc1]<br>N-((R)-2-Hydroxy-2-((S)-1,2,3,4-tetrahydroisoquinolin-3-yl)ethyl)-6-(2,2,2-trifluoroethoxy)nicotinamide | LCMS-B: RT 2.923 min; m/z 396.1 [M + H]⁺ | AH |
| 58 | 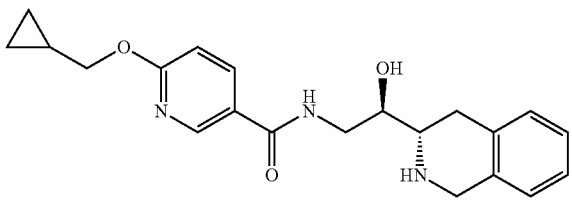 [SMILES: O=C(NC[C@@H](O)[C@@H]1Cc2ccccc2CN1)c1ccc(OCC2CC2)nc1]<br>6-(Cyclopropylmethoxy)-N-((R)-2-hydroxy-2-((S)-1,2,3,4-tetrahydroisoquinolin-3-yl)ethyl)nicotinamide | LCMS-B: RT 2.905 min; m/z 368.2 [M + H]⁺ | AH |
| 59 | 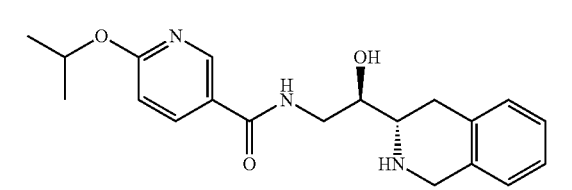 [SMILES: CC(C)Oc1ccc(C(=O)NC[C@@H](O)[C@@H]2Cc3ccccc3CN2)cn1]<br>N-((R)-2-Hydroxy-2-((S)-1,2,3,4-tetrahydroisoquinolin-3-yl)ethyl)-6-isopropoxynicotinamide | LCMS-B: RT 2.892 min; m/z 356.2 [M + H]⁺ | AH |
| 60 | 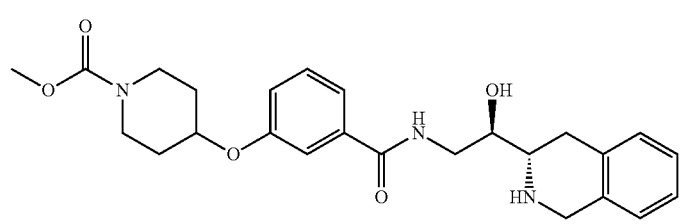 [SMILES: COC(=O)N1CCC(Oc2cccc(C(=O)NC[C@@H](O)[C@@H]3Cc4ccccc4CN3)c2)CC1]<br>Methyl 4-(3-(((R)-2-hydroxy-2-((S)-1,2,3,4-tetrahydroisoquinolin-3-yl)ethyl)carbamoyl)phenoxy)piperidine-1-carboxylate | LCMS-B: RT 2.91 min, m/z 454.2 [M + H]⁺ | AI<br>Treatment with TFA overnight.<br>Carboxylic acid: I48 |

TABLE A-continued

| Ex | Name and Structure | Analytical data | Method |
|---|---|---|---|
| 61 | 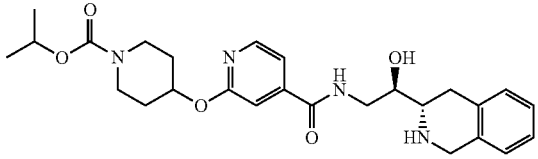 [SMILES: CC(C)OC(=O)N1CCC(Oc2cc(C(=O)NC[C@@H](O)[C@@H]3Cc4ccccc4CN3)ccn2)CC1]<br>Isopropyl 4-((4-(((R)-2-hydroxy-2-((S)-1,2,3,4-tetrahydroisoquinolin-3-yl)ethyl)carbamoyl)pyridin-2-yl)oxy)piperidine-1-carboxylate | LCMS-B: RT 2.99 min, m/z 483.3 [M + H]$^+$ | AI<br>Treatment with TFA overnight.<br>Carboxylic acid: I50 |
| 62 | 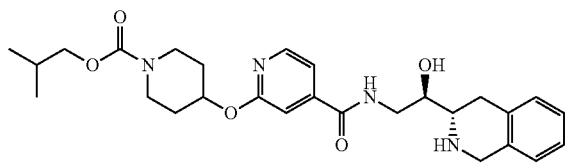 [SMILES: CC(C)COC(=O)N1CCC(Oc2cc(C(=O)NC[C@@H](O)[C@@H]3Cc4ccccc4CN3)ccn2)CC1]<br>Isobutyl 4-((4-(((R)-2-hydroxy-2-((S)-1,2,3,4-tetrahydroisoquinolin-3-yl)ethyl)carbamoyl)pyridin-2-yl)oxy)piperidine-1-carboxylate | LCMS-B: RT 3.04 min, m/z 497.2 [M + H]$^+$ | AI<br>Treatment with TFA overnight.<br>Carboxylic acid: I51 |
| 63 | 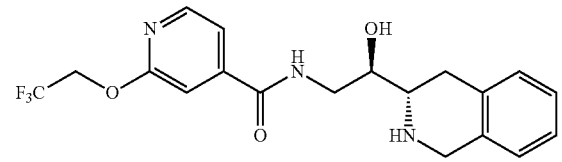 [SMILES: O=C(NC[C@@H](O)[C@@H]1Cc2ccccc2CN1)c1ccnc(OCC(F)(F)F)c1]<br>N-((R)-2-hydroxy-2-((S)-1,2,3,4-tetrahydroisoquinolin-3-yl)ethyl)-2-(2,2,2-trifluoroethoxy)isonicotinamide | LCMS-B: RT 2.90 min, m/z 396.1 [M + H]$^+$, 394.1 [M − H]$^-$ | AI<br>Treatment with TFA for 4 hours. |
| 64 | 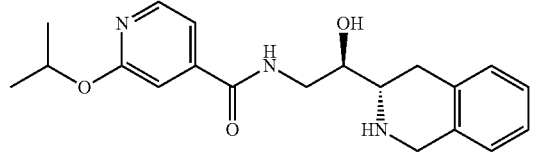 [SMILES: CC(C)Oc1cc(C(=O)NC[C@@H](O)[C@@H]2Cc3ccccc3CN2)ccn1]<br>N-((R)-2-hydroxy-2-((S)-1,2,3,4-tetrahydroisoquinolin-3-yl)ethyl)-2-isopropoxyisonicotinamide | LCMS-B: RT 2.86 min, m/z 356.2 [M + H]$^+$, 354.2 [M − H]$^-$ | AI<br>Treatment with TFA for 4 hours. |
| 65 | 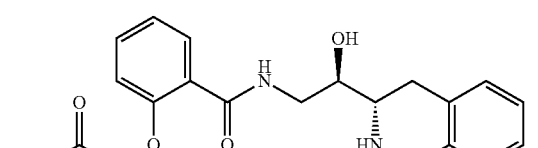<br>2-(2-Amino-2-oxoethoxy)-N-((R)-2-hydroxy-2-((S)-1,2,3,4-tetrahydroisoquinolin-3-yl)ethyl)benzamide | LCMS-A: RT 1.64, 1.79 min; m/z 370.2 [M + H]$^+$ | AJ |

TABLE A-continued

| Ex | Name and Structure | Analytical data | Method |
|---|---|---|---|
| 66 | 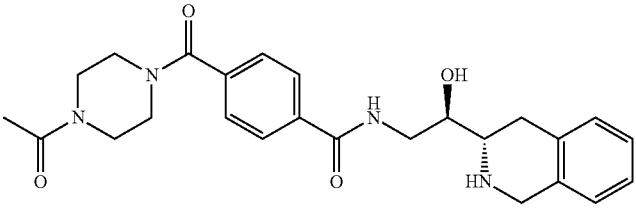 [SMILES: CC(=O)N1CCN(C(=O)c2ccc(C(=O)NC[C@@H](O)[C@@H]3Cc4ccccc4CN3)cc2)CC1]

4-(4-Acetylpiperazine-1-carbonyl)-N-((R)-2-hydroxy-2-((S)-1,2,3,4-tetrahydroisoquinolin-3-yl)ethyl)benzamide | LCMS-A: RT 1.75 min; m/z 451.3 [M + H]⁺ | AJ<br>Lithium salt:<br>I55 |
| 67 | 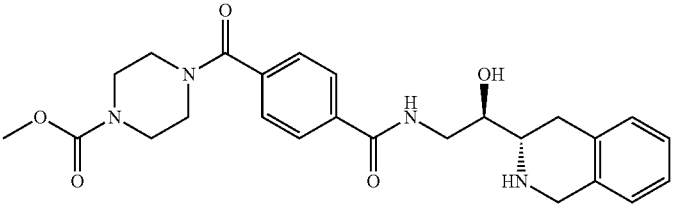 [SMILES: COC(=O)N1CCN(C(=O)c2ccc(C(=O)NC[C@@H](O)[C@@H]3Cc4ccccc4CN3)cc2)CC1]

Methyl 4-(4-(((R)-2-hydroxy-2-((S)-1,2,3,4-tetrahydroisoquinolin-3-yl)ethyl)carbamoyl)benzoyl)piperazine-1-carboxylate | LCMS-A: RT 4.48 min; m/z 467.3 [M + H]⁺ | AJ<br>Lithium salt:<br>I57 |
| 68 | 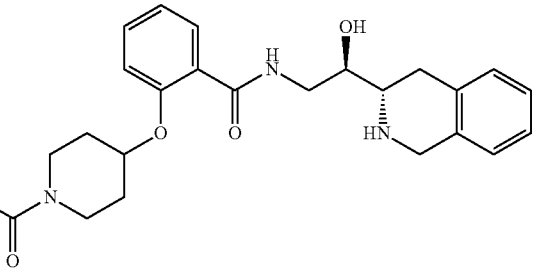

2-((1-Acetylpiperidin-4-yl)oxy)-N-((R)-2-hydroxy-2-((S)-1,2,3,4-tetrahydroisoquinolin-3-yl)ethyl)benzamide | LCMS-A: RT 4.55 min; m/z 438.3 [M + H]⁺ | AJ<br>Carboxylic acid:<br>I58 |
| 69 | 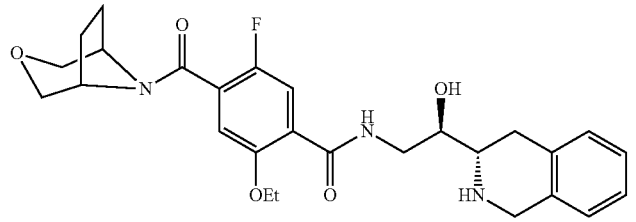 [SMILES: CCOc1cc(C(=O)N2C3CCC2COC3)c(F)cc1C(=O)NC[C@@H](O)[C@@H]1Cc2ccccc2CN1]

4-((3-Oxa-8-azabicyclo[3.2.1]octane-8-carbonyl)-2-ethoxy-5-fluoro-N-((R)-2-hydroxy-2-((S)-1,2,3,4-tetrahydroisoquinolin-3-yl)ethyl)benzamide | LCMS-B: RT 2.88 min; m/z 498.2 [M + H]⁺ | AK<br>Lithium salt:<br>I61 |

| Ex | Name and Structure | Analytical data | Method |
|---|---|---|---|
| 70 | 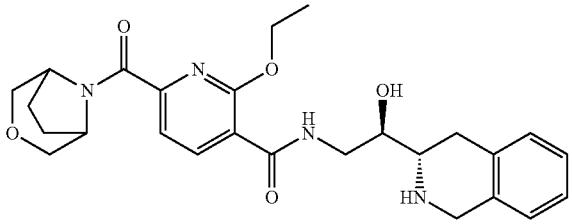 [SMILES: CCOc1nc(C(=O)N2C3CCC2COC3)ccc1C(=O)NC[C@@H](O)[C@@H]1Cc2ccccc2CN1]<br>6-(3-Oxa-8-azabicyclo[3.2.1]octane-8-carbonyl)-2-ethoxy-N-((R)-2-hydroxy-2-((S)-1,2,3,4-tetrahydroisoquinolin-3-yl)ethyl)nicotinamide | $^1$H NMR (400 MHz, Methanol-$d_4$) δ 8.44 (d, J = 8.0 Hz, 1H), 7.52 (d, J = 8.0 Hz, 1H), 7.17-7.08 (m, 4H), 4.70-4.64 (m, 2H), 4.54-4.46 (m, 2H), 4.14 (s, 2H), 3.99-3.95 (m, 1H), 3.91-3.87 (m,1H), 3.81-3.67 (m, 4H), 3.61-3.55 (m, 1H), 3.18-3.13 (m, 1H), 2.99-2.97 (m, 2H), 2.09-1.97 (m, 4H), 1.44 (t, J = 7.2 Hz, 3H).<br>LCMS-C: RT 4.77 min, m/z 481.0 [M + H]$^+$ | AL<br>Carboxylic acid: I65 |
| 71 | 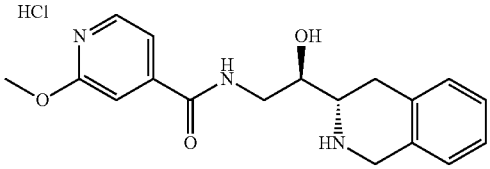 [SMILES: Cl ; COc1cc(C(=O)NC[C@@H](O)[C@@H]2Cc3ccccc3CN2)ccn1]<br>N-((R)-2-Hydroxy-2-((S)-1,2,3,4-tetrahydroisoquinolin-3-yl)ethyl)-2-methoxyisonicotinamide dihydrochloride | $^1$H NMR (400 MHz, Methanol-$d_4$) δ 8.36 (d, J = 6.0 Hz, 1H), 7.58-7.57 (m, 2H), 7.31-7.21 (m, 4H), 4.51-4.47 (m, 1H) 4.39-4.31 (m, 2H), 4.12(s, 3H), 3.71-3.66 (m, 2H), 3.60-3.56 (m, 1H), 3.36-3.32 (m, 1H), 3.24-3.19 (m, 1H).<br>LCMS-C: RT 2.64 min, m/z 328.0 [M + H]$^+$ for free base | AL |
| 72 | 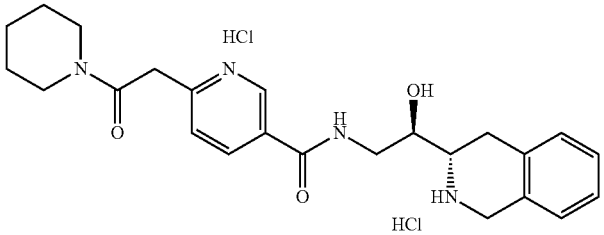 [SMILES: O=C(NC[C@@H](O)[C@@H]1Cc2ccccc2CN1)c1ccc(CC(=O)N2CCCCC2)nc1 ; Cl ; Cl]<br>N-((R)-2-Hydroxy-2-((S)-1,2,3,4-tetrahydroisoquinolin-3-yl)ethyl)-6-(2-oxo-2-(piperidin-1-yl)ethyl)nicotinamide dihydrochloride | $^1$H NMR (400 MHz, Methanol-$d_4$) δ 9.24 (s, 1H), 8.87 (dd, J = 8.0, 1.6 Hz, 1H), 8.01 (d, J = 8.0 Hz, 1H), 7.31-7.21 (m, 4H), 4.51-4.32 (m, 3H), 3.74-3.69 (m, 2H), 3.63-3.56 (m, 5H), 3.37-3.31 (m, 2H), 3.30 (m, 1H), 3.25-3.19 (m, 1H), 1.76-1.66 (m, 4H), 1.60-1.55 (m, 2H).<br>LCMS-C: RT 0.98 min, m/z 423.3 [M + H]$^+$ for free base | AL<br>Carboxylic acid: I70 |
| 73 | 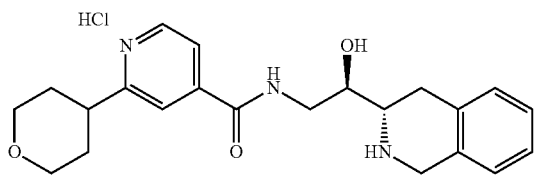<br>N-((R)-2-Hydroxy-2-((S)-1,2,3,4-tetrahydroisoquinolin-3-yl)ethyl)-2-(tetrahydro-2H-pyran-4-yl)isonicotinamide dihydrochloride | $^1$H NMR (400 MHz, Methanol-$d_4$) δ 8.87-8.85 (m, 1H), 8.39 (s, 1H), 8.28 (m, 1H), 7.30-7.23 (m, 4H), 4.52-4.35 (m, 3H), 4.12 (d, J = 10.8 Hz, 2H), 3.76-3.58 (m, 5H), 3.40-3.38 (m, 2H), 3.24-3.20 (m, 1H), 2.01-1.98 (m, 4H).<br>LCMS-C: RT 0.61 min, m/z 382.3 [M + H]$^+$ for free base | AL<br>Carboxylic acid: I75 |

TABLE A-continued

| Ex | Name and Structure | Analytical data | Method |
|---|---|---|---|
| 74 | 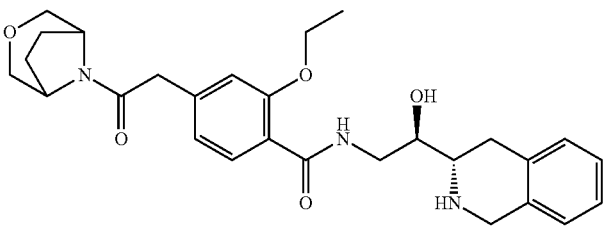 [SMILES: CCOc1cc(CC(=O)N2C3CCC2COC3)ccc1C(=O)NC[C@@H](O)[C@@H]1Cc2ccccc2CN1]<br>4-(2-(3-Oxa-8-azabicyclo[3.2.1]octan-8-yl)-2-oxoethyl)-2-ethoxy-N-(R)-2-hydroxy-2-((S)-1,2,3,4-tetrahydroisoquinolin-3-yl)ethyl)benzamide | $^1$H NMR (400 MHz, Methanol-d$_4$) δ 7.94 (d, J = 8.0 Hz, 1H), 7.16-7.07 (m, 4H), 7.06-6.97 (m, 2H), 4.51 (d, J = 5.8 Hz, 1H), 4.31 (d, J = 5.6 Hz, 1H), 4.27-4.19 (m, 2H), 4.03 (d, J = 4.6 Hz, 2H), 3.89-3.83 (m, 1H), 3.81-3.72 (m, 3H), 3.63-3.52 (m, 4H), 3.40 (d, J = 11.0 Hz, 1H), 2.99-2.94 (m, 1H), 2.91-2.81 (m, 2H), 2.04-1.96 (m, 2H), 1.92-1.83 (m, 2H), 1.48 (t, J = 7.0 Hz, 3H).<br>LCMS-C: RT 1.92 min, m/z 494.4 [M + H]$^+$ | AL<br>Carboxylic acid: I79 |
| 75 | 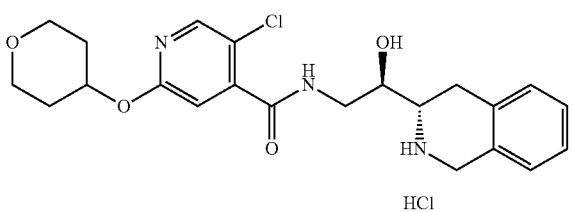<br>5-Chloro-N-((R)-2-hydroxy-2-((S)-1,2,3,4-tetrahydroisoquinolin-3-yl)ethyl)-2-((tetrahydro-2H-pyran-4-yl)oxy)isonicotinamide dihydrochloride | $^1$H NMR (400 MHz, Methanol-d$_4$) δ 8.17 (s, 1H), 7.32-7.22 (m, 4H), 6.92 (s, 1H), 5.26-5.18 (m, 1H), 4.51-4.35 (m, 2H), 4.30-4.26 (m, 1H), 3.97-3.89 (m, 2H), 3.71-3.51 (m, 5H), 3.25-3.14 (m, 2H), 2.11-1.99 (m, 2H), 1.79-1.68 (m, 2H).<br>LCMS-C: RT 3.56 min, m/z 432.2 [M + H]$^+$ for free base | AL<br>Carboxylic acid: I81 |
| 76 | 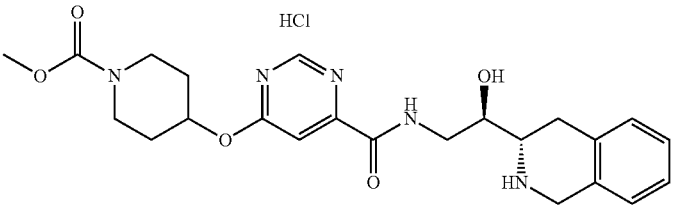<br>Methyl 4-((6-(((R)-2-hydroxy-2-((S)-1,2,3,4-tetrahydroisoquinolin-3-yl)ethyl)carbamoyl)pyrimidin-4-yl)oxy)piperidine-1-carboxylate dihydrochloride | $^1$H NMR (400 MHz, Methanol-d$_4$) δ 8.80 (s, 1H), 7.40 (s, 1H), 7.32-7.24 (m, 3H), 7.21 (d, J = 7.3 Hz, 1H), 5.46-5.40 (m, 1H), 4.49-4.34 (m, 2H), 4.28-4.23 (m, 1H), 3.85-3.75 (m, 2H), 3.72-3.68 (m, 3H), 3.67-3.62 (m, 1H), 3.59-3.53 (m, 1H), 3.45-3.34 (m, 3H), 3.26-3.18 (m, 2H), 2.08-2.00 (m, 2H), 1.81-1.72 (m, 2H).<br>LCMS-C: RT 3.79 min, m/z 456.2 [M + H]$^+$ for free base | AM<br>Lithium salt: I86 |
| 77 | 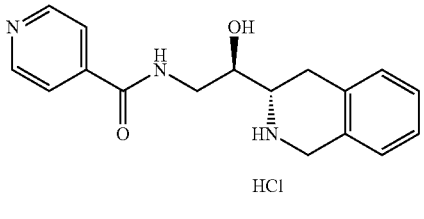<br>N-((R)-2-Hydroxy-2-((S)-1,2,3,4-tetrahydroisoquinolin-3-yl)ethyl)isonicotinamide dihydrochloride | $^1$H NMR (400 MHz, Methanol-d$_4$) δ 9.02 (d, J = 6.2 Hz, 2H), 8.46 (d, J = 6.3 Hz, 2H), 7.33-7.20 (m, 4H), 4.51 (d, J = 15.6 Hz, 1H), 4.41-4.34 (m, 2H), 3.78-3.70 (m, 2H), 3.65-3.58 (m, 1H), 3.39-3.33 (m, 1H), 3.27-3.19 (m, 1H).<br>LCMS-C: RT 0.33 min, m/z 298.1 [M + H]$^+$ for free base | AL |

TABLE A-continued

| Ex | Name and Structure | Analytical data | Method |
|---|---|---|---|
| 78 | 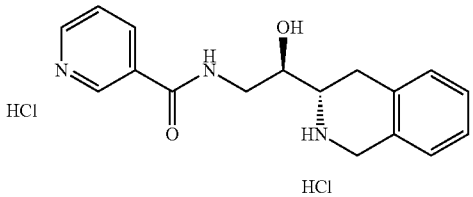 [SMILES: Cl ; O=C(NC[C@@H](O)[C@@H]1Cc2ccccc2CN1)c1cccnc1 ; Cl]<br>N-((R)-2-Hydroxy-2-((S)-1,2,3,4-tetrahydroisoquinolin-3-yl)ethyl)nicotinamide dihydrochloride | $^1$H NMR (400 MHz, Methanol-$d_4$) δ 9.33 (s, 1H), 9.02 (d, J = 8.0, Hz, 1H), , 9.00 (d, J = 5.6, Hz, 1H), 8.18 (dd, J = 8.0, 5.6 Hz, 1H), 7.35-7.18 (m, 4H), 4.50 (d, J = 15.7 Hz, 1H), 4.42-4.32 (m, 2H), 3.79-3.70 (m, 2H), 3.67-3.57 (m, 1H), 3.39-3.33 (m, 1H), 3.27-3.19 (m, 1H). LCMS-C: RT 0.34 min, m/z 298.2 [M + H]$^+$ for free base | AL |
| 79 | 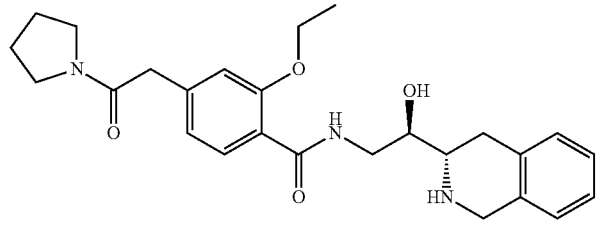<br>2-Ethoxy-N-((R)-2-hydroxy-2-((S)-1,2,3,4-tetrahydroisoquinolin-3-yl)ethyl)-4-(2-oxo-2-(pyrrolidin-1-yl)ethyl)benzamide hydrochloride | $^1$H NMR (400 MHz, Methanol-$d_4$) δ 7.88 (d, J = 8.0 Hz, 1H), 7.32-7.20 (m, 4H), 7.05 (s, 1H), 6.95 (d, J = 7.9 Hz, 1H), 4.49-4.36 (m, 2H), 4.29-4.17 (m, 3H), 3.78-3.69 (m, 3H), 3.65-3.52 (m, 4H), 3.44 (t, J = 6.8 Hz, 2H), 3.29-3.10 (m, 2H), 2.01-1.85 (m, 4H), 1.43 (t, J = 6.8 Hz, 3H). LCMS-C: RT 2.02 min, m/z 452.2 [M + H]$^+$ for free base | AL<br>Carboxylic acid: I88 |
| 80 | 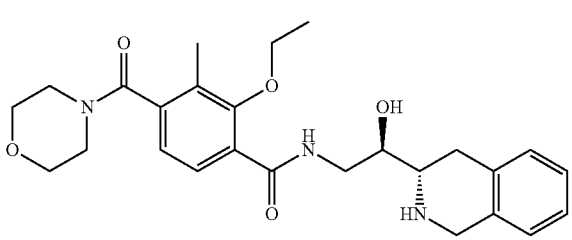<br>2-Ethoxy-N-((R)-2-hydroxy-2-((S)-1,2,3,4-tetrahydroisoquinolin-3-yl)ethyl)-3-methyl-4-(morpholine-4-carbonyl)benzamide hydrochloride | $^1$H NMR (400 MHz, Methanol-$d_4$) δ 7.63 (d, J = 7.7 Hz, 1H), 7.33-7.20 (m, 4H), 7.07 (d, J = 7.8 Hz, 1H), 4.44 (m, 2H), 4.25 (m, 1H), 4.02-3.92 (m, 2H), 3.84-3.70 (m, 5H), 3.68-3.52 (m, 4H), 3.23 (m, 3H), 2.25 (s, 3H), 1.44-1.29 (m, 4H). LCMS-C: RT 1.10 min, m/z 468.3 [M + H]$^+$ for free base | AL<br>Carboxylic acid: I95 |
| 81 | 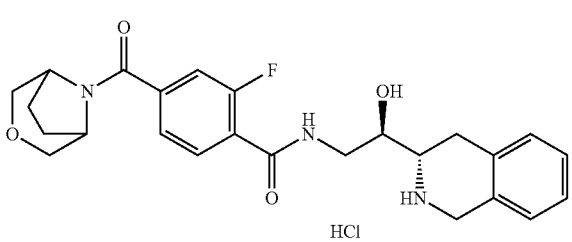 [SMILES: O=C(NC[C@@H](O)[C@@H]1Cc2ccccc2CN1)c1ccc(C(=O)N2C3CCC2COC3)cc1F ; Cl]<br>4-(3-Oxa-8-azabicyclo[3.2.1]octane-8-carbonyl)-2-fluoro-N-((R)-2-hydroxy-2-((S)-1,2,3,4-tetrahydroisoquinolin-3-yl)ethyl)benzamide hydrochloride | $^1$H NMR (400 MHz, Methanol-$d_4$) δ 7.87-7.83 (m, 1H), 7.42-7.37 (m, 2H), 7.31-7.21 (m, 4H), 4.64 (s, 1H), 4.53-4.27 (m, 3H), 3.94 (s, 1H), 3.85-3.56 (m, 7H), 3.56-3.28 (m, 1H, overlap), 3.21 (dd, J = 17.2, 4.4 Hz, 1H), 2.07-2.01 (m, 4H). LCMS-C: RT 0.48 min, m/z 454.3 [M + H]$^+$ for free base | AL<br>Carboxylic acid: I97 |

TABLE A-continued

| Ex | Name and Structure | Analytical data | Method |
|---|---|---|---|
| 82 | 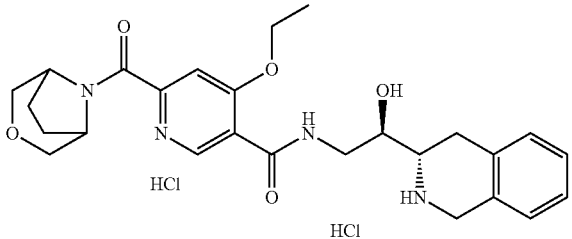 [SMILES: CCOc1cc(C(=O)N2C3CCC2COC3)ncc1C(=O)NC[C@@H](O)[C@@H]1Cc2ccccc2CN1 ; Cl ; Cl]<br>6-(3-Oxa-8-azabicyclo[3.2.1]octane-8-carbonyl)-4-ethoxy-N-((R)-2-hydroxy-2-((S)-1,2,3,4-tetrahydroisoquinolin-3-yl)ethyl)nicotinamide dihydrochloride | $^1$H NMR (400 MHz, Methanol-$d_4$) δ 8.97 (s, 1H), 7.74 (s, 1H), 7.31-7.22 (m, 4H), 4.68 (s, 1H), 4.54-4.48 (m, 3H), 4.47-4.27 (m, 3H), 3.86-3.59 (m, 7H), 3.56-3.29 (m, 1H, obscured by solvent), 3.20 (dd, J = 16.8, 4.0 Hz, 1H), 2.09-2.08 (m, 4H), 1.49 (t, J = 6.8 Hz, 3H).<br>LCMS-C: RT 3.18 min, m/z 481.1 [M + H]$^+$ for free base | AL<br>Carboxylic acid: I103 |
| 83 | 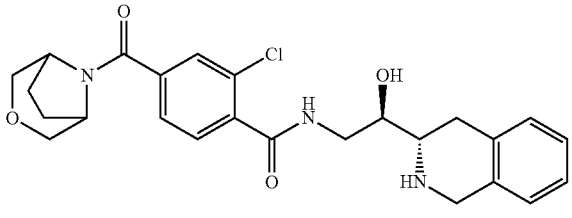 [SMILES: O=C(NC[C@@H](O)[C@@H]1Cc2ccccc2CN1)c1ccc(C(=O)N2C3CCC2COC3)cc1Cl]<br>4-(3-Oxa-8-azabicyclo[3.2.1]octane-8-carbonyl)-2-chloro-N-((R)-2-hydroxy-2-((S)-1,2,3,4-tetrahydroisoquinolin-3-yl)ethyl)benzamide | $^1$H NMR (400 MHz, Methanol-$d_4$) δ 7.61-7.57 (m, 2H), 7.51-7.49 (m, 1H), 7.17-7.09 (m, 4H), 4.63 (s, 1H), 4.15 (s, 2H), 4.01-3.94 (m, 2H), 3.82-3.80 (m, 1H), 3.72-3.64 (m, 3H), 3.59-3.56 (m, 2H), 3.21-3.17 (m, 1H), 3.00-2.99 (m, 2H), 2.06-2.01 (m, 4H).<br>LCMS-C: RT 3.25 min, m/z 470.2 [M + H]$^+$ | AL<br>Carboxylic acid: I105 |
| 84 | 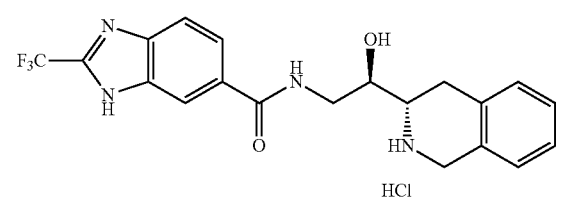<br>N-((R)-2-Hydroxy-2-((S)-1,2,3,4-tetrahydroisoquinolin-3-yl)ethyl)-2-(trifluoromethyl)-1H-benzo[d]imidazole-6-carboxamide dihydrochloride | $^1$H NMR (400 MHz, Methanol-$d_4$) δ 8.28 (s, 1H), 7.96-7.93 (m, 1H), 7.77 (d, J = 8.4 Hz, 1H), 7.32-7.21 (m, 4H), 4.51-4.35 (m, 2H), 4.30-4.26 (m, 1H), 3.71-3.58 (m, 3H), 3.28-3.26 (m, 1H).<br>LCMS-C: RT 3.51 min, m/z 405.1 [M + H]$^+$ for free base | AL<br>Carboxylic acid: I106 |
| 85 | 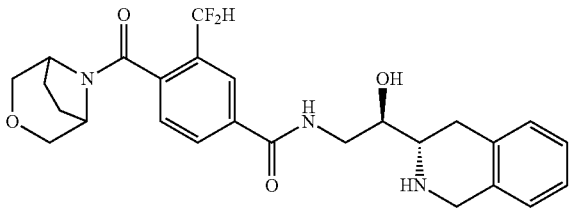 [SMILES: O=C(NC[C@@H](O)[C@@H]1Cc2ccccc2CN1)c1ccc(C(=O)N2C3CCC2COC3)c(C(F)F)c1]<br>4-(3-Oxa-8-azabicyclo[3.2.1]octane-8-carbonyl)-3-(difluoromethyl)-N-((R)-2-hydroxy-2-((S)-1,2,3,4-tetrahydroisoquinolin-3-yl)ethyl)benzamide | $^1$H NMR (400 MHz, Methanol-$d_4$) δ 8.22 (s, 1H), 8.10 (d, J = 7.6 Hz, 1H), 7.61 (d, J = 7.6 Hz, 1H), 7.24-7.14 (m, 4H), 7.02-6.88 (m, 1H), 4.69 (s, 1H), 4.32-4.22 (m, 2H), 4.15-4.14 (m, 1H), 3.83-3.80 (m, 1H), 4.74-3.66 (m, 4H), 3.61-3.48 (m, 2H), 3.42-3.37 (m, 1H), 3.20-3.07 (m, 2H), 2.09-1.99 (m, 4H).<br>LCMS-C: RT 2.05 min, m/z 486.2 [M + H]$^+$ | AL<br>Carboxylic acid: I110 |

TABLE A-continued

| Ex | Name and Structure | Analytical data | Method |
|---|---|---|---|
| 86 | 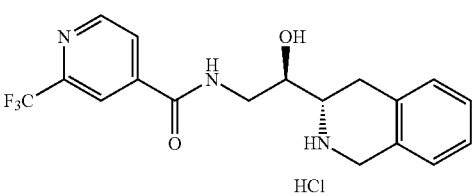<br>N-((R)-2-Hydroxy-2-((S)-1,2,3,4-tetrahydroisoquinolin-3-yl)ethyl)-2-(trifluoromethyl)isonicotinamide dihydrochloride | $^1$H NMR (400 MHz, Methanol-$d_4$) δ 8.88 (d, J = 4.8 Hz, 1H), 8.23 (s, 1H), 8.07 (d, J = 4.8 Hz, 1H), 7.31-7.21 (m, 4H), 4.51-4.47 (m, 1H), 4.39-4.31 (m, 2H), 3.71-3.66 (m, 2H), 3.61-3.56 (m, 1H), 3.37 (m, 1H), 3.24-3.19 (m, 1H).<br>LCMS-C: RT 3.43 min, m/z 366.3 [M + H]$^+$ for free base | AL |
| 87 | 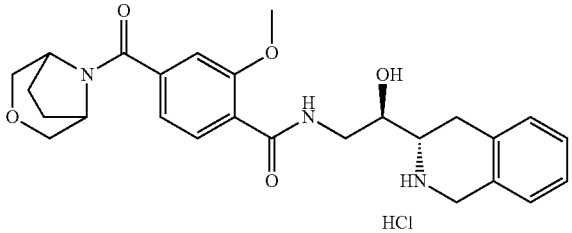 [SMILES: COc1cc(C(=O)N2C3CCC2COC3)ccc1C(=O)NC[C@@H](O)[C@@H]1Cc2ccccc2CN1 ; Cl]<br>4-(3-Oxa-8-azabicyclo[3.2.1]octane-8-carbonyl)-N-((R)-2-hydroxy-2-((S)-1,2,3,4-tetrahydroisoquinolin-3-yl)ethyl)-2-methoxybenzamide hydrochloride | $^1$H NMR (400 MHz, Methanol-$d_4$) δ 7.96 (d, J = 7.6 Hz, 1H), 7.31-7.22 (m, 5H), 7.17 (dd, J = 8.0, 1.2 Hz, 1H), 4.65 (br s, 1H), 4.96-4.36 (m, 2H), 4.28-4.24 (m, 1H), 3.97 (s, 3H), 3.84-3.81 (m, 1H), 3.75-3.71 (m, 3H), 3.67-3.56 (m, 4H), 3.27-3.23 (m, 2H), 2.08-1.98 (m, 4H).<br>LCMS-C: RT 1.03 min, m/z 466.2 [M + H]$^+$ for free base. | AL<br>Carboxylic acid: I112 |
| 88 | 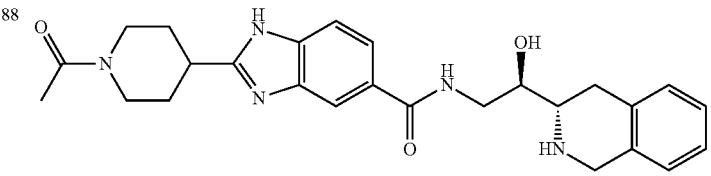<br>2-(1-Acetylpiperidin-4-yl)-N-((R)-2-hydroxy-2-((S)-1,2,3,4-tetrahydroisoquinolin-3-yl)ethyl)-1H-benzo[d]imidazole-5-carboxamide | $^1$H NMR (400 MHz, Methanol-$d_4$) δ 8.33 (s, 1H), 8.12 (d, J = 7.3 Hz, 1H), 7.85 (d, J = 7.2 Hz, 1H), 7.37-7.19 (m, 4H), 4.77-4.69 (m, 1H), 4.53-4.29 (m, 3H), 4.20-4.10 (m, 1H), 3.75-3.57 (m, 4H), 3.28-3.11 (m, 2H), 2.93-2.69 (m, 2H), 2.38-2.22 (m, 2H), 2.17 (s, 3H), 2.00-1.80 (m, 2H).<br>LCMS-C: RT 0.34 min, m/z 462.3 [M + H]$^+$ | AL<br>Carboxylic acid: I117 |
| 89 | 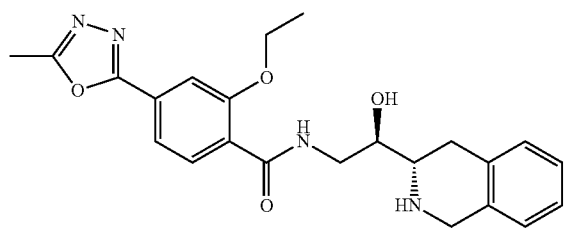 [SMILES: CCOc1cc(-c2nnc(C)o2)ccc1C(=O)NC[C@@H](O)[C@@H]1Cc2ccccc2CN1]<br>2-Ethoxy-N-((R)-2-hydroxy-2-((S)-1,2,3,4-tetrahydroisoquinolin-3-yl)ethyl)-4-(5-methyl-1,3,4-oxadiazol-2-yl)benzamide | $^1$H NMR (400 MHz, Methanol-$d_4$) δ 8.05 (d, J = 8.0 Hz, 1H), 7.71 (s, 1H), 7.68 (d, J = 8.4 Hz, 1H), 7.24-7.21 (m, 3H), 7.18-7.16 (m, 1H), 4.32-4.27(m, 4H), 4.18-4.13 (m, 1H), 3.78-3.72 (m, 1H), 3.64-3.58(m, 1H), 3.48-3.43(m, 1H), 3.21-3.08 (m, 2H), 2.63 (s, 3H), 1.48 (t, J = 6.8 Hz, 3H).<br>LCMS-C: RT 3.57 min, m/z 423.2 [M + H]$^+$ | AL<br>Carboxylic acid: I120 |
| 111 | 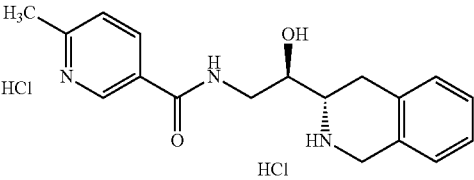 [SMILES: Cl ; Cc1ccc(C(=O)NC[C@@H](O)[C@@H]2Cc3ccccc3CN2)cn1 ; Cl]<br>6-Amino-N-((R)-2-hydroxy-2-((S)-1,2,3,4-tetrahydroisoquinolin-3-yl)ethyl)nicotinamide dihydrochloride | $^1$H NMR (400 MHz, Methanol-$d_4$) δ 8.43(s, 1H), 8.34(d, J = 8.8 Hz, 1H), 7.30-7.20 (m, 4H), 7.06 (d, J = 8.8 Hz, 1H), 4.50-4.46 (m, 1H), 4.38-4.27 (m, 2H), 3.67-3.63 (m, 2H), 3.56-3.53 (m, 1H), 3.27-3.18 (m, 2H).<br>LCMS-C: RT 0.25 min, m/z 313.2 [M + H]$^+$ (free base) | AL |

TABLE A-continued

| Ex | Name and Structure | Analytical data | Method |
|---|---|---|---|
| 112 | 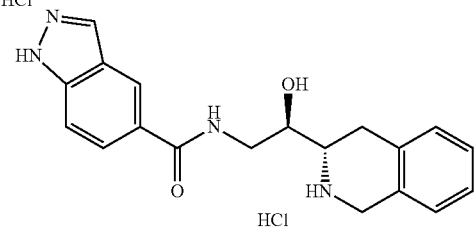<br>N-((R)-2-Hydroxy-2-((S)-1,2,3,4-tetrahydroisoquinolin-3-yl)ethyl)-1H-indazole-5-carboxamide dihydrochloride | $^1$H NMR (400 MHz, Methanol-$d_4$) δ 8.38 (s, 1H), 8.18 (s, 1H), 7.91 (dd, J = 8.8, 1.2 Hz, 1H), 7.60 (d, J = 8.8, 1H), 7.31-7.20 (m, 4H), 4.50-4.46 (m, 1H), 4.39-4.35 (m, 1H), 4.31-4.27 (m, 1H), 3.71-3.58 (m, 3H), 3.36-3.33 (m, 1H), 3.27-3.22 (m, 1H).<br>LCMS-C: RT 2.65 min, m/z 337.2 [M + H]$^+$ (free base) | AL |
| 113 | 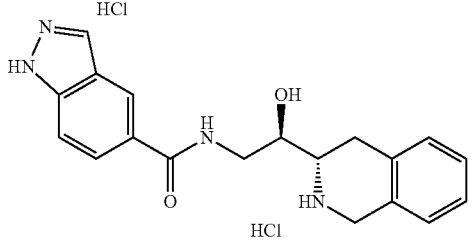 [SMILES: Cl ; O=C(NC[C@@H](O)[C@@H]1Cc2ccccc2CN1)c1ccc2[nH]ncc2c1 ; Cl]<br>N-((R)-2-Hydroxy-2-((S)-1,2,3,4-tetrahydroisoquinolin-3-yl)ethyl)-1H-benzo[d]imidazole-5-carboxamide dihydrochloride | $^1$H NMR (400 MHz, Methanol-$d_4$) δ 9.49 (s, 1H), 8.43 (s, 1H), 8.15(d, J = 8.4 Hz, 1H), 7.94 (d, J = 8.4 Hz, 1H), 7.31-7.21 (m, 4H), 4.52-4.35 (m, 3H), 3.75-3.59 (m, 3H), 3.38-3.33 (m, 1H), 3.27-3.22 (m, 1H).<br>LCMS-C: RT 0.28 min, m/z 337.1 [M + H]$^+$ (free base) | AL |
| 114 | 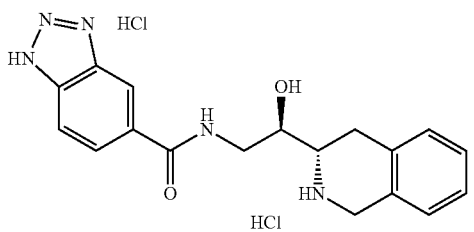 [SMILES: O=C(NC[C@@H](O)[C@@H]1Cc2ccccc2CN1)c1ccc2[nH]nnc2c1 ; Cl ; Cl]<br>N-((R)-2-Hydroxy-2-((S)-1,2,3,4-tetrahydroisoquinolin-3-yl)ethyl)-1H-benzo[d][1,2,3]triazole-5-carboxamide dihydrochloride | $^1$H NMR (400 MHz, Methanol-$d_4$) δ 8.48 (s, 1H), 7.99 (d, J = 9.6 Hz, 1H), 7.91 (d, J = 8.8, 1H), 7.31-7.21 (m, 4H), 4.51-4.47 (m, 1H), 4.39-4.35 (m, 1H), 4.31-4.28 (m, 1H), 3.72-3.59 (m, 3H), 3.37-3.33 (m, 1H), 3.27-3.22 (m, 1H).<br>LCMS-C: RT 2.72 min, m/z 338.1 [M + H]$^+$ (free base) | AL |
| 115 | 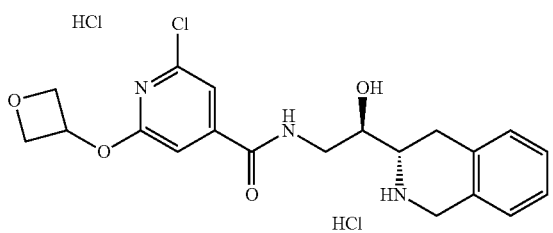 [SMILES: Cl ; O=C(NC[C@@H](O)[C@@H]1Cc2ccccc2CN1)c1cc(Cl)nc(OC2COC2)c1 ; Cl]<br>2-Chloro-N-((R)-2-hydroxy-2-((S)-1,2,3,4-tetrahydroisoquinolin-3-yl)ethyl)-6-(oxetan-3-yloxy)isonicotinamide dihydrochloride | $^1$H NMR (400 MHz, Methanol-$d_4$) δ 8.05 (s, 1H), 7.87 (s, 1H), 7.33-7.22 (m, 4H), 5.67 (t, J = 8.0 Hz, 1H), 5.14-5.06 (m, 1H), 5.00-4.93 (m, 1H), 4.50 (d, J = 15.5 Hz, 1H), 4.40-4.31 (m, 2H), 4.11-4.05 (m, 1H), 3.91-3.86 (m, 1H), 3.76-3.65 (m, 1H), 3.62-3.54 (m, 1H), 3.37-3.33 (m, 2H), 3.23-3.16 (m, 1H).<br>LCMS-C: RT 0.26 min, m/z 404.1, 406.1 [M + H]$^+$ (free base) | AL<br>Carboxylic acid: I121 |

TABLE A-continued

| Ex | Name and Structure | Analytical data | Method |
|---|---|---|---|
| 116 | 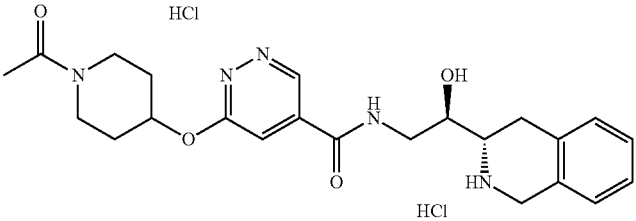 [SMILES: CC(=O)N1CCC(Oc2cc(C(=O)NC[C@@H](O)[C@@H]3Cc4ccccc4CN3)cnn2)CC1 ; Cl ; Cl]<br>6-((1-Acetylpiperidin-4-yl)oxy)-N-((R)-2-hydroxy-2-((S)-1,2,3,4-tetrahydroisoquinolin-3-yl)ethyl)pyridazine-4-carboxamide dihydrochloride | $^1$H NMR (400 MHz, Methanol-$d_4$) δ 9.48 (s, 1H), 8.09 (s, 1H), 7.29-7.23 (m, 4H), 4.51-4.35 (m, 3H), 3.90-3.58 (m, 8H), 3.26-3.16 (m, 2H), 2.25-2.05 (m, 5H), 1.96-1.87 (m, 2H)<br>LCMS-C: RT 0.56 min, m/z 440.2 [M + H]$^+$ (free base) | AL<br>Carboxylic acid: I124 |
| 117 | 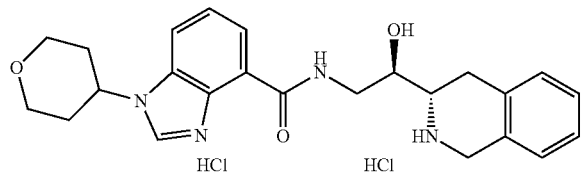 [SMILES: O=C(NC[C@@H](O)[C@@H]1Cc2ccccc2CN1)c1cccc2c1ncn2C1CCOCC1 ; Cl ; Cl]<br>N-((R)-2-Hydroxy-2-((S)-1,2,3,4-tetrahydroisoquinolin-3-yl)ethyl)-1-(tetrahydro-2H-pyran-4-yl)-1H-benzo[d]imidazole-4-carboxamide dihydrochloride | $^1$H NMR (400 MHz, Methanol-$d_4$) δ 9.47 (s, 1H), 8.25 (d, J = 8 Hz, 1H), 8.17 (d, J = 7.2 Hz, 1H), 7.76-7.72 (m, 1H), 7.32-7.21 (m, 4H), 4.51-4.36 (m, 3H), 4.16 (d, J = 11.2 Hz, 2H), 3.82-3.63 (m, 5H), 3.40-3.25 (m, overlap), 2.25 (br s, 4H).<br>LCMS-C: RT 3.25 min, m/z 421.2 [M + H]$^+$ (free base) | AL<br>Carboxylic acid: I129 |
| 118 | 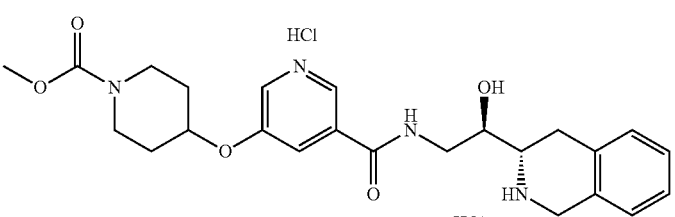<br>Methyl 4-((5-(((R)-2-hydroxy-2-((S)-1,2,3,4-tetrahydroisoquinolin-3-yl)ethyl)carbamoyl)pyridin-3-yl)oxy)piperidine-1-carboxylate dihydrochloride | $^1$H NMR (400 MHz, Methanol-$d_4$) δ 8.82 (s, 1H), 8.69 (s, 1H), 8.51 (s, 1H), 7.31-7.21 (m, 4H), 4.95 (br s, 1H), 4.52-4.34 (m, 3H), 3.81-3.70 (m, 7H), 3.62-3.57 (m, 1H), 3.47-3.42 (m, 2H), 3.37-3.31 (m, 1H, overlap), 3.24-3.21 (m, 1H), 2.06 (br s, 2H), 1.79 (br s, 2H).<br>LCMS-C: RT 3.55 min, m/z 455.2 [M + H]$^+$ (free base) | AL<br>Lithium salt: I135 |
| 119 | 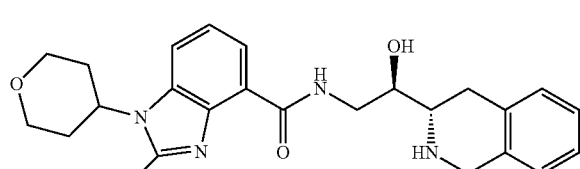<br>N-((R)-2-Hydroxy-2-((S)-1,2,3,4-tetrahydroisoquinolin-3-yl)ethyl)-2-methyl-1-(tetrahydro-2H-pyran-4-yl)-1H-benzo[d]imidazole-4-carboxamide dihydrochloride | $^1$H NMR (400 MHz, Methanol-$d_4$) δ 8.27 (d, J = 8.4 Hz, 1H), 8.09 (d, J = 7.6 Hz, 1H), 7.67 (t, J = 8.0 Hz, 1H), 7.32-7.21 (m, 4H), 4.99-4.93 (m, 1H), 4.51-4.35 (m, 3H), 4.19-4.15 (dd, J = 11.6, 4.0 Hz, 2H), 3.80-3.62 (m, 5H), 3.40-3.25 (m, 2H, overlap), 3.02 (s, 3H), 2.65-2.55 (m, 2H), 2.05-2.02 (m, 2H).<br>LCMS-C: RT 2.89 min, m/z 435.2 [M + H]$^+$ (free base) | AL<br>Carboxylic acid: I131 |

TABLE A-continued

| Ex | Name and Structure | Analytical data | Method |
|---|---|---|---|
| 120 | 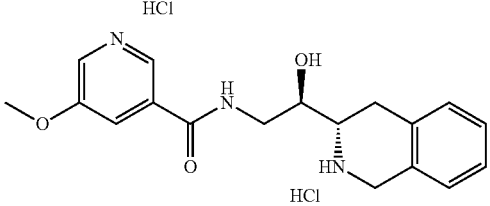 [SMILES: Cl ; COc1cncc(C(=O)NC[C@@H](O)[C@@H]2Cc3ccccc3CN2)c1 ; Cl]<br>N-((R)-2-Hydroxy-2-((S)-1,2,3,4-tetrahydroisoquinolin-3-yl)ethyl)-5-methoxynicotinamide dihydrochloride | $^1$H NMR (400 MHz, Methanol-d$_4$) δ 8.88 (s, 1H), 8.70 (s, 1H), 8.56 (s, 1H), 7.31-7.21 (m, 4H), 4.52-4.49 (m, 1H), 4.39-4.3 (m, 2H), 4.10 (s, 3H), 3.75-2.72 (m, 2H), 3.63-3.58 (m, 1H), 3.37-3.33 (m, 1H), 3.26-3.20 (m, 1H).<br>LCMS-C: RT 0.52 min, m/z 328.1 [M + H]$^+$ (free base) | AL<br>Carboxylic acid: I137 |
| 126 | 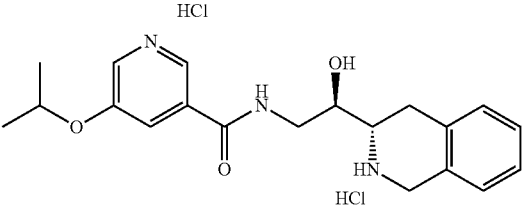 [SMILES: Cl ; CC(C)Oc1cncc(C(=O)NC[C@@H](O)[C@@H]2Cc3ccccc3CN2)c1 ; Cl]<br>N-((R)-2-Hydroxy-2-((S)-1,2,3,4-tetrahydroisoquinolin-3-yl)ethyl)-5-isopropoxynicotinamide dihydrochloride | $^1$H NMR (400 MHz, Methanol-d$_4$) δ 8.80 (s, 1H), 8.69 (s, 1H), 8.39 (s, 1H), 7.31-7.21 (m, 4H), 4.54 (d, J = 7.6 Hz, 1H), 4.39-4.34 (m, 2H), 3.74-3.69 (m, 2H), 3.62-3.57 (m, 1H), 3.39-3.33 (m, 1H), 3.25-3.20 (m, 1H), 3.13-3.07 (m, 1H), 1.46 (d, J = 6.0, 6H).<br>LCMS-C: RT 1.63 min, m/z 357.0 [M + H]$^+$ | AL<br>Carboxylic acid: I139 |

Examples 30-47, 56 & 90-97 (Table B)

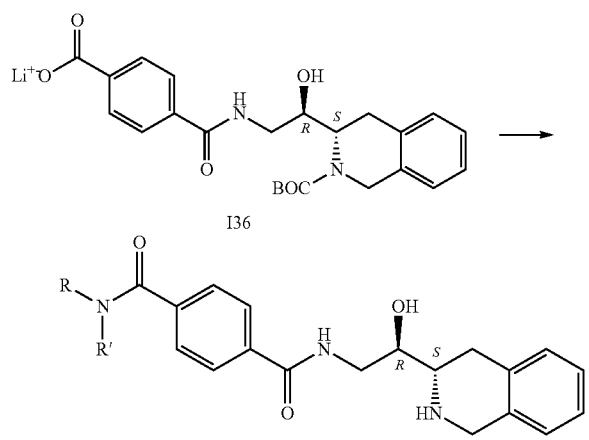

General Method BA:

Lithium 4-(((R)-2-((S)-2-(tert-butoxycarbonyl)-1,2,3,4-tetrahydroisoquinolin-3-yl)-2-hydroxyethyl)carbamoyl) benzoate (I36) (30 mg, 0.067 mmol), the respective amine (0.067 mmol), triethylamine (0.028 mL, 0.20 mmol), DMF (0.5 mL) and HATU (38 mg, 0.10 mmol) were stood at room temperature. After 18 hours the mixture was diluted with water (1.5 mL) and DCM (1 mL). The mixture was passed through a phase separator cartridge and the collected DCM phase was diluted with 4.0 M HCl in 1,4-dioxane (1 mL). After 4 hours the mixture was diluted with methanol (1 mL) and loaded onto a 0.5 g SCX cartridge. The cartridge was washed with methanol (10 mL) and eluted with 2M ammonia in methanol (5 mL). The basic eluate was concentrated to give the amide products.

General Procedure BB:

To a solution of the respective amine (0.20 mmol, 1 equiv) in DMF (1 mL) and MeCN (5 mL) were added a pre-stirred solution of lithium 4-(((R)-2-((S)-2-(tert-butoxycarbonyl)-1, 2,3,4-tetrahydroisoquinolin-3-yl)-2-hydroxyethyl)carbamoyl)benzoate (I36) (69 mg, 0.20 mmol, 1 equiv), DIPEA (104 µL, 0.60 mmol, 3 equiv) and HATU (114 mg, 0.30 mmol, 1.5 equiv) in DMF (1 mL). The reaction was stirred at room temperature for 16 hours. The mixture was quenched with a saturated aqueous solution of NaHCO$_3$ (5 mL) and extracted with DCM (3×5 mL) utilizing a phase separation cartridge. The organic filtrates were dried in vacuo to give an oil which was taken up in 2M HCl in 1,4-dioxane (2 mL) and stirred at room temperature for 20 hours. The reaction was dried in vacuo and then purified by solid-phase extraction (1 g SCX-2 cartridge, 3 column volumes of methanol followed by 3 column volumes of 0.2 M methanolic ammonia), then concentrated to give the amide products.

General Procedure BC

Lithium 4-(((R)-2-((S)-2-(tert-butoxycarbonyl)-1,2,3,4-tetrahydroisoquinolin-3-yl)-2-hydroxyethyl)carbamoyl) benzoate I36 (30 mg, 0.067 mmol), the respective amine or amine hydrochloride (0.067 mmol), triethylamine (0.028 mL, 0.20 mmol), DMF (0.5 mL) and HATU (38 mg, 0.10 mmol) were stood at room temperature. After 18 hours, the mixture was diluted with water (1.5 mL) and DCM (1 mL). The mixture was passed through a phase separator cartridge and the DCM filtrate diluted with 4 M HCl/1,4-dioxane (1 mL). After 4 hours, the mixture was diluted with methanol (1 mL) and loaded onto a 1 g SCX cartridge. The cartridge was washed with methanol (20 mL) and eluted with 2 M ammonia in methanol (12 mL). The basic eluate was concentrated to give the desired compound.

TABLE B

| Ex | Structure | LCMS | Method |
|----|-----------|------|--------|
| 30 | 4-(4-(Difluoromethyl)-4-hydroxypiperidine-1-carbonyl)-N-((R)-2-hydroxy-2-((S)-1,2,3,4-tetrahydroisoquinolin-3-yl)ethyl)benzamide | LCMS-B: RT 3.20 min; m/z 474.2 [M + H]$^+$ | BA |
| 31 | N$^1$-((R)-2-Hydroxy-2-((S)-1,2,3,4-tetrahydroisoquinolin-3-yl)ethyl)-N$^4$-((tetrahydro-2H-pyran-4-yl)methyl)terephthalamide | LCMS-B: RT 3.18 min; m/z 438.2 [M + H]$^+$ | BA |
| 32 | N-((R)-2-Hydroxy-2-((S)-1,2,3,4-tetrahydroisoquinolin-3-yl)ethyl)-4-(4-(hydroxymethyl)piperidine-1-carbonyl)benzamide | LCMS-B: RT 3.14 min; m/z 438.2 [M + H]$^+$ | BA |
| 33 | 4-(4-(Ethylsulfonyl)piperazine-1-carbonyl)-N-((R)-2-hydroxy-2-((S)-1,2,3,4-tetrahydroisoquinolin-3-yl)ethyl)benzamide | LCMS-B: RT 3.21 min; m/z 501.2 [M + H]$^+$ | BA |

TABLE B-continued

| Ex | Structure | LCMS | Method |
|---|---|---|---|
| 34 | 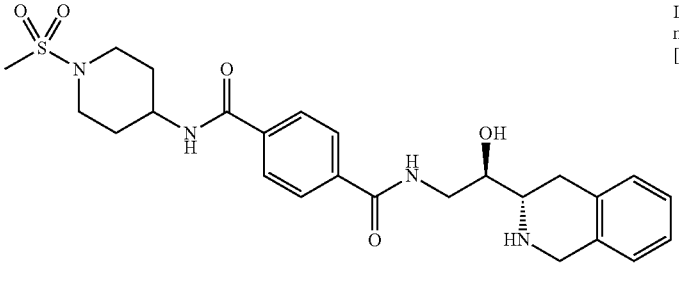<br>N¹-((R)-2-Hydroxy-2-((S)-1,2,3,4-tetrahydroisoquinolin-3-yl)ethyl)-N⁴-(1-(methylsulfonyl)piperidin-4-yl)terephthalamide hydrochloride | LCMS-B: RT 3.14 min; m/z 501.2 [M + H]⁺ (free base) | BA Precipitated from HCl/1,4-dioxane, collected, washed with MeOH and dried to give the title compound. |
| 35 | 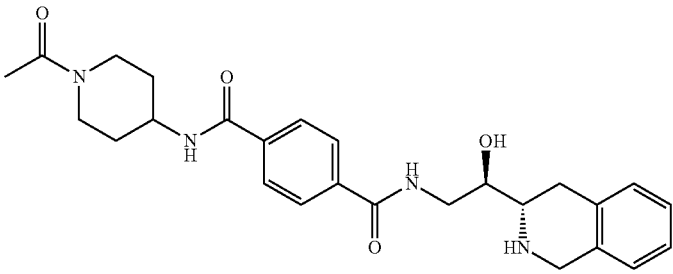<br>N¹-(1-Acetylpiperidin-4-yl)-N⁴-((R)-2-hydroxy-2-((S)-1,2,3,4-tetrahydroisoquinolin-3-yl)ethyl)terephthalamide | LCMS-B: RT 3.11 min; m/z 465.3 [M + H]⁺ | BA |
| 36 | 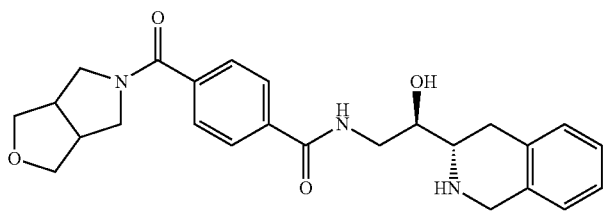 [SMILES: O=C(NC[C@@H](O)[C@@H]1Cc2ccccc2CN1)c1ccc(C(=O)N2CC3COCC3C2)cc1]<br>4-(cis-Hexahydro-1H-furo[3,4-c]pyrrole-5-carbonyl)-N-((R)-2-hydroxy-2-((S)-1,2,3,4-tetrahydroisoquinolin-3-yl)ethyl)benzamide | LCMS-B: RT 3.12 min; m/z 436.3 [M + H]⁺ | BA |
| 37 | 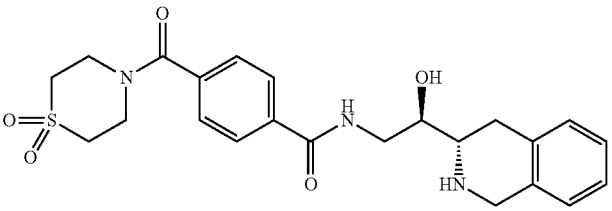 [SMILES: O=C(NC[C@@H](O)[C@@H]1Cc2ccccc2CN1)c1ccc(C(=O)N2CCS(=O)(=O)CC2)cc1]<br>4-(1,1-Dioxidothiomorpholine-4-carbonyl)-N-((R)-2-hydroxy-2-((S)-1,2,3,4-tetrahydroisoquinolin-3-yl)ethyl)benzamide | LCMS-B: RT 3.13 min; m/z 458.2 [M + H]⁺ | BA |

TABLE B-continued

| Ex | Structure | LCMS | Method |
|---|---|---|---|
| 38 | N-((R)-2-Hydroxy-2-((S)-1,2,3,4-tetrahydroisoquinolin-3-yl)ethyl)-4-(3-methoxy-8-azabicyclo[3.2.1]octane-8-carbonyl)benzamide | LCMS-B: RT 3.26 min; m/z 464.2 [M + H]+ | BA |
| 39 | N1-((R)-2-Hydroxy-2-((S)-1,2,3,4-tetrahydroisoquinolin-3-yl)ethyl)-N4-isopropyl-N4-methylterephthalamide | LCMS-B: RT 3.28 min; m/z 396.2 [M + H]+ | BA |
| 40 | N-((R)-2-Hydroxy-2-((S)-1,2,3,4-tetrahydroisoquinolin-3-yl)ethyl)-4-(1,4-oxazepane-4-carbonyl)benzamide | LCMS-B: RT 3.20 min; m/z 424.2 [M + H]+ | BA |
| 41 | N-((R)-2-Hydroxy-2-((S)-1,2,3,4-tetrahydroisoquinolin-3-yl)ethyl)-4-(4-methyl-3-oxopiperazine-1-carbonyl)benzamide | LCMS-B: RT 3.12 min; m/z 437.2 [M + H]+ | BA |
| 42 | N-((R)-2-Hydroxy-2-((S)-1,2,3,4-tetrahydroisoquinolin-3-yl)ethyl)-4-(3-hydroxy-8-azabicyclo[3.2.1]octane-8-carbonyl)benzamide | LCMS-B: RT 3.19 min; m/z 450.2 [M + H]+ | BA |

TABLE B-continued

| Ex | Structure | LCMS | Method |
|---|---|---|---|
| 43 | N-((R)-2-Hydroxy-2-((S)-1,2,3,4-tetrahydroisoquinolin-3-yl)ethyl)-4-(3-hydroxypiperidine-1-carbonyl)benzamide | LCMS-B: RT 3.10 min, m/z 424 [M + H]$^+$ | BB |
| 44 | N$^1$-(4,4-Difluorocyclohexyl)-N$^4$-((R)-2-hydroxy-2-((S)-1,2,3,4-tetrahydroisoquinolin-3-yl)ethyl)terephthalamide | LCMS-B: RT 3.32 min, m/z 458 [M + H]$^+$ | BB |
| 45 | N-((R)-2-Hydroxy-2-((S)-1,2,3,4-tetrahydroisoquinolin-3-yl)ethyl)-4-(4-hydroxypiperidine-1-carbonyl)benzamide | LCMS-B: RT 3.10 min, m/z 424 [M + H]$^+$ | BB |
| 46 | 4-(4-(Difluoromethyl)piperidine-1-carbonyl)-N-((R)-2-hydroxy-2-((S)-1,2,3,4-tetrahydroisoquinolin-3-yl)ethyl)benzamide | LCMS-B: RT 3.29 min, m/z 458 [M + H]$^+$ | BB |
| 47 | N-((R)-2-Hydroxy-2-((S)-1,2,3,4-tetrahydroisoquinolin-3-yl)ethyl)-4-(3-hydroxypyrrolidine-1-carbonyl)benzamide | LCMS-B: RT 3.10 min, m/z 410.2 [M + H]$^+$ | BB |

| Ex | Structure | LCMS | Method |
|---|---|---|---|
| 56 | N¹-((R)-2-Hydroxy-2-((S)-1,2,3,4-tetrahydroisoquinolin-3-yl)ethyl)-N⁴-(pyridin-2-ylmethly)terephthalamide | LCMS-B: RT 3.12 min; m/z 431.2 [M + H]⁺ | BA |
| 90 | N-((R)-2-Hydroxy-2-((S)-1,2,3,4-tetrahydroisoquinolin-3-yl)ethyl)-4-(pyrrolidine-1-carbonyl)benzamide | LCMS-B: RT 2.81 min; m/z 394.2 [M + H]⁺ | BC |
| 91 | 4-(7-Azabicyclo[2.2.1]heptane-7-carbonyl)-N-((R)-2-hydroxy-2-((S)-1,2,3,4-tetrahydroisoquinolin-3-yl)ethyl)benzamide | LCMS-B: RT 2.88 min; m/z 420.2 [M + H]⁺ | BC |
| 92 | N-((R)-2-Hydroxy-2-((S)-1,2,3,4-tetrahydroisoquinolin-3-yl)ethyl)-4-(4-methoxypiperidine-1-carbonyl)benzamide | LCMS-B: RT 2.82 min; m/z 438.2 [M + H]⁺ | BC |
| 93 | N-((R)-2-Hydroxy-2-((S)-1,2,3,4-tetrahydroisoquinolin-3-yl)ethyl)-4-(1,2-oxazinane-2-carbonyl)benzamide | LCMS-B: RT 2.83 min; m/z 410.2 [M + H]⁺ | BC |

TABLE B-continued

| Ex | Structure | LCMS | Method |
|---|---|---|---|
| 94 | 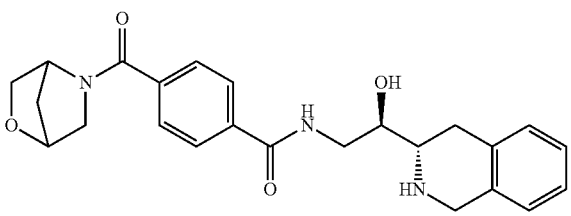 [SMILES: O=C(NC[C@@H](O)[C@@H]1Cc2ccccc2CN1)c1ccc(C(=O)N2CC3CC2CO3)cc1]<br>4-(2-Oxa-5-azabicyclo[2.2.1]heptane-5-carbonyl)-N-((R)-2-hydroxy-2-((S)-1,2,3,4-tetrahydroisoquinolin-3-yl)ethyl)benzamide | LCMS-B: RT 2.75 min; m/z 422.2 [M + H]$^+$ | BC Racemic bridged amine used |
| 95 | 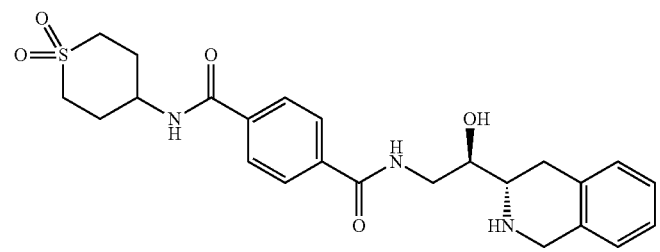 [SMILES: O=C(NC[C@@H](O)[C@@H]1Cc2ccccc2CN1)c1ccc(C(=O)NC2CCS(=O)(=O)CC2)cc1]<br>N$^1$-(1,1-Dioxidotetrahydro-2H-thiopyran-4-yl)-N$^4$-((R)-2-hydroxy-2-((S)-1,2,3,4-tetrahydroisoquinolin-3-yl)ethyl)terephthalamide | LCMS-B: RT 2.74 min; m/z 472.2 [M + H]$^+$ | BC |
| 96 | 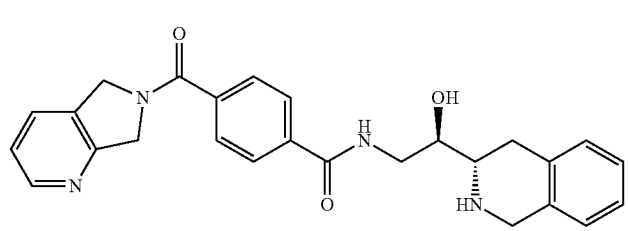 [SMILES: O=C(NC[C@@H](O)[C@@H]1Cc2ccccc2CN1)c1ccc(C(=O)N2Cc3cccnc3C2)cc1]<br>4-(6,7-Dihydro-5H-pyrrolo[3,4-b]pyridine-6-carbonyl)-N-((R)-2-hydroxy-2-((S)-1,2,3,4-tetrahydroisoquinolin-3-yl)ethyl)benzamide | LCMS-B: RT 2.78 min; m/z 443.2 [M + H]$^+$ | BC |
| 97 | 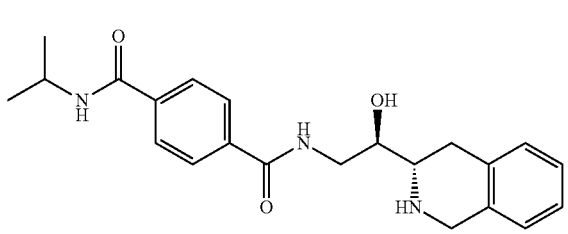 [SMILES: CC(C)NC(=O)c1ccc(C(=O)NC[C@@H](O)[C@@H]2Cc3ccccc3CN2)cc1]<br>N$^1$-((R)-2-Hydroxy-2-((S)-1,2,3,4-tetrahydroisoquinolin-3-yl)ethyl)-N$^4$-isopropylterephthalamide | LCMS-B: RT 2.80 min; m/z 382.2 [M + H]$^+$ | BC |

Example 48: 4-Chloro-N—((R)-2-hydroxy-2-((S)-1,2,3,4-tetrahydroisoquinolin-3-yl)ethyl)benzamide

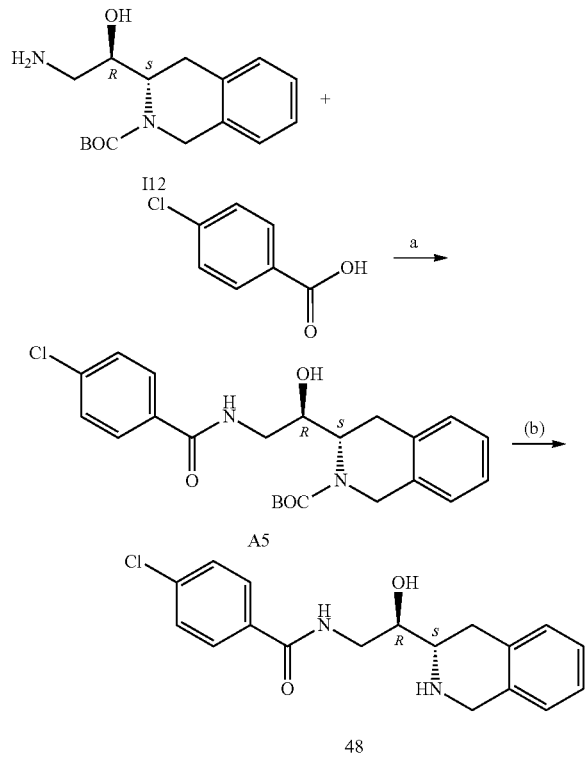

(a) tert-Butyl (S)-3-((R)-2-(4-chlorobenzamido)-1-hydroxyethyl)-3,4-dihydroisoquinoline-2(1H)-carboxylate (A5)

To a solution of 4-chlorobenzoic acid (0.058 g, 0.37 mmol) in DCM (10 mL) were added DIPEA (129 mg, 1.02 mmol) and HATU (0.14 g, 0.37 mmol). The mixture was stirred for 30 minutes, then tert-butyl (S)-3-((R)-2-amino-1-hydroxyethyl)-3,4-dihydroisoquinoline-2(1H)-carboxylate I12 (0.10 g, 0.34 mmol) was added. The resulting mixture was stirred at room temperature overnight, diluted with DCM (40 mL) and washed with water (50 mL), saturated NaHCO₃ (50 mL), water (50 mL), and brine (50 mL), dried over Na₂SO₄ and concentrated. The residue was purified by prep TLC (5% methanol/DCM) to give the title compound (100 mg, 68% yield) as a white solid. ¹H NMR (400 MHz, d₄-MeOD) δ 7.81-7.77 (m, 2H), 7.54-7.44 (m, 2H), 7.17-7.14 (m, 4H), 4.86-4.79 (m, 1H), 4.44-4.29 (m, 2H), 3.81-3.61 (m, 2H), 3.23-3.08 (m, 2H), 2.97-2.92 (m, 1H), 1.52-1.49 (m, 9H); LCMS-C: RT 3.09 min; m/z 453.2 [M+Na]⁺.

(b) 4-Chloro-N—((R)-2-hydroxy-2-((S)-1,2,3,4-tetrahydroisoquinolin-3-yl)ethyl)benzamide (48)

A mixture of tert-butyl (S)-3-((R)-2-(4-chlorobenzamido)-1-hydroxyethyl)-3,4-dihydroisoquinoline-2(1H)-carboxylate A5 (0.10 g, 0.23 mmol) in HCl/EtOAc (2 M, 4 mL) was stirred at room temperature overnight. The solvent was removed and the residue was diluted with saturated NaHCO₃ (15 mL). The aqueous layer was extracted with DCM (4×20 mL). The combined organic extracts were dried over Na₂SO₄ and concentrated. The residue was purified by prep TLC (10% methanol/DCM) to give the title compound (35 mg, 46% yield) as an off-white solid. ¹H NMR (400 MHz, d₄-MeOD) δ 7.86-7.84 (d, 2H, J=8.4 Hz), 7.49-7.47 (d, 2H, J=8.4 Hz), 7.26-7.16 (m, 4H), 4.38-4.26 (m, 2H), 4.19-4.15 (m, 1H), 3.67-3.44 (m, 3H), 3.24-3.10 (m, 2H); LCMS-C: RT 1.93 min; m/z 331.1 [M+H]⁺

Example 49: 4-(3-Oxa-8-azabicyclo[3.2.1]octane-8-carbonyl)-N—((R)-2-hydroxy-2-((S)-1,2,3,4-tetrahydroisoquinolin-3-yl)ethyl)benzamide hydrochloride

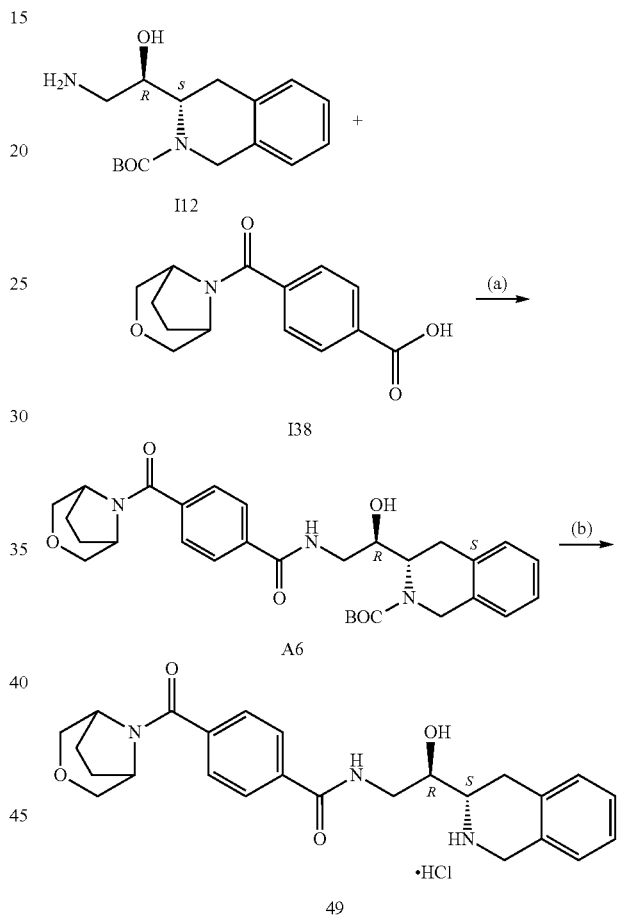

(a) tert-Butyl (3S)-3-((1R)-2-(4-(3-oxa-8-azabicyclo[3.2.1]octane-8-carbonyl)benzamido)-1-hydroxyethyl)-3,4-dihydroisoquinoline-2(1H)-carboxylate (A6)

To a mixture of tert-butyl (S)-3-((R)-2-amino-1-hydroxyethyl)-3,4-dihydroisoquinoline-2(1H)-carboxylate I12 (100 mg, 0.342 mmol), 4-(3-oxa-8-azabicyclo[3.2.1]octane-8-carbonyl)benzoic acid I38 (98.7 mg, 0.378 mmol), HOBt (5 mg, 0.03 mmol) and DIPEA (88.4 mg, 0.7 mmol) in DCM (5 mL) was added EDCl.HCl (80.9 mg, 0.422 mmol). The resultant mixture was stirred at room temperature overnight. The mixture was washed with sodium bicarbonate (6 mL) and the aqueous phase was extracted with DCM (2×3 mL). The combined organic extracts were washed with brine, dried over sodium sulfate and concentrated. The residue was purified by prep TLC (7% methanol/dichloromethane) to give the title compound (58 mg, 32% yield) as an off-white solid. LCMS-C: RT 2.75 min, m/z 558.3 [M+Na]$^+$ (b) 4-(3-Oxa-8-azabicyclo[3.2.1]octane-8-carbonyl)-N—((R)-2-hydroxy-2-((S)-1,2,3,4-tetrahydroisoquinolin-3-yl)ethyl)benzamide hydrochloride (49)

tert-Butyl (3S)-3-((1R)-2-(4-(3-oxa-8-azabicyclo[3.2.1]octane-8-carbonyl)benzamido)-1-hydroxyethyl)-3,4-dihydroisoquinoline-2(1H)-carboxylate A6 (55 mg, 0.10 mmol) was dissolved in ethyl acetate (3 mL), and HCl in EtOAc (2 M, 1.5 mL) was added. The mixture was stirred at room temperature overnight. The solid was collected by filtration and dissolved in water (5 mL), the aqueous solution was washed with diethyl ether (3 mL) and the remaining aqueous phase was freeze-dried to give the title compound (40 mg, 83% yield) as a white solid. $^1$H NMR (400 MHz, d$_4$-MeOD) δ 8.01-7.93 (m, 2H), 7.63-7.57 (m, 2H), 7.33-7.19 (m, 4H), 4.61-4.69 (m, 1H), 4.52-4.43 (m, 1H), 4.43-4.25 (m, 2H), 3.97-3.91 (m, 1H), 3.86-3.77 (m, 1H), 3.76-3.61 (m, 4H), 3.61-3.53 (m, 2H), 3.31-3.28 (m, 1H), 3.26-3.19 (m, 1H), 2.11-1.93 (m, 4H); LCMS-C: RT 3.14 min; m/z 436.2 [M+H]$^+$ (free base)

Example 50: 4-(3-Oxa-8-azabicyclo[3.2.1]octane-8-carbonyl)-2-ethoxy-N—((R)-2-hydroxy-2-((S)-1,2,3,4-tetrahydroisoquinolin-3-yl)ethyl)benzamide hydrochloride

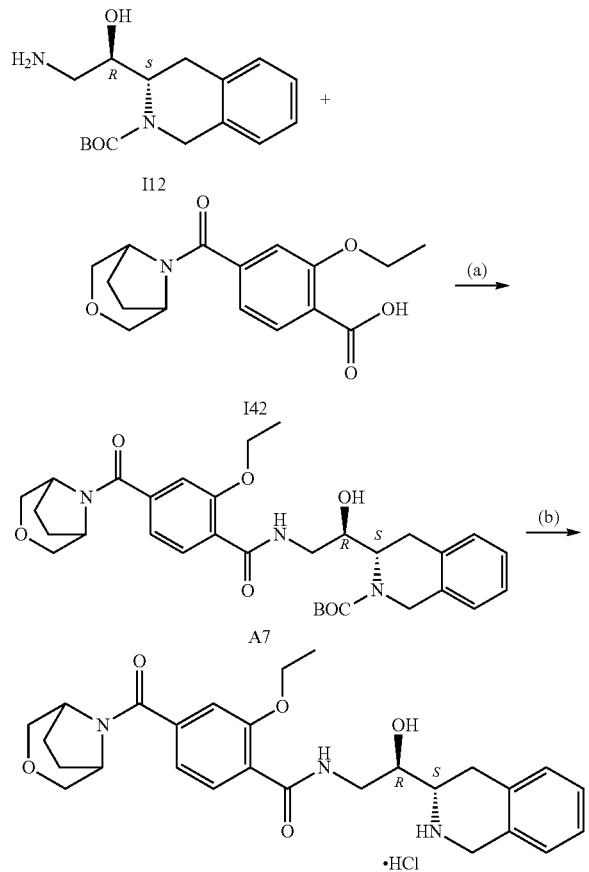

(a) tert-Butyl (3S)-3-((1R)-2-(4-(3-oxa-8-azabicyclo[3.2.1]octane-8-carbonyl)-2-ethoxybenzamido)-1-hydroxyethyl)-3,4-dihydroisoquinoline-2(1H)-carboxylate (A7)

To a mixture of tert-butyl (S)-3-((R)-2-amino-1-hydroxyethyl)-3,4-dihydroisoquinoline-2(1H)-carboxylate I12 (0.30 g, 1.0 mmol), 4-(3-oxa-8-azabicyclo[3.2.1]octane-8-carbonyl)-2-ethoxybenzoic acid I42 (0.34 g, 1.1 mmol), HOBt (0.014 g, 0.10 mmol) and DIPEA (0.27 g, 2.1 mmol) in dichloromethane (5 mL) was added EDCl.HCl (0.24 g, 1.2 mmol). The resulting mixture stirred overnight at room temperature. The mixture was washed with saturated sodium bicarbonate (6 mL) and the aqueous layer extracted with dichloromethane (3×10 mL). The combined organic extracts were washed with brine, dried over sodium sulfate and concentrated. The residue was purified by column chromatography (2% methanol/dichloromethane) to give the title compound (0.23 g, 38% yield) as an off-white solid. LCMS-C: RT 2.86 min, m/z 580.4 [M+H]$^+$ (b) 4-(3-Oxa-8-azabicyclo[3.2.1]octane-8-carbonyl)-2-ethoxy-N—((R)-2-hydroxy-2-((S)-1,2,3,4-tetrahydroisoquinolin-3-yl)ethyl)benzamide hydrochloride (50)

tert-Butyl (3 S)-3-((1R)-2-(4-(3-oxa-8-azabicyclo[3.2.1]octane-8-carbonyl)-2-ethoxybenzamido)-1-hydroxyethyl)-3,4-dihydroisoquinoline-2(1H)-carboxylate A7 (0.22 g, 0.4 mmol) was dissolved in ethyl acetate (5 mL) and HCl/EtOAc (2 M, 2.5 mL) was added. The mixture was stirred at room temperature overnight. The solid was collected by filtration and rinsed with ethyl acetate (20 mL). The solid was dried under vacuum to give the title compound (0.13 g, 72% yield) as an off-white solid. $^1$H NMR (400 MHz, d$_4$-MeOD) δ 7.98-7.96 (m, 1H), 7.30-7.22 (m, 5H), 7.18-7.15 (m, 1H), 4.64 (br s, 1H), 4.51-4.36 (m, 2H), 4.29-4.20 (m, 3H), 3.95 (br s, 1H), 3.84-3.78 (m, 1H), 3.75-3.55 (m, 6H), 3.23-3.15 (m, 2H), 2.05-1.95 (m, 4H), 1.47-1.38 (m, 3H); LCMS-C: RT 3.51 min; m/z 480.3 [M+H]$^+$ (free base)

Alternate Synthesis Method (a) tert-Butyl (3S)-3-((1R)-2-(4-(3-oxa-8-azabicyclo[3.2.1]octane-8-carbonyl)-2-ethoxybenzamido)-1-hydroxyethyl)-3,4-dihydroisoquinoline-2(1H)-carboxylate (A7)

To a mixture of tert-butyl (S)-3-((R)-2-amino-1-hydroxyethyl)-3,4-dihydroisoquinoline-2(1H)-carboxylate I12 (2.7 g, 9.2 mmol), 4-(3-oxa-8-azabicyclo[3.2.1]octane-8-carbonyl)-2-ethoxybenzoic acid I42 (3.1 g, 10.2 mmol), HOBt (0.13 g, 0.9 mmol) and DIPEA (4.8 g, 36.9 mmol) in dichloromethane (40 mL) was added EDCl.HCl (3.6 g, 18.5 mmol). The resulting mixture stirred overnight at room temperature. The mixture was washed with saturated sodium bicarbonate (20 mL) and the aqueous layer extracted with dichloromethane (2×15 mL). The combined organic extracts were washed with brine, dried over sodium sulfate and concentrated. The residue was purified by column chromatography (50% ethyl acetate/petroleum ether) to give the title compound (2.9 g, 55%) as an off-white solid. LCMS-C: RT 2.86 min, m/z 580.4 [M+H]$^+$ (b) 4-(3-Oxa-8-azabicyclo[3.2.1]octane-8-carbonyl)-2-ethoxy-N—((R)-2-hydroxy-2-((S)-1,2,3,4-tetrahydroisoquinolin-3-yl)ethyl)benzamide hydrochloride (50)

tert-Butyl (3S)-3-((1R)-2-(4-(3-oxa-8-azabicyclo[3.2.1]octane-8-carbonyl)-2-ethoxybenzamido)-1-hydroxyethyl)-

3,4-dihydroisoquinoline-2(1H)-carboxylate A7 (2.9 g, 5.0 mmol) was dissolved in HCl/EtOAc (2 M, 100 mL). The mixture was stirred at room temperature overnight then the solvent removed. The solid was washed with diethyl ether (2×30 mL) then taken up in water (40 mL) and lyophilized to give the title compound (2.35 g, 98%) as a yellow solid. $^1$H NMR (400 MHz, d$_4$-MeOD) δ 7.98-7.96 (m, 1H), 7.30-7.22 (m, 5H), 7.18-7.15 (m, 1H), 4.64 (br s, 1H), 4.51-4.36 (m, 2H), 4.29-4.20 (m, 3H), 3.95 (br s, 1H), 3.84-3.78 (m, 1H), 3.75-3.55 (m, 6H), 3.23-3.15 (m, 2H), 2.05-1.95 (m, 4H), 1.47-1.38 (m, 3H); LCMS-C: RT 3.51 min; m/z 480.3 [M+H]$^+$ (free base)

Example 51: 6-((1-Acetylpiperidin-4-yl)amino)-N—((R)-2-hydroxy-2-((S)-1,2,3,4-tetrahydroisoquinolin-3-yl)ethyl)pyrimidine-4-carboxamide dichloride

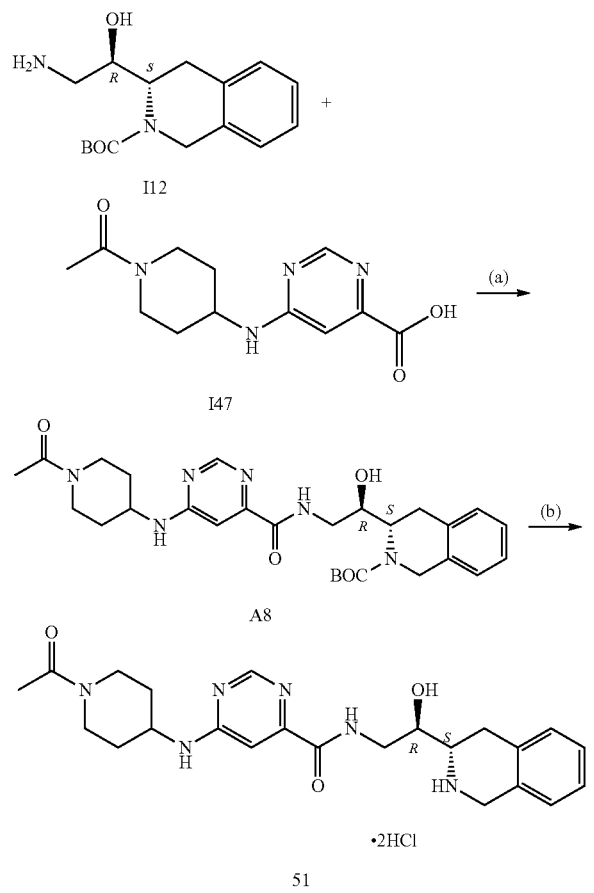

(a) tert-Butyl (S)-3-((R)-2-(6-((1-acetylpiperidin-4-yl)amino)pyrimidine-4-carboxamido)-1-hydroxyethyl)-3,4-dihydroisoquinoline-2(1H)-carboxylate (A8)

To a solution of 6-((1-acetylpiperidin-4-yl)amino)pyrimidine-4-carboxylic acid I47 (95 mg, 0.34 mmol) in DCM (5 mL) were added tert-butyl (S)-3-((R)-2-amino-1-hydroxyethyl)-3,4-dihydroisoquinoline-2(1H)-carboxylate I12 (99 mg, 0.34 mmol), HOBt (4 mg, 0.03 mmol), DIPEA (220 mg, 1.70 mmol) and EDCl.HCl (130 mg, 0.678 mmol). The resulting mixture was stirred at room temperature overnight.

The mixture was diluted with DCM (50 mL), the organic layer was washed with saturated aqueous NaHCO$_3$ (50 mL) and brine (50 mL), dried over Na$_2$SO$_4$ and concentrated. The residue was purified by prep TLC (0-10% MeOH/DCM) to give the title compound (50 mg, 26%) as a yellow solid. LCMS-C: RT 2.72 min; m/z 539.3 [M+H]$^+$ (b) 6-((1-Acetylpiperidin-4-yl)amino)-N—((R)-2-hydroxy-2-((S)-1,2,3,4-tetrahydroisoquinolin-3-yl)ethyl)pyrimidine-4-carboxamide dichloride (51)

A mixture of tert-butyl (S)-3-((R)-2-(6-((1-acetylpiperidin-4-yl)amino)pyrimidine-4-carboxamido)-1-hydroxyethyl)-3,4-dihydroisoquinoline-2(1H)-carboxylate A8 (50 mg, 0.093 mmol) in HCl/EtOAc (2 M, 3 mL) was stirred at room temperature overnight. The solvent was removed under reduced pressure and the solid washed with EtOAc (10 mL) to give the title compound (35 mg, 46% yield) as a pale yellow solid. $^1$H NMR (400 MHz, d$_4$-MeOD) δ 8.68 (s, 0.70H), 8.57 (s, 0.21H), 7.99 (s, 0.20H), 7.41 (s, 0.68H), 7.30-7.21 (m, 4H), 4.58-4.35 (m, 5H), 4.05-3.99 (m, 1H), 3.73-3.68 (m, 2H), 3.60-3.55 (m, 1H), 3.35-3.31 (m, 3H, overlapped), 2.97-2.86 (m, 1H), 2.15-2.04 (m, 5H), 1.67-1.54 (m, 2H). LCMS-C: RT 3.04 min; m/z 439.3 [M+H]$^+$ (free base)

Example 52: N—((S)-2-Hydroxy-2-((S)-1,2,3,4-tetrahydroisoquinolin-3-yl)ethyl)-4-(morpholine-4-carbonyl)benzamide hydrochloride

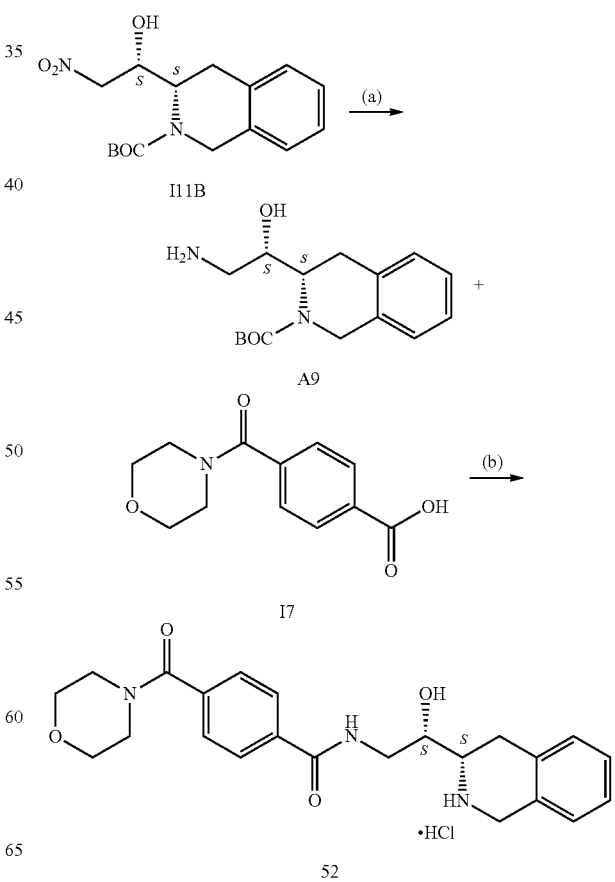

(a) tert-Butyl (S)-3-((S)-2-amino-1-hydroxyethyl)-3,4-dihydroisoquinoline-2(1H)-carboxylate (A9)

Analogous to the preparation of I12, treatment of tert-butyl (S)-3-((S)-1-hydroxy-2-nitroethyl)-3,4-dihydroisoquinoline-2(1H)-carboxylate (I11B) with Pd/C in the presence of hydrogen gave the title compound. LCMS-B: RT 3.24 min, m/z 293.3 [M+H]+

(b) N—((S)-2-Hydroxy-2-((S)-1,2,3,4-tetrahydroisoquinolin-3-yl)ethyl)-4-(morpholine-4-carbonyl)benzamide hydrochloride (52)

Analogous to the preparation of 28, coupling of tert-butyl (S)-3-((S)-2-amino-1-hydroxyethyl)-3,4-dihydroisoquinoline-2(1H)-carboxylate (A9) with 4-(morpholine-4-carbonyl)benzoic acid 17, followed by treatment with HCl in 1,4-dioxane gave the title compound. $^1$H NMR (400 MHz, $d_6$-DMSO) δ 9.17 (d, J=11.3 Hz, 1H), 8.97 (d, J=11.1 Hz, 1H), 8.80 (t, J=5.8 Hz, 1H), 7.99-7.89 (m, 2H), 7.52-7.44 (m, 2H), 7.31-7.17 (m, 4H), 4.39-4.21 (m, 3H), 3.18-3.08 (m, 2H), 3.01 (dd, J=17.0, 11.3 Hz, 2H) Some protons obscured by residual solvent. LCMS-B: RT 3.13 min; m/z 410.3 [M+H]+ (free base); m/z 408.3 [M−H]− (free base)

Example 53: N—((S)-2-hydroxy-2-((R)-1,2,3,4-tetrahydroisoquinolin-3-yl)ethyl)-4-(morpholine-4-carbonyl)benzamide hydrochloride

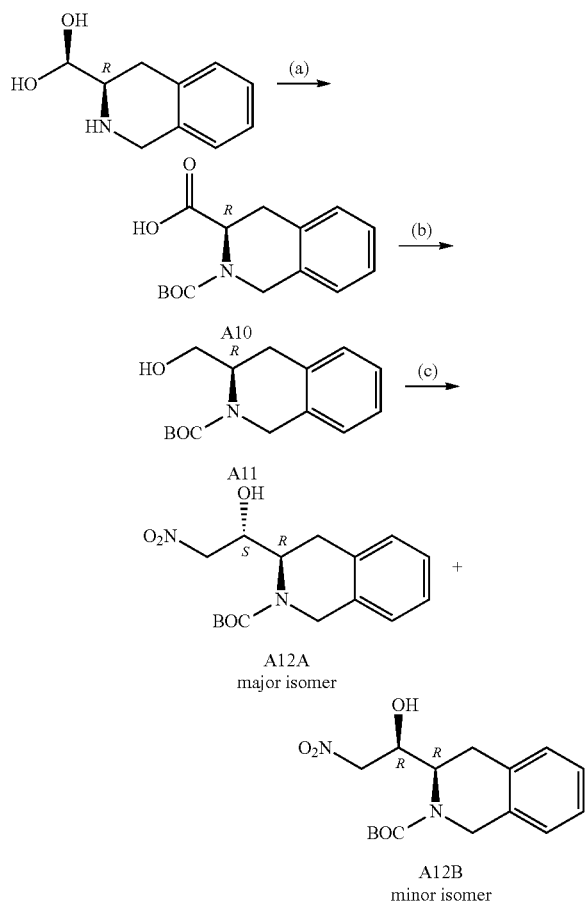

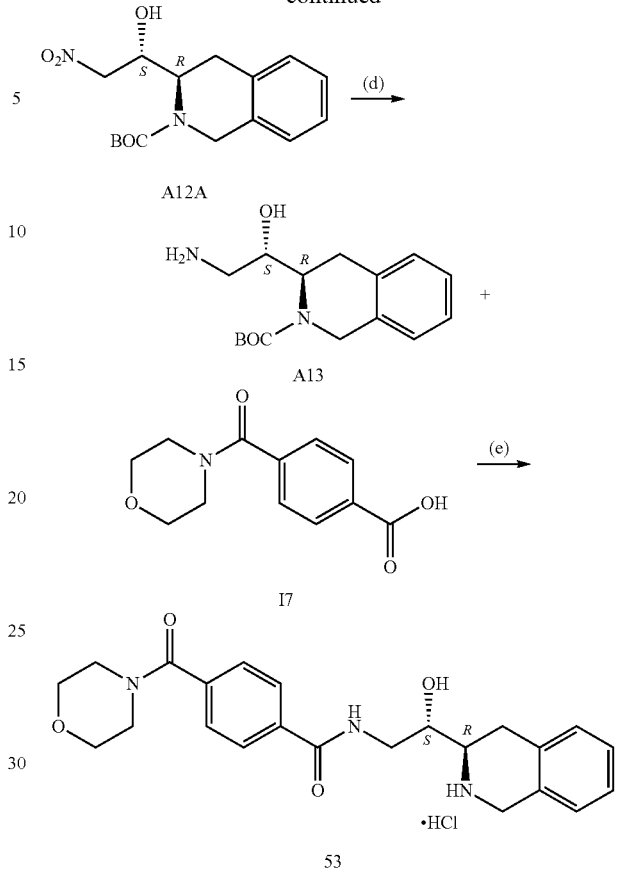

(a) (R)-2-(tert-Butoxycarbonyl)-1,2,3,4-tetrahydroisoquinoline-3-carboxylic acid (A10)

Analogous to the preparation of I8, treatment of (R)-1,2,3,4-tetrahydroisoquinoline-3-carboxylic acid with Boc anhydride gave the title compound. LCMS-B: RT 3.61 min; m/z 300.2 [M+Na]+; 178.2 [M-Boc+2H]+; m/z 276.2 [M−H]−

(b) tert-Butyl (R)-3-(hydroxymethyl)-3,4-dihydroisoquinoline-2(1H)-carboxylate (A11)

Analogous to the preparation of I9, treatment of (R)-2-(tert-butoxycarbonyl)-1,2,3,4-tetrahydroisoquinoline-3-carboxylic acid (A10) with CDI and sodium borohydride gave the title compound. LCMS-B: RT 3.66 min; m/z 164.2 [M-Boc+2H]+

(c) tert-Butyl (R)-3-((S)-1-hydroxy-2-nitroethyl)-3,4-dihydroisoquinoline-2(1H)-carboxylate (A12A) and tert-butyl (R)-3-((R)-1-hydroxy-2-nitroethyl)-3,4-dihydroisoquinoline-2(1H)-carboxylate (A12B)

Analogous to the preparation of intermediates I11A and I11B, oxidation of tert-butyl (R)-3-(hydroxymethyl)-3,4-dihydroisoquinoline-2(1H)-carboxylate (A11) followed by treatment with nitromethane and potassium fluoride gave the title compounds. Data for major isomer tert-butyl (R)-3-((S)-1-hydroxy-2-nitroethyl)-3,4-dihydroisoquinoline-2(1H)-carboxylate A12A:

¹H NMR (400 MHz, d₄-MeOD) δ 7.24-7.14 (m, 4H), 4.84-4.68 (m, 1H), 4.65-4.49 (m, 1H), 4.49-4.40 (m, 1H), 4.36-3.98 (m, 3H), 3.19 (dd, J=15.9, 3.2 Hz, 1H), 2.92 (dd, J=15.8, 5.6 Hz, 1H), 1.51 (s, 9H). LCMS-B: RT 3.72 min; m/z 223.2 [M-Boc+2H]⁺; m/z 321.3 [M−H]⁻

Data for minor isomer tert-butyl (R)-3-((R)-1-hydroxy-2-nitroethyl)-3,4-dihydroisoquinoline-2(1H)-carboxylate A12B:

¹H NMR (400 MHz, d₄-MeOD) δ 7.23-7.12 (m, 4H), 4.75 (d, J=16.4 Hz, 1H), 4.61-4.49 (m, 1H), 4.42-4.22 (m, 4H), 3.06 (dd, J=16.3, 6.1 Hz, 1H), 2.91 (d, J=16.4 Hz, 1H), 1.49 (s, 9H). LCMS-B: RT 3.73 min; m/z 223.2 [M-Boc+2H]⁺; m/z 321.1 [M−H]⁻

(d) tert-Butyl (R)-3-((S)-2-amino-1-hydroxyethyl)-3,4-dihydroisoquinoline-2(1H)-carboxylate (A13)

Analogous to the preparation of I12, treatment of tert-butyl (R)-3-((S)-1-hydroxy-2-nitroethyl)-3,4-dihydroisoquinoline-2(1H)-carboxylate (A12A) with Pd/C in the presence of hydrogen gave the title compound. ¹H NMR (400 MHz, d₄-MeOD) δ 7.21-7.08 (m, 4H), 4.84-4.73 (m, 1H), 4.37-4.08 (m, 2H), 3.42-3.30 (m, overlaps with solvent), 3.18 (dd, J=16.0, 2.6 Hz, 1H), 2.91 (dd, J=16.0, 5.6 Hz, 1H), 2.70-2.54 (m, 1H), 1.51 (s, 9H). LCMS-B RT 3.34 min; m/z 293.3 [M+H]⁺, 237.2 [M-ᵗBu+2H]⁺, 193.2 [M-Boc+2H]⁺

(e) N—((S)-2-Hydroxy-2-((R)-1,2,3,4-tetrahydroisoquinolin-3-yl)ethyl)-4-(morpholine-4-carbonyl)benzamide hydrochloride (53)

Analogous to the preparation of 28, coupling of tert-butyl (R)-3-((S)-2-amino-1-hydroxyethyl)-3,4-dihydroisoquinoline-2(1H)-carboxylate (A13) with 4-(morpholine-4-carbonyl)benzoic acid I7, followed by treatment with HCl with 1,4-dioxane gave the title compound. ¹H NMR (400 MHz, d₆-DMSO) δ 9.48-9.38 (m, 1H), 9.03-8.89 (m, 1H), 8.81 (t, J=5.7 Hz, 1H), 7.92 (d, J=8.3 Hz, 2H), 7.48 (d, J=8.3 Hz, 2H), 7.30-7.18 (m, 4H), 5.98 (d, J=5.2 Hz, 1H), 4.44-4.33 (m, 1H), 4.21 (d, J=15.1 Hz, 2H), 3.17-3.08 (m, overlaps with solvent), 1.31-1.22 (m, 4H). LCMS-B: RT 3.12 min; m/z 410.3 [M+H]⁺ (free base); m/z 408.2 [M−H]⁻ (free base)

Example 54: N—((R)-2-Hydroxy-2-((R)-1,2,3,4-tetrahydroisoquinolin-3-yl)ethyl)-4-(morpholine-4-carbonyl)benzamide hydrochloride

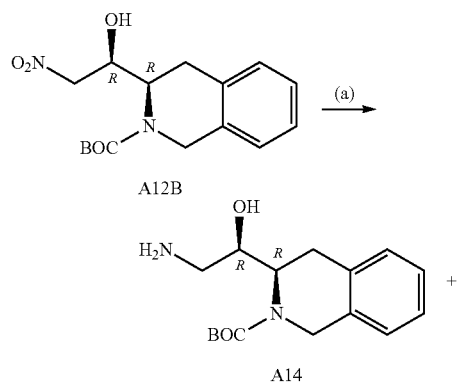

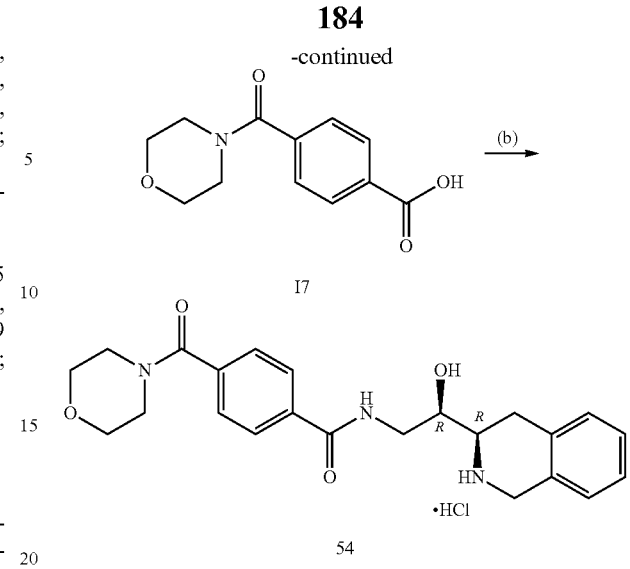

(a) tert-Butyl (R)-3-((R)-2-amino-1-hydroxyethyl)-3,4-dihydroisoquinoline-2(1H)-carboxylate (A14)

Analogous to the preparation of I12, treatment of tert-butyl (R)-3-((R)-1-hydroxy-2-nitroethyl)-3,4-dihydroisoquinoline-2(1H)-carboxylate (A12B) with Pd/C in the presence of hydrogen gave the title compound. LCMS-A: RT 4.65 min, m/z 293.2 [M+H]⁺

(b) N—((R)-2-Hydroxy-2-((R)-1,2,3,4-tetrahydroisoquinolin-3-yl)ethyl)-4-(morpholine-4-carbonyl)benzamide hydrochloride (54)

Analogous to the preparation of 28, coupling of tert-butyl (R)-3-((R)-2-amino-1-hydroxyethyl)-3,4-dihydroisoquinoline-2(1H)-carboxylate (A14) with 4-(morpholine-4-carbonyl)benzoic acid 17, followed by treatment with HCl in 1,4-dioxane gave the title compound. LCMS-B: RT 3.11 min; m/z 410.3 [M+H]⁺ (free base)

Example 55: 4-(3-Oxa-9-azabicyclo[3.3.1]nonane-9-carbonyl)-2-ethoxy-N—((R)-2-hydroxy-2-((S)-1,2,3,4-tetrahydroisoquinolin-3-yl)ethyl)benzamide

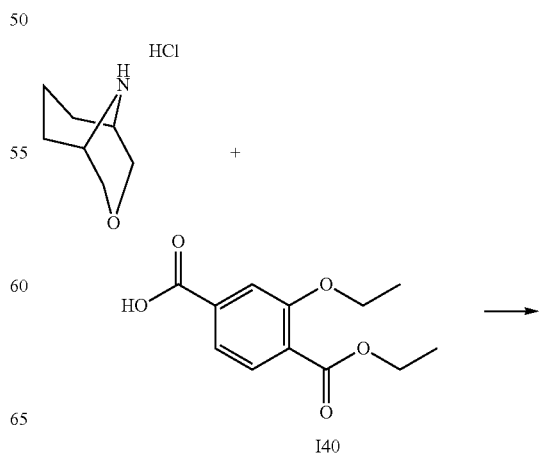

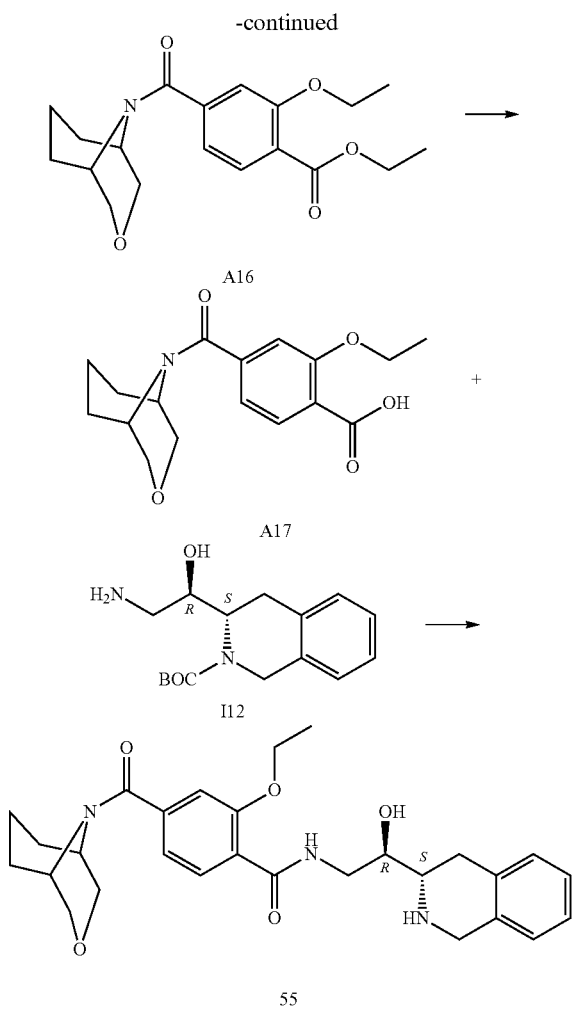

(a) Ethyl (3-oxa-9-azabicyclo[3.3.1]nonane-9-carbonyl)-2-ethoxybenzoate A16

To a solution of the acid 3-ethoxy-4-(ethoxycarbonyl) benzoic acid I40 (73 mg, 0.31 mmol, 1 equiv) in DMF (2 mL) and MeCN (5 mL) was added DIPEA (160 µL, 0.917 mmol, 3 equiv), HATU (174 mg, 0.458 mmol, 1.5 equiv) and the amine; 3-oxa-9-azabicyclo[3.3.1]nonane hydrochloride (50 mg, 0.31 mmol, 1 equiv) and the reaction was stirred overnight at room temperature. The mixture was quenched with a saturated aqueous solution of NaHCO₃ (5 mL) and extracted with DCM (3×5 mL). The combined organic layers were dried in vacuo and the resultant oil was purified by column chromatography (24 g SiO₂ cartridge, 0-65% EtOAc in petroleum benzine 40-60° C.) to give the title compound (88 mg, 83% yield) as a yellow oil. LCMS-B: RT 3.28 min, m/z 348 [M+H]⁺

(b) 4-(3-Oxa-9-azabicyclo[3.3.1]nonane-9-carbonyl)-2-ethoxybenzoic acid A17

To a solution of ethyl (3-oxa-9-azabicyclo[3.3.1]nonane-9-carbonyl)-2-ethoxybenzoate A16 (88 mg, 0.25 mmol, 1 equiv) in THF:H₂O:MeOH (3:1:0.5, 9 mL) was added LiOH—H₂O (32 mg, 0.76 mmol, 3 equiv). The reaction was stirred at room temperature for 16 hours before the reaction was quenched by the addition of a 0.5 M aqueous solution of citric acid (10 mL). The solution was extracted with EtOAc (3×15 mL), the combined organic layers were washed with water (30 mL), brine (30 mL), dried over MgSO₄ and evaporated in vacuo. The resultant crude was purified by column chromatography (12 g SiO₂ cartridge, 0-100% EtOAc in petroleum benzine 40-60° C.) to give the title compound (55 mg, 68% yield) as a colourless oil. ¹H NMR (400 MHz, d₄-MeOD) δ 7.84 (d, J=7.8 Hz, 1H), 7.14 (d, J=1.3 Hz, 1H), 7.05 (dd, J=7.8, 1.4 Hz, 1H), 4.52 (s, 1H), 4.20 (q, J=7.0 Hz, 2H), 4.07-3.99 (m, 1H), 3.93-3.72 (m, 3H), 3.60 (s, 1H), 2.02-1.95 (m, obscured by EtOAc solvent), 1.92-1.78 (m, 2H), 1.75-1.64 (m, 1H), 1.45 (t, J=7.0 Hz, 3H), 1.40-1.27 (m, 2H). LCMS-B: RT 3.00 min, m/z 320.2 [M+H]⁺

(c) 4-(3-Oxa-9-azabicyclo[3.3.1]nonane-9-carbonyl)-2-ethoxy-N—((R)-2-hydroxy-2-((S)-1,2,3,4-tetrahydroisoquinolin-3-yl)ethyl)benzamide 55

To a solution of 4-(3-oxa-9-azabicyclo[3.3.1]nonane-9-carbonyl)-2-ethoxybenzoic acid A17 (55 mg, 0.17 mmol, 1 equiv), DIPEA (90 µL, 0.52 mmol, 3 equiv) and HATU (98 mg, 0.26 mmol, 1.5 equiv) in DMF (2 mL) was added a solution of the amine tert-butyl (S)-3-((R)-2-amino-1-hydroxyethyl)-3,4-dihydroisoquinoline-2(1H)-carboxylate I12 (50 mg, 0.17 mmol, 1 equiv) in DMF (2 mL). The reaction was stirred at room temperature overnight, then quenched with a saturated aqueous solution of NaHCO₃ (15 mL) and extracted with EtOAc (3×15 mL). The combined organic layers were washed with water (30 mL), brine (30 mL), dried over MgSO₄ and concentrated in vacuo. DCM:TFA (4 mL, 1:1) was added and the reaction stirred at room temperature overnight. The reaction mixture was concentrated in vacuo and then purified by solid-phase extraction (2×1 g SCX-2 cartridge, 3 column volumes of methanol followed by 3 column volumes of 0.2 M methanolic ammonia) to give the crude product which was further purified by column chromatography (12 g SiO₂ cartridge, 50-100% EtOAc modified by the addition of 1% v/v of 3.5 M methanolic ammonia in petroleum benzine 40-60° C. followed by 0-20% MeOH in EtOAc modified by the addition of 1% v/v of 2.0 M methanolic ammonia). The product fractions were combined and dried in vacuo to give title compound (19 mg, 22% yield) as a glassy yellow solid. ¹H NMR (400 MHz, d₄-MeOD) δ 8.02 (d, J=7.9 Hz, 1H), 7.15-7.07 (m, 5H), 7.08-6.98 (m, 1H), 4.52 (s, 1H), 4.25 (q, J=7.0 Hz, 2H), 4.07-3.98 (m, 3H), 3.91-3.81 (m, 3H), 3.83-3.72 (m, 2H), 3.63-3.52 (m, 2H), 3.02-2.90 (m, 1H), 2.92-2.79 (m, 2H), 2.65-2.52 (m, 1H), 2.04-1.95 (m, 2H), 1.92-1.76 (m, 2H), 1.74-1.63 (m, 1H), 1.48 (t, J=7.0 Hz, 3H). LCMS-B: RT 2.89 min, m/z 494.3 [M+H]⁺

Determination of Stereochemistry

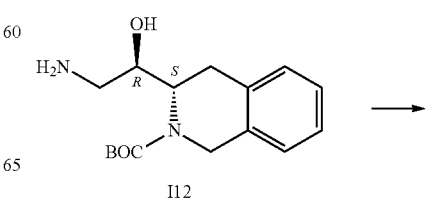

I12

-continued

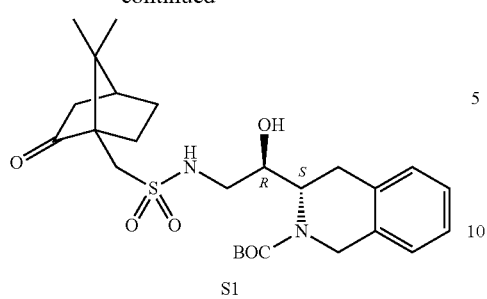

S1

The amine I12 (30 mg, 0.10 mmol), DCM (1 mL) and triethylamine (0.028 mL, 0.21 mmol) and (1S)-(+)-10-camphorsulfonyl chloride (26 mg, 0.10 mmol) were stood at room temperature. After three hours the mixtures was purified by chromatography (4 g silica cartridge, 0-100% ethyl acetate/hexanes then 0-100% methanol/ethyl acetate) to give the camphorsulfonamide (20 mg, 39% yield). LCMS-B: RT 3.95 min m/z (positive ion) 407.3 [M-Boc+2H]

Crystals of the sulfonamide S1 were grown by vial-in-vial vapour diffusion (S1 dissolved in ethyl acetate, sealed in a larger vial with hexane) over approximately five months. The crystals were studied by X-ray crystallography by the Monash University X-ray Diffraction Service, and a structure obtained. The structure unambiguously confirms the relative and absolute stereochemistry of the tetrahydroisoquinoline and alcohol stereocentres in the product of the preceding nitroaldol reaction. The following table sets out the data derived from the structure:

| | |
|---|---|
| Empirical formula | C26H38N2O6S |
| Formula weight | 506.64 |
| Temperature | 123(2) K |
| Wavelength | 1.54184 Å |
| Crystal system, space group | Monoclinic, P 21 |
| Unit cell dimensions | a = 11.7820(6) Å alpha = 90° |
| | b = 7.0492(5) Å beta = 100.331(5)° |
| | c = 16.1515(12) Å gamma = 90° |
| Volume | 1319.69(15) Å$^3$ |
| Z, Calculated density | 1.275 Mg/m$^3$ |
| Absorption coefficient | 1.440 mm$^{-1}$ |
| F(000) | 544 |
| Crystal size | 0.25 × 0.08 × 0.05 mm |
| Theta range for data collection | 2.78 to 66.92° |
| Limiting indices | −14 <= h <= 13, −8 <= k <= 8, |
| | −19 <= l <= 19 |
| Reflections collected/unique | 13367/4558 [R(int) = 0.0667] |
| Completeness to theta = 66.92 | 98.8% |
| Absorption correction | Semi-empirical from equivalents |
| Max. and min. transmission | 1.00000 and 0.72746 |
| Refinement method | Full-matrix least-squares on F^2 |
| Data/restraints/parameters | 4558/3/329 |
| Goodness-of-fit on F^2 | 1.070 |
| Final R indices [I > 2sigma(I)] | R1 = 0.0413, wR2 = 0.1047 |
| R indices (all data) | R1 = 0.0445, wR2 = 0.1093 |
| Absolute structure parameter | −0.012(16) |
| Largest diff. peak and hole | 0.248 and −0.395 e · Å$^{-3}$ |

Example 98: 6-Chloro-N—((R)-2-hydroxy-2-((S)-1,2,3,4-tetrahydroisoquinolin-3-yl)ethyl)nicotinamide hydrochloride 98

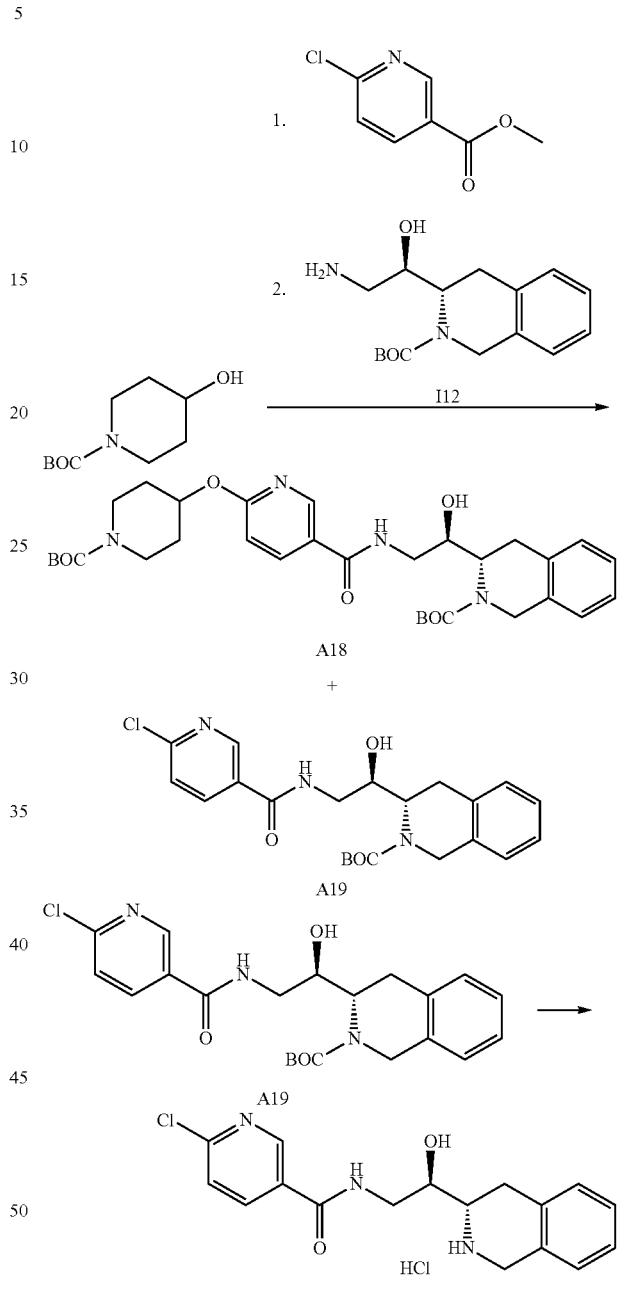

(a) tert-Butyl (S)-3-((R)-2-(6-chloronicotinamido)-1-hydroxyethyl)-3,4-dihydroisoquinoline-2(1H)-carboxylate A19 and tert-butyl (S)-3-((R)-2-(6-((1-(tert-butoxycarbonyl)piperidin-4-yl)oxy)nicotinamido)-1-hydroxyethyl)-3,4-dihydroisoquinoline-2(1H)-carboxylate A18

To a solution of tert-butyl 4-hydroxypiperidine-1-carboxylate (0.766 g, 3.81 mmol) in anhydrous THF (25 mL) under an atmosphere of nitrogen was added NaH (60% dispersion in mineral oil, 0.457 g, 11.42 mmol) in portions at 0° C. The reaction mixture was allowed to warm to room temperature and was stirred for 20 minutes, cooled to 0° C. and methyl 6-chloronicotinate (0.300 g, 1.748 mmol) was added in anhydrous THF (5 mL). The mixture was allowed to warm to room temperature and was then heated at reflux for 48 hours. The reaction was quenched with water (20 mL) and the resulting mixture was allowed to stir at room temperature for 24 hours, then acidified to pH 3 (checked with pH paper) by addition of 0.5 M aqueous citric acid and extracted with EtOAc (2×50 mL). The combined organic layers were washed with brine (70 mL), dried (Na₂SO₄), filtered and concentrated in vacuo then purified by column chromatography (Isolera Biotage, 24 g SiO₂ cartridge, 0-100% EtOAc in petroleum benzine 40-60° C.). The resulting residue was dissolved in DMF (4 mL) and Et₃N (0.074 mL, 0.527 mmol) followed by HATU (0.080 g, 0.211 mmol) were added. The mixture was then stirred at room temperature for 10 minutes before tert-butyl (S)-3-((R)-2-amino-1-hydroxyethyl)-3,4-dihydroisoquinoline-2(1H)-carboxylate I12 (0.046 g, 0.158 mmol) was added. The reaction was stirred at room temperature for 20 hours, then diluted with EtOAc (50 mL) and washed with saturated aqueous NaHCO₃ (50 mL), brine (50 mL), dried (Na₂SO₄), filtered and concentrated in vacuo to give the crude product. This material was purified by column chromatography (Isolera Biotage, 12 g SiO₂ cartridge, 0-60% EtOAc in petroleum benzine 40-60° C.) to give the title compounds A19 (0.008 g, 19% yield) and A18 (20 mg, 66% yield) as colourless gums.

A19: LCMS-B: RT 3.346 min, m/z 430.1 [M−H]⁻
A18: LCMS-B: RT 3.532 min, m/z 597.3 [M+H]⁺

(b) 6-Chloro-N—((R)-2-hydroxy-2-((S)-1,2,3,4-tetrahydroisoquinolin-3-yl)ethyl)nicotinamide hydrochloride 98 tert-Butyl (S)-3-((R)-2-(6-chloronicotinamido)-1-hydroxyethyl)-3,4-dihydroisoquinoline-2(1H)-carboxylate A19 (0.020 g, 0.035 mmol) was dissolved in 1,4-dioxane (2 mL) and 4 M HCl in 1,4-dioxane solution (0.43 mL) was added and the reaction was then stirred at room temperature for 20 hours. The precipitate formed in the reaction mixture was allowed to sediment on the bottom of the flask. Solvent was carefully removed with a pipette, diethyl ether (~2 mL) was added and then removed with a pipette. The diethyl ether wash was repeated 4 times and the residue dried on high-vacuum to give the title compound (0.008 g, 52% yield) as an off-white solid. LCMS-B: RT 2.753 min, m/z 332.1 [M+H]⁺ for free base.

Example 99: N—((R)-2-Hydroxy-2-((S)-1,2,3,4-tetrahydroisoquinolin-3-yl)ethyl)-6-(piperidin-4-yloxy)nicotinamide trihydrochloride 99

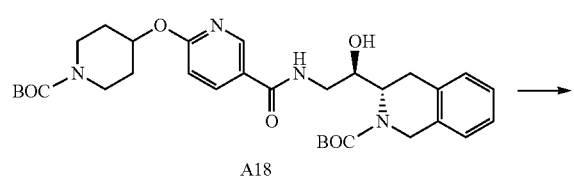

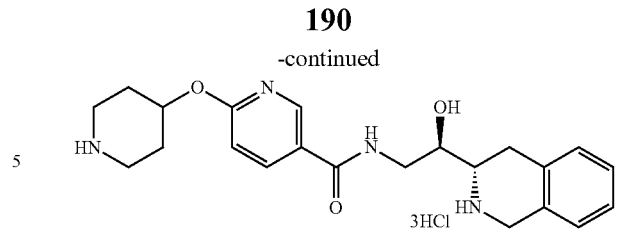

tert-Butyl (S)-3-((R)-2-(6-((1-(tert-butoxycarbonyl)piperidin-4-yl)oxy)nicotinamido)-1-hydroxyethyl)-3,4-dihydroisoquinoline-2(1H)-carboxylate A18 (0.008 g, 75% purity, 0.010 mmol) was dissolved in 1,4-dioxane (1 mL) and 4 M HCl in 1,4-dioxane solution (0.13 mL) was added and the reaction was then stirred at room temperature for 20 hours. The precipitate formed in the reaction mixture was allowed to sediment on the bottom of the flask. Solvent was carefully removed with a pipette, diethyl ether (~2 mL) was added and then removed with a pipette. The diethyl ether wash was repeated 4 times and the residue dried on high-vacuum to give the title compound (0.004 g, 75% yield) as an off-white solid. LCMS-B: RT 1.739 min, m/z 397 [M+H] for free base.

Example 100: Methyl 4-((5-(((R)-2-hydroxy-2-((S)-1,2,3,4-tetrahydroisoquinolin-3-yl)ethyl)carbamoyl)pyridin-2-yl)oxy)piperidine-1-carboxylate 100

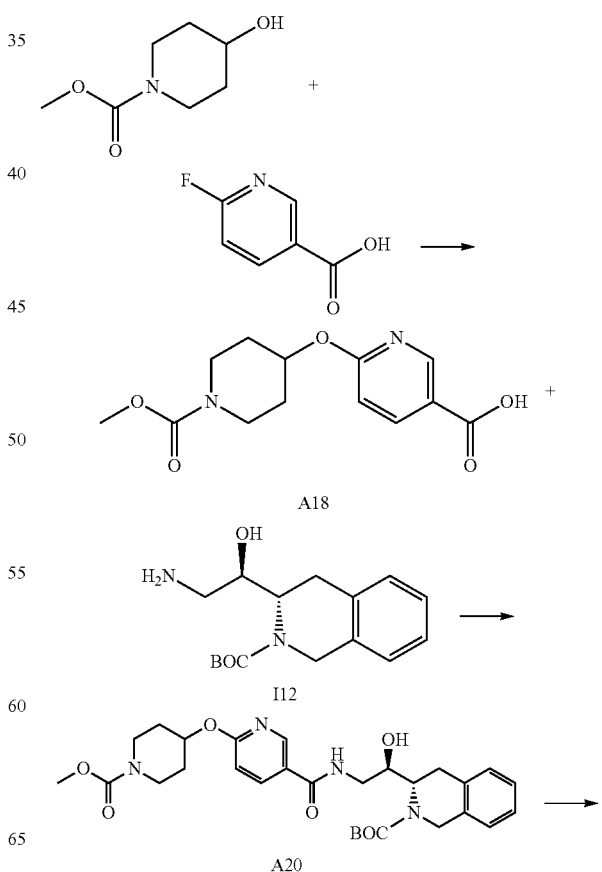

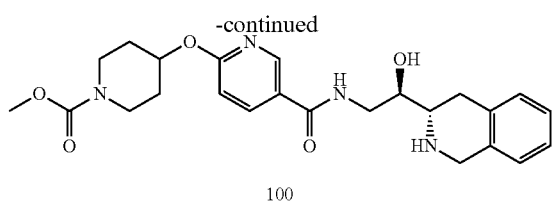

(a) 6-((1-(Methoxycarbonyl)piperidin-4-yl)oxy)nicotinic acid A18

Methyl 4-hydroxypiperidine-1-carboxylate (0.45 g, 2.84 mmol) was dissolved in anhydrous THF (10 mL) under an atmosphere of nitrogen. Sodium tert-butoxide (0.55 g, 5.67 mmol) was added in portions and the resulting mixture was stirred at room temperature for 20 minutes. 6-Fluoronicotinic acid (0.20 g, 1.42 mmol) was then added and the mixture was heated at 60° C. for 20 hours. The reaction was quenched with water (20 mL), then acidified to pH 3 (checked with pH paper) by addition of 0.5 M aqueous citric acid and extracted with EtOAc (2×70 mL). The combined organic layers were washed with brine (70 mL), dried ($Na_2SO_4$), filtered and concentrated in vacuo. The crude product was purified by chromatography (Isolera Biotage, 12 g $SiO_2$ cartridge, 0-100% EtOAc in petroleum benzine 40-60° C.) to give the title compound (0.068 g, 17% yield, 80% purity) as a white solid. LCMS-B: RT 3.030 min, m/z 279.1 [M−H]−

(b) tert-Butyl (S)-3-((R)-1-hydroxy-2-(6-((1-(methoxycarbonyl)piperidin-4-yl)oxy)nicotinamido)ethyl)-3,4-dihydroisoquinoline-2(1H)-carboxylate A20

6-((1-(Methoxycarbonyl)piperidin-4-yl)oxy)nicotinic acid A18 (80% purity, 0.063 g, 0.178 mmol) was dissolved in DMF (4 mL) and $Et_3N$ (0.075 mL, 0.535 mmol) followed by HATU (0.102 g, 0.268 mmol) were added. The mixture was then stirred at room temperature for 10 minutes before tert-butyl (S)-3-((R)-2-amino-1-hydroxyethyl)-3,4-dihydroisoquinoline-2(1H)-carboxylate I12 (0.052 g, 0.178 mmol) was added. The reaction was then stirred at room temperature for 20 hours then diluted with EtOAc (50 mL) and washed with saturated aqueous $NaHCO_3$ (50 mL), brine (50 mL), dried ($Na_2SO_4$), filtered and concentrated in vacuo to give the crude product. This was purified by column chromatography (Isolera Biotage, 12 g $SiO_2$ cartridge, 0-100% EtOAc in petroleum benzine 40-60° C.) to give the title compound (0.050 g, 50% yield) as a colourless gum. LCMS-B: RT 3.385 min, m/z 555.3 [M+H]+

(c) Methyl 4-((5-(((R)-2-hydroxy-2-((S)-1,2,3,4-tetrahydroisoquinolin-3-yl)ethyl)carbamoyl)pyridin-2-yl)oxy)piperidine-1-carboxylate 100 tert-Butyl (S)-3-((R)-1-hydroxy-2-(6-((1-(methoxycarbonyl)piperidin-4-yl)oxy)nicotinamido)ethyl)-3,4-dihydroisoquinoline-2(1H)-carboxylate A20 (0.05 g, 0.09 mmol) was dissolved in 1,4-dioxane (2.5 mL) and 4 M HCl in 1,4-dioxane solution (1.13 mL) was added and the reaction was then stirred at room temperature for 20 hours. The volatiles were removed in vacuo and the residue was taken up in EtOAc (50 mL) and 1 M aqueous NaOH (50 mL). The layers were separated and the aqueous layer was extracted with EtOAc (50 mL), the combined organics were washed with brine (70 mL), dried ($Na_2SO_4$), filtered and concentrated in vacuo to give the title compound (0.023 g, 56% yield) as an off-white solid. 1H NMR (400 MHz, Methanol-d4) δ 8.64 (dd, J=2.6, 0.7 Hz, 1H), 8.10 (dd, J=8.7, 2.5 Hz, 1H), 7.16-7.01 (m, 4H), 6.83 (dd, J=8.7, 0.8 Hz, 1H), 5.35-5.28 (m, 1H), 4.09-3.97 (m, 2H), 3.89 (dt, J=7.0, 4.7 Hz, 1H), 3.84-3.76 (m, 2H), 3.70 (s, 3H), 3.68-3.62 (m, 1H), 3.54 (dd, J=13.8, 7.0 Hz, 1H), 3.44-3.34 (m, 2H), 2.99-2.85 (m, 3H), 2.06-1.97 (m, 2H), 1.78-1.67 (m, 2H). LCMS-B: RT 2.887 min, m/z 455.2 [M+H]+

Example 101: N—((R)-2-Hydroxy-2-((S)-1,2,3,4-tetrahydroisoquinolin-3-yl)ethyl)-6-morpholinonicotinamide 101

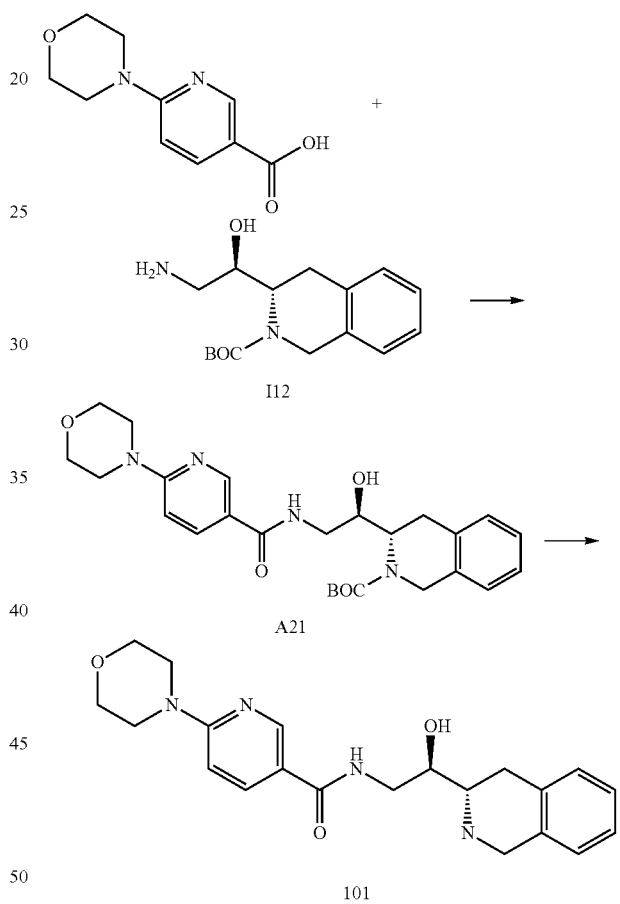

(a) tert-Butyl (S)-3-((R)-1-hydroxy-2-(6-morpholinonicotinamido)ethyl)-3,4-dihydroisoquinoline-2(1H)-carboxylate A21

6-Morpholinonicotinic acid (0.050 g, 0.240 mmol) was dissolved in DMF (4 mL) and $Et_3N$ (0.100 mL, 0.720 mmol) followed by HATU (0.137 g, 0.360 mmol) were added. The mixture was then stirred at room temperature for 10 minutes before tert-butyl (S)-3-((R)-2-amino-1-hydroxyethyl)-3,4-dihydroisoquinoline-2(1H)-carboxylate I12 (0.070 g, 0.240 mmol) was added. The reaction was then stirred at room temperature for 20 hours then diluted with EtOAc (70 mL) and washed with saturated aqueous $NaHCO_3$ (70 mL), brine (70 mL), dried ($Na_2SO_4$), filtered and concentrated in vacuo to give the crude product. This was purified by column chromatography (Isolera Biotage, 12 g SiO$_2$ cartridge, 0-100% EtOAc in petroleum benzine 40-60° C.) to give the title compound (0.061 g, 53% yield) as a colourless gum. LCMS-B: RT 3.222 min, m/z 483.3 [M+H]$^+$ (b) N—((R)-2-Hydroxy-2-((S)-1,2,3,4-tetrahydroisoquinolin-3-yl)ethyl)-6-morpholinonicotinamide 101 tert-Butyl (S)-3-((R)-1-hydroxy-2-(6-morpholinonicotinamido)ethyl)-3,4-dihydroisoquinoline-2(1H)-carboxylate A21 (0.061 g, 0.126 mmol) was dissolved in 1,4-dioxane (2.5 mL) and 4 M HCl in 1,4-dioxane solution (1.6 mL) was added and the reaction was then stirred at room temperature for 16 hours. The volatiles were removed in vacuo and the residue was taken up in EtOAc (70 mL) and 1 M aqueous NaOH (50 mL). The layers were separated and the aqueous layer was extracted with EtOAc (70 mL), the combined organics were washed with brine (70 mL), dried (Na$_2$SO$_4$), filtered and concentrated in vacuo to give the title compound (0.045 g, 93% yield) as a white solid. $^1$H NMR (400 MHz, Methanol-d$_4$) δ 8.62 (dd, J=2.5, 0.7 Hz, 1H), 7.99 (dd, J=9.0, 2.5 Hz, 1H), 7.15-7.01 (m, 4H), 6.85-6.79 (m, 1H), 4.10-3.98 (m, 2H), 3.88 (dt, J=6.9, 4.7 Hz, 1H), 3.81-3.74 (m, 4H), 3.66-3.51 (m, 6H), 3.00-2.85 (m, 3H). LCMS-B: RT 2.711 min, m/z 383.1 [M+H]$^+$ Example 102: 2-((1-Acetylpiperidin-4-yl)oxy)-N—((R)-2-hydroxy-2-((S)-1,2,3,4-tetrahydroisoquinolin-3-yl)ethyl)isonicotinamide 102

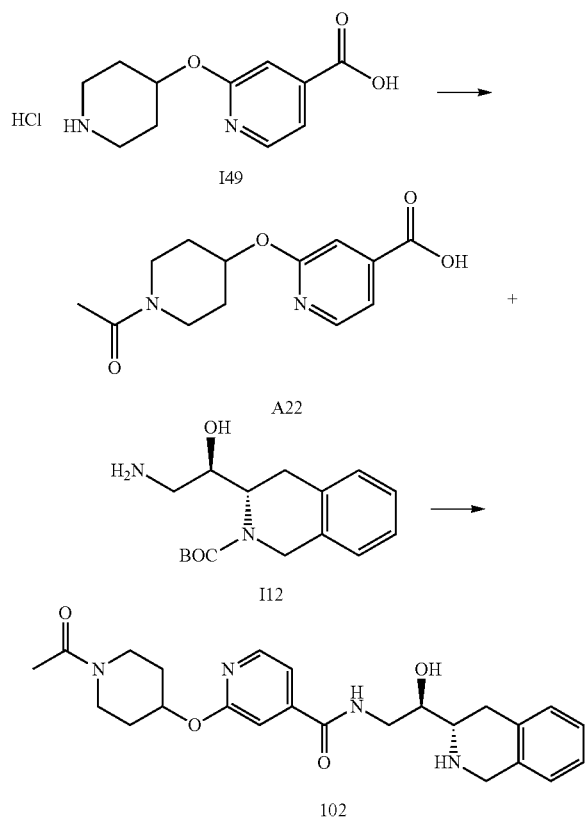

(a) 2-((1-Acetylpiperidin-4-yl)oxy)isonicotinic acid A22

To a solution of 2-(piperidin-4-yloxy)isonicotinic acid dihydrochloride I49 (0.150 g, 0.508 mmol, 1 equiv) in anhydrous THF (10 mL) and triethylamine (0.319 mL, 2.29 mmol, 4.5 equiv) was slowly added acetyl chloride (0.073 mL, 1.0 mmol, 2 equiv). After the addition, the mixture was stirred overnight at ambient temperature and then at 50° C. for an additional 24 hours. The solvent was removed in vacuo, a 0.5 M aqueous solution of NaOH was added (20 mL) and the solution was stirred for 1 hour. The reaction was acidified to pH=3 with a 0.5 M aqueous citric acid solution, extracted with EtOAc (3×30 mL) and the combined organic extracts washed with water (50 mL), brine (50 mL), dried (Na$_2$SO$_4$) and evaporated. The crude product was purified by column chromatography (12 g SiO$_2$ cartridge, 0-100% EtOAc in petroleum benzine 40-60° C.) to give the title compound (75 mg, 56% yield) as a white solid. $^1$H NMR (400 MHz, CDCl$_3$) δ 8.28 (dd, J=5.2, 0.9 Hz, 1H), 7.46 (dd, J=5.3, 1.4 Hz, 1H), 7.37 (s, 1H), 5.34 (tt, J=7.2, 3.6 Hz, 1H), 3.97-3.85 (m, 1H), 3.80-3.67 (m, 1H), 3.65-3.54 (m, 1H), 3.49-3.38 (m, 1H), 2.17 (s, 3H), 2.11-1.93 (m, 2H), 1.93-1.74 (m, 2H), 1.30-1.18 (m, 1H). LCMS-B: RT 0.80 min, m/z 265.1 [M+H]$^+$, 263.1 [M−H]$^−$.

(b) 2-((1-Acetylpiperidin-4-yl)oxy)-N—((R)-2-hydroxy-2-((S)-1,2,3,4-tetrahydroisoquinolin-3-yl)ethyl)isonicotinamide 102

To a solution of 2-((1-acetylpiperidin-4-yl)oxy)isonicotinic acid A22 (45 mg, 0.17 mmol, 1 equiv), DIPEA (89 μL, 0.51 mmol, 3 equiv) and HATU (98 mg, 0.26 mmol, 1.5 equiv) was added a solution of tert-butyl (S)-3-((R)-2-amino-1-hydroxyethyl)-3,4-dihydroisoquinoline-2(1H)-carboxylate I12 (50 mg, 0.17 mmol, 1 equiv) in DMF (2 mL). The reaction was stood at room temperature for 16 hours, quenched with a saturated aqueous solution of NaHCO$_3$ (5 mL) and extracted with DCM (×3) utilizing a phase separation cartridge. The organic filtrates were reduced under a stream of air, DCM:TFA (4 mL, 1:1) was added and the reaction stood at room temperature overnight. Additional TFA (2 mL) was added and the solution stirred for 2 more days. The reaction mixture was concentrated under a stream of air and then purified by solid-phase extraction (1 g SCX-2 cartridge, 3 column volumes of methanol followed by 3 column volumes of 0.2 M methanolic ammonia). The crude product was further purified by column chromatography (12 g SiO$_2$ cartridge, 50-100% EtOAc (modified by the addition of 1% v/v of 3.5 M methanolic ammonia) in petroleum benzine 40-60° C.) followed by 0-30% MeOH in EtOAc modified by the addition of 1% v/v of 2.0 M methanolic ammonia) to give the title compound (28 mg, 38% yield) as a pale yellow oil. $^1$H NMR (400 MHz, Methanol-d$_4$) δ 8.23 (d, J=5.3 Hz, 1H), 7.30 (d, J=5.4 Hz, 1H), 7.22-7.03 (m, 5H), 5.36-5.26 (m, 1H), 4.15 (s, 2H), 4.06-3.96 (m, 1H), 3.94-3.83 (m, 1H), 3.83-3.72 (m, 1H), 3.65 (dd, J=13.8, 5.0 Hz, 1H), 3.59-3.44 (m, 3H), 3.21-3.12 (m, 1H), 3.05-2.92 (m, 2H), 2.12 (s, 3H), 2.14-1.94 (m, 2H), 1.88-1.66 (m, 2H). LCMS-B: RT 2.79 min, m/z 439.2 [M+H]$^+$.

Example 103: 4-(3-Oxa-9-azabicyclo[3.3.1]nonane-9-carbonyl)-N—((R)-2-hydroxy-2-((S)-1,2,3,4-tetrahydroisoquinolin-3-yl)ethyl)benzamide 103

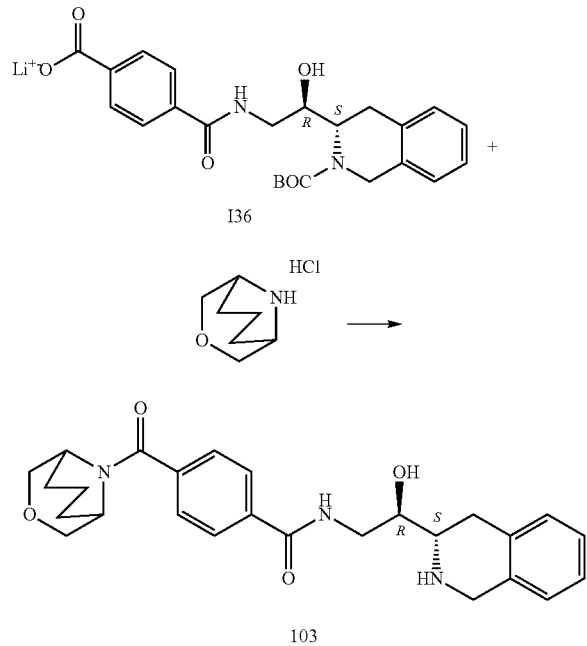

103

Example 104: N—((R)-2-Hydroxy-2-((S)-1,2,3,4-tetrahydroisoquinolin-3-yl)ethyl)-2-((tetrahydrofuran-3-yl)oxy)isonicotinamide bis(2,2,2-trifluoroacetate) 104

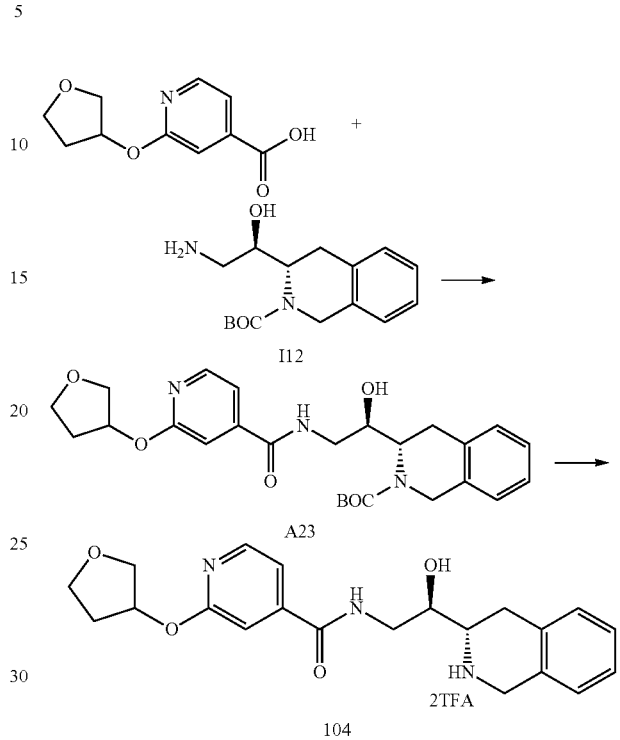

104

To a solution of lithium 4-(((R)-2-((S)-2-(tert-butoxycarbonyl)-1,2,3,4-tetrahydroisoquinolin-3-yl)-2-hydroxyethyl)carbamoyl)benzoate I36 (150 mg, 0.336 mmol, 1 equiv), DIPEA (176 μL, 1.01 mmol, 3 equiv) and HATU (192 mg, 0.504 mmol, 1.5 equiv) in DMF (2 mL) was added a solution of 3-oxa-9-azabicyclo[3.3.1]nonane hydrochloride (55 mg, 0.34 mmol, 1 equiv) in MeCN (10 mL). The reaction was stirred at room temperature overnight, quenched with a saturated aqueous solution of $NaHCO_3$ (15 mL) and extracted with EtOAc (3×40 mL). The combined organic layers were washed with water (50 mL), brine (50 mL), dried over $MgSO_4$ and concentrated in vacuo. DCM:TFA (8 mL, 1:1) was added and the reaction stirred at room temperature overnight. The reaction mixture was concentrated in vacuo and purified by solid-phase extraction (2×1 g SCX-2 cartridge, 3 column volumes of methanol followed by 3 column volumes of 0.2 M methanolic ammonia). The basic eluate was dried in vacuo and further purified by column chromatography (12 g $SiO_2$ cartridge, 50-100% EtOAc (modified by the addition of 1% v/v of 3.5 M methanolic ammonia) in petroleum benzine 40-60° C. followed by 0-20% MeOH in EtOAc modified by the addition of 1% v/v of 3.5 M methanolic ammonia) to give the title compound (26 mg, 17% yield) as a colourless oil. $^1$H NMR (400 MHz, Methanol-$d_4$) δ 7.95 (d, J=8.3 Hz, 2H), 7.54 (d, J=8.3 Hz, 2H), 7.34-7.18 (m, 4H), 4.56-4.34 (m, 3H), 4.30-4.23 (m, 1H), 4.03 (d, J=11.7 Hz, 1H), 3.91-3.74 (m, 3H), 3.71-3.52 (m, 4H), 3.38-3.16 (m, obscured by solvent), 2.66-2.52 (m, 1H), 2.02-1.94 (m, 2H), 1.91-1.77 (m, 2H), 1.74-1.64 (m, 1H). LCMS-B: RT 2.83 min, m/z 450.2 [M+H]$^+$ (a) tert-Butyl (3S)-3-((1R)-1-hydroxy-2-(2-((tetrahydrofuran-3-yl)oxy)isonicotinamido)ethyl)-3,4-dihydroisoquinoline-2(1H)-carboxylate A23

2-((Tetrahydrofuran-3-yl)oxy)isonicotinic acid (100 mg, 0.48 mmol), tert-butyl (S)-3-((R)-2-amino-1-hydroxyethyl)-3,4-dihydroisoquinoline-2(1H)-carboxylate I12 (140 mg, 0.48 mmol), DMF (1.5 mL), triethylamine (0.200 mL, 1.43 mmol) and HATU (273 mg, 0.72 mmol) were stirred at 30° C. After 2 hours, the mixture was added to water (30 mL) and the precipitate collected by filtration. The solid was washed with water (15 mL) and air-dried. The solid was dissolved in methanol (10 mL) and sodium tert-butoxide (50 mg) was added. After 1.5 hours the mixture was evaporated, chromatography (12 g silica cartridge, 0-100% ethyl acetate/hexanes) gave the title compound (81 mg, 35% yield) as a white solid. LCMS-A: RT 6.39 min; m/z 484.3 [M+H]$^+$ (b) N—((R)-2-Hydroxy-2-((S)-1,2,3,4-tetrahydroisoquinolin-3-yl)ethyl)-2-((tetrahydrofuran-3-yl)oxy)isonicotinamide bis(2,2,2-trifluoroacetate) 104 tert-Butyl (3S)-3-((1R)-1-hydroxy-2-(2-((tetrahydrofuran-3-yl)oxy)isonicotinamido)ethyl)-3,4-dihydroisoquinoline-2(1H)-carboxylate A23 (32 mg, 0.066 mmol) was taken up in DCM:TFA (1:1, 4 mL) and stirred overnight at room temperature. The solvent was removed in vacuo to give the title compound (14 mg, 35% yield) as a pale brown oil. $^1$H NMR (400 MHz, Methanol-$d_4$) δ 8.24 (d, J=5.5 Hz, 1H), 7.35-7.14 (m, 6H), 5.61-5.53 (m, 1H), 4.48 (d, J=15.7 Hz, 1H), 4.36 (d, J=15.6 Hz, 1H), 4.25 (td, J=6.5, 3.1 Hz, 1H), 4.07-3.81 (m, 4H), 3.72-3.48 (m, 3H), 3.20 (dd, J=17.0, 4.8 Hz, 1H), 2.70 (s, 1H), 2.36-2.23 (m, 1H), 2.16-2.07 (m, 1H). LCMS-B: RT 2.85 min, m/z 384.2 [M+H]$^+$ for free base.

Example 105: Methyl (1R,3r,5S)-3-((4-(((R)-2-hydroxy-2-((S)-1,2,3,4-tetrahydroisoquinolin-3-yl)ethyl)carbamoyl)pyridin-2-yl)oxy)-8-azabicyclo[3.2.1]octane-8-carboxylate 105

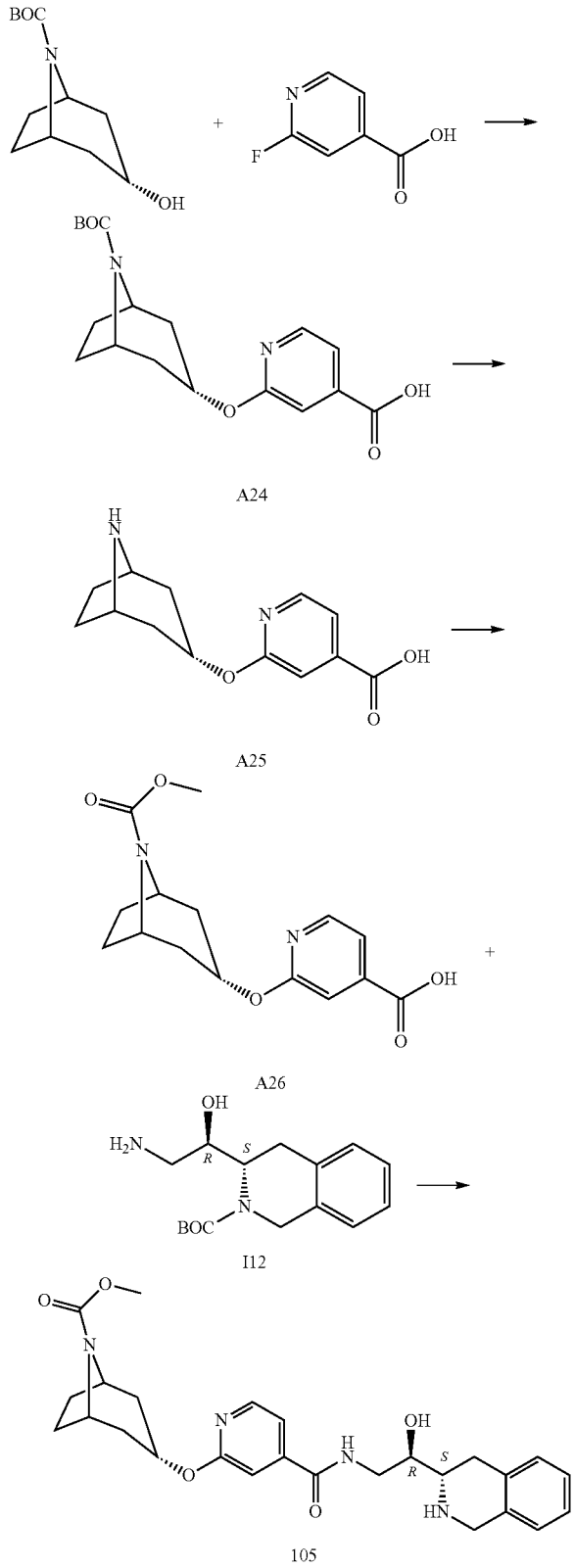

(a) 2-(((1R,3r,5S)-8-(tert-Butoxycarbonyl)-8-azabicyclo[3.2.1]octan-3-yl)oxy)isonicotinic acid A24

A solution of endo-8-Boc-3-hydroxy-8-azabicyclo[3.2.1]octane (0.500 g, 2.20 mmol, 1.2 equiv) in anhydrous DMF (5 mL) was added to a stirring suspension of sodium hydride (60% dispersion in mineral oil, 0.293 g, 7.33 mmol, 4 equiv) in anhydrous DMF (5 mL) under an atmosphere of nitrogen. The mixture was stirred at room temperature for 10 minutes before a solution of 2-fluoroisonicotinic acid (0.259 g, 1.83 mmol, 1 equiv) in DMF (5 mL) was added. The mixture was then stirred for a further 16 hours at room temperature. H$_2$O (~20 mL) was carefully added and the pH of the aqueous mixture was adjusted to ~3 with a 0.5 M solution of aqueous citric acid. The aqueous layer was extracted with EtOAc (3×30 mL), the organic layers were combined, washed with brine, dried (Na$_2$SO$_4$) and the solvent removed in vacuo. The resulting residue was purified by column chromatography (Biotage Isolera, 40 g SiO$_2$ cartridge, 0-100% EtOAc in petroleum benzine 40-60° C.) to give the title compound (328 mg, contaminated with starting material endo-8-Boc-3-hydroxy-8-azabicyclo[3.2.1]octane) as a white solid. The impure material was carried through to the next step without further purification and analysis.

(b) 2-(((1R,3r,5S)-8-Azabicyclo[3.2.1]octan-3-yl)oxy)isonicotinic acid dihydrochloride A25

To 2-(((1R,3r,5S)-8-(tert-butoxycarbonyl)-8-azabicyclo[3.2.1]octan-3-yl)oxy)isonicotinic acid A24 (328 mg) in 1,4-dioxane (20 mL) was added a 4 M solution of HCl in 1,4-dioxane (1.42 mL, 5.65 mmol). The reaction was then stirred at room temperature overnight. A further 5 mL of 4 M solution of HCl in 1,4-dioxane (20 mmol) was added and the reaction was stirred at 35° C. for an additional 24 hours before the reaction was dried in vacuo to give the impure title compound (300 mg) as a white solid. LCMS-B: RT 0.42 min, m/z 249.1 [M+H]$^+$ for the free base.

(c) 2-(((1R,3r,5S)-8-(Methoxycarbonyl)-8-azabicyclo[3.2.1]octan-3-yl)oxy)isonicotinic acid A26

Methyl chloroformate (72 µL, 0.93 mmol) was added drop-wise to a mixture of impure 2-(((1R,3r,5S)-8-azabicyclo[3.2.1]octan-3-yl)oxy)isonicotinic acid dihydrochloride A25 (150 mg) and sodium hydroxide (75 mg, 1.9 mmol) in water (10 mL). The reaction was stirred at ambient temperature overnight, acidified to pH=3 with a 0.5 M aqueous solution of citric acid and extracted with EtOAc (3×20 mL). The combined organic layers were dried over Na$_2$SO$_4$, filtered, and the filtrate concentrated in vacuo. The resulting oil was purified by column chromatography (12 g SiO$_2$ cartridge, 0-60% EtOAc in petroleum benzine 40-60° C.) to give the title compound (98 mg, 69% yield) as a white solid. LCMS-B: RT 3.09 min, m/z 307.1 [M+H]$^+$.

(d) Methyl (1R,3r,5S)-3-((4-(((R)-2-hydroxy-2-((S)-1,2,3,4-tetrahydroisoquinolin-3-yl)ethyl)carbamoyl)pyridin-2-yl)oxy)-8-azabicyclo[3.2.1]octane-8-carboxylate 105

To a solution of 2-(((1R,3r,5S)-8-(methoxycarbonyl)-8-azabicyclo[3.2.1]octan-3-yl)oxy)isonicotinic acid A26 (0.17 mmol, 1 equiv), DIPEA (89 µL, 0.51 mmol, 3 equiv) and HATU (98 mg, 0.26 mmol, 1.5 equiv) was added a solution of tert-butyl (S)-3-((R)-2-amino-1-hydroxyethyl)-3,4-dihydroisoquinoline-2(1H)-carboxylate I12 (50 mg, 0.17 mmol, 1 equiv) in DMF (2 mL). The reaction was stood at room temperature for 16 hours, quenched with a saturated aqueous solution of NaHCO$_3$ (5 mL) and extracted with DCM (×3) utilizing a phase separation cartridge. The organic filtrates were reduced under a stream of air, DCM:TFA (4 mL, 1:1) was added and the reaction stood at room temperature overnight. The reaction mixture was concentrated under a stream of air and then purified by solid-phase extraction (1 g SCX-2 cartridge, 3 column volumes of methanol followed by 3 column volumes of 0.2 M methanolic ammonia) to give the crude product. This was further purified by column chromatography (12 g SiO$_2$ cartridge, 50-100% EtOAc (modified by the addition of 1% v/v of 3.5 M methanolic ammonia) in petroleum benzine 40-60° C. followed by 0-30% MeOH in EtOAc modified by the addition of 1% v/v of 2.0 M methanolic ammonia) to give the title compound. LCMS-B: RT 2.90 min, m/z 481.2 [M+H]$^+$.

Example 106: 4-(3-Oxa-8-azabicyclo[3.2.1]octane-8-carbonyl)-2-(difluoromethyl)-N—((R)-2-hydroxy-2-((S)-1,2,3,4-tetrahydroisoquinolin-3-yl)ethyl)benzamide 106

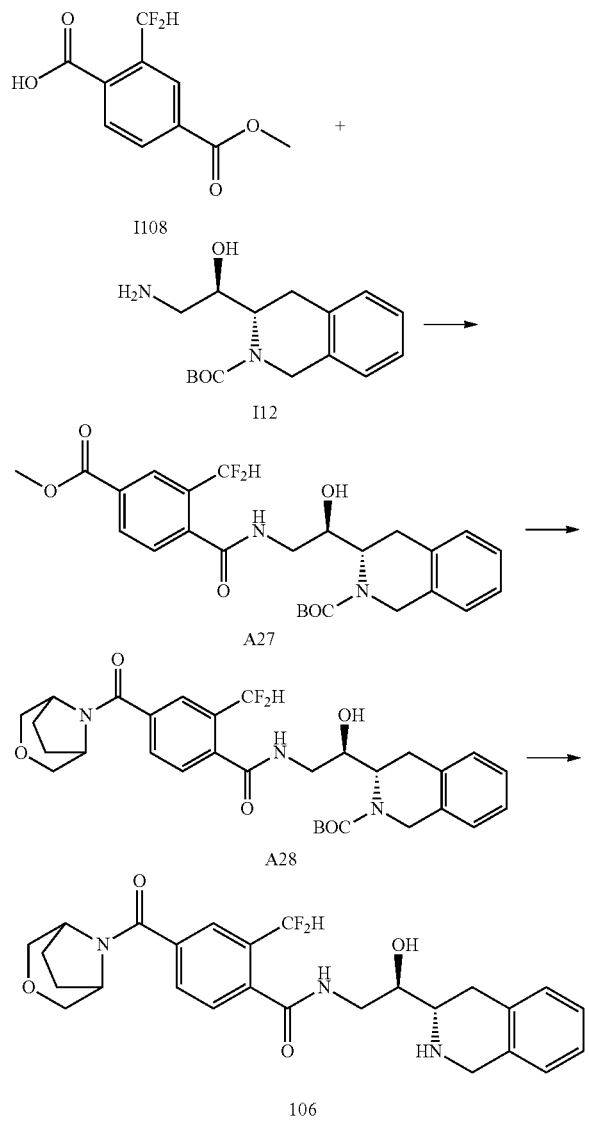

(a) tert-Butyl (S)-3-((R)-2-(2-(difluoromethyl)-4-(methoxycarbonyl)benzamido)-1-hydroxyethyl)-3,4-dihydroisoquinoline-2(1H)-carboxylate A27

To a solution of tert-butyl (S)-3-((R)-2-amino-1-hydroxyethyl)-3,4-dihydroisoquinoline-2(1H)-carboxylate I12 (191 mg, 0.65 mmol) in DCM (5 mL) was added 2-(difluoromethyl)-4-(methoxycarbonyl)benzoic acid I108 (150 mg, 0.65 mmol), HOBt (8.8 mg, 0.065 mmol), DIPEA (337 mg, 2.6 mmol) and EDCl (260 mg, 1.3 mmol). The resulting mixture was stirred at room temperature overnight. The reaction mixture was washed with saturated NaHCO$_3$ solution, the organic layer was washed with brine (3 mL×2), dried (Na$_2$SO$_4$) and concentrated. The residue was purified by prep TLC (DCM:methanol=50:1) to give the title compound as a white solid (89 mg, 27%). LCMS-C: RT 3.07 min; m/z 527.2 [M+Na]$^+$.

(b) tert-Butyl (3S)-3-((1R)-2-(4-(3-oxa-8-azabicyclo[3.2.1]octane-8-carbonyl)-2-(difluoromethyl)-benzamido)-1-hydroxyethyl)-3,4-dihydroisoquinoline-2(1H)-carboxylate A28

To a solution of tert-butyl (S)-3-((R)-2-(2-(difluoromethyl)-4-(methoxycarbonyl)benzamido)-1-hydroxyethyl)-3,4-dihydroisoquinoline-2(1H)-carboxylate A27 (80 mg, 0.16 mmol) in a mixture of THF (5 mL), methanol (0.5 mL) and water (0.5 mL) was added LiOH.H$_2$O (33.3 mg, 0.79 mmol). The resulting mixture was then stirred at room temperature overnight. The solvent was removed, and the residue was diluted with water (5 mL). The pH of the aqueous mixture was adjusted to 6 by addition of a 2 M HCl solution, then extracted with DCM (3 mL×3). The combined organic layers were washed with brine (2 mL×2), dried (Na$_2$SO$_4$) and concentrated to give an off-white solid (76 mg). A solution of 3-oxa-8-azabicyclo[3.2.1]octane hydrochloride (23 mg, 0.15 mmol) in DCM (5 mL) was added to the intermediate (75 mg), HOBt (2.1 mg, 0.015 mmol), DIPEA (79 mg, 0.61 mmol) and EDCl (59 mg, 0.3 mmol). The resulting mixture was stirred at room temperature overnight. The reaction mixture was washed with NaHCO$_3$ solution, the organic layer was washed with brine (3 mL×2), dried (Na$_2$SO$_4$) and concentrated. The residue was purified by prep TLC (DCM:methanol=50:1) to give the title compound as a white solid (51 mg, 57%): LCMS-C: RT 2.88 min; m/z 608.3 [M+Na]$^+$.

(c) 4-(3-Oxa-8-azabicyclo[3.2.1]octane-8-carbonyl)-2-(difluoromethyl)-N—((R)-2-hydroxy-2-((S)-1,2,3,4-tetrahydroisoquinolin-3-yl)ethyl)benzamide 106

A solution of tert-butyl (3S)-3-((1R)-2-(4-(3-oxa-8-azabicyclo[3.2.1]octane-8-carbonyl)-2-(difluoromethyl)-benzamido)-1-hydroxyethyl)-3,4-dihydroisoquinoline-2(1H)-carboxylate A28 (45 mg, 0.077 mmol) in saturated HCl/EtOAc solution (5 mL) was stirred at room temperature overnight. The reaction mixture was diluted with NaHCO$_3$ solution and the organic layer washed with brine (3 mL×2), dried (Na$_2$SO$_4$) and concentrated. The residue was purified by prep TLC (DCM:methanol=40:1) to give the crude compound. The product was washed with diethyl ether (4 mL×2) then taken up in methanol (4 drops) and water (4 mL) and lyophilized to give the title compound as an off-white solid (9 mg). $^1$H NMR (400 MHz, Methanol-d$_4$) δ 7.82 (s, 1H), 7.76-7.70 (m, 2H), 7.24-7.10 (m, 5H), 4.66 (s, 1H), 4.27-4.19 (m, 2H), 4.09-4.08 (m, 1H), 3.93-3.92 (m, 1H), 3.84-3.81 (m, 1H), 3.73-3.51 (m, 6H), 3.13-3.03 (m, 2H), 2.06-2.01 (m, 4H). LCMS-C: RT 3.46 min; m/z 486.0 [M+H]$^+$.

Example 107: N—((R)-2-Hydroxy-2-((S)-1,2,3,4-tetrahydroisoquinolin-3-yl)ethyl)-6-(oxetan-3-ylamino)pyrimidine-4-carboxamide 107

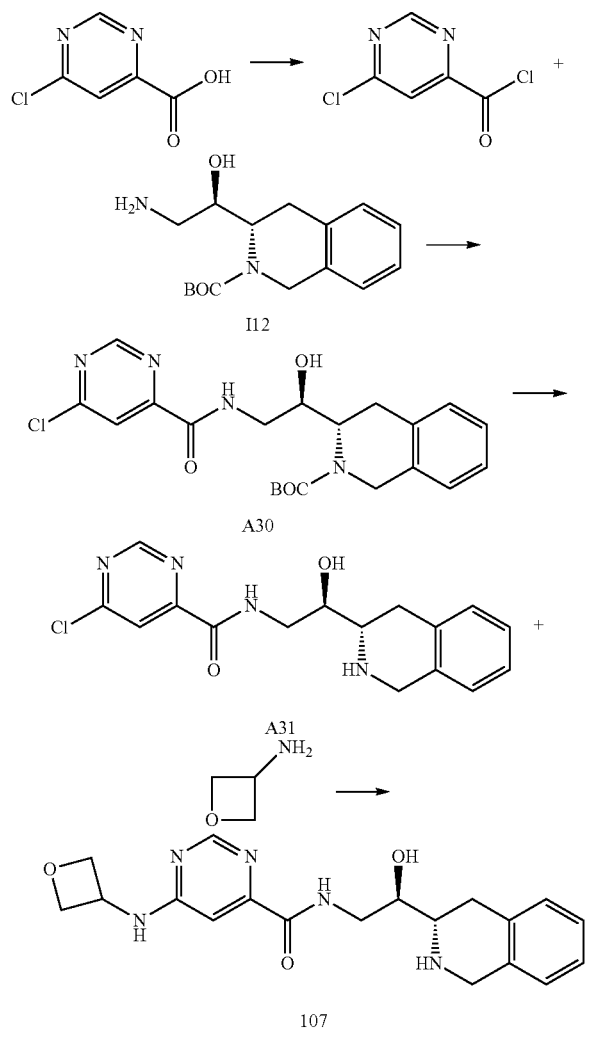

(a) 6-Chloropyrimidine-4-carbonyl chloride A29

To a solution of 6-hydroxypyrimidine-4-carboxylic acid (1.0 g, 7.1 mmol) in EtOAc (20 mL) was added oxalyl chloride (3.6 g, 28.4 mmol) dropwise. The mixture was stirred at room temperature for 30 minutes then DMF (0.1 mL) was added and the mixture heated at reflux overnight. The solvent was removed to give the crude product as an oil (1.2 g, 95%) which was used without purification. LCMS-C of a MeOH quench: RT 0.64 min; m/z 173.0, 175.0 [M+H]$^+$.

(b) (S)-tert-Butyl3-((R)-2-(6-chloropyrimidine-4-carboxamido)-1-hydroxyethyl)-3,4-dihydroisoquinoline-2(1H)-carboxylate A30

To a solution of (S)-tert-butyl 3-((R)-2-amino-1-hydroxyethyl)-3,4-dihydroisoquinoline-2(1H)-carboxylate I12 (500 mg, 1.7 mmol) and Et$_3$N (688 mg, 6.8 mmol) in DCM (20 mL) at 0° C. was added a solution of 6-chloropyrimidine-4-carbonyl chloride A29 (300 mg, 1.7 mmol) in DCM (4 mL) dropwise. The mixture was allowed to warm to room temperature and stirred for 2 hours. The mixture was diluted with DCM (50 mL) and the organic layer washed with water (50 mL) and brine (50 mL), dried (Na$_2$SO$_4$) and concentrated. The residue was purified by column chromatography (100% petroleum ether to 25% EtOAc in petroleum ether) to give the title compound as an off-white solid (420 mg, 57%). LCMS-C: RT 2.96 min; m/z 455.1, 457.2 [M+Na]$^+$.

(c) 6-Chloro-N—((R)-2-hydroxy-2-((S)-1,2,3,4-tetrahydroisoquinolin-3-yl)ethyl)pyrimidine-4-carboxamide dihydrochloride A31

A mixture of (S)-tert-butyl3-((R)-2-(6-chloropyrimidine-4-carboxamido)-1-hydroxyethyl)-3,4-dihydroisoquinoline-2(1H)-carboxylate A30 (100 mg, 0.23 mmol) in saturated HCl/EtOAc (3 mL) was stirred at room temperature for 3 hours. The solvent was removed to give the crude product as a yellow solid (100 mg, 94%). The crude product was without further purification. LCMS-C: RT 0.69 min; m/z 333.2 [M+H]$^+$ (d) N—((R)-2-hydroxy-2-((S)-1,2,3,4-tetrahydroisoquinolin-3-yl)ethyl)-6-(oxetan-3-ylamino)pyrimidine-4-carboxamide 107

To a solution of 6-chloro-N—((R)-2-hydroxy-2-((S)-1,2,3,4-tetrahydroisoquinolin-3-yl)ethyl)pyrimidine-4-carboxamide dihydrochloride A31 (85 mg, 0.23 mmol) in i-PrOH (5 mL) were added oxetan-3-amine (20 mg, 0.28 mmol) and Et$_3$N (93 mg, 0.92 mmol). The mixture was heated at 60° C. overnight. The solvent was removed under reduced pressure and the residue obtained dissolved in water (15 mL). The pH was adjusted to pH 8-9 by addition of solid NaHCO$_3$. The aqueous layer was extracted with 10% MeOH/DCM (30 mL×5). The combined organic layers were dried (Na$_2$SO$_4$) and concentrated. The solid was washed with diethyl ether (10 mL×2) to give the title compound as a white solid (27 mg, 29%): $^1$H NMR (400 MHz, DMSO-d$_6$) δ 8.69-8.68 (m, 1H), 8.52-8.49 (m, 2H), 7.13-7.01 (m, 5H), 5.11 (d, J=5.2 Hz, 1H), 5.00 (br s, 1H), 4.82 (t, J=6.8 Hz, 2H), 4.48-4.45 (m, 2H), 3.94-3.82 (m, 2H), 3.68-3.59 (m, 2H), 3.32-3.29 (m, 1H, obscured by solvent), 2.83-2.59 (m, 4H); LCMS-C: RT 2.88 min; m/z 370.3 [M+H]$^+$.

Example 108: 4-(3-Oxa-8-azabicyclo[3.2.1]octane-8-carbonyl)-2-ethoxy-N—((R)-2-hydroxy-2-((S)-7-methyl-1,2,3,4-tetrahydroisoquinolin-3-yl)ethyl)benzamide 108

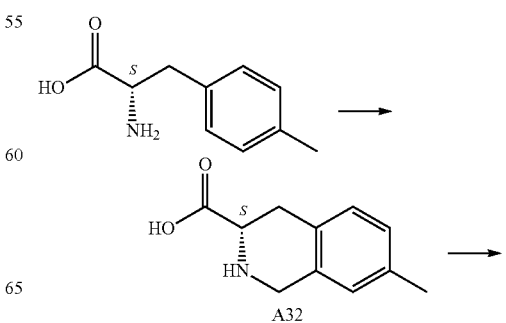

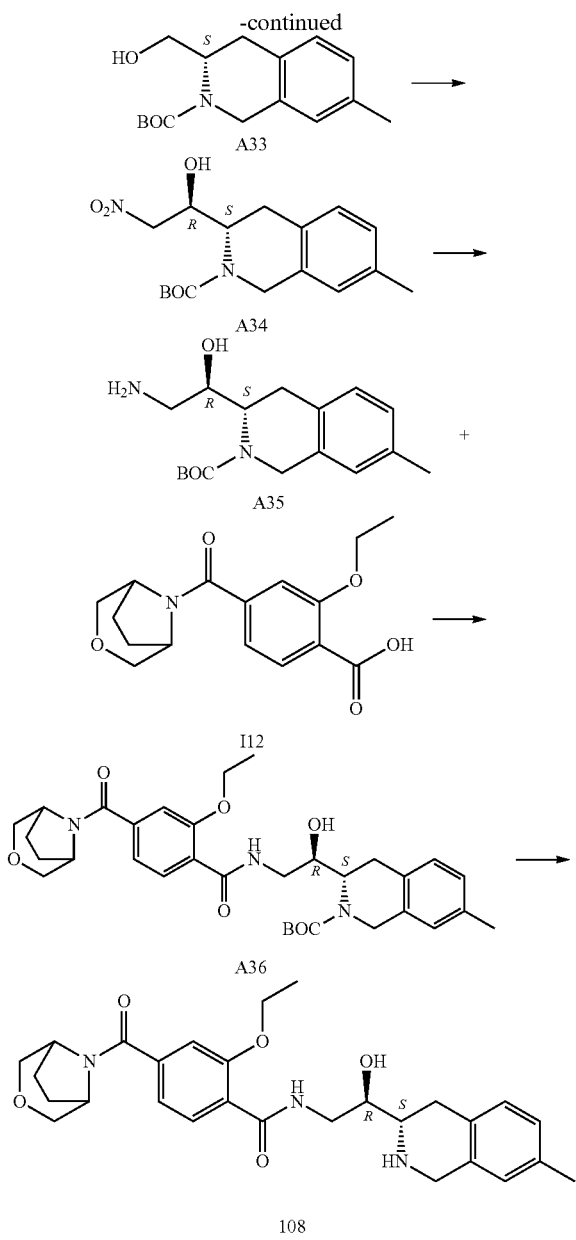

(a) (S)-7-Methyl-1,2,3,4-tetrahydroisoquinoline-3-carboxylic acid A32

To a solution of (S)-2-amino-3-(p-tolyl)propanoic acid (500 mg, 2.8 mol) in 48% aqueous HBr (5 mL) was added formaldehyde (0.82 mL, 22.3 mmol) gradually at 40° C. The mixture was then stirred at 75° C. for 5 hours. The reaction was cooled to 0° C., filtered and washed with DCM (2×10 mL). The solid was collected to provide the title compound as a white solid (440 mg, 82%). LCMS-C: RT 1.40 min; m/z 192.2 [M+H]$^+$.

(b) (S)-tert-Butyl 3-(hydroxymethyl)-7-methyl-3,4-dihydroisoquinoline-2(1H)-carboxylate A33

(S)-7-Methyl-1,2,3,4-tetrahydroisoquinoline-3-carboxylic acid A32 (700 mg, 3.7 mmol) was stirred vigorously in 1,4-dioxane (10 mL) and water (5 mL). NaHCO$_3$ (922 mg, 11 mmol) and Boc$_2$O (880 mg, 4.0 mmol) were added and the reaction was stirred vigorously. After 6 days, the mixture was concentrated in vacuo and the residue dissolved in water (20 mL). A 30% w/v aqueous solution of NaHSO$_4$ (30 mL) was added and the mixture extracted with DCM (3×50 mL). The pooled organic extracts were washed with brine, dried over Na$_2$SO$_4$ and concentrated in vacuo to give a yellow oil. This material was dissolved in THF (150 mL) and CDI (579 mg, 3.6 mmol) was added. The mixture was stirred for 3 hours at room temperature then cooled to 0° C. A solution of NaBH$_4$ (135 mg, 3.6 mmol) in water (4 mL) was added dropwise. The mixture was stirred vigorously at room temperature for 3 hours then concentrated in vacuo. The residue was partitioned between water (20 mL) and ethyl acetate (20 mL) and the aqueous phase extracted with ethyl acetate (2×20 mL), the combined organic extracts washed with 5% w/v aqueous NaHSO$_4$ (20 mL) and brine (20 mL), dried (Na$_2$SO$_4$) and concentrated in vacuo. The residue was purified by column chromatography (5% EtOAc/petroleum ether) to give the title compound as a pale oil (262 mg, 26% yield over 2 steps): LCMS-C: RT 2.91 min; m/z 300.2 [M+Na]

(c) tert-Butyl (S)-3-((R)-1-hydroxy-2-nitroethyl)-7-methyl-3,4-dihydroisoquinoline-2(1H)-carboxylate A34

To a solution of (S)-tert-butyl 3-(hydroxymethyl)-7-methyl-3,4-dihydroisoquinoline-2(1H)-carboxylate A33 (280 mg, 1.0 mmol) in a mixture of DCM (10 mL) and DMSO (2 mL) at 0° C. was added triethylamine (306 mL, 3.0 mmol) and pyridine-sulfur trioxide complex (482 mg, 3.0 mmol). The mixture was stirred at 0° C. for 10 minutes then allowed warm to room temperature and stirred a further 4 hours. The reaction was quenched by addition of saturated aqueous NaHCO$_3$ (20 mL) and water (20 mL), and the aqueous layer extracted with diethyl ether (3×150 mL). The pooled organic extracts were washed with 1:1 water:saturated aqueous NH$_4$Cl (100 mL) and brine (100 mL), dried (Na$_2$SO$_4$) and concentrated in vacuo to give the crude intermediate as an orange oil which was used without further purification.

A solution of N$^1$,N$^2$-bis(4-chlorobenzyl)benzene-1,2-diamine (44 mg, 0.12 mmol) and Cu(OAc)$_2$.H$_2$O (20 mg, 0.1 mmol) in ethanol (5 mL) was stirred at 23° C. for 1 hour. A solution of the crude intermediate from above (275 mg) in ethanol (5 mL) was then added to the catalyst solution and the mixture was cooled to 0° C. and stirred for 30 minutes. CH$_3$NO$_2$ (600 mg, 10.0 mmol) was added and stirring continued at 0° C. for 5 days. The mixture was concentrated and the residue purified by chromatography (5% EtOAc/petroleum ether) to give the title compound (160 mg, 48% yield over 2 steps) as a yellow oil. LCMS-C: RT 2.92 min; m/z 359.2 [M+Na]$^+$ (d) tert-Butyl (S)-3-((R)-2-amino-1-hydroxyethyl)-7-methyl-3,4-dihydroisoquinoline-2(1H)-carboxylate A35

To a solution of tert-butyl (S)-3-((R)-1-hydroxy-2-nitroethyl)-7-methyl-3,4-dihydroisoquinoline-2(1H)-carboxylate A34 (160 mg, 0.47 mmol) in absolute ethanol (10 mL) was added 10% Pd/C (50% wet with water, 160 mg). The reaction was stirred vigorously under a hydrogen atmosphere overnight. The mixture was filtered through Celite and the Celite washed with absolute ethanol (40 mL). The pooled filtrates were concentrated in vacuo to give the title compound as a yellow solid (110 mg, 76%): LCMS-C: RT 2.21 min; m/z 307.2 [M+H]$^+$

(e) (3S)-tert-Butyl 3-((1R)-2-(4-(3-oxa-8-azabicyclo[3.2.1]octane-8-carbonyl)-2-ethoxybenzamido)-1-hydroxyethyl)-7-methyl-3,4-dihydroisoquinoline-2(1H)-carboxylate A36

To a solution of 4-(3-oxa-8-azabicyclo[3.2.1]octane-8-carbonyl)-2-ethoxybenzoic acid I42 (110 mg, 0.36 mmol) and tert-butyl (S)-3-((R)-2-amino-1-hydroxyethyl)-7-methyl-3,4-dihydroisoquinoline-2(1H)-carboxylate A35 (110 mg, 0.36 mmol) in DCM (10 mL) were added DIPEA (186 mg, 1.44 mmol), HOBt (11 mg, 0.072 mmol), and EDCl.HCl (138 mg, 0.72 mmol). The resulting mixture was stirred at room temperature overnight. Water (20 mL) was added to the reaction mixture and the aqueous extracted with DCM (3×20 mL). The combined organic layers were dried (Na$_2$SO$_4$) and concentrated to give the crude product which was purified by column chromatography (DCM:MeOH=50:1) to give the title compound as a yellow oil (140 mg, 65%): LCMS-C: RT 3.10 min; m/z 594.3 [M+H]$^+$.

(f) 4-(3-Oxa-8-azabicyclo[3.2.1]octane-8-carbonyl)-2-ethoxy-N—((R)-2-hydroxy-2-((S)-7-methyl-1,2,3,4-tetrahydroisoquinolin-3-yl)ethyl)benzamide 108

A solution of (3S)-tert-butyl 3-((1R)-2-(4-(3-oxa-8-azabicyclo[3.2.1]octane-8-carbonyl)-2-ethoxybenzamido)-1-hydroxyethyl)-7-methyl-3,4-dihydroisoquinoline-2(1H)-carboxylate A36 (140 mg, 0.23 mmol) in saturated HCl/EtOAc solution (10 mL) was stirred at room temperature for 3 hours. The mixture was concentrated and the residue obtained suspended in saturated aqueous NaHCO$_3$ solution (20 mL). The aqueous mixture was extracted with DCM (3×20 mL) and the combined organic layers dried (Na$_2$SO$_4$) and concentrated to give a crude residue which was purified by prep TLC (DCM:MeOH=10:1) to give the title compound as a white solid (50 mg, 43%). $^1$H NMR (400 MHz, Methanol-d$_4$) δ 7.99 (d, J=8.0 Hz, 1H), 7.22 (s, 1H), 7.17-7.06 (m, 3H), 6.99 (s, 1H), 4.64 (s, 1H), 4.32-4.22 (m, 4H), 4.15-4.11 (m, 1H), 3.96 (br s, 1H), 3.83-3.81 (m, 1H), 3.74-3.70 (m, 3H), 3.62-3.57 (m, 2H), 3.45-3.40 (m, 1H), 3.16-3.04 (m, 2H), 2.30 (s, 3H), 2.07-2.00 (m, 4H), 1.44 (t, J=7.2 Hz, 3H). LCMS-C: RT 2.16 min, m/z 494.3 [M+H]$^+$.

Example 109: N-((1R)-1-Hydroxy-1-((S)-1,2,3,4-tetrahydroisoquinolin-3-yl)propan-2-yl)-4-(morpholine-4-carbonyl)benzamide hydrochloride 109

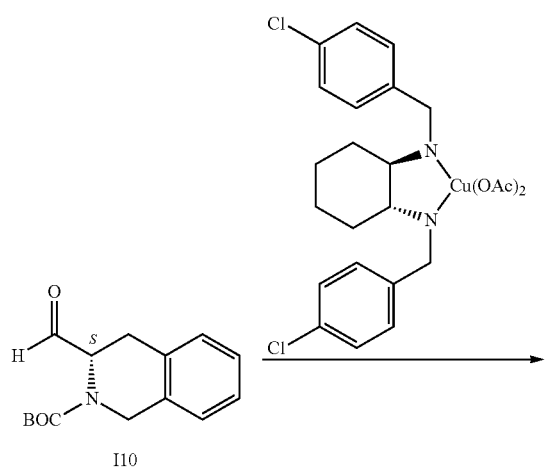

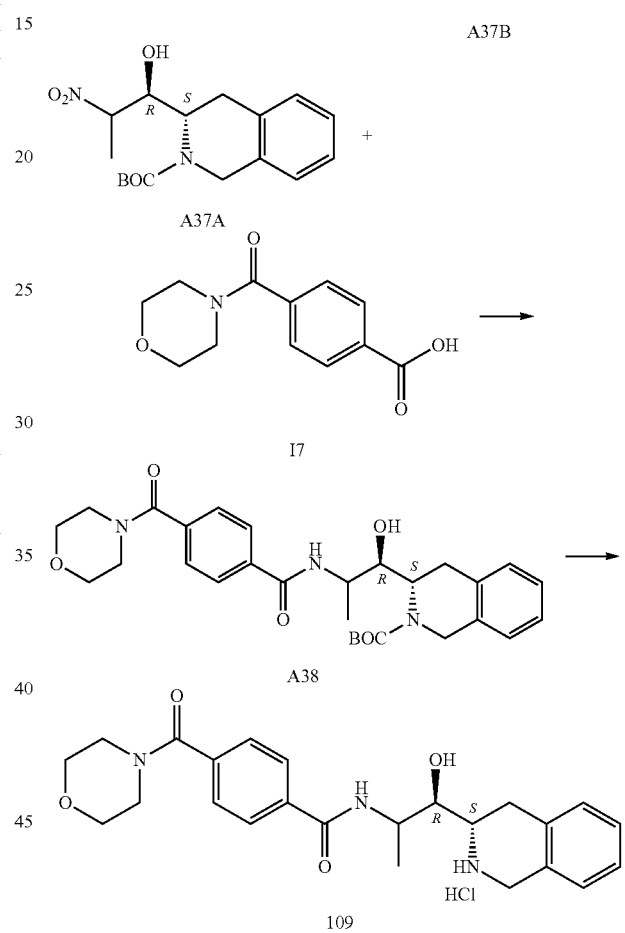

(a) tert-Butyl (3S)-3-((1S)-1-hydroxy-2-nitropropyl)-3,4-dihydroisoquinoline-2(1H)-carboxylate A37A and tert-butyl (3S)-3-((1R)-1-hydroxy-2-nitropropyl)-3,4-dihydroisoquinoline-2(1H)-carboxylate A37 B tert-Butyl (S)-3-formyl-3,4-dihydroisoquinoline-2(1H)-carboxylate I10 (3.55 mmol @ 100% conversion), absolute ethanol (10 mL), nitroethane (2.53 mL, 35.5 mmol) and the copper catalyst (see above FIGURE, prepared according to Tetrahedron: Asymmetry (2008) 2310-2315) (169 mg, 10 mol %) were stirred at room temperature. After four days the mixture was concentrated in vacuo, chromatography (12 g SiO$_2$ cartridge, 0-20% ethyl acetate/hexanes) gave title compounds A37A (pale yellow syrup, 231 mg) and A37B (brighter yellow syrup, 306 mg).

Data for tert-butyl (3S)-3-((1S)-1-hydroxy-2-nitropropyl)-3,4-dihydroisoquinoline-2(1H)-carboxylate A37A:

¹H NMR (400 MHz, Methanol-d₄) δ 7.29-6.99 (m, 4H), 5.03-3.95 (m, overlaps with solvent), 3.16 (dd, J=16.2, 2.4 Hz, 1H), 2.93 (dd, J=15.9, 5.6 Hz, 1H), 1.65-1.37 (m, 12H).

Data for tert-butyl (3S)-3-((1R)-1-hydroxy-2-nitropropyl)-3,4-dihydroisoquinoline-2(1H)-carboxylate A37B:

¹H NMR (400 MHz, Methanol-d₄) δ 7.23-7.09 (m, 4H), 4.99-4.64 (m, overlaps with solvent), 4.37-3.95 (m, overlaps with solvent), 3.14 (dd, J=15.5, 6.2 Hz, 1H), 2.84 (dd, J=15.5, 6.2 Hz, 1H), 1.55 (d, J=6.8 Hz, 3H), 1.50 (s, 9H). LCMS-A: 6.58 min; m/z 237.2 [M-Boc+2H]⁺

Determination of Stereochemistry for A37A and A37B:

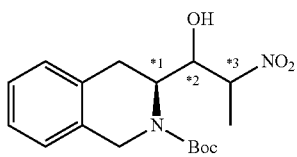 [SMILES: CC(C(O)[C@@H]1Cc2ccccc2CN1C(=O)OC(C)(C)C)[N+](=O)[O-]]

The ring stereocentre *1 is set in the starting material, (S)-1,2,3,4-tetrahydroisoquinoline-3-carboxylic acid. Based on ¹H NMR coupling constants for nitro compounds A37A and A37B and comparison to the known related systems (i.e. I11A and I11B) coupling constants (configuration which is confirmed by X-ray), stereocentre *2 in compound A37A has been assigned syn with respect to the heteroatoms (i.e. *1,*2=S,S) and compound A37B has been assigned anti with respect to the heteroatoms (i.e. *1,*2=S,R).

The stereochemistry at *3 has been left undefined, however a single signal is observed for the methyl group in the ¹H NMR for A37B, so A37B (and by extension A37A) are presumed to be a single diastereomers.

(b) tert-Butyl (3S)-3-((1R)-1-hydroxy-2-(4-(morpholine-4-carbonyl)benzamido)propyl)-3,4-dihydroisoquinoline-2(1H)-carboxylate A38 tert-Butyl (3S)-3-((1S)-1-hydroxy-2-nitropropyl)-3,4-dihydroisoquinoline-2(1H)-carboxylate A37A (231 mg, 0.69 mmol), absolute ethanol (10 mL), Pd/C (50% wet with water, 200 mg) were stirred under hydrogen. After 18 hours, the mixture was filtered through Celite and the Celite washed with absolute ethanol (20 mL). The combined filtrates were evaporated to give the crude amine which was used in the next step without purification.

The amine (164 mg), 4-(morpholine-4-carbonyl)benzoic acid I7 (126 mg, 0.535 mmol), acetonitrile (5 mL), DMF (1 mL), DIPEA (0.186 mL, 1.07 mmol) and HATU (305 mg 0.803 mmol) were stirred at room temperature. After 18 hours, the mixture was quenched with water (1 mL) and the acetonitrile removed in vacuo. The aqueous residue was diluted with water (25 mL) and DCM (25 mL). The DCM phase was separated and concentrated in vacuo. Chromatography (12 g silica cartridge, 0-100% ethyl acetate/hexanes) gave the title compound as an off white solid after trituration with DCM/hexanes (48 mg, 13% yield over 2 steps). LCMS-B: RT 3.25 min; m/z 424.2 [M-Boc+2H]⁺

(c) N-((1R)-1-Hydroxy-1-((S)-1,2,3,4-tetrahydroisoquinolin-3-yl)propan-2-yl)-4-(morpholine-4-carbonyl)benzamide hydrochloride 109 tert-Butyl (3S)-3-((1R)-1-hydroxy-2-(4-(morpholine-4-carbonyl)benzamido)propyl)-3,4-dihydroisoquinoline-2(1H)-carboxylate A38 (48 mg, 0.091 mmol), 1,4-dioxane (2 mL) and 4.0 M HCl in 1,4-dioxane (2 mL) were stood at room temperature. After 1.5 hours the mixture was diluted with diethyl ether (50 mL), the solvent decanted from the precipitate and the precipitate washed with further diethyl ether (2×50 mL). The diethyl ether extracts were discarded and the precipitate was dried in vacuo to give the title compound as a white solid (8.7 mg, 21% yield). LCMS-B: RT 2.75 min; m/z 424.2 [M+H]⁺ for free base.

Example 110: N-((1S)-1-Hydroxy-1-((S)-1,2,3,4-tetrahydroisoquinolin-3-yl)propan-2-yl)-4-(morpholine-4-carbonyl)benzamide hydrochloride 110

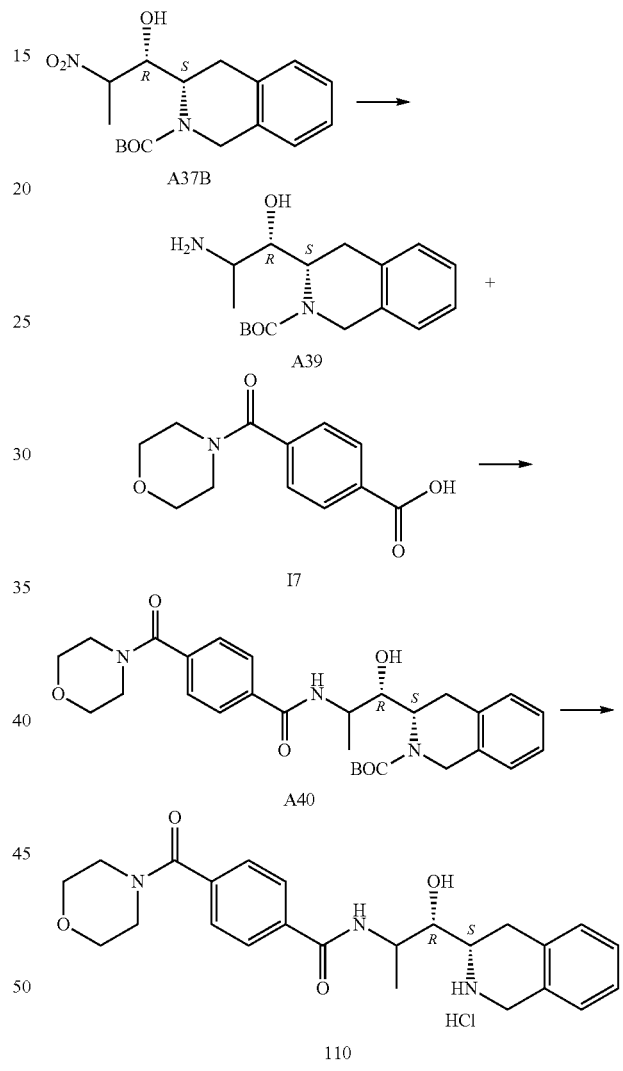

(a) tert-Butyl (3S)-3-((1S)-2-amino-1-hydroxypropyl)-3,4-dihydroisoquinoline-2(1H)-carboxylate A39 tert-Butyl (3S)-3-((1R)-1-hydroxy-2-nitropropyl)-3,4-dihydroisoquinoline-2(1H)-carboxylate A37B (306 mg, 0.91 mmol), absolute ethanol (10 mL) and Pd/C (50% wet with water, 200 mg) were stirred under hydrogen. After 18 hours, the mixture was filtered through Celite and the Celite washed with absolute ethanol (20 mL). The combined filtrates were evaporated to give the title compound as a colourless syrup (250 mg, 90% yield). LCMS-A: RT 4.76 min; m/z 307.2 [M-Boc+2H]⁺

(b) tert-Butyl (3S)-3-((1S)-1-hydroxy-2-(4-(morpholine-4-carbonyl)benzamido)propyl)-3,4-dihydroisoquinoline-2(1H)-carboxylate A40 tert-Butyl (3S)-3-((1S)-2-amino-1-hydroxypropyl)-3,4-dihydroisoquinoline-2(1H)-carboxylate A39 (153 mg, 0.499 mmol), 4-(morpholine-4-carbonyl)benzoic acid I7 (117 mg, 0.499 mmol), acetonitrile (5 mL), DMF (1 mL), DIPEA (0.174 mL, 0.999 mmol) and HATU (285 mg 0.749 mmol) were stirred at room temperature. After 18 hours, the mixture was quenched with water (1 mL) and the acetonitrile removed in vacuo. The aqueous residue was diluted with water (25 mL) and DCM (25 mL). The DCM phase was separated and concentrated in vacuo. Chromatography (12 g silica cartridge, 0-100% ethyl acetate/hexanes) gave the title compound as an off white solid after trituration with DCM/hexanes (96 mg, 37% yield). LCMS-B: RT 3.20 min; m/z 424.2 [M-Boc+2H]$^+$; 468.2 [M-tBu+2H]$^+$; 524.3 [M+H]$^+$ (c) N-((1S)-1-Hydroxy-1-((S)-1,2,3,4-tetrahydroisoquinolin-3-yl)propan-2-yl)-4-(morpholine-4-carbonyl)benzamide hydrochloride 110 tert-Butyl (3S)-3-((1S)-1-hydroxy-2-(4-(morpholine-4-carbonyl)benzamido)propyl)-3,4-dihydroisoquinoline-2(1H)-carboxylate A40 (96 mg, 0.183 mmol), 1,4-dioxane (2 mL) and 4.0 M HCl in 1,4-dioxane (2 mL) were stood at room temperature. After 1.5 hours, the mixture was diluted with diethyl ether (50 mL), the solvent decanted from the precipitate and the precipitate washed with further diethyl ether (2×50 mL). The diethyl ether extracts were discarded and the precipitate was dried in vacuo to give the title compound as a white solid (46 mg, 55% yield). LCMS-B: RT 2.75 min; m/z 424.3 [M+H]$^+$ for free base.

Example 121: N—((R)-2-Hydroxy-2-((S)-1,2,3,4-tetrahydroisoquinolin-3-yl)ethyl)-6-(methylamino)nicotinamide dihydrochloride 121

(a) (S)-tert-Butyl 3-((R)-1-hydroxy-2-(6-(methylamino)nicotinamido)ethyl)-3,4-dihydroisoquinoline-2(1H)-carboxylate A41

To a solution of (S)-tert-butyl 3-((R)-2-(6-chloronicotinamido)-1-hydroxyethyl)-3,4-dihydroisoquinoline-2(1H)-carboxylate A19 (50 mg, 0.12 mmol, 1.0 eq) in EtOH (1 mL) was added a solution of methylamine in THF (2M, 0.23 mL), and the reaction was heated in the microwave at 130° C. for 3 hours. The solvent was removed and the residue purified by preparative TLC (DCM:MeOH=15:1) to give the title compound (25 mg, 49%) as a white solid. LCMS-C: RT 2.36 min; m/z 427.2 [M+H]$^+$ (b) N—((R)-2-Hydroxy-2-((S)-1,2,3,4-tetrahydroisoquinolin-3-yl)ethyl)-6-(methylamino)nicotinamide dihydrochloride 121

To a solution of (S)-tert-butyl 3-((R)-1-hydroxy-2-(6-(methylamino)nicotinamido)ethyl)-3,4-dihydroisoquinoline-2(1H)-carboxylate A41 (20 mg, 0.07 mmol, 1.0 eq) in diethyl ether (2 mL) was added a solution of saturated HCl in diethyl ether (2 mL). The reaction was stirred at room temperature for 2 hours then concentrated and the residue obtained was washed with diethyl ether to give the title compound (15 mg, 79%) as a yellow solid. $^1$H NMR (400 MHz, Methanol-d$_4$) δ 8.44 (s, 1H), 8.30 (br s, 1H), 7.30-7.21 (m, 4H), 7.10 (d, J=8.8 Hz, 1H), 4.51-4.30 (m, 3H), 3.69-3.64 (m, 2H), 3.58-3.53 (m, 1H), 3.35-3.28 (m, 1H, overlap), 3.24-3.18 (m, 1H), 3.09 (s, 3H). LCMS-C: RT 0.65 min; m/z 327.2 [M+H]$^+$ (free base)

Example 122: N—((R)-2-Hydroxy-2-((S)-1,2,3,4-tetrahydroisoquinolin-3-yl)ethyl)-6-((((tetrahydro-2H-pyran-4-yl)methyl)amino)nicotinamide dihydrochloride 122

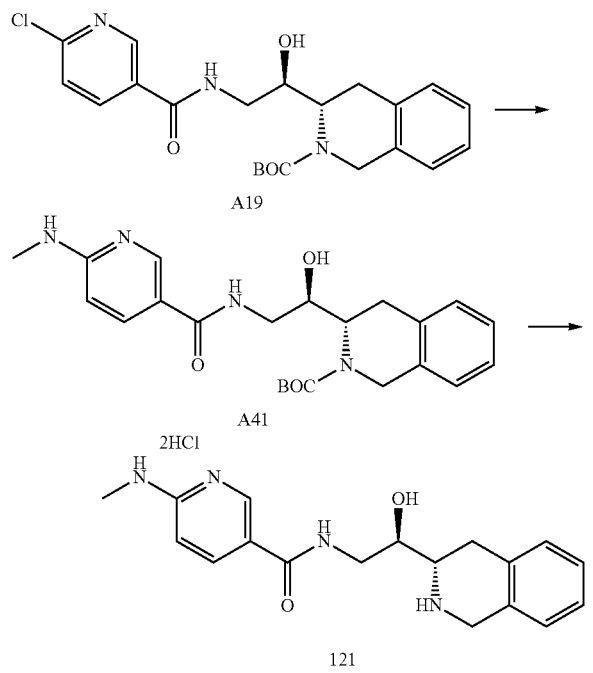

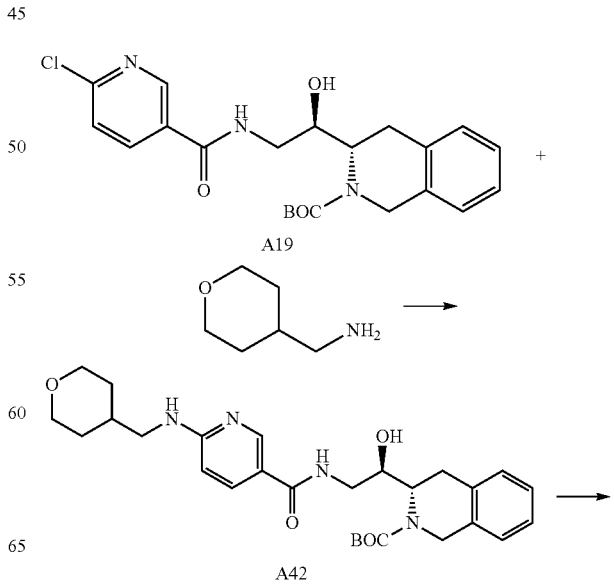

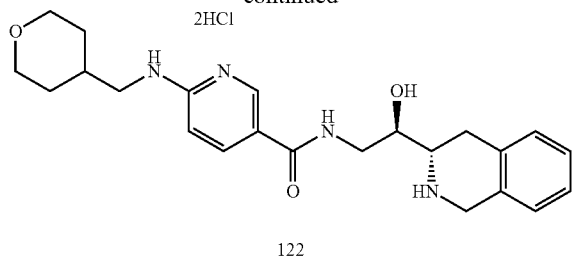

122

(a) (S)-tert-Butyl 3-((R)-1-hydroxy-2-(6-(((tetra-hydro-2H-pyran-4-yl)methyl)amino)nicotinamido) ethyl)-3,4-dihydroisoquinoline-2(1H)-carboxylate A42

A solution of (S)-tert-butyl 3-((R)-2-(6-chloronicotinamido)-1-hydroxyethyl)-3,4-dihydroisoquinoline-2(1H)-carboxylate A19 (50 mg, 0.12 mmol, 1.0 eq) and (tetrahydro-2H-pyran-4-yl)methanamine (55 mg, 0.48 mmol, 4.0 eq) in tert-butanol (1 mL) was heated in the microwave at 170° C. for 4 hours. The solvent was removed and the crude residue purified by preparative TLC (DCM:MeOH=15:1) to give the title compound (10 mg, 16%) as a white solid. LCMS-C: RT 2.53 min; m/z 511.3 [M+H]+

(b) N—((R)-2-Hydroxy-2-((S)-1,2,3,4-tetrahydroisoquinolin-3-yl)ethyl)-6-(((tetrahydro-2H-pyran-4-yl)methyl)amino)nicotinamide dihydrochloride I22

To a solution of (S)-tert-butyl 3-((R)-1-hydroxy-2-(6-(((tetrahydro-2H-pyran-4-yl)methyl)amino)nicotinamido) ethyl)-3,4-dihydroisoquinoline-2(1H)-carboxylate A42 (10 mg, 0.02 mmol, 1.0 eq) in diethyl ether (2 mL) was added a solution of saturated HCl in diethyl ether (2 mL). The reaction was stirred at room temperature for 2 hours then concentrated and the residue obtained was washed with diethyl ether to give the title compound (7 mg, 78%) as a yellow solid. $^1$H NMR (400 MHz, Methanol-$d_4$) δ 8.41 (s, 1H), 8.32-8.28 (m, 1H), 7.33-7.21 (m, 4H), 7.15-7.13 (m, 1H), 4.50-4.47 (m, 1H), 4.39-4.35 (m, 1H), 4.30-4.26 (m, 1H), 3.99-3.96 (m, 2H), 3.69-3.64 (m, 2H), 3.57-3.52 (m, 1H), 3.47-3.41 (m, 2H), 3.35-3.33 (m, overlap), 3.23-3.18 (m, 1H), 2.03-1.94 (m, 1H), 1.78-1.75 (m, 2H), 1.45-1.34 (m, 4H). LCMS: RT 2.45 min; m/z 411.2 [M+H]+ (free base)

Example 123: 4-(3-Oxa-8-azabicyclo[3.2.1]octane-8-carbonyl)-2-ethoxy-N—((S)-2-hydroxy-2-((R)-1,2,3,4-tetrahydroisoquinolin-3-yl)ethyl)benzamide hydrochloride 123

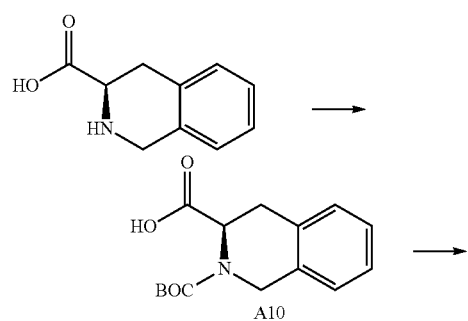

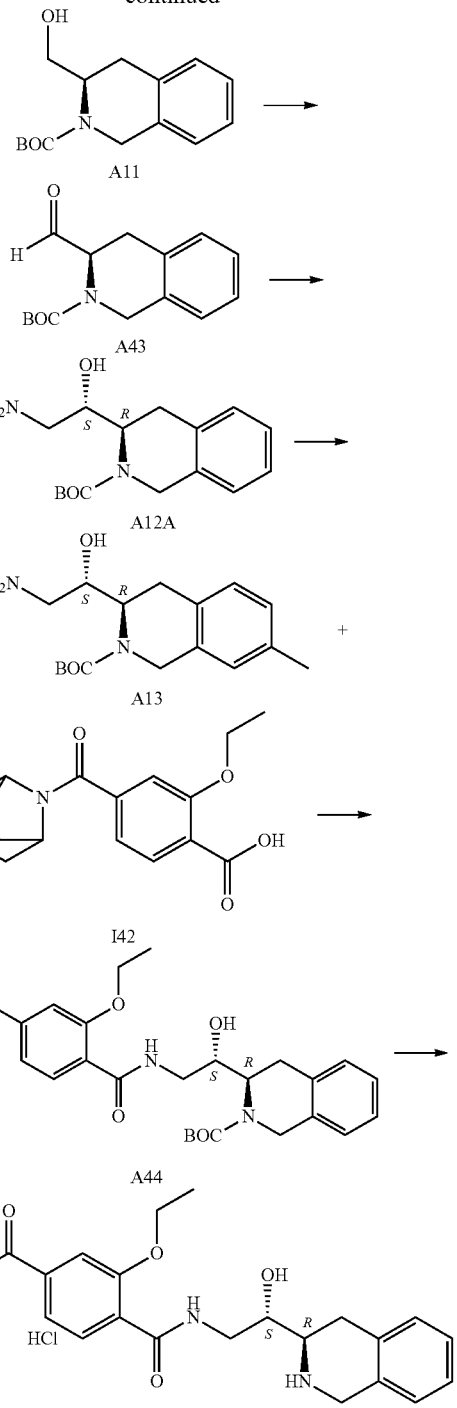

123

(a) Alternate Synthesis of (R)-2-(tert-Butoxycarbonyl)-1,2,3,4-tetrahydroisoquinoline-3-carboxylic acid A10

A mixture of (R)-1,2,3,4-tetrahydroisoquinoline-3-carboxylic acid (3.0 g, 16.9 mmol, 1.0 eq) in 1,4-dioxane (60 mL) and water (30 mL) was vigorously stirred. NaHCO$_3$ (2.8 g, 33.8 mmol, 2.0 eq) and Boc$_2$O (4.1 g, 18.6 mmol, 1.1 eq) were added and the reaction stirred vigorously at room temperature for 6 days. The mixture was concentrated in vacuo and the residue was dissolved in water (100 mL). A 30% w/v aqueous solution of NaHSO$_4$ (30 mL) was added and the mixture extracted with CHCl$_3$ (3×200 mL). The pooled organic extracts were washed with brine, dried (Na$_2$SO$_4$) and concentrated to give the title compound (3.9 g, 85%) as an oil. LCMS-C: RT 2.65 min; m/z 300.1 [M+Na]$^+$ (b) Alternate Synthesis of (R)-tert-Butyl 3-(hydroxymethyl)-3,4-dihydroisoquinoline-2(1H)-carboxylate A11

(R)-2-(tert-Butoxycarbonyl)-1,2,3,4-tetrahydroisoquinoline-3-carboxylic acid A10 (3.7 g, 13.5 mmol, 1.0 eq) was dissolved in THF (10 mL). CDI (4.4 g, 27.2 mmol, 2.0 eq) was added and the mixture was stirred for 30 minutes at room temperature then cooled to 0° C. A solution of NaBH$_4$ (616 mg, 16.3 mmol, 1.2 eq) in water (8 mL) was added dropwise and the reaction stirred vigorously at 0° C. for 4 hours. The reaction was quenched with acetone (20 mL) and concentrated in vacuo. The residue was suspended in water (100 mL) and extracted with ethyl acetate (4×50 mL), the combined organic extracts were washed with 5% w/v aqueous NaHSO$_4$ (100 mL) and brine (100 mL), dried (Na$_2$SO$_4$) and concentrated in vacuo. The residue was purified by chromatography (5%-17% EtOAc/petroleum ether) to give the title compound (1.0 g, 28%) as a pale yellow oil. LCMS-C: RT 2.68 min; m/z 286.1 [M+Na]$^+$ (c) (R)-tert-Butyl 3-formyl-3,4-dihydroisoquinoline-2(1H)-carboxylate A43

To a solution of (R)-tert-butyl 3-(hydroxymethyl)-3,4-dihydroisoquinoline-2(1H)-carboxylate A11 (1.0 g, 3.8 mmol, 1.0 eq) in a mixture of DCM (25 mL) and DMSO (5 mL) at 0° C. was added triethylamine (1.15 g, 11.4 mmol, 3.0 eq) and pyridine-sulfur trioxide complex (1.8 g, 11.4 mmol, 3.0 eq). The mixture was stirred at 0° C. for 10 minutes then allowed to warm to room temperature. After 3 hours, saturated sodium bicarbonate (50 mL) and water (50 ml) were added and the mixture extracted with diethyl ether (3×150 mL). The pooled ether extracts were washed with 1:1 water: saturated aqueous NH$_4$Cl (100 mL) and brine (100 mL), dried (Na$_2$SO$_4$) and concentrated to give the crude product as an orange oil which was used in the next step directly without further purification.

(d) Alternate synthesis of (R)-tert-Butyl 3-((S)-1-hydroxy-2-nitroethyl)-3,4-dihydroisoquinoline-2(1H)-carboxylate A12A To a solution of (R)-tert-butyl 3-formyl-3,4-dihydroisoquinoline-2(1H)-carboxylate A43 (3.8 mmol @ 100% conversion) in i-propanol (50 mL) at 0° C. was added nitromethane (928 mg, 15.2 mmol, 4.0 eq) and potassium fluoride (221 mg, 3.8 mmol, 1.0 eq). The reaction was allowed to warm to room temperature and stirred for 2 days. The reaction was diluted with NaHCO$_3$ (50 mL) and water (200 mL) and extracted with diethyl ether (100 mL×3). The organic layers were washed with brine (100 mL), dried (Na$_2$SO$_4$) and concentrated in vacuo. The crude product was purified by column (5% EtOAc/petroleum ether) to give the title compound (345 mg, 29%) as a pale yellow oil. LCMS-C: RT 2.67 min; m/z 345.1 [M+Na]$^+$ (e) Alternate synthesis of (R)-tert-Butyl 3-((S)-2-amino-1-hydroxyethyl)-3,4-dihydroisoquinoline-2(1H)-carboxylate A13

To a solution of (R)-tert-butyl 3-((S)-1-hydroxy-2-nitroethyl)-3,4-dihydroisoquinoline-2(1H)-carboxylate A12A (345 mg, 0.15 mmol) in absolute ethanol (25 mL) was added 10% Pd/C (50% wet with water, 350 mg) and the mixture was stirred vigorously under hydrogen atmosphere overnight. The catalyst was removed by filtration through Celite and the Celite washed with absolute ethanol (30 mL). The pooled filtrates were concentrated to give the title compound (260 mg, 83%) as a yellow solid: LCMS-C: RT 2.10 min; m/z 293.2 [M+H]$^+$ (f) (3R)-tert-Butyl 3-((1S)-2-(4-(3-oxa-8-azabicyclo [3.2.1]octane-8-carbonyl)-2-ethoxybenzamido)-1-hydroxyethyl)-3,4-dihydroisoquinoline-2(1H)-carboxylate A44

To a mixture of 4-(3-oxa-8-azabicyclo[3.2.1]octane-8-carbonyl)-2-ethoxybenzoic acid I42 (59 mg, 0.19 mmol, 1.1 eq) and (R)-tert-butyl 3-((S)-2-amino-1-hydroxyethyl)-3,4-dihydroisoquinoline-2(1H)-carboxylate A13 (51 mg, 0.175 mmol, 1.0 eq) in DCM (5 mL) were added DIPEA (90 mg, 0.70 mmol, 4.0 eq), HOBt (3 mg, 0.02 mmol, 0.1 eq), and EDCl.HCl (67 mg, 0.35 mmol, 2.0 eq). The resulting mixture was stirred at room temperature overnight. The reaction was diluted with saturated aqueous NaHCO$_3$ (30 mL) and extracted with DCM (3×30 mL). The combined organic layers were dried (Na$_2$SO$_4$) and concentrated to give the crude product which was purified by preparative TLC (5% MeOH/DCM) to give the title compound (80 mg, 79%) as a white solid. LCMS-C: RT 2.88 min; m/z 580.3 [M+H]$^+$ (g) 4-(3-Oxa-8-azabicyclo[3.2.1]octane-8-carbonyl)-2-ethoxy-N—((S)-2-hydroxy-2-((R)-1,2,3,4-tetrahydroisoquinolin-3-yl)ethyl)benzamide hydrochloride 123

To a solution of (3R)-tert-butyl 3-((1S)-2-(4-(3-oxa-8-azabicyclo[3.2.1]octane-8-carbonyl)-2-ethoxybenzamido)-1-hydroxyethyl)-3,4-dihydroisoquinoline-2(1H)-carboxylate A44 (70 mg, 0.12 mmol, 1.0 eq) in diethyl ether (5 mL) was added a solution of saturated HCl in diethyl ether (5 mL) and the reaction was stirred at room temperature overnight. The mixture was concentrated and the residue washed with diethyl ether to give the title compound (57 mg, 92%) as a yellow solid. $^1$H NMR (400 MHz, Methanol-d$_4$) δ 7.97 (d, J=8.0 Hz, 1H), 7.32-7.22 (m, 5H), 7.15 (d, J=8.0 Hz, 1H), 4.64 (s, 1H), 4.49-4.37 (m, 2H), 4.27-4.22 (m, 3H), 3.95 (br s, 1H), 3.83-3.57 (m, 7H), 3.34-3.27 (m, overlap), 3.22-3.16 (m, 1H), 2.06-2.00 (m, 4H), 1.43 (t, J=6.8 Hz, 3H). LCMS-C: RT 2.05 min, m/z 480.3 [M+H]$^+$ (free base)

Example 124: N—((R)-2-Hydroxy-2-((S)-1,2,3,4-tetrahydroisoquinolin-3-yl)ethyl)-2-((1-(2,2,2-trifluoroethyl)piperidin-4-yl)oxy)isonicotinamide 124

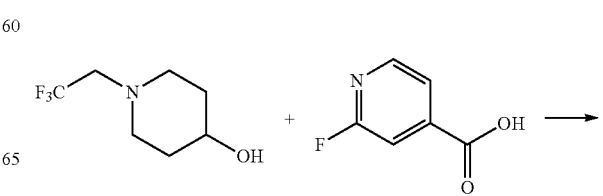

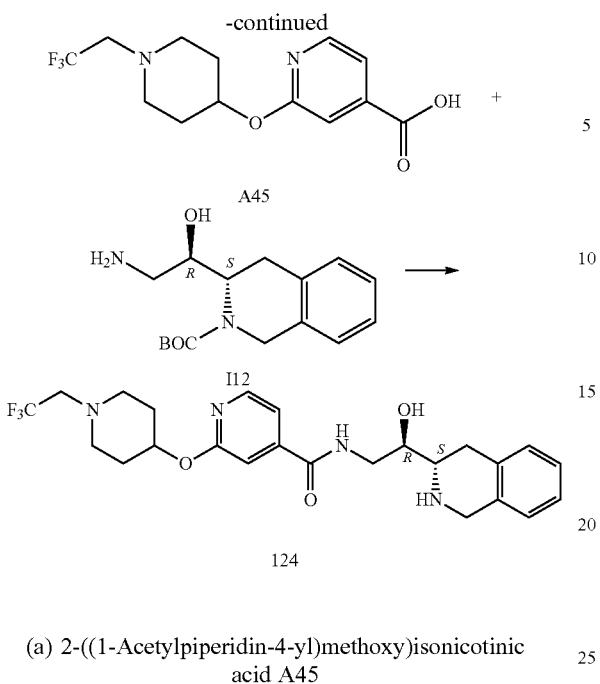

(a) 2-((1-Acetylpiperidin-4-yl)methoxy)isonicotinic acid A45

A solution of (1-(2,2,2-trifluoroethyl)piperidin-4-yl)methanol (253 mg, 1.38 mmol, 1.3 equiv) in anhydrous DMF (5 mL) was added to a stirring suspension of sodium hydride (60% dispersion in mineral oil, 0.170 g, 24.0 mmol, 4 equiv) in anhydrous DMF (5 mL) under an atmosphere of nitrogen. The mixture was stirred at room temperature for 10 minutes before a solution of 2-fluoroisonicotinic acid (0.150 g, 1.06 mmol, 1 equiv) in DMF (5 mL) was added. The mixture was then stirred overnight. H$_2$O (~10 mL) was carefully added and the pH of the aqueous mixture was adjusted to ~3 with a 0.5 M solution of aqueous citric acid. The aqueous was extracted with EtOAc (3×30 mL), the organics were combined, washed with brine, dried (Na$_2$SO$_4$) and the solvent removed in vacuo. The resultant residue was purified by column chromatography (Biotage Isolera, 12 g SiO$_2$ cartridge, 0-55% EtOAc in petroleum benzene 40-60° C.) to give the title compound (172 mg, 53% yield) as a white solid. $^1$H NMR (400 MHz, Methanol-d$_4$) δ 8.23 (dd, J=5.2, 0.8 Hz, 1H), 7.40 (dd, J=5.2, 1.4 Hz, 1H), 7.24 (dd, J=1.3, 0.7 Hz, 1H), 5.08 (tt, J=8.0, 3.9 Hz, 1H), 3.10 (q, J=9.9 Hz, 2H), 3.01-2.88 (m, 2H), 2.70-2.59 (m, 2H), 2.12-1.96 (m, 2H), 1.91-1.70 (m, 2H). LCMS-B: RT 2.99 min, m/z 305.1 [M+H]$^+$.

b) N—((R)-2-Hydroxy-2-((S)-1,2,3,4-tetrahydroisoquinolin-3-yl)ethyl)-2-((1-(2,2,2-trifluoroethyl)piperidin-4-yl)oxy)isonicotinamide 124

To a solution of 2-((1-acetylpiperidin-4-yl)methoxy)isonicotinic acid A45 (70 mg, 0.23 mmol, 1 equiv), DIPEA (120 μL, 0.69 mmol, 3 equiv) and HATU (131 mg, 0.345 mmol, 1.5 equiv) in DMF (4 mL) was added a solution of tert-butyl (S)-3-((R)-2-amino-1-hydroxyethyl)-3,4-dihydroisoquinoline-2(1H)-carboxylate I12 (67 mg, 0.23 mmol, 1 equiv) in DMF (2 mL). The reaction was stood at room temperature overnight, quenched with a saturated aqueous solution of 1 M NaOH (5 mL) and stirred for 3 hours. The solution was extracted with DCM (3×10 mL) utilizing a phase separation cartridge. The organic filtrates were reduced under a stream of air, DCM:TFA (8 mL, 1:1 v/v) was added and the reaction stood at room temperature overnight. The reaction mixture was concentrated under a stream of air and then purified by solid-phase extraction (1 g SCX-2 cartridge, 3 column volumes of methanol followed by 3 column volumes of 0.2 M methanolic ammonia) to give the title compound (62 mg, 56% yield) as a white solid. $^1$H NMR (400 MHz, Methanol-d$_4$) δ 8.21 (dd, J=5.3, 0.8 Hz, 1H), 7.27 (dd, J=5.3, 1.5 Hz, 1H), 7.16-7.08 (m, 4H), 7.07-7.02 (m, 1H), 5.15-5.04 (m, 1H), 4.09-3.95 (m, 2H), 3.93-3.84 (m, 1H), 3.65 (dd, J=13.8, 4.6 Hz, 1H), 3.53 (dd, J=13.8, 7.2 Hz, 1H), 3.16-3.02 (m, 2H), 3.02-2.81 (m, 5H), 2.71-2.50 (m, 2H), 2.03 (d, J=8.1 Hz, 2H), 1.89-1.70 (m, 2H). LCMS-B: RT 2.87 min, m/z 479.2 [M+H]$^+$.

Example 125: 4-(3-Oxa-8-azabicyclo[3.2.1]octane-8-carbonyl)-2-ethoxy-N—((R)-2-hydroxy-2-((S)-6-methyl-1,2,3,4-tetrahydroisoquinolin-3-yl)ethyl)benzamide hydrochloride 125

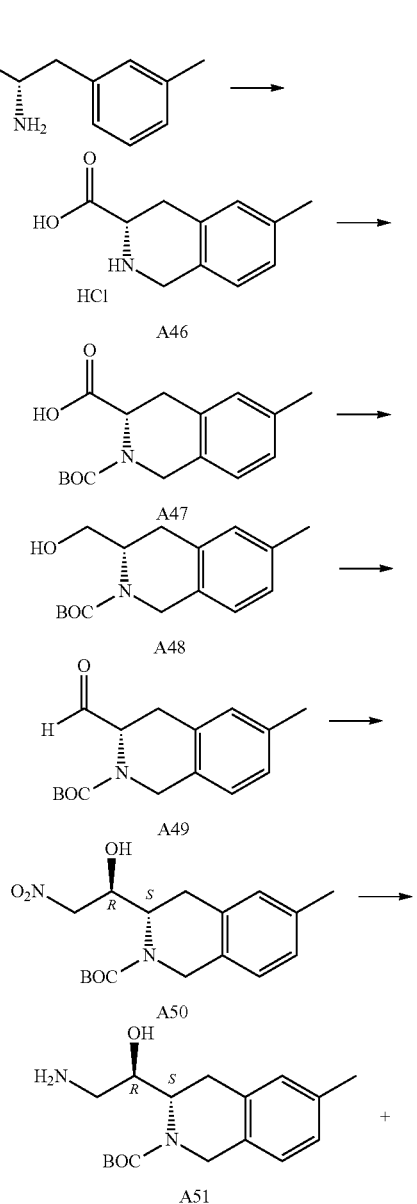

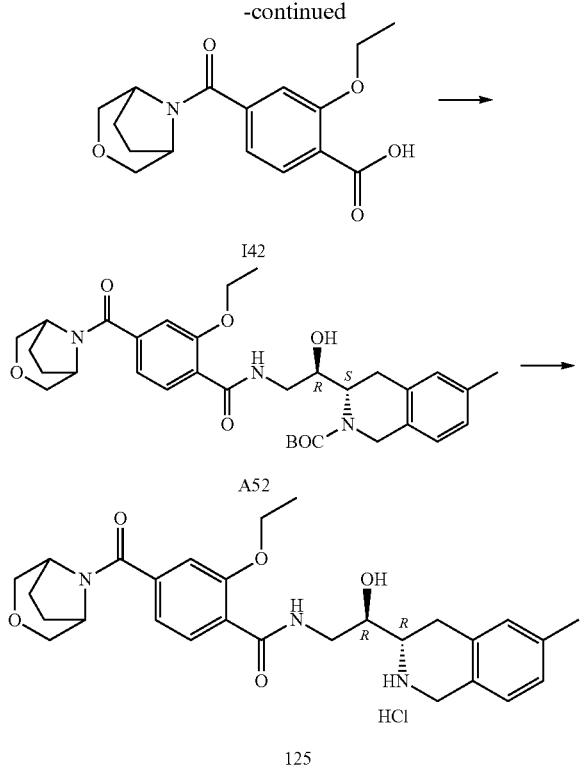

(a)(S)-6-Methyl-1,2,3,4-tetrahydroisoquinoline-3-carboxylic acid hydrochloride A46

To a solution of (S)-2-amino-3-(m-tolyl)propanoic acid (1.0 g, 5.6 mmol) in concentrated HCl (10 mL) was added formaldehyde (1.5 mL, 37-40% gradually at 40° C. The mixture was heated at 100° C. for 3 hours, then cooled to 0° C. and the solid precipitate was collected by filtration and washed with dichloromethane (40 mL). The solid was dried to give the title compound as a grey solid (300 mg), purity about 70%: LCMS-C: RT 2.93 min; m/z 192.1 [M+H]+ (free base).

(b) (S)-2-(tert-Butoxycarbonyl)-6-methyl-1,2,3,4-tetrahydroisoquinoline-3-carboxylic acid A47

To a vigorously stirred suspension of (S)-6-methyl-1,2,3,4-tetrahydroisoquinoline-3-carboxylic acid hydrochloride A46 (300 mg, 1.3 mmol) in a mixture of 1,4-dioxane (20 mL) and water (10 mL) at 40° C. was added NaHCO$_3$ (316 mg, 4.0 mmol) and Boc$_2$O (316 mg, 1.5 mmol) and the reaction was stirred for 7 days. The mixture was concentrated in vacuo and the residue dissolved in water (10 mL). A 30% w/v aqueous solution of NaHSO$_4$ (20 mL) was added and the mixture extracted with DCM (4×40 mL). The pooled organic extracts were washed with brine, dried (Na$_2$SO$_4$) and concentrated to give the title compound as an off-white solid (530 mg, 100%): LCMS-C: RT 2.89 min; m/z 192.2 [M-Boc+2H]+, 314.2 [M+Na]+.

(c) (S)-tert-Butyl 3-(hydroxymethyl)-6-methyl-3,4-dihydroisoquinoline-2(1H)-carboxylate A48

To a solution of (S)-2-(tert-butoxycarbonyl)-7-methyl-1,2,3,4-tetrahydroisoquinoline-3-carboxylic acid A47 (530 mg, 1.8 mmol) in THF (10 mL) was added CDI (590 mg, 3.6 mmol). The reaction was stirred for 2 hours at room temperature then cooled to 0° C. A solution of NaBH$_4$ (138 mg, 3.6 mmol) in water (15 mL) was added dropwise and the mixture stirred vigorously at room temperature for 3 hours. The reaction was concentrated in vacuo and the residue obtained partitioned between water (20 mL) and ethyl acetate (20 mL). The aqueous layer was extracted with ethyl acetate (3×30 mL) and the combined organic extracts dried (Na$_2$SO$_4$) and concentrated. The residue was purification by chromatography (5% EtOAc/petroleum ether) to give the title compound as a white solid (207 mg, 41%). LCMS-C: RT 2.91 min; m/z 300.3 [M+Na]+

(d) (S)-tert-Butyl 3-formyl-6-methyl-3,4-dihydroisoquinoline-2(1H)-carboxylate A49

To a solution of (S)-tert-butyl 3-(hydroxymethyl)-7-methyl-3,4-dihydroisoquinoline-2(1H)-carboxylate A48 (250 mg, 0.9 mmol) in a mixture of DCM (10 mL) and DMSO (3 mL) at 0° C. was added triethylamine (304 mL, 3.0 mmol) and pyridine-sulfur trioxide complex (477 mg, 3.0 mmol). The mixture was stirred at 0° C. for 10 minutes then allowed to warm to room temperature. After 4 hours, saturated sodium bicarbonate (20 mL) and water (20 ml) were added and the mixture was extracted with diethyl ether (5×30 mL). The pooled ether extracts were washed with 1:1 water: saturated aqueous NH$_4$Cl (20 mL), dried (Na$_2$SO$_4$) and concentrated to give the crude product as an orange oil which was used in next step without purification. LCMS-C: RT 2.96 min; m/z 330.2 [M+MeOH+Na]+

(e) tert-butyl (S)-3-((R)-1-hydroxy-2-nitroethyl)-6-methyl-3,4-dihydroisoquinoline-2(1H)-carboxylate A50

A solution of N,N-bis(4-chlorobenzyl)benzene-1,2-diamine (40 mg, 0.11 mmol) and Cu(OAc)$_2$.H$_2$O (18 mg, 0.09 mmol) in ethanol (2 mL) was stirred at room temperature for 1 hour. A solution of (S)-tert-butyl 3-formyl-7-methyl-3,4-dihydroisoquinoline-2(1H)-carboxylate A49 (260 mg, 0.9 mmol) in ethanol (3 mL) was added, the reaction mixture was cooled to 0° C. and stirred for 30 minutes, CH$_3$NO$_2$ (541 mg, 9.0 mmol) was added and stirring continued at 0° C. for 2 days. The mixture was concentrated and the residue was purified by preparative TLC (25% EtOAc/petroleum ether) to give the title compound (50 mg, 17%) as an oil. LCMS-C: RT 2.92 min; m/z 359.3 [M+Na]+

(f) tert-Butyl (S)-3-((R)-2-amino-1-hydroxyethyl)-6-methyl-3,4-dihydroisoquinoline-2(1H)-carboxylate A51

A mixture of tert-butyl (S)-3-((R)-1-hydroxy-2-nitroethyl)-6-methyl-3,4-dihydroisoquinoline-2(1H)-carboxylate A50 (50 mg, 0.15 mmol) and 10% Pd/C (50% wet with water, 80 mg) in absolute ethanol (5 mL) was stirred vigorously under hydrogen atmosphere for 3 days. The catalyst was removed by filtration through Celite and the Celite was washed with absolute ethanol (50 mL). The pooled filtrates were concentrated to give the title compound as a yellow solid (20 mg, 43%). LCMS-C: RT 2.42 min; m/z 307.2 [M+H]+

(g) (3S)-tert-Butyl 3-((1R)-2-(4-(3-oxa-8-azabicyclo[3.2.1]octane-8-carbonyl)-2-ethoxybenzamido)-1-hydroxyethyl)-6-methyl-3,4-dihydroisoquinoline-2(1H)-carboxylate A52

To a solution of 4-(3-oxa-8-azabicyclo[3.2.1]octane-8-carbonyl)-2-ethoxybenzoic acid I42 (77 mg, 0.25 mmol) and tert-butyl (S)-3-((R)-2-amino-1-hydroxyethyl)-6-methyl-3,4-dihydroisoquinoline-2(1H)-carboxylate A51 (70 mg, 0.23 mmol) in DCM (10 mL) were added DIPEA (119 mg, 0.92 mmol), HOBt (3 mg, 0.02 mmol) and EDCl.HCl (111 mg, 0.58 mmol). The resulting mixture was stirred at room temperature overnight. A saturated aqueous solution of NaHCO$_3$ (30 mL) was added and the aqueous layer extracted with DCM (3×30 mL). The combined organic layers were dried (Na$_2$SO$_4$) and concentrated to give the crude product which was purified by preparative TLC (DCM:MeOH=20:1) to give the title compound as a yellow oil (56 mg, 41%). $^1$H NMR (400 MHz, Methanol-d$_4$) δ 8.07-8.02 (m, 1H), 7.21 (s, 1H), 7.16-7.13 (m, 1H), 7.02-6.98 (m, 3H), 4.64 (br s, 1H), 4.39-4.23 (m, 4H), 3.96 (br s, 1H), 3.85-3.56 (m, 7H), 3.19-3.13 (m, 2H), 2.92-2.87 (m, 1H), 2.29 (s, 3H), 2.05-2.00 (m, 4H), 1.50-1.43 (m, 12H). LCMS-C: RT 6.01 min; m/z 594.0 [M+H]$^+$.

(h) 4-(3-Oxa-8-azabicyclo[3.2.1]octane-8-carbonyl)-2-ethoxy-N—((R)-2-hydroxy-2-((S)-6-methyl-1,2,3,4-tetrahydroisoquinolin-3-yl)ethyl)benzamide hydrochloride 125

A solution of (3S)-tert-butyl 3-((1R)-2-(4-(3-oxa-8-azabicyclo[3.2.1]octane-8-carbonyl)-2-ethoxybenzamido)-1-hydroxyethyl)-7-methyl-3,4-dihydroisoquinoline-2(1H)-carboxylate A52 (56 mg, 0.23 mmol) in diethyl ether (5 mL) at 0° C. was added a solution of saturated HCl in diethyl ether (5 mL) and the reaction stirred for 3 hours. The mixture was concentrated and the residue washed with diethyl ether to give the title compound (25 mg, 52%) as an off-white solid. $^1$H NMR (400 MHz, Methanol-d$_4$) δ 7.96 (d, J=8.0 Hz, 1H), 7.22 (s, 1H), 7.17-7.10 (m, 4H), 4.64 (br s, 1H), 4.39-4.21 (m, 5H), 3.96 (br s, 1H), 3.83-3.80 (m, 1H), 3.73-3.69 (m, 3H), 3.63-3.58 (m, 3H), 3.26-3.22 (m, 1H), 3.16-3.11 (m, 1H), 2.32 (s, 3H), 2.07-2.00 (m, 4H), 1.43 (t, J=6.8 Hz, 3H). LCMS-C: RT 2.12 min, m/z 494.1 [M+H]$^+$ (free base).

Assays

PRMT5 Biochemical Assay

Compounds of the invention may be tested for in vitro activity in the following assay: A histone H4 derived peptide is used as substrate (amino acid sequence: Ser-Gly-Arg-Gly-Lys-Gly-Gly-Lys-Gly-Leu-Gly-Lys-Gly-Gly-Ala-Lys-Arg-His-Arg-Lys-Val-N H$_2$). Full-length PRMT5 enzyme (NCBI Reference sequence NP_006100.2) was co-expressed with His$_6$-MEP50 in insect cells and purified via Nickel immobilized metal affinity and gel filtration chromatography ("the enzyme").

The 6 μL assay reactions are run in Greiner brand black 384-well low volume plates. All reactions contained assay buffer (phosphate buffered saline, 0.01% (v/v) Tween-20, 0.01% (w/v) albumin from chicken egg white, 1 mM dithiothreitol, 200 nM peptide substrate, 1 μM S-Adenosyl methionine, and 15 ng/reaction enzyme, with the enzyme being omitted from negative control reactions. Compounds were added in a volume of 100 nL from dilution series prepared in DMSO, positive and negative control reactions receiving the same volume DMSO without compound. The plates were sealed with adhesive seals and incubated for 4 hours at 37° C. Reaction progress was measured using the Transcreener™ EPIGEN methyltransferase assay (Bell-Brook Labs, Madison, Wis.) as recommended by the manufacturer. To each reaction 2 μL detection mix were added, containing coupling enzymes, fluorescence polarisation tracer, and AMP antibody. Plates were incubated for 90 min before being read on a PerkinElmer EnVision™ plate reader in fluorescence polarisation mode. IC$_{50}$ values were obtained from the raw readings by calculating percent inhibition (%1) for each reaction relative to controls on the same plate (% I=(I−CN)/(CP−CN) where CN/CP are the averages of the negative/positive reactions, respectively), then fitting the % I data vs. compound concentration [I] to % I=(A+((B−A)/(1+((C/[I])^D)))) where A is the lower asymptote, B is the upper asymptote, C is the IC$_{50}$ value, and D is the slope.

| Example Number | IC$_{50}$ (μM) |
|---|---|
| 1 | 4.686 |
| 2 | 0.763 |
| 53 | 22.020 |

PRMT5 Biomarker Assay

Compounds of the invention may be tested for potency to inhibit symmetrical dimethylation of arginine in the following assay:

The cell line TE11 was seeded at a density of 12,000 cells per well in 96 well tissue culture plates in DME medium and 10% foetal bovine serum, and allowed to adhere overnight under standard culture conditions (37° C., 5% CO$_2$). Compound dilutions prepared in DMSO were added to the medium, with negative control wells reserved for treatment with DMSO only and positive controls receiving a potent PRMT5 inhibitor. The concentration of the inhibitor had been previously determined to give maximum inhibition of the methylation. After incubation for 72 h, cells were washed twice in ice-cold PBS, lysed in lysis buffer (20 mM Tris pH 7.4, 135 mM NaCl, 1.5 mM MgCl$_2$, 1 mM EGTA, 10% glycerol and 1% Triton-X100), centrifuged at 15,000×g and the supernatants collected for subsequent analysis. The methylation level was determined using the EpiQuik™ Global Di-Methyl Histone H4R$^3$ Quantification ELISA Kit (Epigentek, Farmingdale, N.Y.) as per the manufacturer's recommendations; in parallel the total protein amount in the lysate was quantified using a Lowry protein assay. The methylation level was corrected for the total protein amount of each sample, normalised to the controls, and the data fitted against a four-parameter logistic model to determine the 50% inhibitory concentration (IC$_{50}$).

| Example Number | IC$_{50}$ (μM) |
|---|---|
| 1 | 0.956 |
| 2 | 0.0072 |

Revised PRMT5 Biochemical Assay

Compounds of the invention may be tested for in vitro activity in the following assay: A histone H4 derived peptide is used as substrate (amino acid sequence: Ser-Gly-Arg-Gly-Lys-Gly-Gly-Lys-Gly-Leu-Gly-Lys-Gly-Gly-Ala-Lys-Arg-His-Arg-Lys-Val-N H$_2$). Full-length PRMT5 enzyme (NCBI Reference sequence NP_006100.2) was co-expressed with His$_6$-MEP50 in insect cells and purified via Nickel immobilized metal affinity and gel filtration chromatography ("the enzyme").

The 6 μL reactions are run in Greiner brand black 384-well low volume assay plates. All reactions contained assay buffer (phosphate buffered saline, 0.01% (v/v) Tween-20, 0.01% (w/v) albumin from chicken egg white, 1 mM Dithiothreitol, 1 μM peptide substrate, 1 μM S-Adenosyl methionine, and 15 ng/reaction enzyme, with the enzyme being omitted from negative control reactions. Compounds were added in a volume of 100 nL from dilution series prepared in DMSO, positive and negative control reactions receiving the same volume DMSO without compound. The plates were sealed with adhesive seals and incubated for 4 hours at 37 degree Celsius. Reaction progress was measured using the Transcreener™ EPIGEN methyltransferase assay (Bell-Brook Labs, Madison, Wis.) as recommended by the manufacturer. To each reaction 2 µL detection mix were added, containing coupling enzymes, fluorescence polarisation tracer, and AMP antibody. Plates were incubated for 90 minutes before being read on a PerkinElmer EnVision™ plate reader in fluorescence polarisation mode. $IC_{50}$ values were obtained from the raw readings by calculating percent inhibition (%1) for each reaction relative to controls on the same plate (% I=(I−CN)/(CP−CN) where CN/CP are the averages of the negative/positive reactions, respectively), then fitting the %1 data vs. compound concentration [I] to % I=(A+((B−A)/(1+((C/[I])^D)))) where A is the lower asymptote, B is the upper asymptote, C is the $IC_{50}$ value, and D is the slope.

| Example Number | $IC_{50}$ (µM) |
|---|---|
| 3 | 8.359 |
| 4 | 8.786 |
| 5 | 51.058 |
| 6 | 45.752 |
| 7 | 19.988 |
| 8 | 16.534 |
| 9 | 12.536 |
| 10 | 22.495 |
| 12 | 0.663 |
| 13 | 0.551 |
| 14 | 2.331 |
| 15 | 0.383 |
| 16 | 0.662 |
| 17 | 1.266 |
| 18 | 2.103 |
| 19 | 0.912 |
| 20 | 11.687 |
| 21 | 0.070 |
| 22 | 2.153 |
| 23 | 5.140 |
| 24 | 3.688 |
| 25 | 1.701 |
| 26 | 0.053 |
| 27 | 0.044 |
| 28 | 0.180 |
| 29 | 0.535 |
| 30 | 0.139 |
| 31 | 0.204 |
| 32 | 0.511 |
| 33 | 0.305 |
| 34 | 1.680 |
| 35 | 0.152 |
| 36 | 0.148 |
| 37 | 0.105 |
| 38 | 0.599 |
| 39 | 0.846 |
| 40 | 0.705 |
| 41 | 1.389 |
| 42 | 0.212 |
| 43 | 0.967 |
| 44 | 1.245 |
| 45 | 0.500 |
| 46 | 0.230 |
| 47 | 3.368 |
| 48 | 0.192 |
| 49 | 0.038 |
| 50 | 0.019 |
| 51 | 0.061 |
| 52 | 3.333 |
| 53 | 21.191 |
| 54 | 82.115 |
| 55 | 0.016 |
| 56 | 0.383 |
| 57 | 0.594 |
| 58 | 0.657 |
| 59 | 0.593 |
| 60 | 3.302 |
| 61 | 0.104 |
| 62 | 0.102 |
| 63 | 0.245 |
| 64 | 0.261 |
| 65 | 2.287 |
| 66 | 0.329 |
| 67 | 0.307 |
| 68 | 2.256 |
| 69 | 1.298 |
| 70 | 0.121 |
| 71 | 0.939 |
| 72 | 0.585 |
| 73 | 2.268 |
| 74 | 0.338 |
| 75 | 1.202 |
| 76 | 0.262 |
| 77 | 8.759 |
| 78 | 1.695 |
| 79 | 0.168 |
| 80 | 0.161 |
| 81 | 0.051 |
| 82 | 0.106 |
| 83 | 0.065 |
| 84 | 0.124 |
| 85 | 0.279 |
| 86 | 3.822 |
| 87 | 0.057 |
| 88 | 0.187 |
| 89 | 0.203 |
| 90 | 0.947 |
| 91 | 0.123 |
| 92 | 0.310 |
| 93 | 0.759 |
| 94 | 0.780 |
| 95 | 9.706 |
| 96 | 1.377 |
| 97 | 18.654 |
| 98 | 0.230 |
| 99 | 0.127 |
| 100 | 0.066 |
| 101 | 0.104 |
| 102 | 0.068 |
| 103 | 0.065 |
| 104 | 0.147 |
| 105 | 0.038 |
| 106 | 0.212 |
| 107 | 0.546 |
| 108 | 0.017 |
| 109 | 0.688 |
| 110 | 1.491 |
| 111 | 4.665 |
| 112 | 2.308 |
| 113 | 2.742 |
| 114 | 5.486 |
| 115 | 2.834 |
| 116 | 1.114 |
| 117 | 0.487 |
| 118 | 0.502 |
| 124 | 0.070 |
| 125 | 0.232 |

Revised PRMT5 Biomarker Assay

Compounds of the invention may be tested for potency to inhibit symmetrical dimethylation of arginine in the following assay:

The cell line TE11 was seeded at a density of 6,000 cells per well in 96 well optical quality tissue culture plates in DME medium and 10% foetal bovine serum, and allowed to adhere for 5 hours under standard culture conditions (37 degree Celsius, 5% $CO_2$). Compound dilutions prepared in DMSO were added to the medium, with negative control wells reserved for treatment with DMSO only and positive controls receiving a potent PRMT5 inhibitor compound at 1 µM concentration. After incubation for 72 hours, the cells were fixed with 3.7% formaldehyde in PBS for 30 minutes at room temperature, washed with phosphate buffer saline and blocked with Odyssey blocking buffer (LI-COR, Lincoln, Nebr.). Rabbit anti-Di-Methyl Histone H4 Arginine 3 specific antibody (Epigentek) in Odyssey blocking buffer was added and incubated for 14 hours at 4 degree Celsius. After washing, anti-rabbit secondary antibody labelled with Alexa647 dye (LifeTechnologies) and Hoechst 33342 (1 µg/mL, SigmaAldrich) were added for 1 hour incubation. Plates were washed and read on a PerkinElmer Envision 2103 in fluorescence intensity scanning mode (24 scans across the well area). The methylation level information was corrected for the number of cells as expressed by the Hoechst 33342 stain, converted to percent inhibition relative to controls on the same plate and the data fitted against a four-parameter logistic model to determine the 50% inhibitory concentration ($IC_{50}$ plate-reader based). Alternatively, the plates were imaged on a PerkinElmer Phenix high content imaging platform. Using a Columbus image analysis pipeline, individual nuclei were located by Hoechst 33342 stain and the methylation level was calculated from the Alexa647-related intensity in the same area. The resulting mean intensity per cell was directly converted to percent inhibition as outlined above ($IC_{50}$, imager based).

| Example Number | $IC_{50}$ - plate-reader based (µM) |
|---|---|
| 3 | 1.460 |
| 8 | 2.325 |
| 15 | 0.023 |
| 21 | 0.087 |
| 26 | 0.015 |
| 27 | 0.007 |
| 28 | 0.012 |
| 37 | 0.254 |
| 49 | 0.006 |
| 50 | 0.0003 |
| 51 | 0.015 |
| 55 | 0.0004 |
| 69 | 0.003 |
| 74 | 0.005 |
| 80 | 0.003 |
| 81 | 0.003 |
| 83 | 0.004 |
| 84 | 0.081 |
| 102 | 0.005 |
| 103 | 0.004 |
| 108 | 0.001 |

| Example Number | IC50 - image based (µM) |
|---|---|
| 26 | 0.003 |
| 49 | 0.001 |
| 50 | 0.0003 |
| 55 | 0.0002 |
| 79 | 0.003 |
| 82 | 0.008 |
| 100 | 0.011 |
| 101 | 0.010 |
| 104 | 0.012 |
| 105 | 0.001 |
| 106 | 0.005 |

The invention claimed is:

1. A compound of formula I:

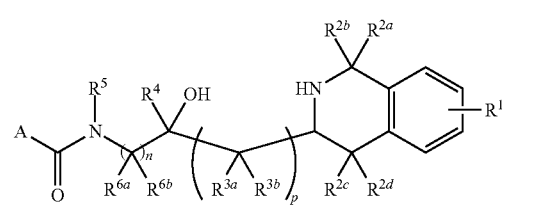

wherein:
n is 1 or 2;
p is 0 or 1;
$R^1$ is optionally one or more halo or methyl groups;
$R^{2a}$ and $R^{2b}$ are independently selected from the group consisting of:
 (i) F;
 (ii) H;
 (iii) Me; and
 (iv) $CH_2OH$;
$R^{2c}$ and $R^{2d}$ are independently selected from the group consisting of:
 (i) F;
 (ii) H;
 (iii) Me; and
 (iv) $CH_2OH$;
$R^{3a}$ and $R^{3b}$ are independently selected from H and Me;
$R^4$ is either H or Me;
$R^5$ is either H or Me;
$R^{6a}$ and $R^{6b}$ are independently selected from H and Me;
A is either
 (i) optionally substituted phenyl;
 (ii) optionally substituted naphthyl; or
 (iii) optionally substituted $C_{5-12}$ heteroaryl;
  wherein when A is substituted, the substituents are independently selected from one of the following groups:
   wherein when A is substituted, the substituents are independently selected from one of the following groups: $C_{1-4}$ alkyl, $C_{1-4}$ fluoroalkyl, $C_{3-6}$ cycloalkyl, $C_{5-6}$ heteroaryl, $C_{5-6}$ heteroaryl methyl, $C_{4-6}$ heterocyclyl, $C_{4-6}$ heterocyclyl methyl, phenyl, benzyl, halo, amido, amidomethyl, acylamido, acylamidomethyl, $C_{1-4}$ alkyl ester, $C_{1-4}$ alkyl ester methyl, $C_{1-4}$ alkyl carbamoyl, $C_{1-4}$ alkyl carbamoyl methyl, $C_{1-4}$ alkylacyl, $C_{1-4}$ alkylacyl methyl, phenylcarbonyl, carboxy, carboxymethyl, ether, amino, aminomethyl, sulfonamido, sulfonamino, sulfone, sulfoxide, nitrile and nitrilemethyl and when A is phenyl, the optional substituent may also be a fused $C_{5-6}$ $N_1$-containing heterocyclic ring.

2. A compound according to claim 1, wherein $R^1$ represents one to four Me or halo groups.

3. A compound according to claim 1, wherein:
 (a) $R^{2a}$, $R^{2b}$, $R^{2c}$ and $R^{2d}$ are all H; or
 (b) $R^{2a}$, $R^{2b}$, $R^{2c}$ and $R^{2d}$ consists of three H and one Me or $CH_2OH$ group; or
 (c) $R^{2a}$, $R^{2b}$, $R^{2c}$ and $R^{2d}$ consists of two H and two Me groups.

4. A compound according to claim 1, wherein:
(a) $R^{3a}$ is H and $R^{3b}$ is Me; or
(b) $R^{3a}$ and $R^{3b}$ are both H; or
(c) $R^{3a}$ and $R^{3b}$ are both Me.

5. A compound according to claim 1, wherein:
(a) $R^{6a}$ is H and $R^{6b}$ is Me; or
(b) $R^{6a}$ and $R^{6b}$ are both H; or
(c) $R^{6a}$ and $R^{6b}$ are both Me.

6. A compound according to claim 1 which is of:

(a) formula Ia

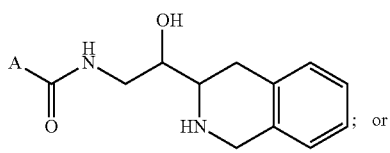

(b) formula Ib

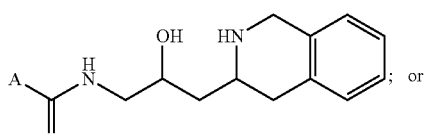

(c) formula Ic

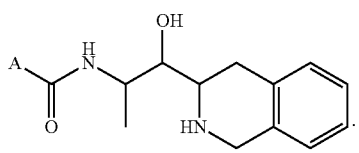

7. A compound according to claim 1, which is a racemate at the carbon atom to which OH is attached.

8. A compound according to claim 1, which is a single enantiomer at the carbon atom to which OH is attached.

9. A compound according to claim 1, wherein A is optionally substituted phenyl, wherein the substituents are selected from: $C_{1-4}$ alkyl, fluoro, chloro, bromo, acetyl, methoxy, ethoxy, —C(=O)Me, —C(=O)Et, —CH$_2$C(=O)Me, phenyl, —CF$_3$, —CF$_2$H, —CN, —CH$_2$CN, —OBn, —OPh, —OCF$_3$, —OCF$_2$H, —O—(C$_6$H$_4$)—CN, —COOH, —CH$_2$COOH, —C(=O)OMe, —C(=O)NH$_2$, —C(=O)NMeH, —C(=O)NMe$_2$, —C(=O)N$^i$PrH, —C(=O)-piperidinyl, —C(=O)-pyrrolidinyl, —C(=O)-morpholino (which may be bridged or substituted with one or two methyl groups), —C(=O)-azetidinyl, —CH$_2$C(=O)NH$_2$, —CH$_2$C(=O)-azetidinyl, —CH$_2$C(=O)NMeH, —CH$_2$C(=O)N$^i$PrH, —CH$_2$C(=O)-pyrrolidinyl, —CH$_2$C(=O)-morpholino, —CH$_2$-morpholino, —CH$_2$-methylpiperazinyl, —OCH$_2$pyridinyl, —OCH$_2$-methyloxadiazolyl, —CH$_2$-imidazolyl, —O-tetrahydropyranyl, —CH$_2$-tetraydropyranyl, —NH-methylpyrazinyl, —CH$_2$-triazolyl, —NHSO$_2$Ph, —NHSO$_2$Me, —SO$_2$NMePh, —SO$_2$NMe$_2$, —SO$_2$NHEt, —SO$_2$CF$_3$, -γ-lactam, —CH$_2$NHC(=O)Me, —CH$_2$NHC(=O)OMe, —CH$_2$NHC(=O)CF$_3$, morpholino, —CH$_2$NH$_2$, —C(=O)Ph, —OCH$_2$-isoxazolyl, —NH-pyrimidinyl, pyridizinyl, pyrimidinyl, pyridinyl, pyrazolyl, methylpyrazolyl, dimethylpyrazolyl, pyrazinyl, pyridazinyl, methyloxadiazolyl, oxadiazolyl, dimethyloxadiazolyl, isoxazolyl, dimethyltriazolyl, imidazolyl, benzimidazolyl and thiadiazolyl.

10. A compound according to claim 9, wherein:
(a) in the ortho position of the phenyl group there is a halo, $C_{1-4}$ alkyl, methoxy or ethoxy substituent; or
(b) in the meta position of the phenyl group there is a $C_{1-4}$ alkyl or $C_{5-6}$ heteroaryl substituent; or
(c) in the para position of the phenyl group there is an amido or amidomethyl substituent; or
(d) the phenyl group bears a halo or methoxy substituent in the ortho position, and an amido or amidomethyl substituent in the para position of the phenyl group; or
(e) the phenyl group bears a halo or methoxy substituent in the ortho position, and an amido or amidomethyl substituent in the para position of the phenyl group; or
(f) in the meta position of the phenyl group there is an amino substituent.

11. A compound according to claim 1, wherein A is:
(a) optionally substituted naphthyl; or
(b) optionally substituted $C_{5-12}$ heteroaryl selected from the group consisting of: pyridinyl, pyrimidinyl, pyrazinyl, isoxazolyl, oxazolyl, thiophenyl, thiazolyl, thiadiazolyl, pyrazolyl, pyridonyl, imidazolyl, benzimidazolyl, imidazopyridinyl and quinolinyl.

12. A compound according to claim 1, wherein A is selected from one of the following groups:

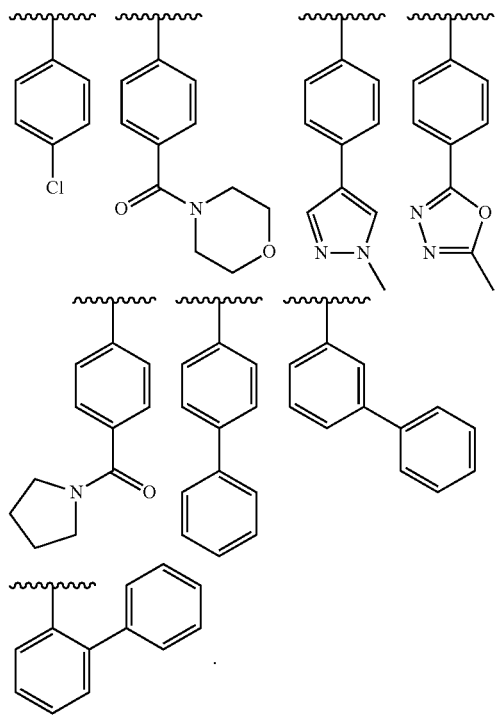

13. A compound according to claim 1, wherein A is selected from one of the following groups:

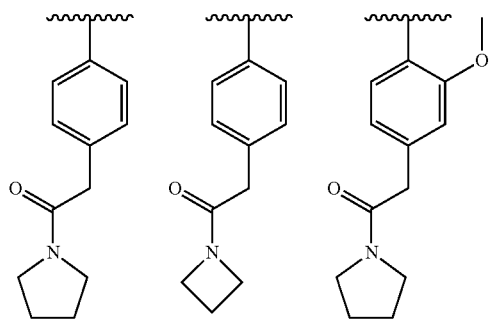

227
-continued
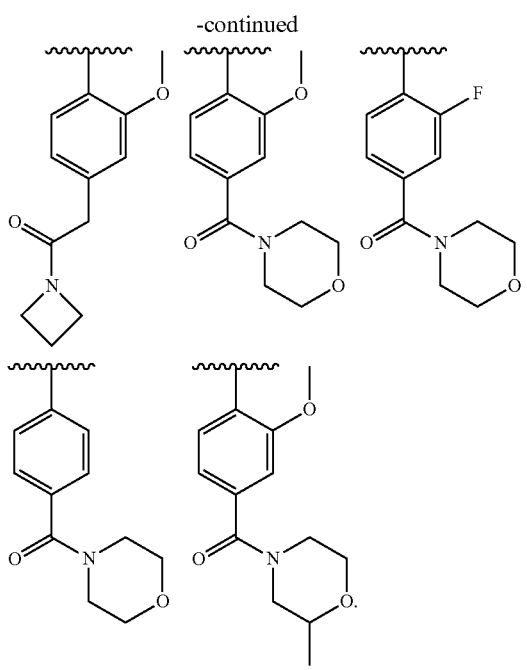
14. A compound according to claim 13, wherein A is selected from one of the following groups:
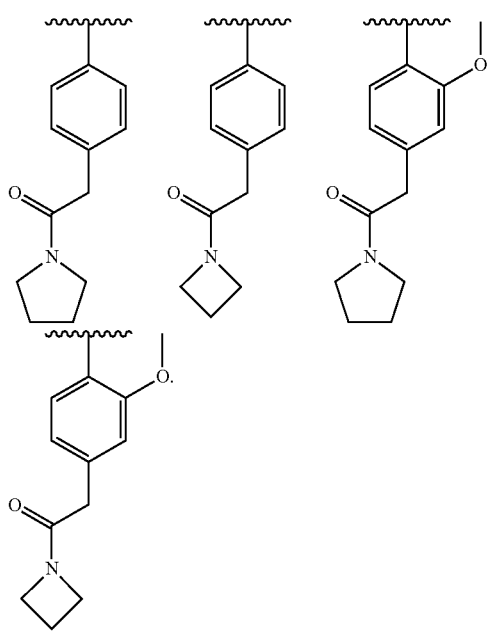
15. A compound according to claim 1, wherein A is selected from one of the following groups:
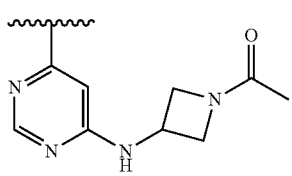
228
-continued
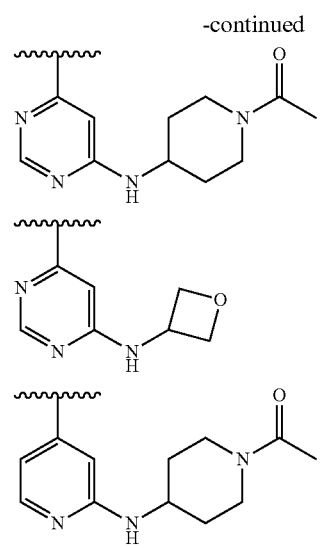
16. A compound according to claim 1, wherein A is selected from one of the following groups:
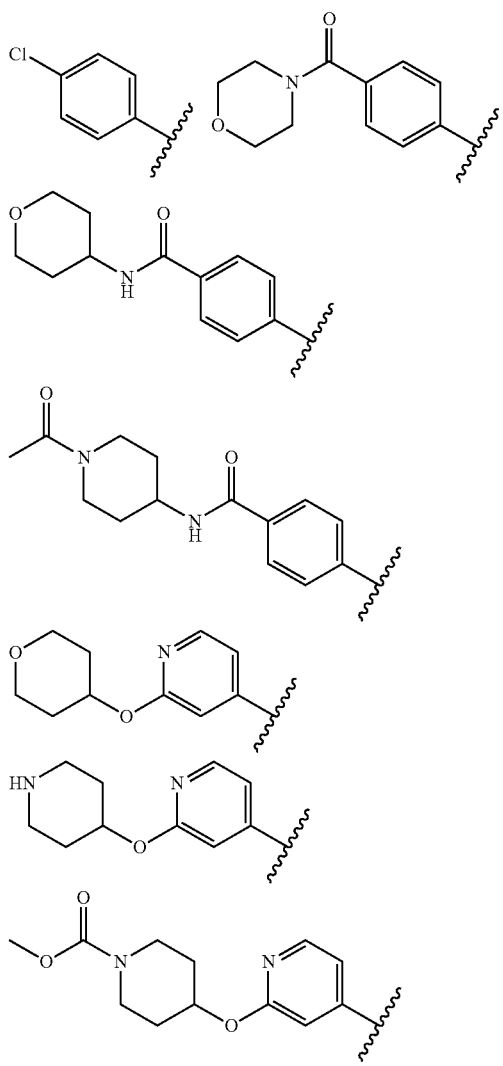

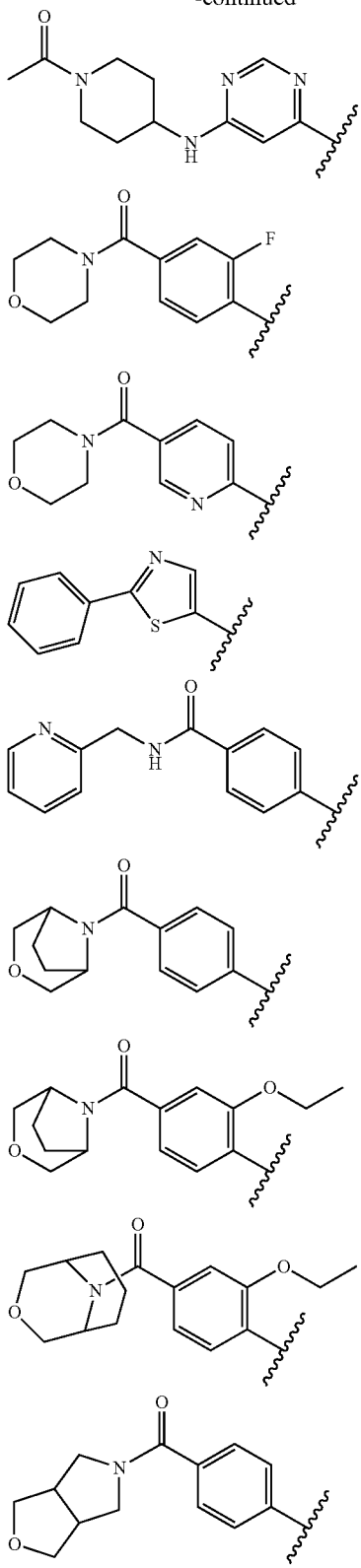
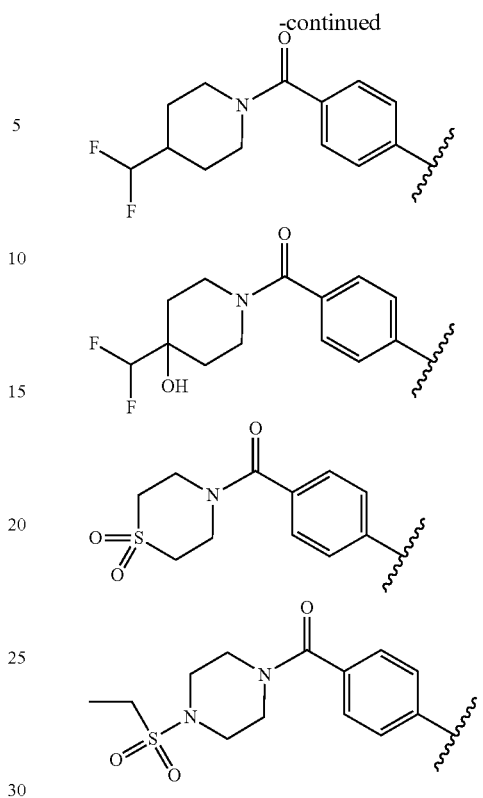

17. A compound according to claim 1, wherein A is selected from
   phenyl with a para-amido substituent;
   phenyl with a para-amido substituent, and an ortho-ethoxy group;
   pyridyl with para ether or amino group, where the ether or amino substituent is a $C_{5-6}$ heterocyclic group, with an optional ortho-ethoxy group; and
   pyridyl with a meta ether group, where the pyridyl N is in the para position.

18. A pharmaceutical composition comprising a compound according to claim 1 and a pharmaceutically acceptable excipient.

19. A method of inhibiting PRMT5 in a patient in need thereof, comprising administering to the patient a PRMT5 inhibiting effective amount of a composition according to claim 18.

20. A method of inhibiting PRMT5 in a patient in need thereof comprising administering to the patient a PRMT5 inhibiting effective amount of a pharmaceutical composition according to claim 18, wherein said inhibition of PRMT5 inhibits γ-globin gene expression during the treatment of hemoglobinopathies.

21. The method of claim 19, wherein said inhibition of PRMT5 treats a cancer that overexpresses PRMT5.

22. The method of claim 21, wherein said cancer is chosen from prostate cancer, lung cancer, melanoma cancer, breast cancer, colorectal cancer, gastric cancer, esophagus carcinoma, lung carcinoma, B-cell lymphoma and B-cell leukemia.

* * * * *